US010428032B2

(12) United States Patent
Horiguchi et al.

(10) Patent No.: US 10,428,032 B2
(45) Date of Patent: Oct. 1, 2019

(54) POLYMERIZABLE COMPOUND AND OPTICALLY ANISOTROPIC BODY

(71) Applicant: DIC Corporation, Tokyo (JP)

(72) Inventors: Masahiro Horiguchi, Kitaadachi-gun (JP); Junichi Mamiya, Kitaadachi-gun (JP); Yoshio Aoki, Kitaadachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 15/769,841

(22) PCT Filed: Aug. 25, 2016

(86) PCT No.: PCT/JP2016/074802
§ 371 (c)(1),
(2) Date: Apr. 20, 2018

(87) PCT Pub. No.: WO2017/068860
PCT Pub. Date: Apr. 27, 2017

(65) Prior Publication Data
US 2018/0312481 A1    Nov. 1, 2018

(30) Foreign Application Priority Data

Oct. 23, 2015 (JP) ................................ 2015-208940

(51) Int. Cl.
| | | |
|---|---|---|
| *C07D 277/82* | (2006.01) |
| *C07D 417/12* | (2006.01) |
| *C08F 20/38* | (2006.01) |
| *C08F 20/36* | (2006.01) |
| *C09K 19/38* | (2006.01) |
| *C08G 65/18* | (2006.01) |
| *C07D 277/84* | (2006.01) |
| *C08G 59/24* | (2006.01) |
| *C08G 65/14* | (2006.01) |
| *C08G 65/22* | (2006.01) |
| *C07C 251/86* | (2006.01) |
| *C09K 19/20* | (2006.01) |
| *C09K 19/34* | (2006.01) |
| *C08G 59/30* | (2006.01) |
| *C09K 19/04* | (2006.01) |

(52) U.S. Cl.
CPC .......... *C07D 277/82* (2013.01); *C07C 251/86* (2013.01); *C07D 277/84* (2013.01); *C07D 417/12* (2013.01); *C08F 20/36* (2013.01); *C08F 20/38* (2013.01); *C08G 59/24* (2013.01); *C08G 59/302* (2013.01); *C08G 65/14* (2013.01); *C08G 65/18* (2013.01); *C08G 65/22* (2013.01); *C09K 19/2028* (2013.01); *C09K 19/3497* (2013.01); *C09K 19/38* (2013.01); *C09K 19/3861* (2013.01); *C07C 2601/14* (2017.05); *C07C 2603/18* (2017.05); *C07C 2603/24* (2017.05); *C09K 2019/0444* (2013.01); *C09K 2019/0448* (2013.01)

(58) Field of Classification Search
CPC ............ C07D 277/82; C08F 222/1006; C09K 19/3838; G02B 1/111; G02B 5/30
USPC ....................................................... 526/257
See application file for complete search history.

(56) References Cited

U.S. PATENT DOCUMENTS

| | | | |
|---|---|---|---|
| 2014/0142266 A1 | 5/2014 | Sakamoto et al. | |
| 2014/0309396 A1 | 10/2014 | Sakamoto et al. | |
| 2015/0175564 A1 | 6/2015 | Sakamoto et al. | |
| 2016/0257659 A1* | 9/2016 | Sakamoto | C07C 251/82 |
| 2017/0260150 A1 | 9/2017 | Nose et al. | |
| 2018/0002276 A1 | 1/2018 | Kadomoto et al. | |
| 2018/0002459 A1 | 1/2018 | Endo et al. | |
| 2018/0002460 A1 | 1/2018 | Endo et al. | |
| 2018/0016502 A1 | 1/2018 | Endo et al. | |
| 2018/0031738 A1 | 2/2018 | Ishii et al. | |
| 2018/0037817 A1 | 2/2018 | Kuwana et al. | |
| 2018/0066189 A1 | 3/2018 | Ishii et al. | |

FOREIGN PATENT DOCUMENTS

| | | | |
|---|---|---|---|
| WO | 2012/147904 A1 | 11/2012 | |
| WO | 2012/176679 A1 | 12/2012 | |
| WO | 2014/010325 A1 | 1/2014 | |
| WO | 2015/064698 A1 | 5/2015 | |
| WO | WO 2015/064698 | * 5/2015 | |
| WO | 2016/088749 A1 | 6/2016 | |
| WO | 2016/114066 A1 | 7/2016 | |

(Continued)

OTHER PUBLICATIONS

International Search Report dated Nov. 15, 2016, issued in counterpart application No. PCT/JP2016/074802. (2 pages).

(Continued)

*Primary Examiner* — William K Cheung
(74) *Attorney, Agent, or Firm* — Westerman, Hattori, Daniels & Adrian, LLP

(57) ABSTRACT

The present invention provides a compound represented by the general formula (I), and a polymerizable composition containing the compound. When the polymerizable composition containing the compound represented by the formula (I) is used to form a filmy product, the resulting filmy product exhibits less change over time in phase difference and reverse wavelength dispersion and when the filmy polymer is irradiated with UV light, peeling from a substrate is unlikely to be caused. Further, the invention provides a polymer obtained through polymerization of the polymerizable composition and an optically anisotropic body obtained using the polymer.

10 Claims, No Drawings

(56) References Cited

FOREIGN PATENT DOCUMENTS

| WO | 2016/114211 A1 | 7/2016 |
| WO | 2016/114252 A1 | 7/2016 |
| WO | 2016/114253 A1 | 7/2016 |
| WO | 2016/114254 A1 | 7/2016 |
| WO | 2016/114255 A1 | 7/2016 |
| WO | 2016/114346 A1 | 7/2016 |
| WO | 2016/114347 A1 | 7/2016 |
| WO | 2016/114348 A1 | 7/2016 |

OTHER PUBLICATIONS

Notification of Reason for Rejection dated Aug. 24, 2017, issued in counterpart Japanese Patent Application No. 2017-539467, w/English translation (10 pages).

Decision to Grant a Patent dated Jan. 18, 2018, issued in counterpart Japanese Patent Application No. 2017-539467, w/English translation (5 pages).

* cited by examiner

POLYMERIZABLE COMPOUND AND OPTICALLY ANISOTROPIC BODY

This application is a national stage of PCT International Application No. PCT/JP2016/074802 filed in Japan on Aug. 25, 2016, which claims priority Japanese Patent Application No. 2015-208940 filed in Japan on Oct. 23, 2015.

TECHNICAL FIELD

The present invention relates to a compound having a polymerizable group, a polymerizable composition and a polymerizable liquid crystal composition containing the compound, and an optically anisotropic body using the polymerizable liquid crystal composition.

BACKGROUND ART

A compound having a polymerizable group (polymerizable compound) is used in various optical materials. For example, a polymerizable composition containing a polymerizable compound, which is in a liquid crystal state, is subjected to alignment, and then subjected to polymerization, thereby making it possible to produce a polymer having a uniform alignment. Such a polymer can be used for polarization plates, retardation plates and the like which are necessary for displays. In many cases, for satisfying necessary optical characteristics, polymerization speed, solubility, melting point, glass transition temperature, polymer transparency, mechanical strength, surface hardness, heat resistance and lightfastness, a polymerizable composition containing two or more kinds of polymerizable compounds is used. In such a case, the polymerizable compound to be used is required to impart good properties to the polymerizable composition without imposing any negative influence on the other characteristics thereof.

For improving the view angle of a liquid crystal display, the wavelength dispersion in terms of birefringence of a retardation film is required to lower or reverse. As a material for that purpose, various polymerizable liquid crystal compounds having reverse wavelength dispersion or low wavelength dispersion have been developed. However, such polymerizable compounds have a problem that, when formed into filmy polymers, they undergo change over time in phase difference and reverse wavelength dispersion, and have a problem that, when formed into filmy polymers and kept irradiated with UV light for a long period of time, peeling from substrates is likely to be caused (PTLs 1, 2 and 3). In the cases where films that are prone to change over time in phase difference and reverse wavelength dispersion or films that are prone to peeling are used, for example, in displays, there may occur a case where the screen color becomes unnatural in long-term use or a case where intended optical characteristics could not be obtained, so that a problem of significantly degrading the quality of display products is caused. Consequently, development of a polymerizable liquid crystal compound that has low wavelength dispersion or reverse wavelength dispersion and can solve these problems has been desired.

CITATION LIST

Patent Literature

[PTL 1] WO2012/147904A1
[PTL 2] WO2014/010325A1
[PTL 3] WO2012/176679A1

SUMMARY OF INVENTION

Technical Problem

An object of the present invention is to provide a polymerizable composition, which is added to a polymerizable composition so as to prepare a filmy polymer, in which the filmy polymer exhibits less change over time in phase difference and reverse wavelength dispersion, and when the filmy polymer is irradiated with UV light, peeling from a substrate is unlikely to be caused. Further, the present invention is to provide a polymer obtained through polymerization of the polymerizable composition and to provide an optically anisotropic body obtained using the polymer.

Solution to Problem

As a result of assiduous studies for solving the above-mentioned problems, the present inventors have reached development of a low wavelength dispersion and/or reverse wavelength dispersion compound having a specific molecular structure. Specifically, the present invention provides a compound represented by the following general formula (I):

[Chem. 1]

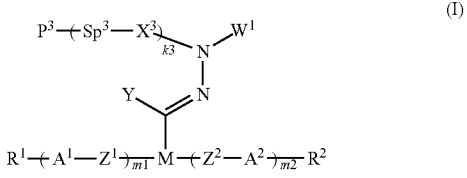

(wherein $P^3$ represents a polymerizable group, and the polymerizable group is a group that polymerizes through radical polymerization, cationic polymerization or anionic polymerization;

$Sp^3$ represents a spacer group, and plural $Sp^3$'s, if any, may be the same or different;

$X^3$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C— or a single bond, and plural $X^3$'s, if any, may be the same or different, provided that $P^3$—$(Sp^3$-$X^3)_{k3}$— does not contain an —O—O— bond;

k3 represents an integer of 1 to 10;

$A^1$ and $A^2$ each independently represent a 1,4-phenylene group, a 1,4-cyclohexylene group, a bicyclo[2,2,2]octane-1,4-diyl group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalane-2,6-diyl group or a 1,3-dioxane-2,5-diyl group, and these groups may be unsubstituted or substituted with one or more substituents L's;

L represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— or two or more (—$CH_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and arbitrary hydrogen atoms in the alkyl group may be substituted with a fluorine atom, or L may represent a group represented by $P^L$—$(Sp^L-X^L)_{kL}$, in which $P^L$ represents a polymerizable group, and the polymerizable group is a group that polymerizes through radical polymerization, cationic polymerization or anionic polymerization, $Sp^L$ represents a spacer group or a single bond, and plural $Sp^L$'s, if any, may be the same or different, $X^L$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C— or a single bond, and plural $X^L$'s, if any, may be the same or different (provided that $P^L$—$(Sp^L-X^L)_{kL}$— does not contain an —O—O— bond), kL represents an integer of 0 to 10, and plural L's, if any, in the compound may be the same or different;

$Z^1$ and $Z^2$ each independently represent —O—, —S—, —$OCH_2$—, —$CH_2O$—, —$CH_2CH_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—, —N=CH—, —CH=N—N=CH—, —CF=CF—, —C≡C— or a single bond, plural $Z^1$'s, if any, may be the same or different, plural $Z^2$'s, if any, may be the same or different;

m1 and m2 each independently represent an integer of 0 to 6, provided that m1+m2 represents an integer of 0 to 6;

M represents an optionally-substituted trivalent aromatic group;

Y represents a hydrogen atom, a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— or two or more (—$CH_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and arbitrary hydrogen atoms in the alkyl group may be substituted with a fluorine atom;

$W^1$ represents a group that contains an aromatic group and/or a nonaromatic group optionally substituted and having 1 to 40 carbon atoms, and the aromatic group may be a hydrocarbon ring or a hetero ring, the nonaromatic group may be a hydrocarbon group or a group where at least one arbitrary carbon atom of a hydrocarbon group is substituted with a hetero atom, provided that the group $W^1$ does not contain an —O—O— bond;

$R^1$ represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms in which one —$CH_2$— or two or more (—$CH_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—, —CF=CF— or —C≡C—, and arbitrary hydrogen atoms in the alkyl group may be substituted with a fluorine atom, or $R^1$ represents a group represented by $P^1$—$(Sp^1-X^1)_{k1}$— (where $P^1$ represents a polymerizable group, and the polymerizable group is a group that polymerizes through radical polymerization, cationic polymerization or anionic polymerization, $Sp^1$ represents a spacer group, plural $Sp^1$'s, if any, may be the same or different, $X^1$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C— or a single bond, plural $X^1$'s, if any, may be the same or different, provided that $P^1$—$(Sp^1-X^1)_{k1}$— does not contain an —O—O— bond, and k1 represents an integer of 0 to 10); and $R^2$ represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms in which one —$CH_2$— or two or more (—$CH_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—, —CF=CF— or —C≡C—, and arbitrary hydrogen atoms in the alkyl group may be substituted with a fluorine atom, or $R^2$ represents a group represented by $P^2$—$(Sp^2-X^2)_{k2}$— (where $P^2$ represents a polymerizable group, and the polymerizable group is a group that polymerizes through radical polymerization, cationic polymerization or anionic polymerization, $Sp^2$ represents a spacer group, plural $Sp^2$'s, if any, may be the same or different, $X^2$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C— or a single bond, plural $X^2$'s, if any, may be the same or different, provided that $P^2$—$(Sp^2\text{-}X^2)_{k2}$— does not contain an —O—O— bond, and k2 represents an integer of 0 to 10)), and also provides a polymerizable composition containing the compound, as well as resins, resin additives, oils, filters, adhesives, pressure-sensitive adhesives, oils and fats, inks, medicines, cosmetics, detergents, building materials, wrapping materials, liquid crystal materials, organic EL materials, organic semiconductor materials, electronic materials, display elements, electronic devices, communication devices, automotive parts, aircraft parts, machine parts, agricultural chemicals and foods using the compound, and products using these, and provides a polymerizable liquid crystal composition, a polymer obtained through polymerization of the polymerizable liquid crystal composition, and an optically anisotropic body using the polymer.

Advantageous Effects of Invention

The compound of the present invention is useful as a constituent member of a polymerizable composition. In addition, the optically anisotropic body using the polymerizable liquid crystal composition containing the compound of the present invention exhibits less change over time in phase difference and reverse wavelength dispersion and is unlikely to cause peeling from a substrate when irradiated with UV light, and is therefore useful for optical materials such as retardation films, etc.

DESCRIPTION OF EMBODIMENTS

The present invention provides a compound having a specific structure, and also provides not only a polymerizable composition containing the compound, but also resins, resin additives, oils, filters, adhesives, pressure-sensitive adhesives, oils and fats, inks, medicines, cosmetics, detergents, building materials, wrapping materials, liquid crystal materials, organic EL materials, organic semiconductor materials, electronic materials, display elements, electronic devices, communication devices, automotive parts, aircraft parts, machine parts, agricultural chemicals and foods each using the compound, products using these, a polymerizable liquid crystal composition, a polymer obtained through polymerization of the polymerizable liquid crystal composition, and an optically anisotropic body using the polymer.

In a graph drawn by plotting a wavelength λ of an incident light running on a retardation film on the horizontal axis and plotting a birefringence Δn thereof on the vertical axis, in the case where the birefringence Δn becomes larger while the wavelength λ becomes shorter, the film is generally referred to as "normal dispersion" by those skilled in the art, and in the case where the birefringence Δn becomes smaller while the wavelength λ becomes shorter, the film is generally referred to as "reverse wavelength dispersion" or "reverse dispersion". In the present invention, a compound which constitutes a retardation film having a Re(450)/Re(550) of 0.95 or less, which is the value calculated by dividing the in-plane phase difference thereof at a wavelength of 450 nm (Re (450)) by the in-plane phase difference thereof at a wavelength of 550 nm (Re(550)), is referred to as a reverse wavelength dispersion compound, and a compound which constitutes a retardation film having a Re(450)/Re(550) of more than 0.95 or less and 1.05 or less is referred to as a low wavelength dispersion compound. The measurement method for phase difference is as described below.

<<Measurement of Phase Difference>>

A polyimide solution for an alignment film is applied onto a glass substrate having a thickness of 0.7 mm according to a spin coating method, then dried at 100° C. for 10 minutes, and thereafter baked at 200° C. for 60 minutes to form a coating film. The resultant coating film is rubbed using a commercially available rubbing device.

A cyclopentanone solution containing 20% by mass of a target compound to be evaluated is applied onto the rubbed substrate, and dried at 100° C. for 2 minutes. The resultant coating film is cooled down to room temperature, and then, using a high-pressure mercury lamp, this is irradiated with UV rays at an intensity of 30 mW/cm$^2$ for 30 seconds to give a target film to be evaluated. The phase difference of the resultant film is measured using a retardation film/optical material inspection apparatus RETS-100 (manufactured by Otsuka Electronics Co., Ltd.).

In the case where the target compound to be evaluated does not dissolve in cyclopentanone, chloroform is used as the solvent. In the case where the target compound does not exhibit liquid crystallinity by itself, a composition prepared by adding the target compound (10% by mass, 20% by mass or 30% by mass) to a matrix liquid crystal composed of a compound represented by the following formula (A) (50% by mass) and a compound represented by the following formula (B) (50% by mass) is formed into a film:

[Chem. 2]

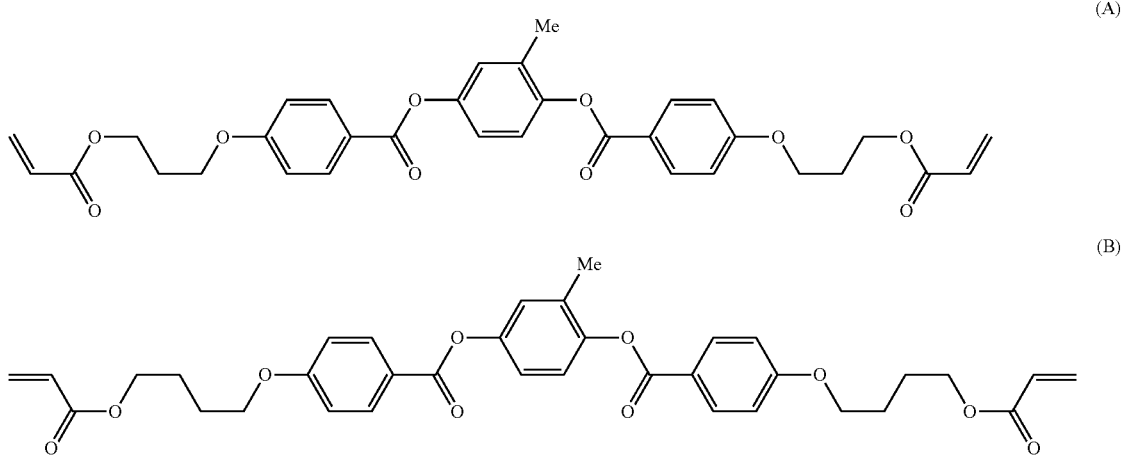

and the phase difference of the compound is determined by extrapolation.

In the general formula (I), $R^1$ represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms in which one —$CH_2$— or two or more (—$CH_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—, —CF=CF— or —C≡C—, and arbitrary hydrogen atoms in the alkyl group may be substituted with a fluorine atom, or $R^1$ represents a group represented by $P^1$—$(Sp^1\text{-}X^1)_{k1}$—. From the viewpoint of liquid crystallinity and easiness in synthesis, $R^1$ preferably represents a hydrogen atom, a fluorine atom, a cyano group, or a linear or branched alkyl group having 1 to 12 carbon atoms in which one —$CH_2$— or two or more (—$CH_2$—)'s not adjacent to each other may be each independently substituted with —O—, —COO—, —OCO— or —O—CO—O—, or represents a group represented by $P^1$—$(Sp^1\text{-}X^1)_{k1}$—, more preferably a hydrogen atom, a fluorine atom, a chlorine atom, a cyano group, or a linear alkyl group or linear alkoxy group having 1 to 12 carbon atoms, or represents a group represented by $P^1$—$(Sp^1\text{-}X^1)_{k1}$—, even more preferably a linear alkyl group or linear alkoxy group having 1 to 12 carbon atoms, or represents a group represented by $P^1$—$(Sp^1\text{-}X^1)_{k1}$—, and from the viewpoints of change over time in phase difference and reverse wavelength dispersion and of peeling from substrate, $R^1$ is especially preferably a group represented by $P^1$—$(Sp^1\text{-}X^1)_{k1}$—.

In the general formula (I), $R^2$ represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms in which one —$CH_2$— or two or more (—$CH_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—, —CF=CF— or —C≡C—, and arbitrary hydrogen atoms in the alkyl group may be substituted with a fluorine atom, or $R^2$ represents a group represented by $P^2$—$(Sp^2\text{-}X^2)_{k2}$—. From the viewpoint of liquid crystallinity and easiness in synthesis, $R^2$ preferably represents a hydrogen atom, a fluorine atom, a cyano group, or a linear or branched alkyl group having 1 to 12 carbon atoms in which one —$CH_2$— or two or more (—$CH_2$—)'s not adjacent to each other may be each independently substituted with —O—, —COO—, —OCO— or —O—CO—O—, or represents a group represented by $P^2$—$(Sp^2\text{-}X^2)_{k2}$—, more preferably a hydrogen atom, a fluorine atom, a chlorine atom, a cyano group, or a linear alkyl group or linear alkoxy group having 1 to 12 carbon atoms, or represents a group represented by $P^2$—$(Sp^2\text{-}X^2)_{k2}$—, even more preferably a linear alkyl group or linear alkoxy group having 1 to 12 carbon atoms, or represents a group represented by $P^2$—$(Sp^2\text{-}X^2)_{k2}$—, and from the viewpoints of change over time in phase difference and reverse wavelength dispersion and of peeling from substrate, $R^2$ is especially preferably a group represented by $P^2$—$(Sp^2\text{-}X^2)_{k2}$—.

In the general formula (I), from the viewpoint of stability over time in reverse wavelength dispersion and phase difference and of difficulty in peeling occurrence, more preferably, $R^1$ is a group represented by $P^1$—$(Sp^1\text{-}X^1)_{k1}$— and $R^2$ is any other group than a group represented by $P^2$—$(Sp^2\text{-}X^2)_{k2}$—, or $R^1$ is any other group than a group represented by $P^1$—$(Sp^1\text{-}X^1)_{k1}$— and $R^2$ is a group represented by $P^2$—$(Sp^2\text{-}X^2)_{k2}$—, or $R^1$ is a group represented by $P^1$—$(Sp^1\text{-}X^1)_{k1}$— and $R^2$ is a group represented by $P^2$—$(Sp^2\text{-}X^2)_{k2}$—; and especially preferably, $R^1$ is a group represented by $P^1$—$(Sp^1\text{-}X^1)_{k1}$— and $R^2$ is a group represented by $P^2$—$(Sp^2\text{-}X^2)_{k2}$—.

$P^1$ and $P^2$, if present, and $P^3$ in the general formula (I), each independently represent a polymerizable group, and the polymerizable group is a group that polymerizes through radical polymerization, cationic polymerization or anionic polymerization, and each is preferably selected from the following formulae (P-1) to (P-19):

[Chem. 3]

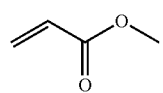
(P-1)

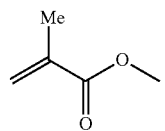
(P-2)

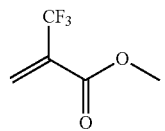
(P-3)

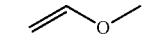
(P-4)

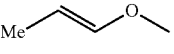
(P-5)

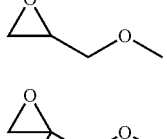
(P-6)

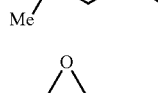
(P-7)

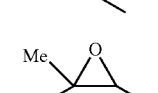
(P-8)

(P-9)

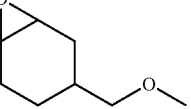
(P-10)

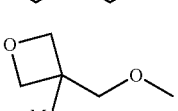
(P-11)

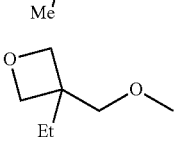
(P-12)

-continued

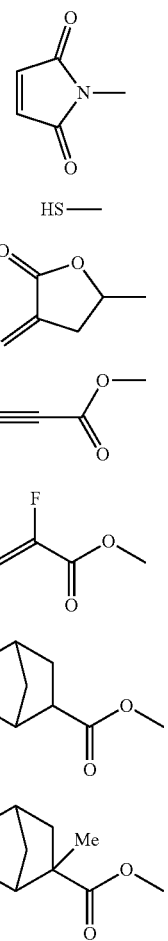

(P-13)

(P-14)

(P-15)

(P-16)

(P-17)

(P-18)

(P-19)

In particular, in the case where UV polymerization is carried out as the polymerization method, the formula (P-1), the formula (P-2), the formula (P-3), the formula (P-4), the formula (P-6), the formula (P-10), the formula (P-12), the formula (P-14) or the formula (P-17) is preferred, the formula (P-1), the formula (P-2), the formula (P-3), the formula (P-6), the formula (P-10) or the formula (P-12) is more preferred, the formula (P-1), the formula (P-2) or the formula (P-3) is further preferred, and the formula (P-1) or the formula (P-2) is especially preferred.

$Sp^1$ and $Sp^2$, if present, and $Sp^3$ in the general formula (I), each independently represent a spacer group, and plural groups with respect to each of $Sp^1$, $Sp^2$ and $Sp^3$, if any, may be the same or different. From the viewpoint of liquid crystallinity, easiness in availability of raw materials and easiness in synthesis, it is preferable that $Sp^1$ and $Sp^2$, if present, and $Sp^3$ each independently represents an alkylene group having 1 to 20 carbon atoms in which one —$CH_2$— or two or more (—$CH_2$—)'s not adjacent to each other may be each independently substituted with —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF— or —C≡C—; and the plural groups with respect to each of $Sp^1$, $Sp^2$ and $Sp^3$, if any, may be the same or different, it is more preferable that $Sp^1$ and $Sp^2$, if present, and $Sp^3$ each independently represents a linear alkylene group having 1 to 20 carbon atoms in which one —$CH_2$— or two or more (—$CH_2$—)'s not adjacent to each other may be each independently substituted with —O—, —COO—, —OCO— or —OCO—O—; the plural groups with respect to each of $Sp^1$, $Sp^2$ and $Sp^3$, if any, may be the same or different, and it is even more preferable that $Sp^1$ and $Sp^2$, if present, and $Sp^3$ each independently represents a linear alkylene group having 1 to 12 carbon atoms in which one —$CH_2$— or two or more (—$CH_2$—)'s not adjacent to each other may be each independently substituted with —O—; and the plural groups with respect to each of $Sp^1$, $Sp^2$ and $Sp^3$, if any, may be the same or different. From the viewpoint of liquid crystallinity and solubility in solvent, especially preferably, $Sp^1$ and $Sp^2$ each independently represent a linear alkylene group having 1 to 12 carbon atoms, and $Sp^3$ represents a linear alkylene group having 1 to 12 carbon atoms in which one —$CH_2$— or two or more (—$CH_2$—)'s not adjacent to each other may be each independently substituted with —O—.

In the general formula (I), $X^1$ and $X^2$, if present, and $X^3$ each independently represent —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C— or a single bond, and plural groups with respect to each of $X^1$, $X^2$ and $X^3$, if any, may be the same or different. From the viewpoint of easiness in availability of raw materials and easiness in synthesis, plural groups with respect to each of $X^1$, $X^2$ and $X^3$, if any, may be the same or different, it is preferable that $X^1$, $X^2$ and $X^3$ each independently represent —O—, —S—, —$OCH_2$—, —$CH_2O$—, —COO—, —OCO—, —CO—S—, —S—CO—, —O—CO—O—, —COO—$CH_2CH_2$—, —OCO—$CH_2CH_2$—, —$CH_2CH_2$—COO—, —$CH_2CH_2$—OCO— or a single bond, and it is more preferable that $X^1$, $X^2$ and $X^3$ each independently represent —O—, —COO—, —OCO— or a single bond. From the viewpoint of easiness in synthesis, especially preferably, $X^1$ and $X^2$ each are —O— and $X^3$ is a single bond.

In the general formula (I), k1 and k2 each independently represent an integer of 0 to 10. From the viewpoint of liquid crystallinity and easiness in availability of raw materials, preferably, they each independently represent an integer of 0 to 3. From the viewpoint of cure shrinkage of films to be formed, more preferably, they each independently represent an integer of 1 to 3, and especially preferably 1.

In the general formula (I), k3 represents an integer of 1 to 10. From the viewpoint of liquid crystallinity and easiness in availability of raw materials, k3 is preferably an integer of 1 to 3. From the viewpoint of cure shrinkage of films to be formed, k3 is especially preferably 1.

In the general formula (I), the group that directly bonds to the N atom in the group represented by $P^3$—$(Sp^3-X^3)_{k3}$— is, from the viewpoint of easiness in synthesis, preferably —$CH_2$—.

In the general formula (I), the group represented by $P^3$—$(Sp^3\text{-}X^3)_{k3}$— is, from the viewpoint of stability over change in phase difference and reverse wavelength dispersion and of peeling after long-term irradiation with UV light, preferably a group selected from the following formula (P3-1), formula (P3-2) and formula (P3-3):

[Chem. 4]

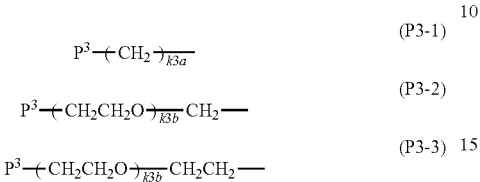

(P3-1)
(P3-2)
(P3-3)

(wherein $P^3$ has the same meaning as in the general formula (I), k3a represents an integer of 2 to 20, and k3b represents an integer of 1 to 6). In the formula (P3-1), k3a is, from the viewpoint of liquid crystallinity, preferably an integer of 2 to 12, and especially preferably an integer of 2 to 8. In the formula (P3-2) and the formula (P3-3), k3b is, from the viewpoint of liquid crystallinity, more preferably an integer of 1 to 3, and especially preferably 1 or 2.

In the general formula (I), $A^1$ and $A^2$ each independently represent a 1,4-phenylene group, a 1,4-cyclohexylene group, a bicyclo[2,2,2]octane-1,4-diyl group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalane-2,6-diyl group or a 1,3-dioxane-2,5-diyl group, and these groups may be unsubstituted or substituted with one or more substituents L's. From the viewpoint of easiness in synthesis, easiness in availability of raw materials and liquid crystallinity, more preferably, $A^1$ and $A^2$ each independently represent a 1,4-phenylene group, a 1,4-cyclohexylene group or a naphthalene-2,6-diyl group, which is unsubstituted or is substituted with one or more substituents L's; even more preferably, each independently represent a group selected from the following formulae (A-1) to (A-11):

[Chem. 5]

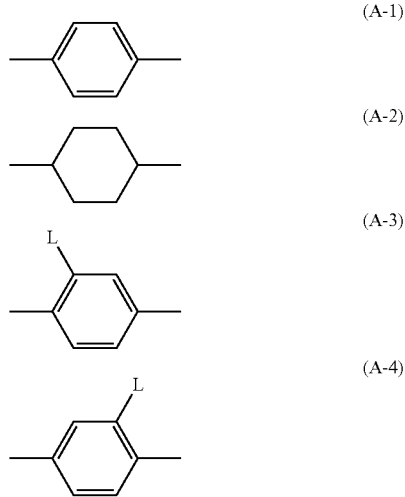

(A-1)
(A-2)
(A-3)
(A-4)

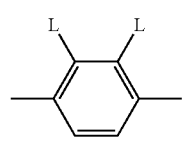
(A-5)

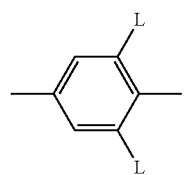
(A-6)

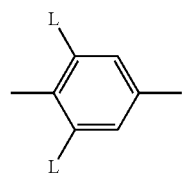
(A-7)

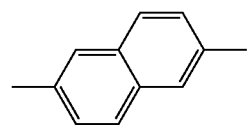
(A-8)

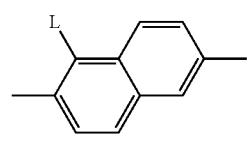
(A-9)

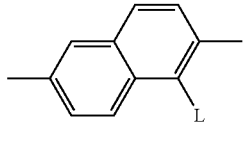
(A-10)

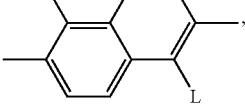
(A-11)

still more preferably, each independently represent a group selected from the formulae (A-1) to (A-8), and especially preferably each independently represent a group selected from the formulae (A-1) to (A-4).

In the general formula (I), L represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— or two or more (—$CH_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and arbitrary hydrogen atoms in the alkyl group may be substituted with a fluorine atom, or L may represent a group represented by $P^L$—$(Sp^L\text{-}X^L)_{kL}$— in which $P^L$ represents a polymerizable group, the polymerizable group is a group that polymerizes through radical polymerization, cationic polymerization or anionic polymerization, $Sp^L$ represents a spacer group or a single bond, plural $Sp^L$'s, if any, may be the same or different, $X^L$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C— or a single bond, plural $X^L$'s, if any, may be the same or different, provided that $P^L$—$(Sp^L$-$X^L)_{kL}$— does not contain an —O—O— bond, kL represents an integer of 0 to 10, and plural L's, if any, in the compound may be the same or different. From the viewpoint of liquid crystallinity and easiness in synthesis, it is preferable that L represents a fluorine atom, a chlorine atom, or a linear or branched alkyl group having 1 to 12 carbon atoms in which arbitrary hydrogen atoms may be substituted with a fluorine atom and one —CH$_2$— or two or more (—CH$_2$—)'s not adjacent to each other may be each independently substituted with a group selected from —O—, —COO— or —OCO—; and plural L's, if any, may be the same or different, it is more preferable that L represents a fluorine atom, a chlorine atom, or a linear or branched alkyl group or alkoxy group having 1 to 12 carbon atoms in which arbitrary hydrogen atoms may be substituted with a fluorine atom; and plural L's, if any, may be the same or different, and it is even more preferable that L represents a fluorine atom, a chlorine atom, or a linear alkyl group or linear alkoxy group having 1 to 8 carbon atoms; and plural L's, if any, may be the same or different, and it is especially preferable that L represents a fluorine atom, a chlorine atom, a methyl group or a methoxy group; and plural L's, if any, may be the same or different. In the case where L represents a group represented by $P^L$—$(Sp^L$-$X^L)_{kL}$, preferred structures of $P^L$, $Sp^L$, $X^L$ and kL are the same as the preferred structures of $P^1$, $Sp^1$, $X^1$ and k1, respectively.

In the general formula (I), $Z^1$ and $Z^2$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C— or a single bond, plural $Z^1$'s, if any, may be the same or different, and plural $Z^2$'s, if any, may be the same or different. From the viewpoint of liquid crystallinity, easiness in availability of raw materials and easiness in synthesis, it is preferable that $Z^1$ and $Z^2$ each is independently —OCH$_2$—, —CH$_2$O—, —COO—, —OCO—, —CF$_2$O—, —OCF$_2$—, —CH$_2$CH$_2$—, —CF$_2$CF$_2$—, —COO—CH$_2$CH$_2$—, —OCO—CH$_2$CH$_2$—, —CH$_2$CH$_2$—COO—, —CH$_2$CH$_2$—OCO— or a single bond; and plural groups with respect to each of $Z^1$ and $Z^2$, if any, may be the same or different, it is more preferable that $Z^1$ and $Z^2$ each is independently —OCH$_2$—, —CH$_2$O—, —COO—, —OCO—, —CF$_2$O—, —OCF$_2$— or a single bond; and plural groups with respect to each of $Z^1$ and $Z^2$, if any, may be the same or different, and it is especially preferable that $Z^1$ and $Z^2$ each is independently —OCH$_2$—, —CH$_2$O—, —COO— or —OCO—.

In the general formula (I), m1 and m2 each independently represent an integer of 0 to 6, provided that m1+m2 represents an integer of 0 to 6. From the viewpoint of solubility in solvent, liquid crystallinity, and stability over time in phase difference and reverse wavelength dispersion, preferably, m1 and m2 each independently represent an integer of 1 to 3, more preferably each independently represent 1 or 2, and especially preferably 2. m1+m2 is preferably an integer of 1 to 4, m1+m2 is more preferably an integer of 2 to 4, m1+m2 is even more preferably 2 or 4, and m1+m2 is especially preferably 4.

In the general formula (I), M represents an optionally-substituted trivalent aromatic group. From the viewpoint of solubility in solvent, liquid crystallinity and easiness in synthesis, M is preferably a group selected from the following formulae (M-1) to (M-6):

[Chem. 6]

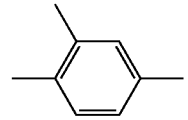
(M-1)

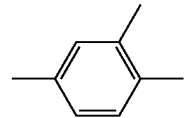
(M-2)

(M-3)

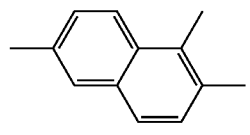
(M-4)

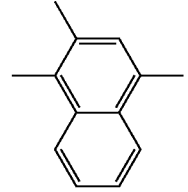
(M-5)

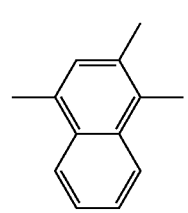
(M-6)

(wherein the two bonds in the horizontal direction each means a bond to $R^1$-$(A^1$-$Z)_{m1}$— or —$(Z^2$-$A^2)_{m2}$-$R^2$, the upper bond means a bond to the remaining group, and these groups may be unsubstituted or substituted with one or more substituents $L^{M}$'s, and arbitrary (—CH=)'s each may be substituted with —N=). From the viewpoint of solubility in solvent, liquid crystallinity and easiness in synthesis, M is more preferably a group selected from the following formulae (M-1-1) to (M-6-1):

[Chem. 7]

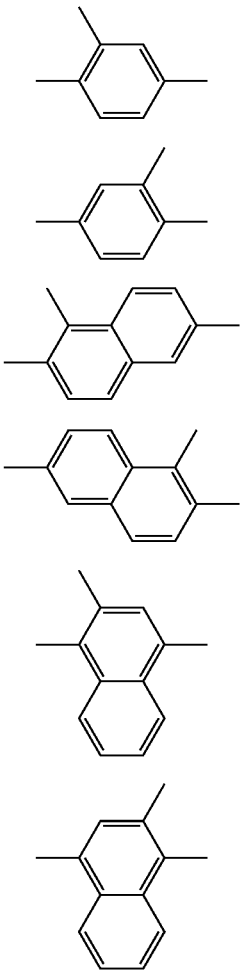

(M-1-1)

(M-2-1)

(M-3-1)

(M-4-1)

(M-5-1)

(M-6-1)

(wherein the two bonds in the horizontal direction each mean a bond to $R^1$-$(A^1$-$Z^1)_{m1}$— or —$(Z^2$-$A^2)_{m2}$-$R^2$, respectively, and the upper bond means a bond to the remaining group.) Especially preferably, M represents a group selected from the formula (M-1-1) or (M-2-1).

With respect to the formulae (M-1) to (M-6), $L^M$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— or two or more (—$CH_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and arbitrary hydrogen atoms in the alkyl group may be substituted with a fluorine atom, or $L^M$ represents a group represented by $P^{LM}$—$(Sp^{LM}$-$X^{LM})_{kLM}$, r in which $P^{LM}$ represents a polymerizable group, and the polymerizable group is a group that polymerizes through radical polymerization, cationic polymerization or anionic polymerization, $Sp^{LM}$ represents a spacer group or a single bond, plural $Sp^{LM}$'s, if any, may be the same or different, $X^{LM}$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C— or a single bond, and plural $X^{LM}$'s, if any, may be the same or different, provided that $P^{LM}$—$(Sp^{LM}$-$X^{LM})_{kLM}$— does not contain an —O—O— bond, kLM represents an integer of 0 to 10, and plural $L^M$'s, if any, in the compound may be the same or different. From the viewpoint of liquid crystallinity and easiness in synthesis, it is preferable that $L^M$ is a fluorine atom, a chlorine atom, a nitro group, a cyano group, a dimethylamino group, or a linear or branched alkyl group having 1 to 12 carbon atoms in which arbitrary hydrogen atoms may be substituted with a fluorine atom and one —$CH_2$— or two or more (—$CH_2$—)'s not adjacent to each other may be each independently substituted with a group selected from —O—, —COO— or —OCO—; and plural $L^M$'s, if any, may be the same or different and; it is more preferable that $L^M$ is a fluorine atom, a chlorine atom, a nitro group, a cyano group, a dimethylamino group, or a linear or branched alkyl group or alkoxy group having 1 to 12 carbon atoms in which arbitrary hydrogen atoms may be substituted with a fluorine atom; and plural $L^M$'s, if any, may be the same or different and, and it is especially preferable that $L^M$ is a fluorine atom, a chlorine atom, a nitro group, a cyano group, a dimethylamino group, a methyl group or a methoxy group. In the case where $L^M$ represents a group represented by $P^{LM}$—$(Sp^{LM}$-$X^{LM})_{kLM}$—, preferred structures of $P^{LM}$, $Sp^{LM}$, $X^{LM}$ and $k^{LM}$ are the same as the preferred structures of $P^1$, $Sp^1$, $X^1$ and k1, respectively.

In the general formula (I), Y represents a hydrogen atom, a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— or two or more (—$CH_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and arbitrary hydrogen atoms in the alkyl group may be substituted with a fluorine atom. From the viewpoint of liquid crystallinity and easiness in synthesis, Y is preferably a hydrogen atom, a fluorine atom, a chlorine atom, a nitro group, a cyano group, or a linear or branched alkyl group having 1 to 20 carbon atoms in which arbitrary hydrogen atoms may be substituted with a fluorine atom and one —CH$_2$— or two or more (—CH$_2$—)'s not adjacent to each other may be each independently substituted with —O—, —S—, —CO—, —COO— or —OCO—, Y is more preferably a hydrogen atom, or a linear or branched alkyl group having 1 to 12 carbon atoms in which arbitrary hydrogen atoms may be substituted with a fluorine atom, Y is even more preferably a hydrogen atom or a linear alkyl group having 1 to 12 carbon atoms, and Y is especially preferably a hydrogen atom.

In the general formula (I), W$^1$ represents a group that contains an aromatic group and/or a nonaromatic group optionally substituted and having 1 to 40 carbon atoms, the aromatic group may be a hydrocarbon ring or a hetero ring, and the nonaromatic group may be a hydrocarbon group or a group where at least one arbitrary carbon atom of a hydrocarbon group is substituted with a hetero atom (provided that the group W$^1$ does not contain an —O—O— bond). From the viewpoint of liquid crystallinity and easiness in synthesis, W$^1$ is preferably a group selected from the following formulae (W-1) to (W-20):

[Chem. 8]

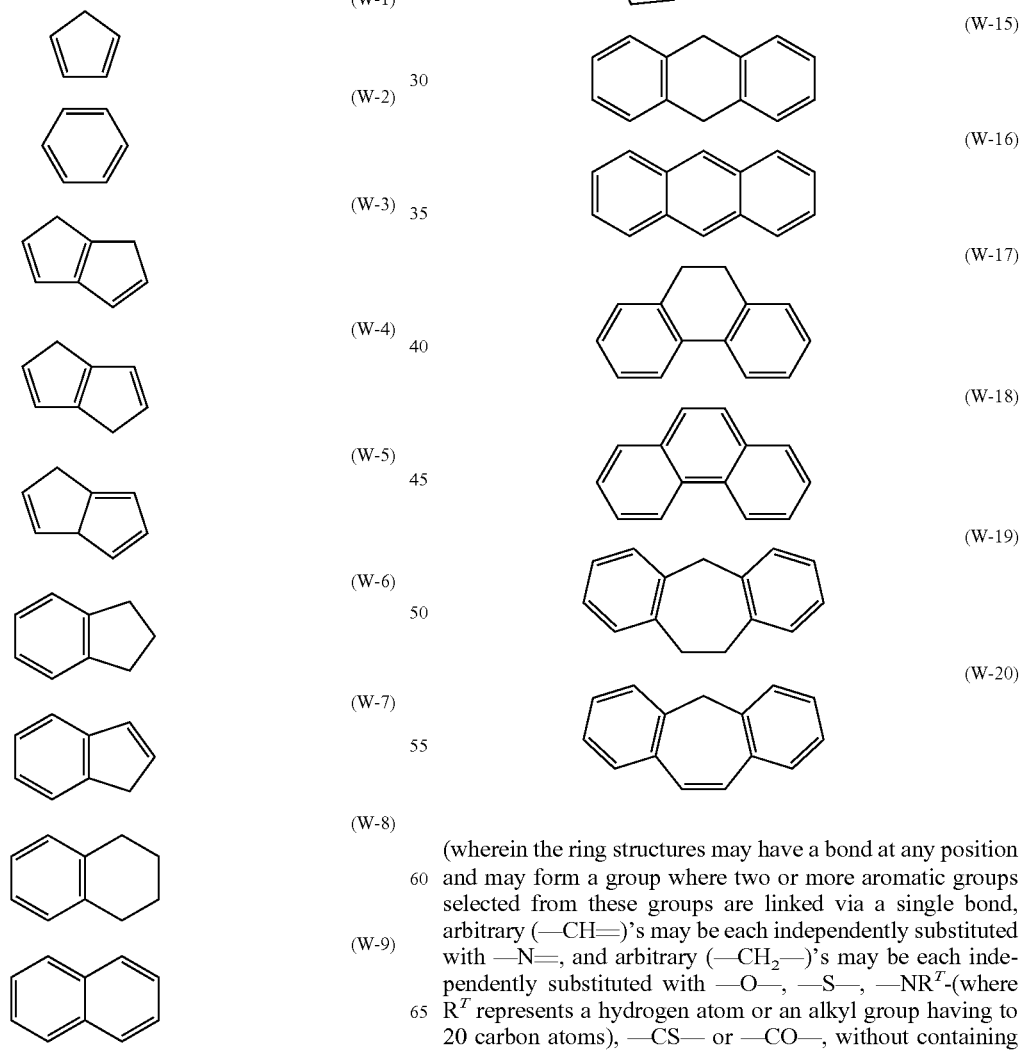

(wherein the ring structures may have a bond at any position and may form a group where two or more aromatic groups selected from these groups are linked via a single bond, arbitrary (—CH═)'s may be each independently substituted with —N═, and arbitrary (—CH$_2$—)'s may be each independently substituted with —O—, —S—, —NR$^T$-(where R$^T$ represents a hydrogen atom or an alkyl group having to 20 carbon atoms), —CS— or —CO—, without containing an —O—O— bond. These groups may be unsubstituted or substituted with one or more substituents $L^W$'s. Here, the wording, "may have a bond at any position" is meant to indicate that, since $W^1$ is a monovalent group, the group may have one bond at an arbitrary position (hereinunder in the present invention, the same shall apply to the wording "may have a bond at any position")).

$L^W$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— or two or more (—$CH_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, and arbitrary hydrogen atoms in the alkyl group may be substituted with a fluorine atom, or $L^W$ represents a group represented by $P^{LW}$—$(Sp^{LW}-X^{LW})_{kLW}$—. From the viewpoint of liquid crystallinity and easiness in synthesis, $L^W$ is preferably a fluorine atom, a chlorine atom, a pentafluorosulfuranyl group, a nitro group, a methylamino group, a dimethylamino group, a diethylamino group, a diisopropylamino group, or a linear or branched alkyl group having 1 to 20 carbon atoms in which arbitrary hydrogen atoms may be substituted with a fluorine atom and one —$CH_2$— or two or more (—$CH_2$—)'s not adjacent to each other may be each independently substituted with a group selected from —O—, —S—, —CO—, —COO—, —OCO—, —O—CO—O—, —CH=CH—, —CF=CF— or —C≡C—, more preferably a fluorine atom, a chlorine atom, or a linear or branched alkyl group having 1 to 12 carbon atoms in which arbitrary hydrogen atoms may be substituted with a fluorine atom and one —$CH_2$— or two or more (—$CH_2$—)'s not adjacent to each other may be each independently substituted with a group selected from —O—, —COO— or —OCO—, even more preferably a fluorine atom, a chlorine atom, or a linear or branched alkyl group or alkoxy group having 1 to 12 carbon atoms in which arbitrary hydrogen atoms may be substituted with a fluorine atom, and especially preferably a fluorine atom, a chlorine atom, or a linear alkyl group or linear alkoxy group having 1 to 8 carbon atoms. In the case where $L^W$ represents a group represented by $P^{LW}$—$(Sp^{LW}-X^{LW})_{kLW}$—, preferred structures of $P^{LW}$, $Sp^{LW}$, $X^{LW}$ and kLW are the same as the preferred structures of $P^1$, $Sp^1$, $X^1$ and k1, respectively.

Preferably, the group represented by the above-mentioned formula (W-1) is a group selected from the following formulae (W-1-1) to (W-1-7), which may be unsubstituted or substituted with one or more of the above-mentioned substituents $L^W$'s:

[Chem. 9]

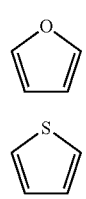
(W-1-1)

(W-1-2)

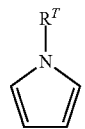
(W-1-3)

(W-1-4)

(W-1-5)

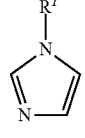
(W-1-6)

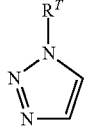
(W-1-7)

(wherein these groups may have a bond at any position, and $R^T$ represents a hydrogen atom or an alkyl group having 1 to 8 carbon atoms.) Preferably, the group represented by the above-mentioned formula (W-2) is a group selected from the following formulae (W-2-1) to (W-2-8), which may be unsubstituted or substituted with one or more of the above-mentioned substituents $L^W$'s:

[Chem. 10]

(W-2-1)

(W-2-2)

(W-2-3)

(W-2-4)

(W-2-5)

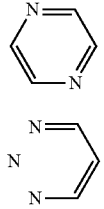
(W-2-6)

-continued

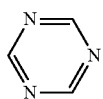
(W-2-7)

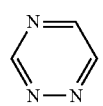
(W-2-8)

(wherein these groups may have a bond at any position.) Preferably, the group represented by the above-mentioned formula (W-3) is a group selected from the following formulae (W-3-1) to (W-3-6), which may be unsubstituted or substituted with one or more of the above-mentioned substituents $L^W$'s:

[Chem. 11]

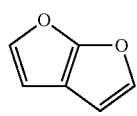
(W-3-1)

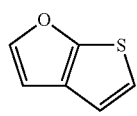
(W-3-2)

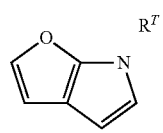
(W-3-3)

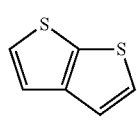
(W-3-4)

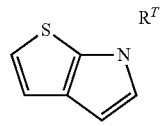
(W-3-5)

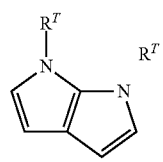
(W-3-6)

(wherein these groups may have a bond at any position, and $R^T$ represents a hydrogen atom or an alkyl group having 1 to 8 carbon atoms.) Preferably, the group represented by the above-mentioned formula (W-4) is a group selected from the following formulae (W-4-1) to (W-4-9), which may be unsubstituted or substituted with one or more of the above-mentioned substituents $L^W$'s:

[Chem. 12]

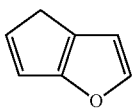
(W-4-1)

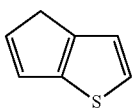
(W-4-2)

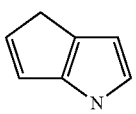
(W-4-3)

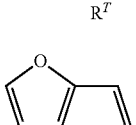
(W-4-4)

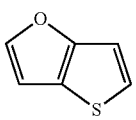
(W-4-5)

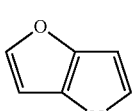
(W-4-6)

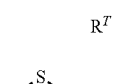
(W-4-7)

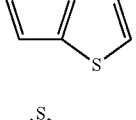
(W-4-8)

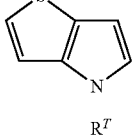
(W-4-9)

(wherein these groups may have a bond at any position, and $R^T$ represents a hydrogen atom or an alkyl group having 1 to 8 carbon atoms.) Preferably, the group represented by the above-mentioned formula (W-5) is a group selected from the following formulae (W-5-1) to (W-5-13), which may be unsubstituted or substituted with one or more of the above-mentioned substituents $L^W$'s:

[Chem. 13]

(W-5-1) 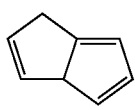

(W-5-2) 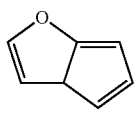

(W-5-3) 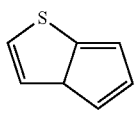

(W-5-4) 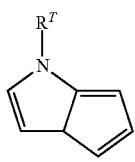

(W-5-5) 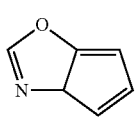

(W-5-6) 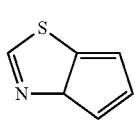

(W-5-7) 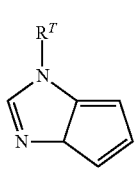

(W-5-8) 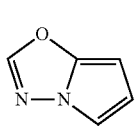

(W-5-9) 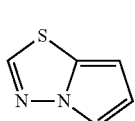

(W-5-10) 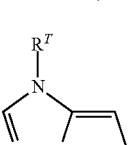

(W-5-11) 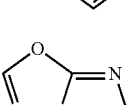

(W-5-12) 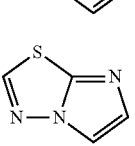

(W-5-13) 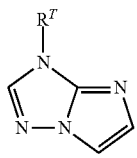

(wherein these groups may have a bond at any position, and $R^T$ represents a hydrogen atom or an alkyl group having 1 to 8 carbon atoms.) Preferably, the group represented by the above-mentioned formula (W-6) is a group selected from the following formulae (W-6-1) to (W-6-12), which may be unsubstituted or substituted with one or more of the above-mentioned substituents $L^W$'s:

[Chem. 14]

(W-6-1) 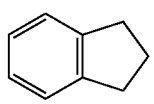

(W-6-2) 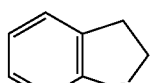

(W-6-3) 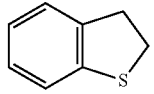

(W-6-4) 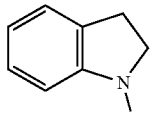

(W-6-5) 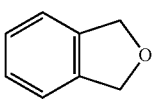

(W-6-6) 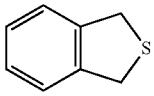

(W-6-7) 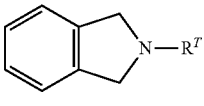

(W-6-8) 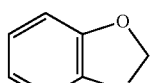

(W-6-9) 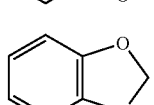

(W-6-10) 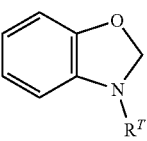

-continued

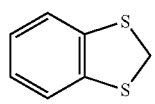
(W-6-11)

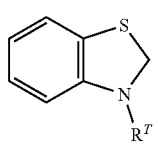
(W-6-12)

(wherein these groups may have a bond at any position, and $R^T$ represents a hydrogen atom or an alkyl group having 1 to 8 carbon atoms.) Preferably, the group represented by the above-mentioned formula (W-7) is a group selected from the following formulae (W-7-1) to (W-7-8), which may be unsubstituted or substituted with one or more of the above-mentioned substituents $L^W$'s:

[Chem. 15]

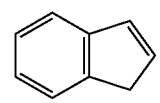
(W-7-1)

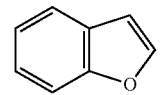
(W-7-2)

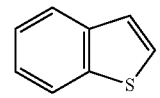
(W-7-3)

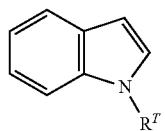
(W-7-4)

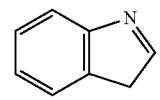
(W-7-5)

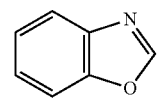
(W-7-6)

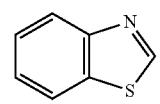
(W-7-7)

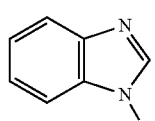
(W-7-8)

(wherein these groups may have a bond at any position, and $R^T$ represents a hydrogen atom or an alkyl group having 1 to 8 carbon atoms.) Preferably, the group represented by the above-mentioned formula (W-8) is a group selected from the following formulae (W-8-1) to (W-8-19), which may be unsubstituted or substituted with one or more of the above-mentioned substituents $L^W$'s:

[Chem. 16]

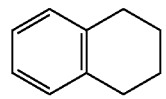
(W-8-1)

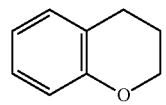
(W-8-2)

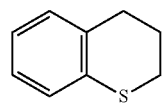
(W-8-3)

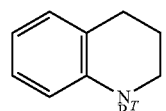
(W-8-4)

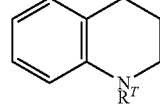
(W-8-5)

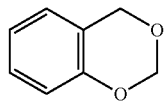
(W-8-6)

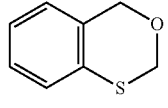
(W-8-7)

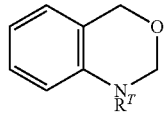
(W-8-8)

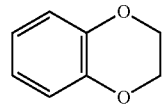
(W-8-9)

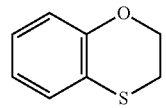
(W-8-10)

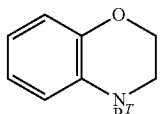
(W-8-11)

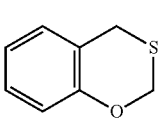
(W-8-12)

(wherein these groups may have a bond at any position, and $R^T$ represents a hydrogen atom or an alkyl group having 1 to 8 carbon atoms.) Preferably, the group represented by the above-mentioned formula (W-9) is a group selected from the following formulae (W-9-1) to (W-9-7), which may be unsubstituted or substituted with one or more of the above-mentioned substituents $L^W$'s:

[Chem. 17]

(wherein these groups may have a bond at any position.) Preferably, the group represented by the above-mentioned formula (W-10) is a group selected from the following formulae (W-10-1) to (W-10-16), which may be unsubstituted or substituted with one or more of the above-mentioned substituents $L^W$'s:

[Chem. 18]

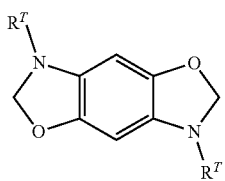 (W-10-7)

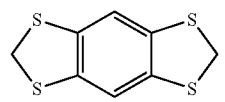 (W-10-8)

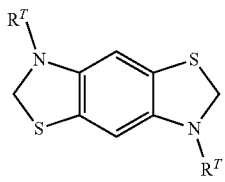 (W-10-9)

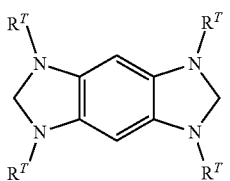 (W-10-10)

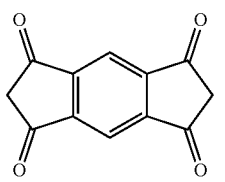 (W-10-11)

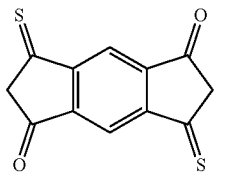 (W-10-12)

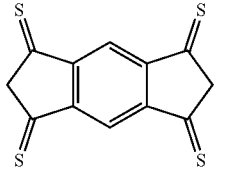 (W-10-13)

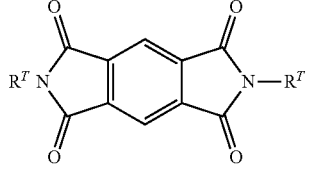 (W-10-14)

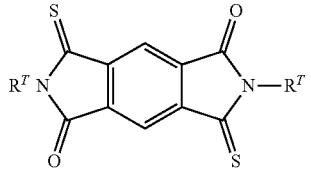 (W-10-15)

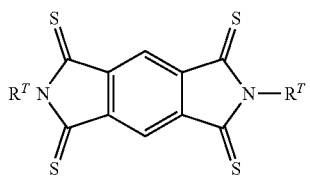 (W-10-16)

(wherein these groups may have a bond at any position, and $R^T$ represents a hydrogen atom or an alkyl group having 1 to 8 carbon atoms.) Preferably, the group represented by the above-mentioned formula (W-11) is a group selected from the following formulae (W-11-1) to (W-11-10), which may be unsubstituted or substituted with one or more of the above-mentioned substituents $L^W$'s:

[Chem. 19]

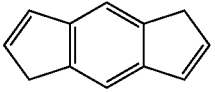 (W-11-1)

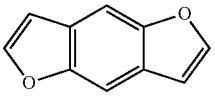 (W-11-2)

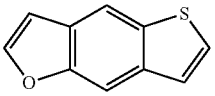 (W-11-3)

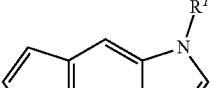 (W-11-4)

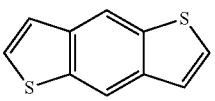 (W-11-5)

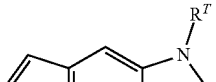 (W-11-6)

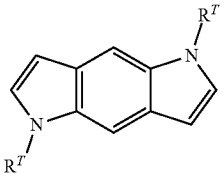 (W-11-7)

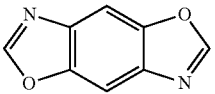 (W-11-8)

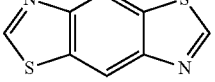 (W-11-9)

(W-11-10)

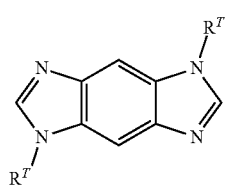

(wherein these groups may have a bond at any position, and $R^T$ represents a hydrogen atom or an alkyl group having 1 to 8 carbon atoms.) Preferably, the group represented by the above-mentioned formula (W-12) is a group selected from the following formulae (W-12-1) to (W-12-4), which may be unsubstituted or substituted with one or more of the above-mentioned substituents $L^W$'s:

[Chem. 20]

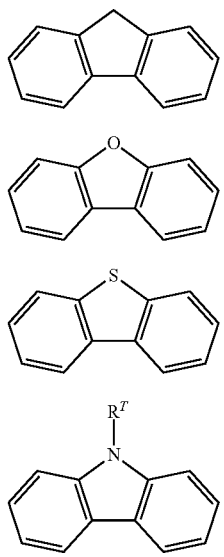

(W-12-1)

(W-12-2)

(W-12-3)

(W-12-4)

(wherein these groups may have a bond at any position, and $R^T$ represents a hydrogen atom or an alkyl group having 1 to 8 carbon atoms.) Preferably, the group represented by the above-mentioned formula (W-13) is a group selected from the following formulae (W-13-1) to (W-13-8), which may be unsubstituted or substituted with one or more of the above-mentioned substituents $L^W$'s:

[Chem. 21]

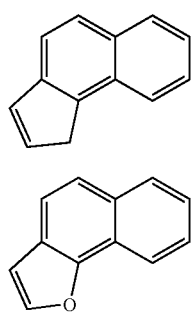

(W-13-1)

(W-13-2)

(W-13-3)

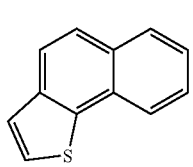

(W-13-4)

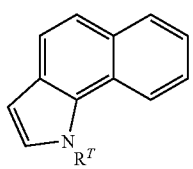

(W-13-5)

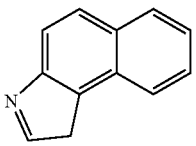

(W-13-6)

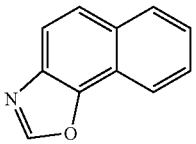

(W-13-7)

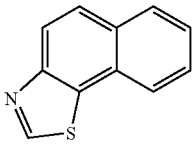

(W-13-8)

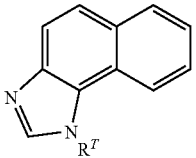

(wherein these groups may have a bond at any position, and $R^T$ represents a hydrogen atom or an alkyl group having 1 to 8 carbon atoms.) Preferably, the group represented by the above-mentioned formula (W-14) is a group selected from the following formulae (W-14-1) to (W-14-8), which may be unsubstituted or substituted with one or more of the above-mentioned substituents $L^W$'s:

[Chem. 22]

(W-14-1)

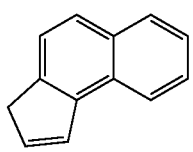

(W-14-2)

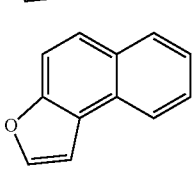

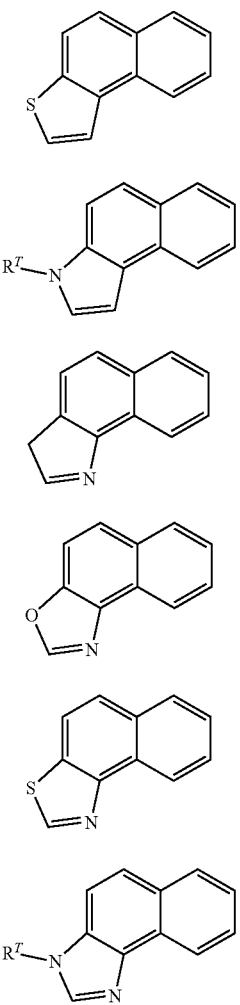

(W-14-3)
(W-14-4)
(W-14-5)
(W-14-6)
(W-14-7)
(W-14-8)

(wherein these groups may have a bond at any position, and $R^T$ represents a hydrogen atom or an alkyl group having 1 to 8 carbon atoms.) Preferably, the group represented by the above-mentioned formula (W-15) is a group selected from the following formulae (W-15-1) to (W-15-10), which may be unsubstituted or substituted with one or more of the above-mentioned substituents $L^W$'s:

[Chem. 23]

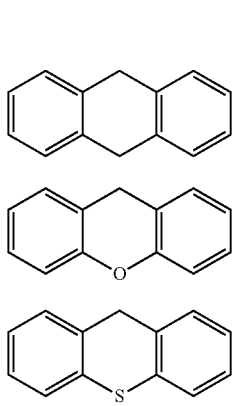

(W-15-1)
(W-15-2)
(W-15-3)

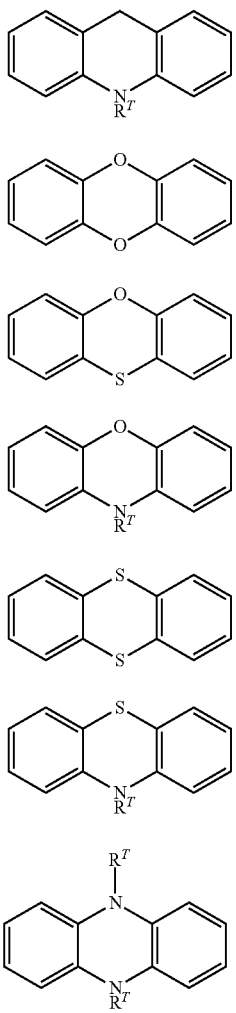

(W-15-4)
(W-15-5)
(W-15-6)
(W-15-7)
(W-15-8)
(W-15-9)
(W-15-10)

(wherein these groups may have a bond at any position, and $R^T$ represents a hydrogen atom or an alkyl group having 1 to 8 carbon atoms.) Preferably, the group represented by the above-mentioned formula (W-16) is a group selected from the following formulae (W-16-1) to (W-16-8), which may be unsubstituted or substituted with one or more of the above-mentioned substituents $L^W$'s:

[Chem. 24]

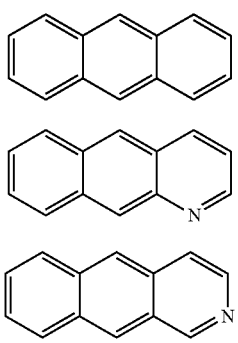

(W-16-1)
(W-16-2)
(W-16-3)

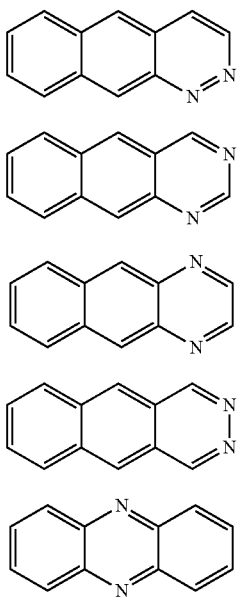

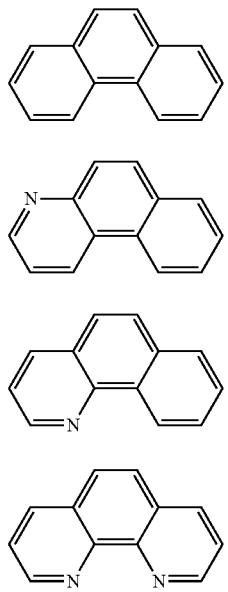

(wherein these groups may have a bond at any position.) Preferably, the group represented by the above-mentioned formula (W-17) is a group selected from the following formulae (W-17-1) to (W-17-4), which may be unsubstituted or substituted with one or more of the above-mentioned substituents $L^W$'s:

[Chem. 25]

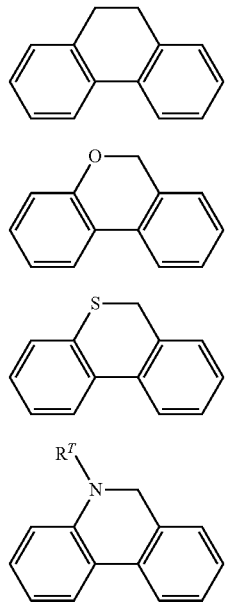

(wherein these groups may have a bond at any position, and $R^T$ represents a hydrogen atom or an alkyl group having 1 to 8 carbon atoms.) Preferably, the group represented by the above-mentioned formula (W-18) is a group selected from the following formulae (W-18-1) to (W-18-4), which may be unsubstituted or substituted with one or more of the above-mentioned substituents $L^W$'s:

[Chem. 26]

(wherein these groups may have a bond at any position.) Preferably, the group represented by the above-mentioned formula (W-19) is a group selected from the following formulae (W-19-1) to (W-19-16), which may be unsubstituted or substituted with one or more of the above-mentioned substituents $L^W$'s:

[Chem. 27]

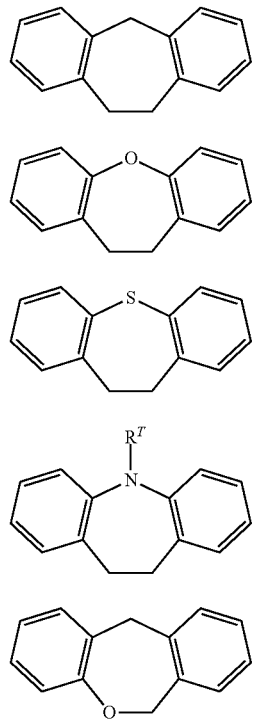

(wherein these groups may have a bond at any position, and $R^T$ represents a hydrogen atom or an alkyl group having 1 to 8 carbon atoms.) Preferably, the group represented by the above-mentioned formula (W-20) is a group selected from the following formulae (W-20-1) to (W-20-4), which may be unsubstituted or substituted with one or more of the above-mentioned substituents $L^W$'s:

[Chem. 28]

(wherein these groups may have a bond at any position, and $R^T$ represents a hydrogen atom or an alkyl group having 1 to 8 carbon atoms.) From the viewpoint of solubility in solvent, liquid crystallinity and reverse wavelength dispersion, $W^1$ is more preferably a group selected from the following formulae (W-7-7-1) to (W-14-7-1):

[Chem. 29]

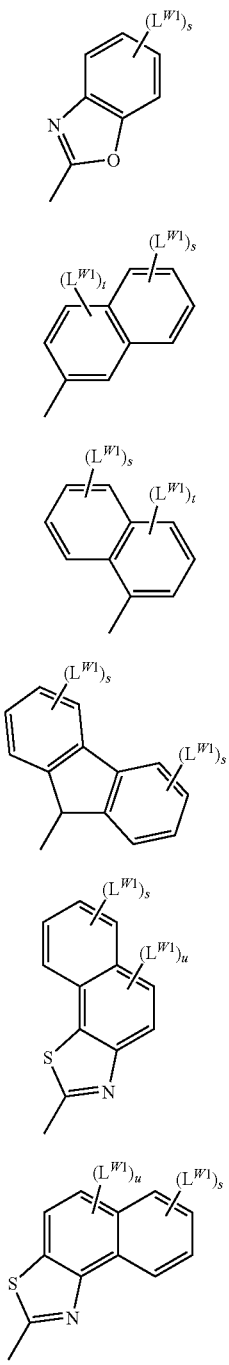

(W-7-6-1)

(W-9-1-1)

(W-9-1-2)

(W-12-1-1)

(W-13-7-1)

(W-14-7-1)

(wherein $L^{W1}$ represents a fluorine atom, a chlorine atom, a nitro group, a cyano group, or a linear or branched alkyl group having 1 to 20 carbon atoms in which one —$CH_2$— or two or more (—$CH_2$—)'s not adjacent to each other may be each independently substituted with —O—, —S—, —CO—, —COO— or —OCO—, and arbitrary hydrogen atoms in the alkyl group may be substituted with a fluorine atom, plural $L^{W1}$'s, if any, in the compound may be the same or different, s represents an integer of 0 to 4, t represents an integer of 0 to 3, and u represents an integer of 0 to 2.) Even more preferably, $W^1$ is a group selected from the following formulae (W-7-7-1-1) to (W-14-7-1-1):

[Chem. 30]

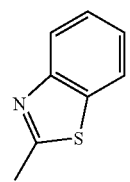

(W-7-7-1-1)

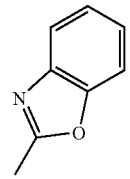

(W-7-6-1-1)

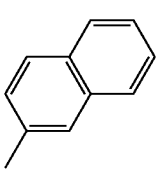

(W-9-1-1-1)

(W-9-1-2-1)

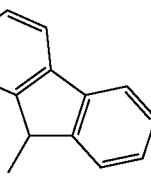

(W-12-1-1-1)

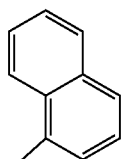

(W-13-7-1-1)

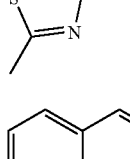

(W-14-7-1-1)

Especially preferably, $W^1$ represents the above-mentioned formula (W-7-7-1-1).

The compound represented by the general formula (I) is, from the viewpoint of stability over time in phase difference and reverse wavelength dispersion, and of difficulty in peeling from substrate after irradiation with UV light, preferably represented by the following general formula (I-i)

[Chem. 31]

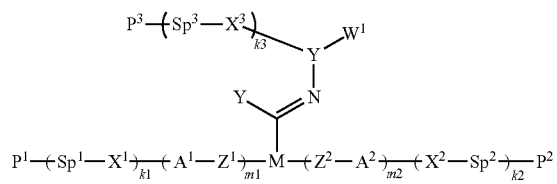

(I-i)

(wherein $P^1$, $P^2$, $P^3$, $Sp^1$, $Sp^2$, $Sp^3$, $X^1$, $X^2$, $X^3$, k1, k2, k3, $A^1$, $A^2$, $Z^1$, $Z^2$, m1, m2, M, Y and $W^1$ each have the same meaning as in the general formula (I)), more preferably represented by the following general formula (I-i-i):

[Chem. 32]

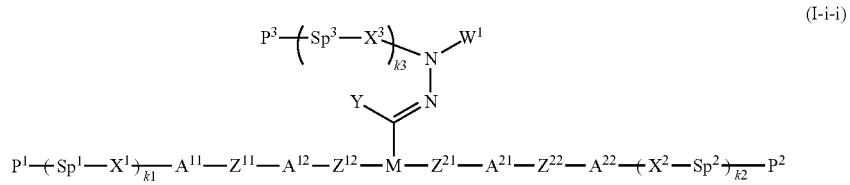

(I-i-i)

(wherein $P^1$, $P^2$, $P^3$, $Sp^1$, $Sp^2$, $Sp^3$, $X^1$, $X^2$, $X^3$, k1, k2, k3, M, Y and $W^1$ each have the same meaning as in the general formula (I), $A^{11}$ and $A^{22}$ each independently represent a 1,4-phenylene group, a 1,4-cyclohexylene group or a naphthalene-2.6-diyl group, and these groups may be unsubstituted or substituted with one or more substituents $L^1$'s, $A^{12}$ and $A^{21}$ each independently represent a 1,4-phenylene group or a 1,4-cyclohexylene group, and these group may be unsubstituted or substituted with one or more substituents $L^2$'s, $L^1$ and $L^2$ each independently have the same meaning as L in the general formula (I), plural $L^1$'s, if any, in the compound may be the same or different, plural $L^2$'s, if any, in the compound may be the same or different, $Z^{11}$ and $Z^{22}$ each independently represent —OCH$_2$—, —CH$_2$O—, —CH$_2$CH$_2$—, —COO—, —OCO—, —CF$_2$O—, —OCF$_2$—, —CH=CH—COO—, —OCO—CH=CH— or a single bond, $Z^{12}$ and $Z^{21}$ each independently represent —OCH$_2$—, —CH$_2$O—, —CH$_2$CH$_2$—, —COO—, —OCO—, —CF$_2$O—, —OCF$_2$—, —COO—CH$_2$CH$_2$—, —OCO—CH$_2$CH$_2$—, —CH$_2$CH$_2$—COO—, —CH$_2$CH$_2$—OCO— or a single bond), and is even more preferably represented by the following general formula (I-i-i-i):

[Chem. 33]

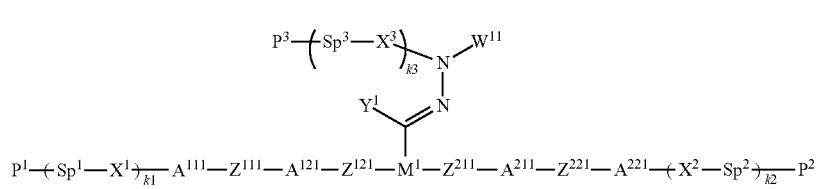

(I-i-i-i)

(wherein $P^1$, $P^2$, $P^3$, $Sp^1$, $Sp^2$, $Sp^3$, $X^1$, $X^2$, $X^3$, k1, k2 and k3 each have the same meaning as in the general formula (I), $A^{111}$ and $A^{221}$ each represent a 1,4-phenylene group, and the group may be unsubstituted or substituted with one or more substituents $L^{11}$'s, $A^{121}$ and $A^{211}$ each represent a 1,4-cyclohexylene group, $L^{11}$ represents a fluorine atom, a chlorine atom, or a linear or branched alkyl group having 1 to 20 carbon atoms in which one —CH$_2$— or two or more (—CH$_2$—)'s not adjacent to each other may be each independently substituted with —O—, —CO—, —COO— or —OCO—, and arbitrary hydrogen atoms in the alkyl group may be substituted with a fluorine atom, plural $L^1$'s, if any, in the compound may be the same or different, $Z^{111}$ and $Z^{221}$ each independently represent —OCH$_2$—, —CH$_2$O—, —COO— or —OCO—, $Z^{121}$ and $Z^{211}$ each independently represent —OCH$_2$—, —CH$_2$O—, —COO— or —OCO—, $M^1$ represents a group selected from the following formula (M-1-1) or (M-2-1):

[Chem. 34]

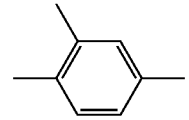

(M-1-1)

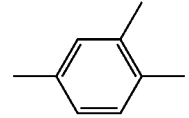

(M-2-1)

(wherein two bonds in the horizontal direction each mean a bond to $Z^{121}$ or $Z^{211}$, and the upper bond means a bond to the remaining group), $Y^1$ represents a hydrogen atom, and $W^{11}$ represents a group selected from the above-mentioned formulae (W-7-7-1) to (W-14-7-1)).

Specifically, the compound represented by the general formula (I) is preferably any of compounds represented by the following formulae (I-1) to (I-103):

[Chem. 35]
(I-1)
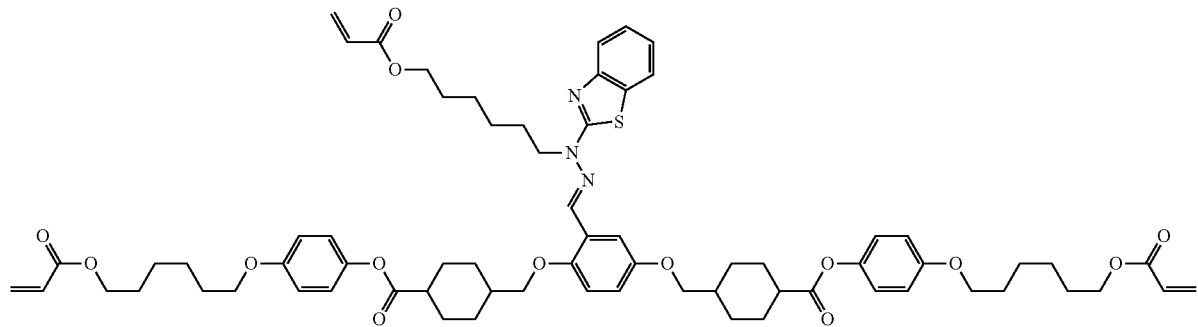
(I-2)
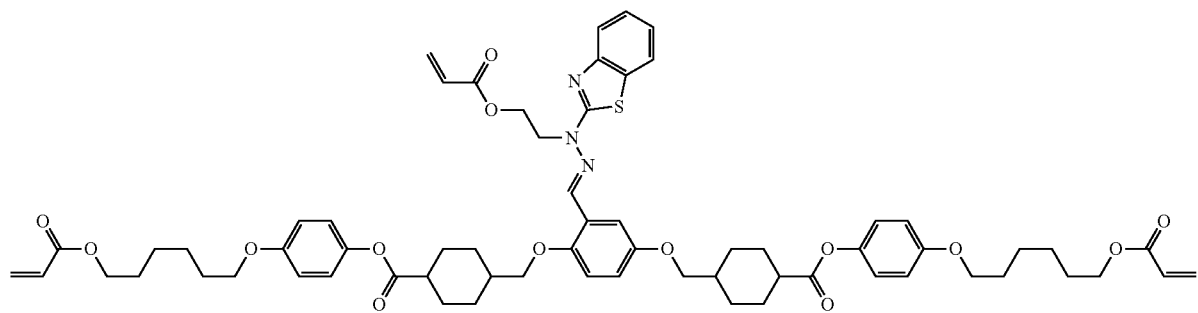
(I-3)
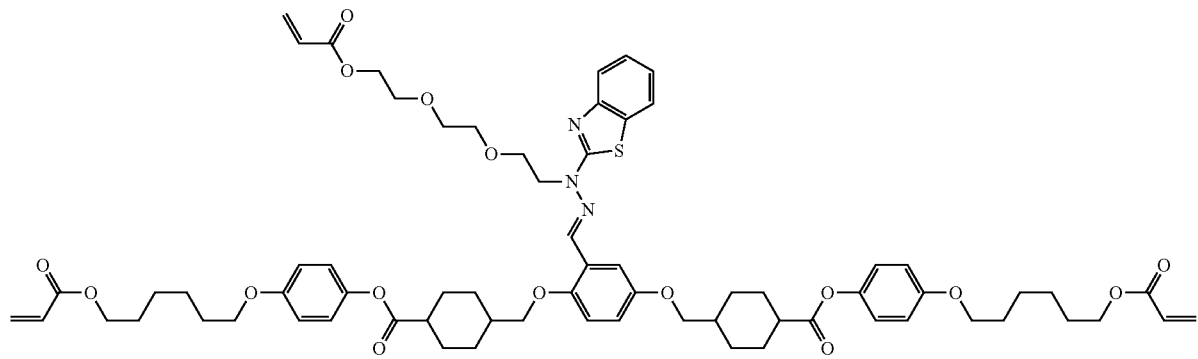
(I-4)
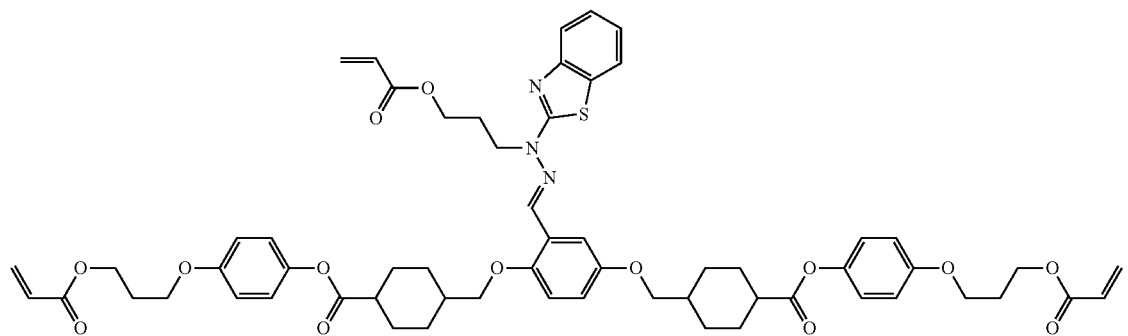

-continued
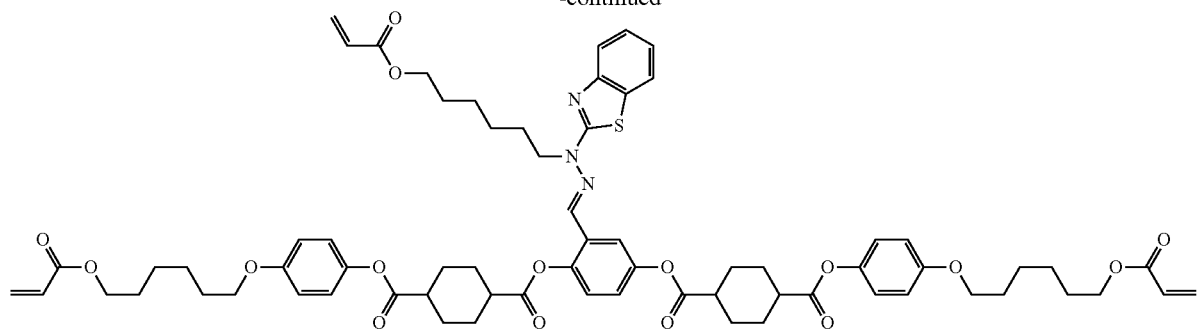
(I-6)
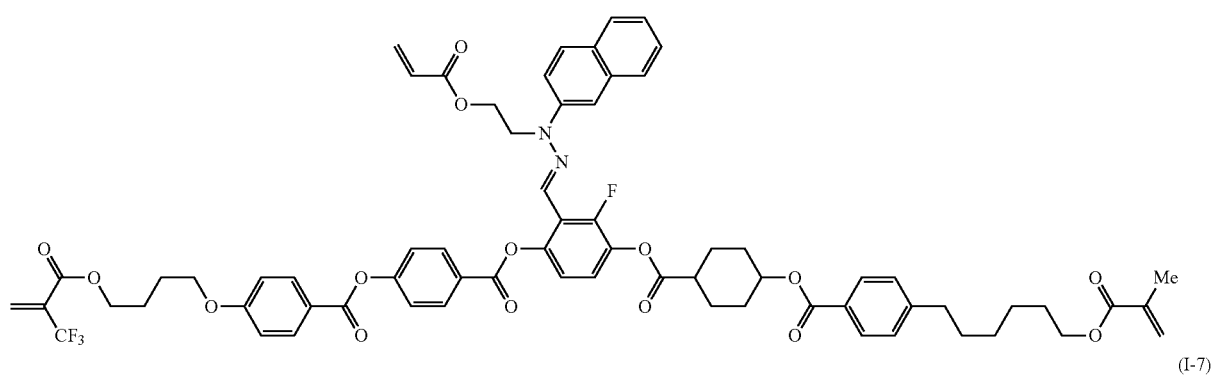
(I-7)
[Chem. 36]
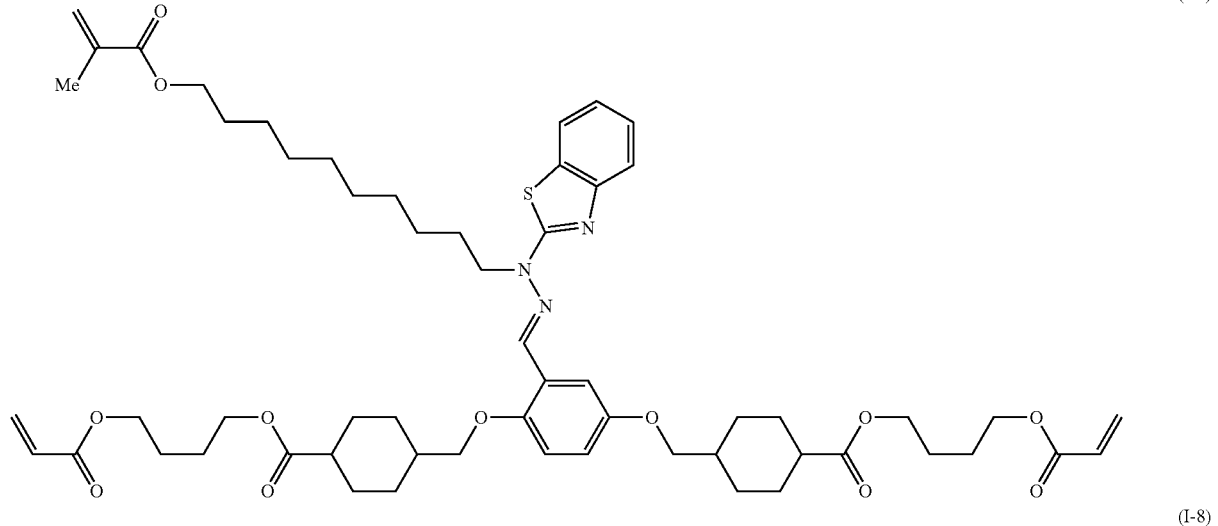
(I-8)
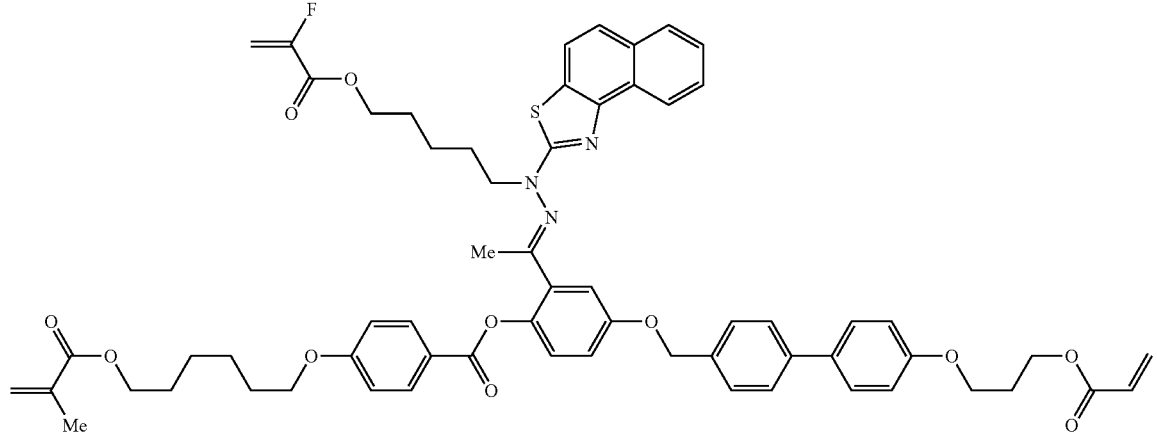

(I-9)
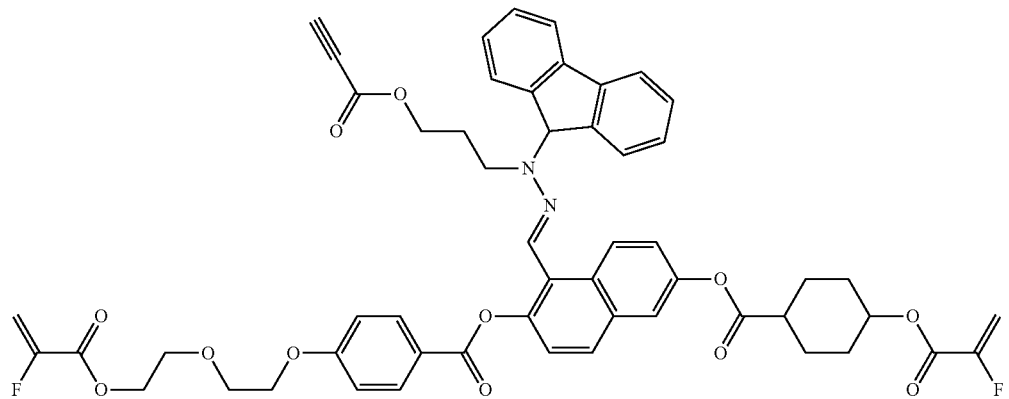
(I-10)
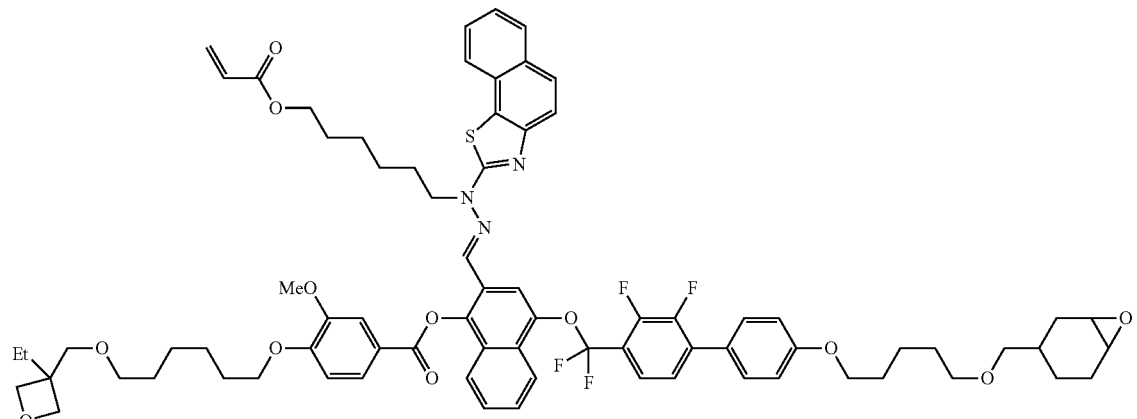
[Chem. 37]
(I-11)
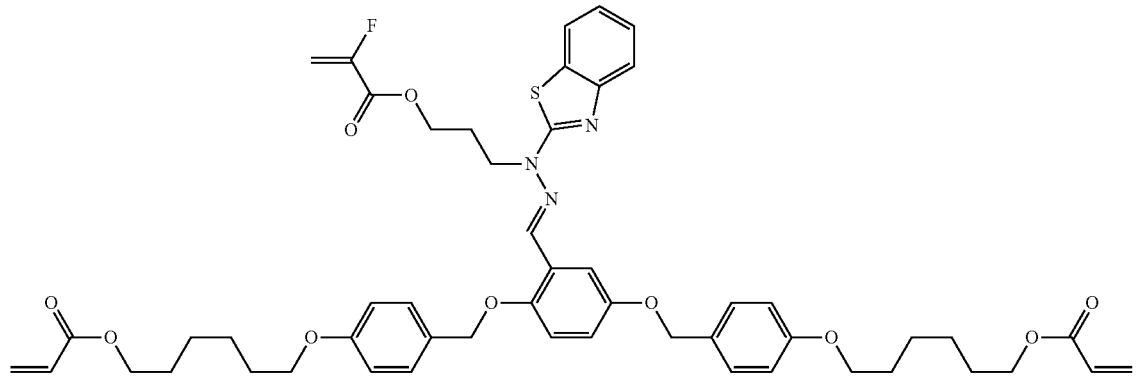
(I-12)
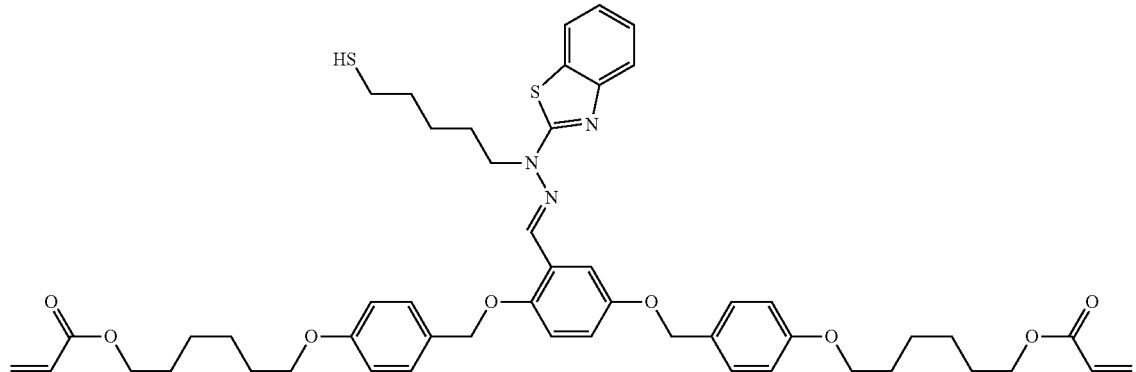

(I-13)
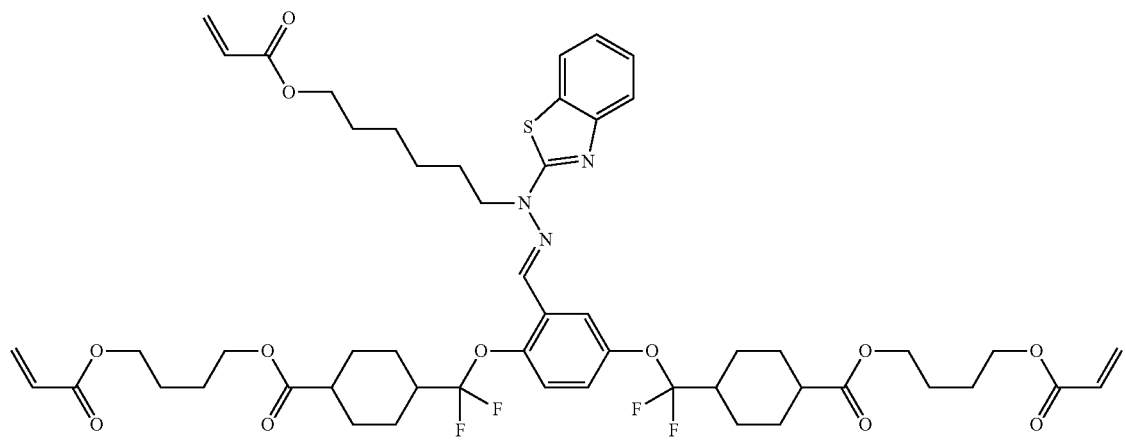
(I-14)
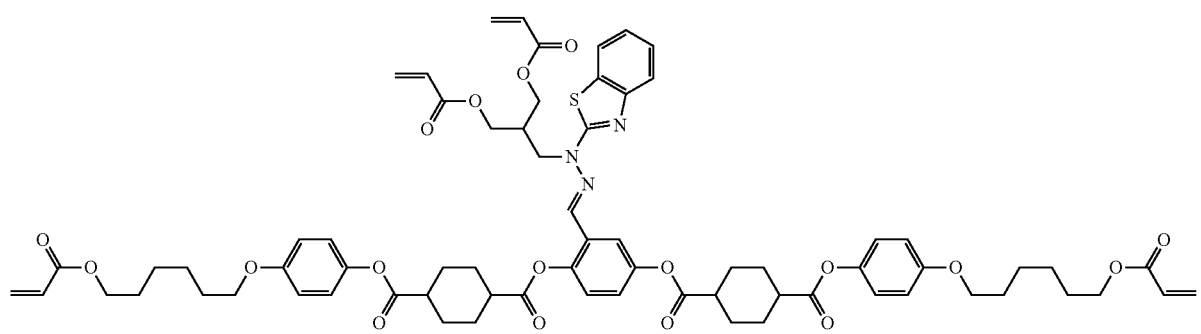
(I-15)
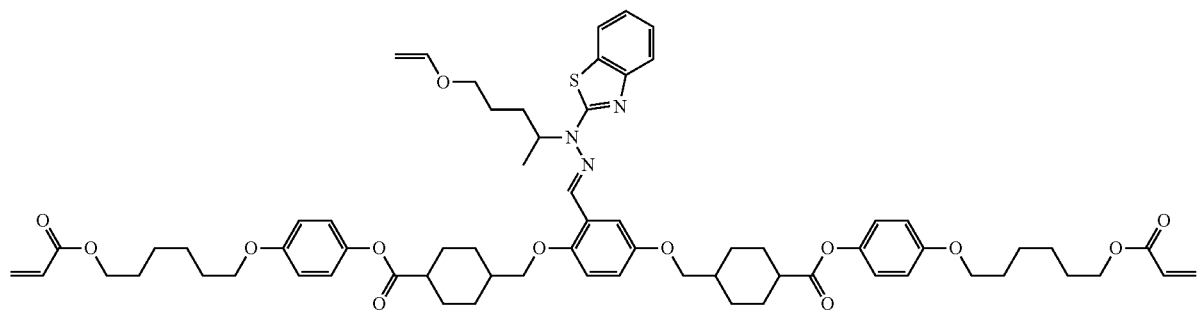
[Chem. 38]
(I-16)
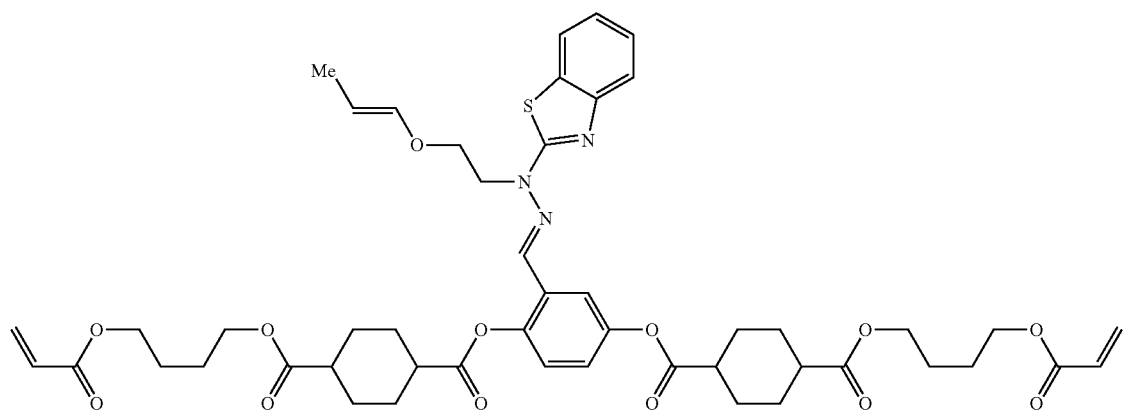

-continued
(I-17)
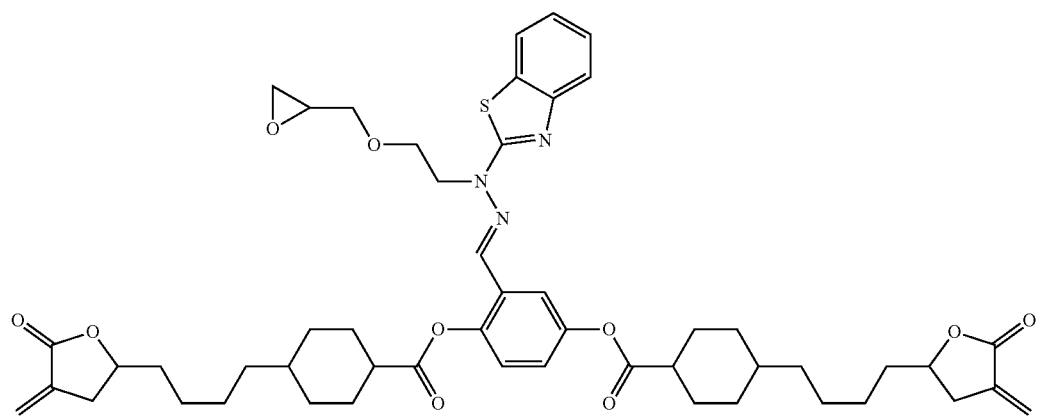
(I-18)
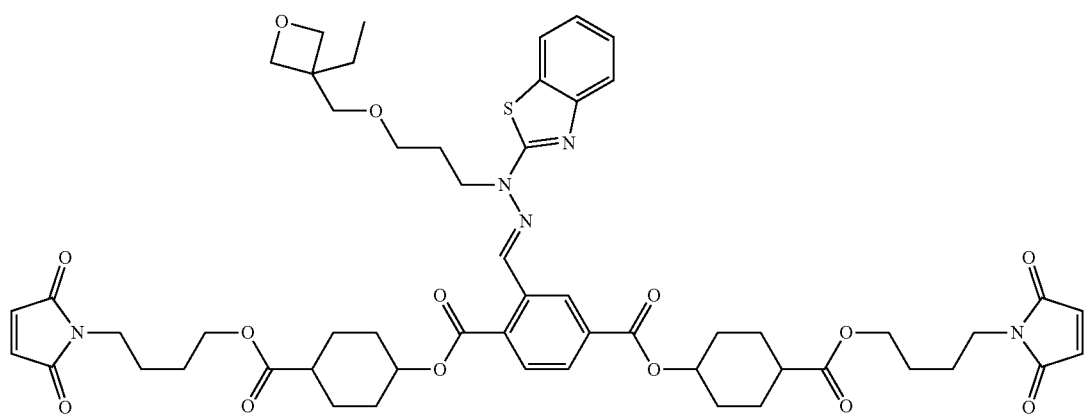
(I-19)
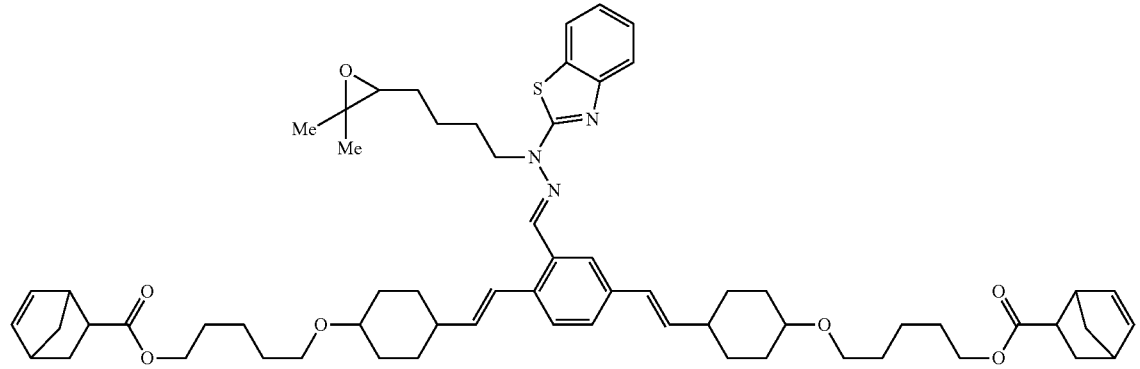
(I-20)
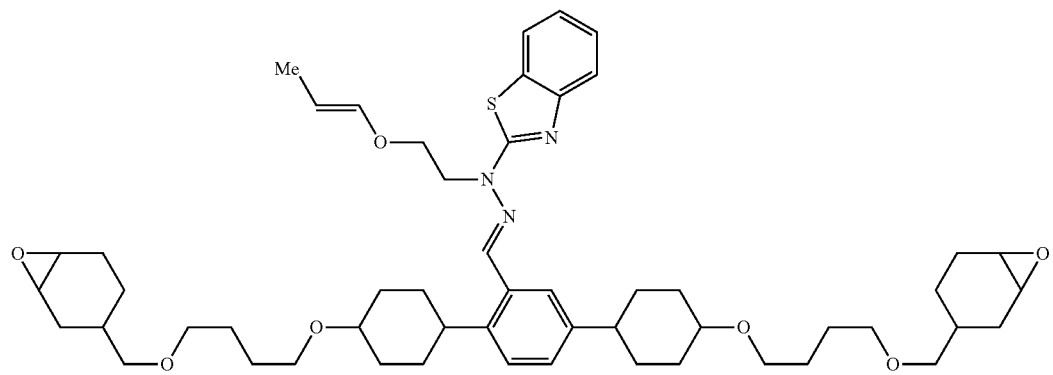

[Chem. 39]
(I-21)
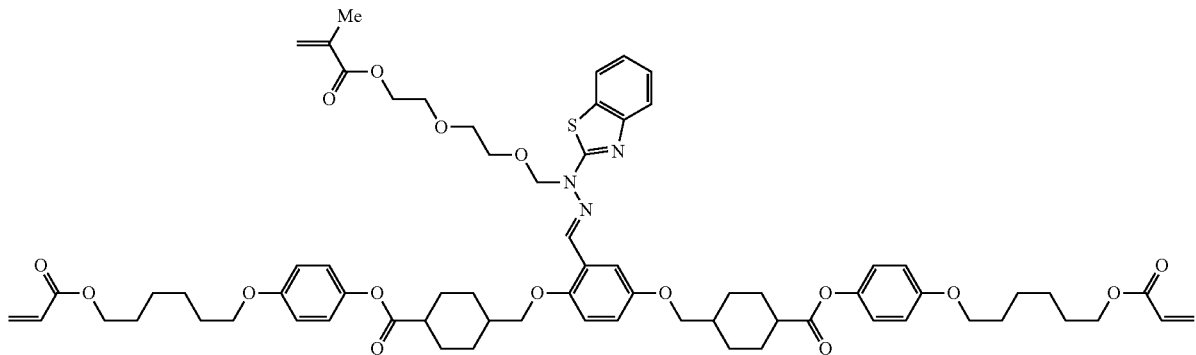
(I-22)
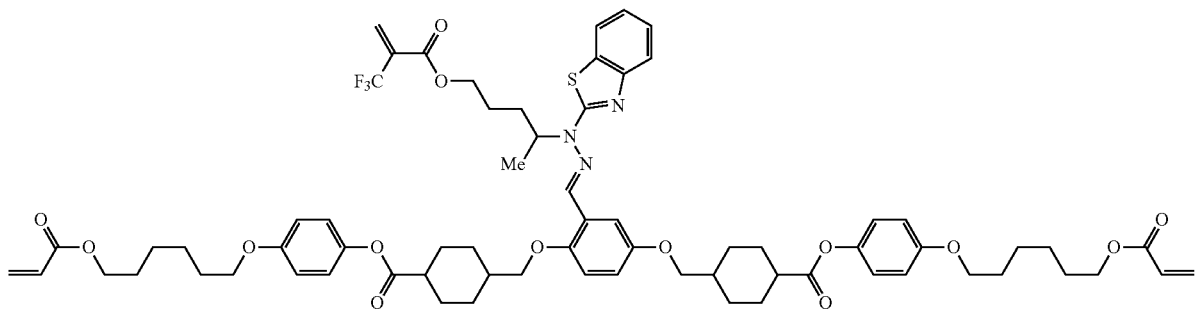
(I-23)
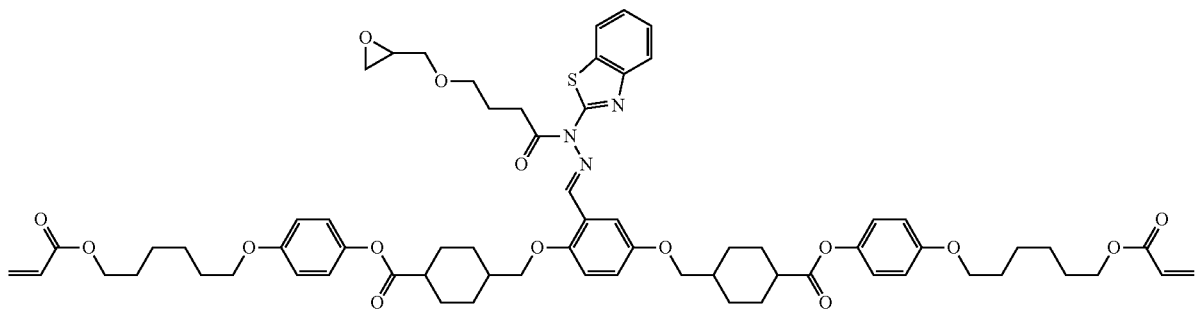
(I-24)
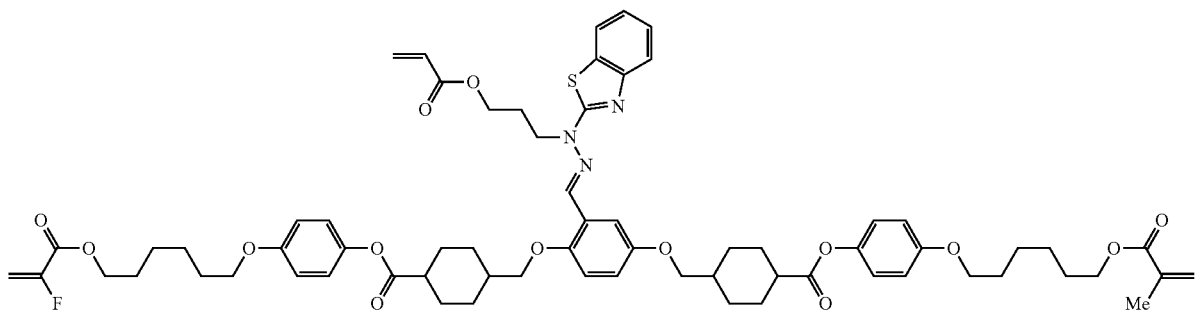

(I-25)
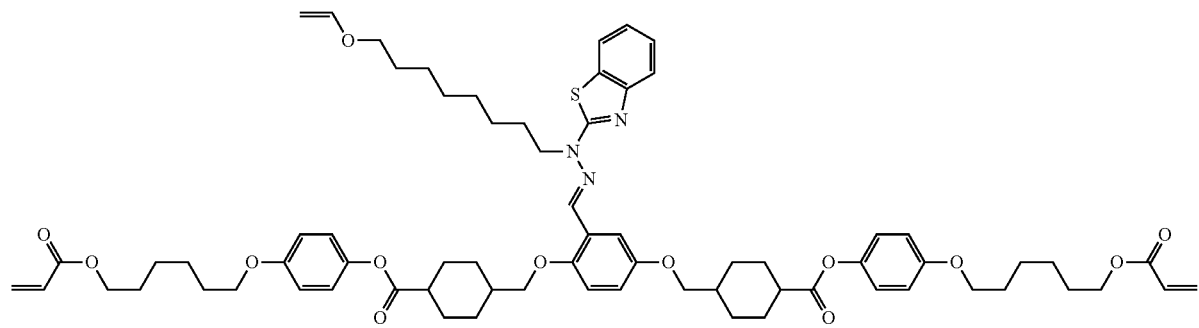
[Chem. 40]
(I-26)
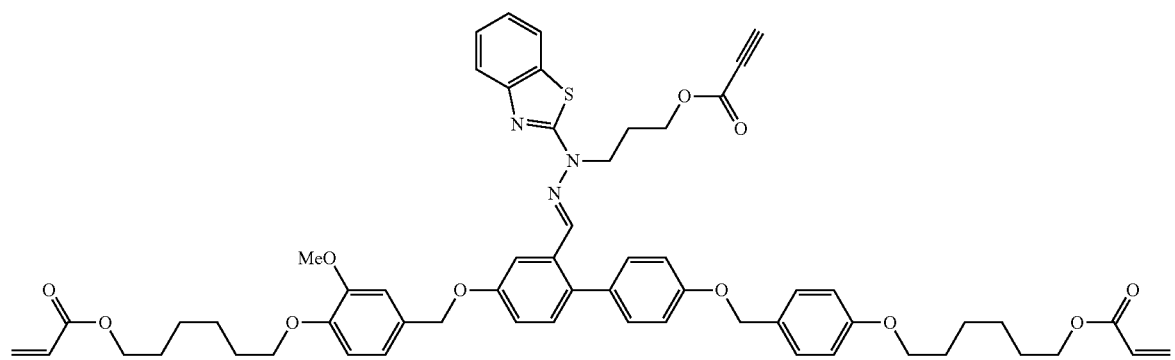
(I-27)
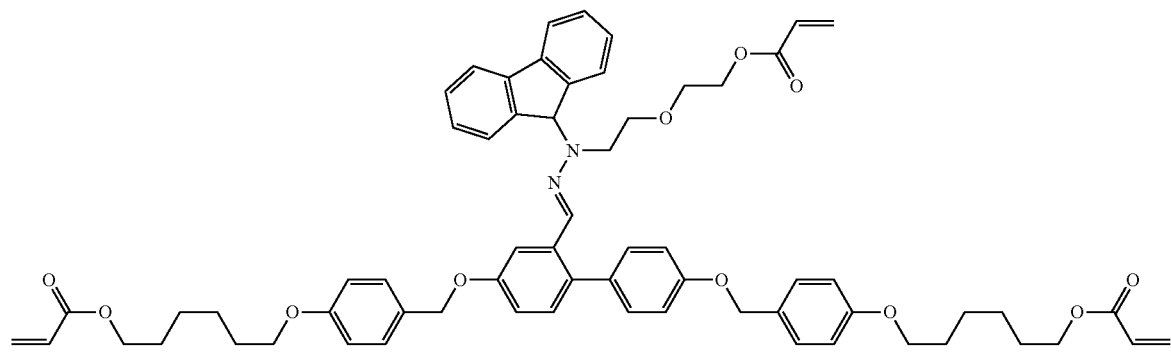
(I-28)
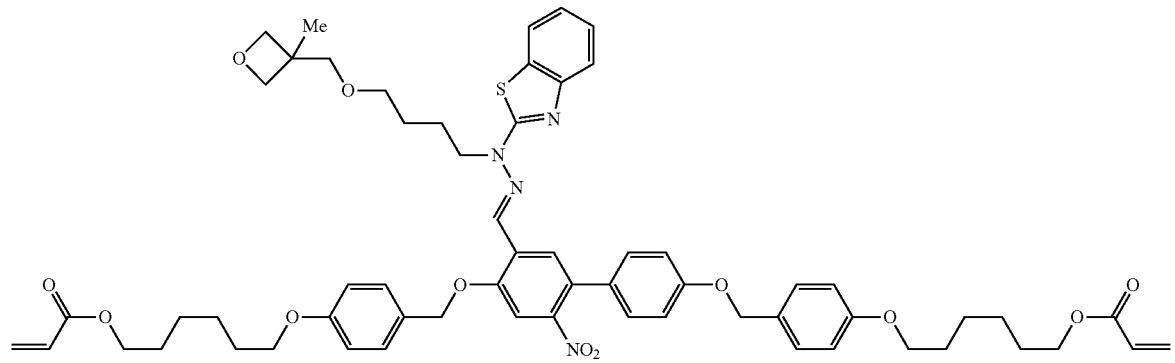

(I-29)
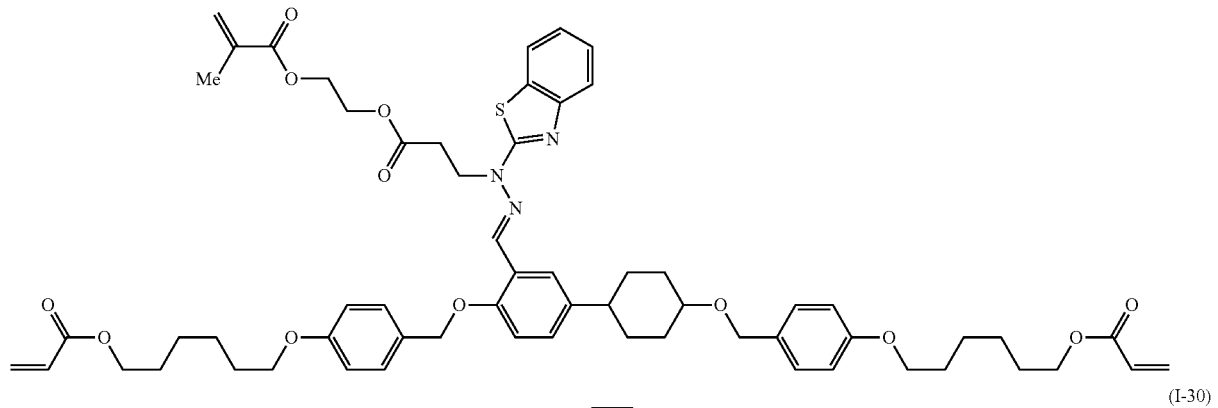
(I-30)
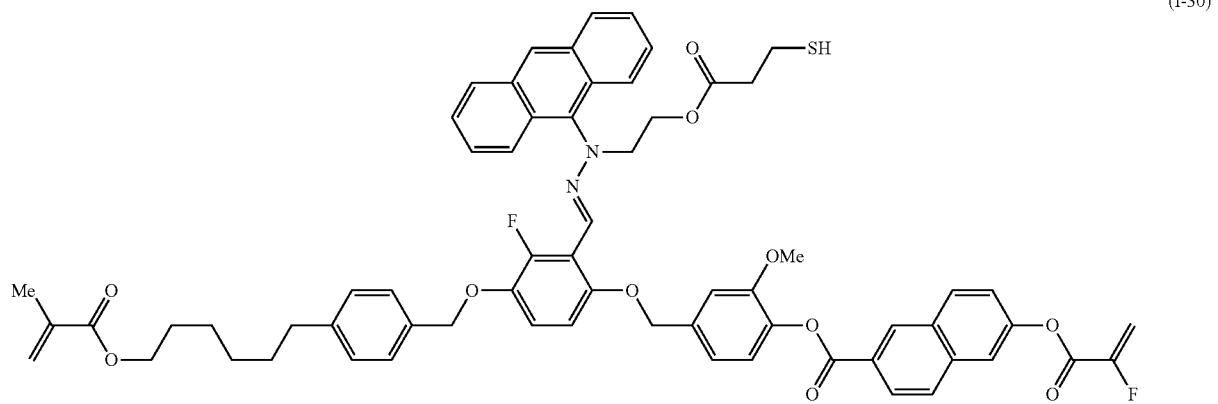
[Chem. 41]
(I-31)
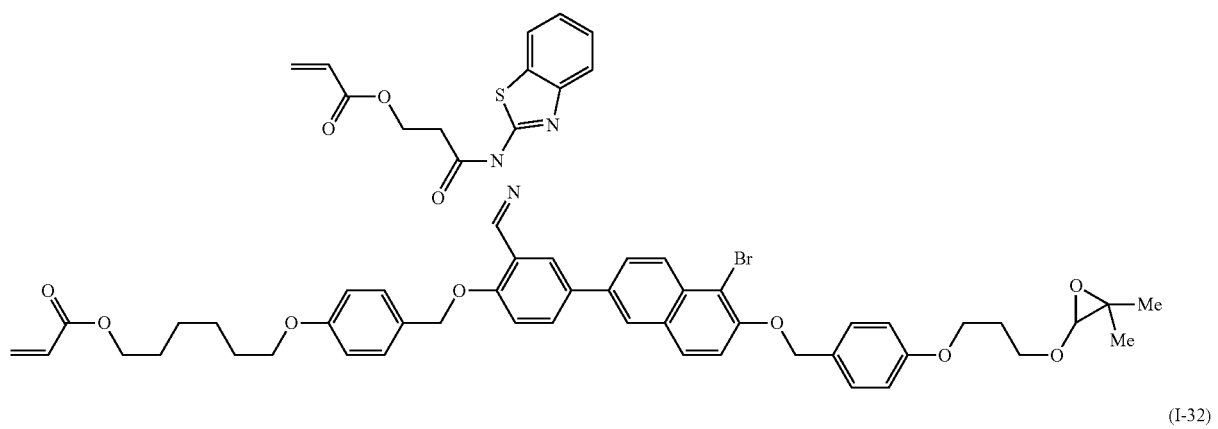
(I-32)
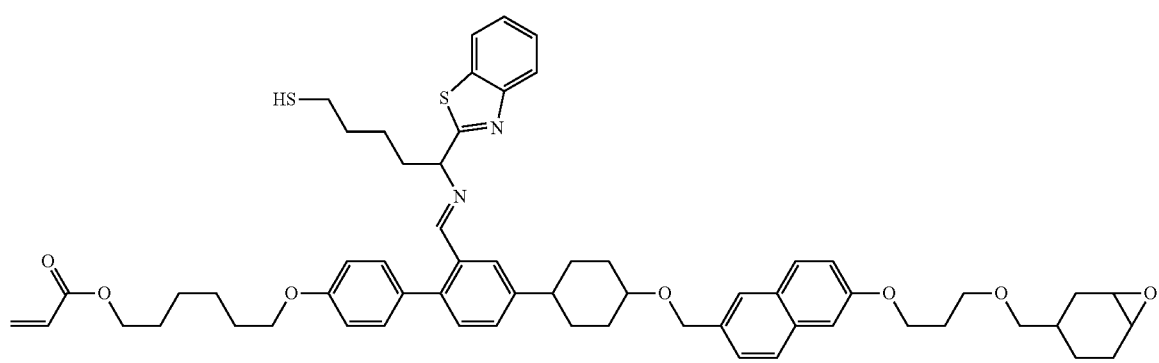

(I-33)
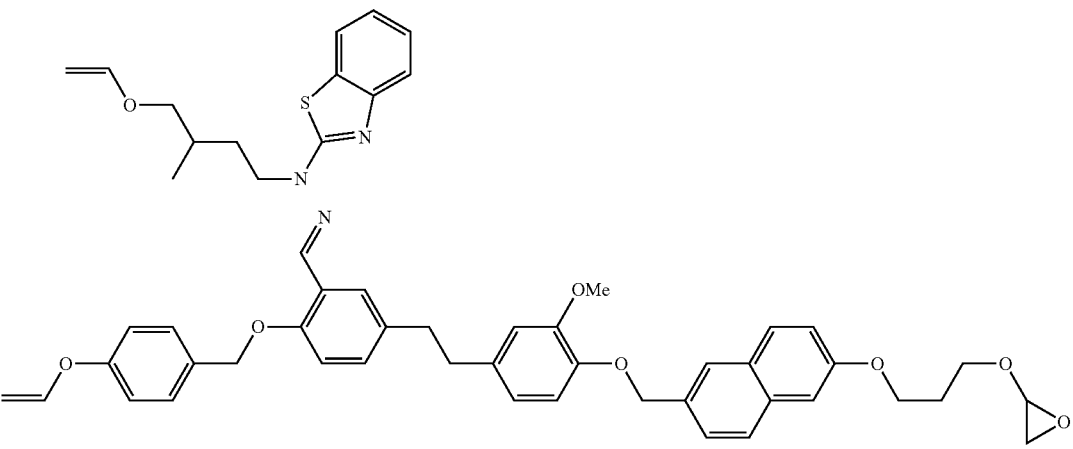
(I-34)
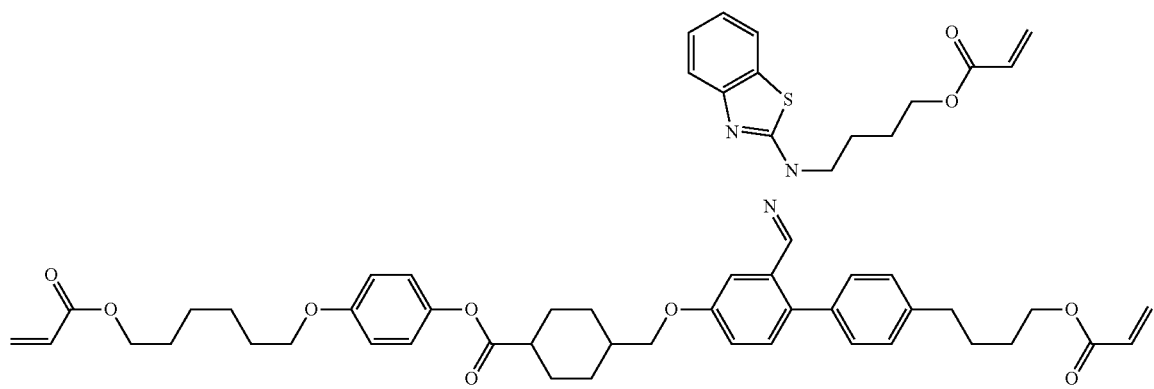
(I-35)
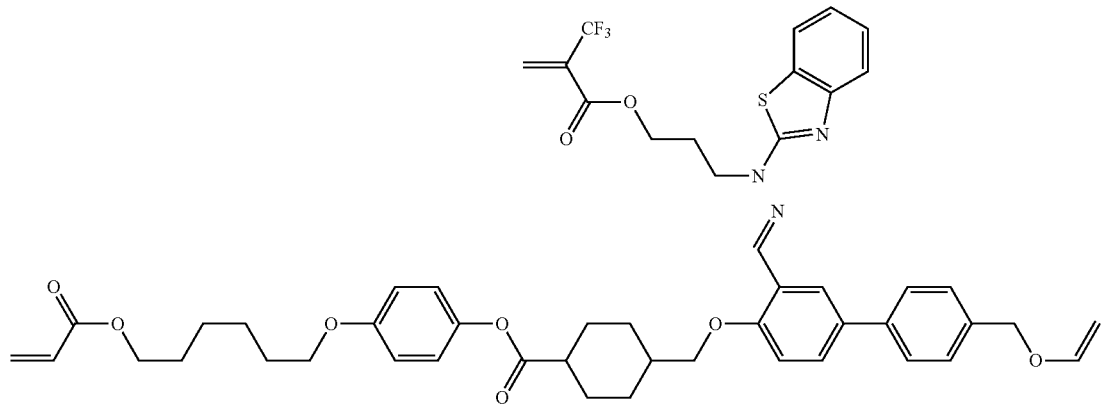

[Chem. 42]
(I-36)
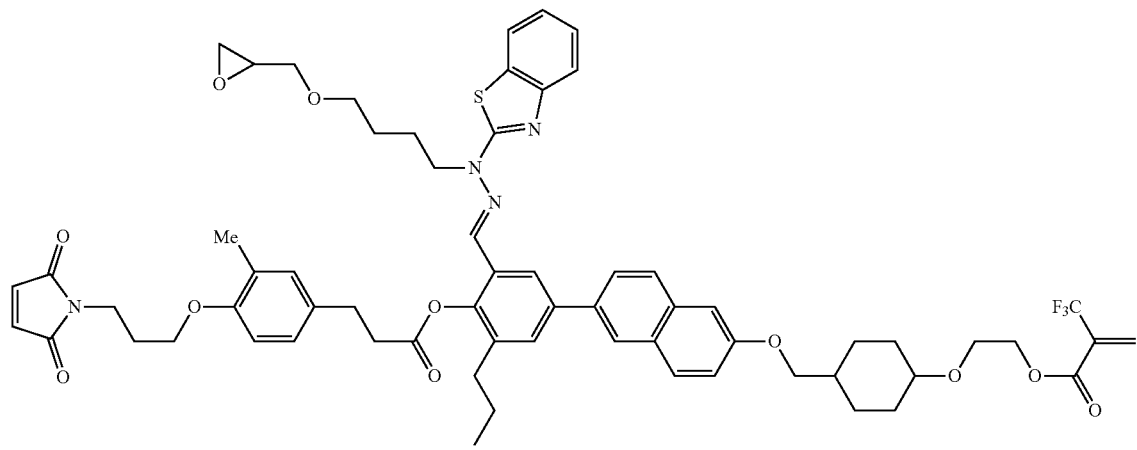
(I-37)
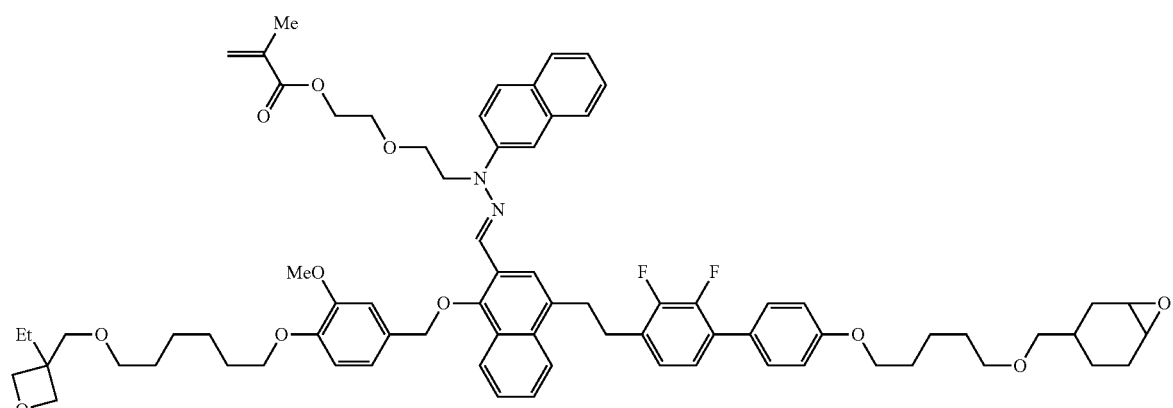
(I-38)
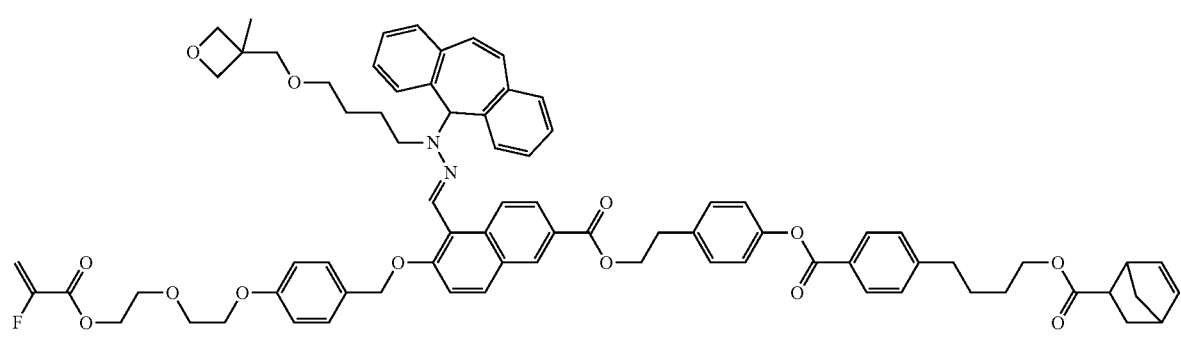
(I-39)
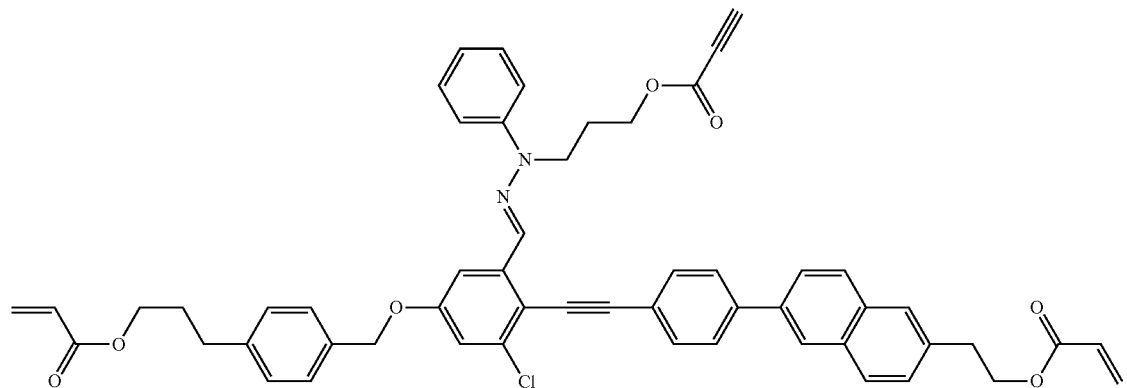

(I-40)
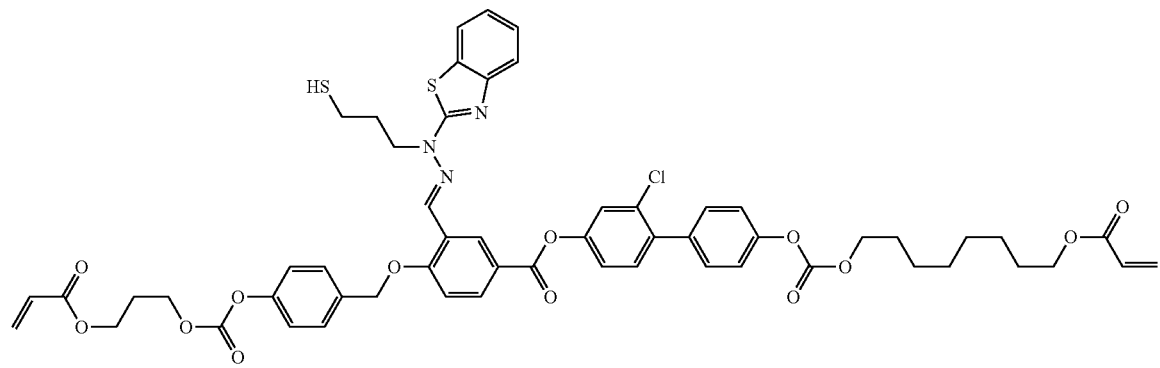
[Chem. 43]
(I-41)
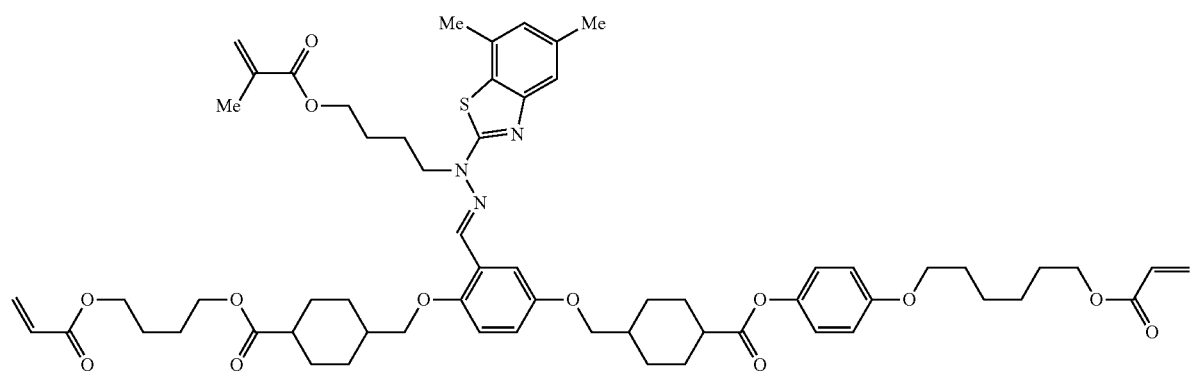
(I-42)
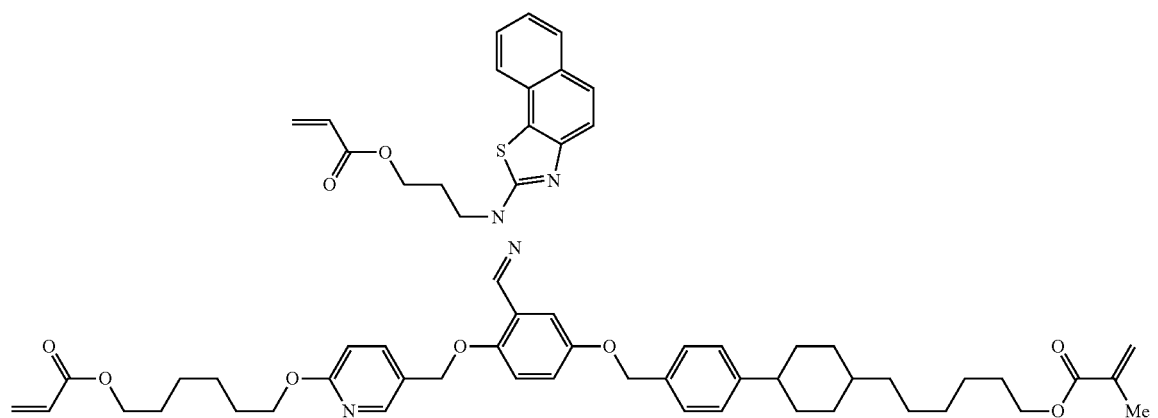

(I-43)
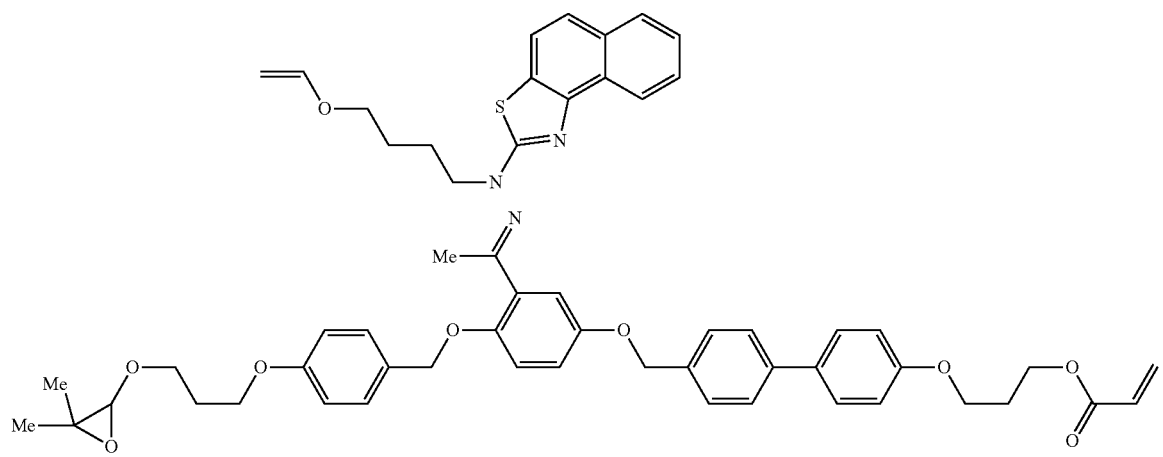
(I-44)
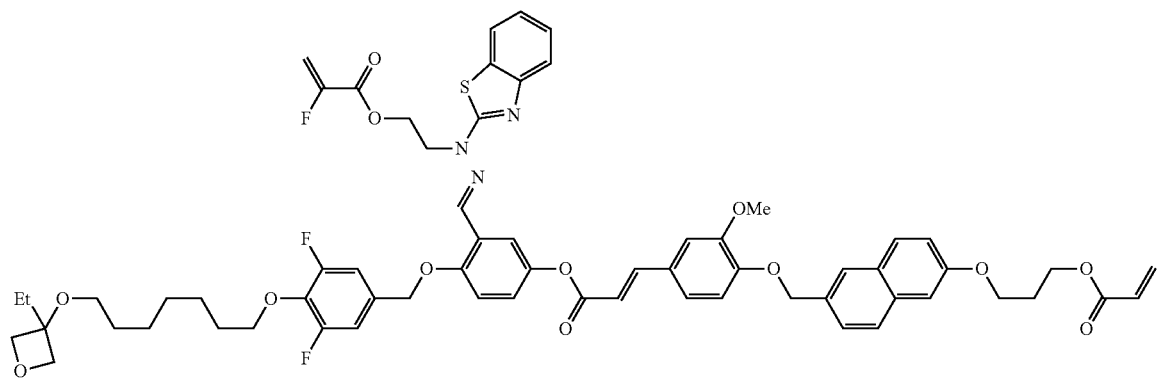
(I-45)
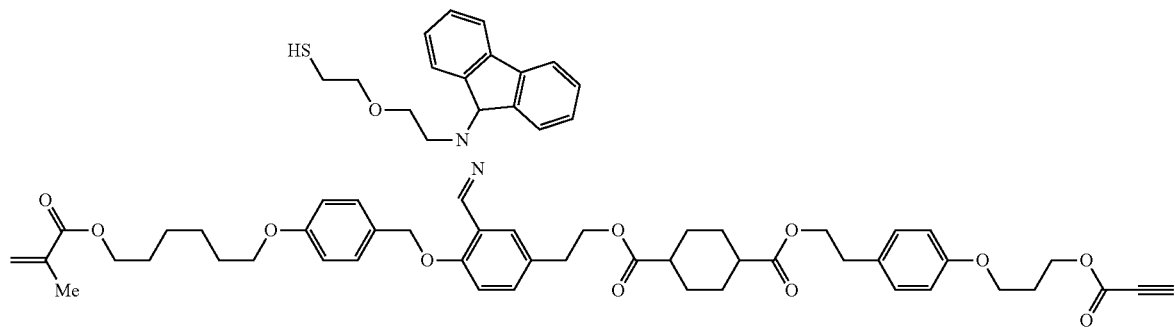

[Chem. 44]
(I-46)
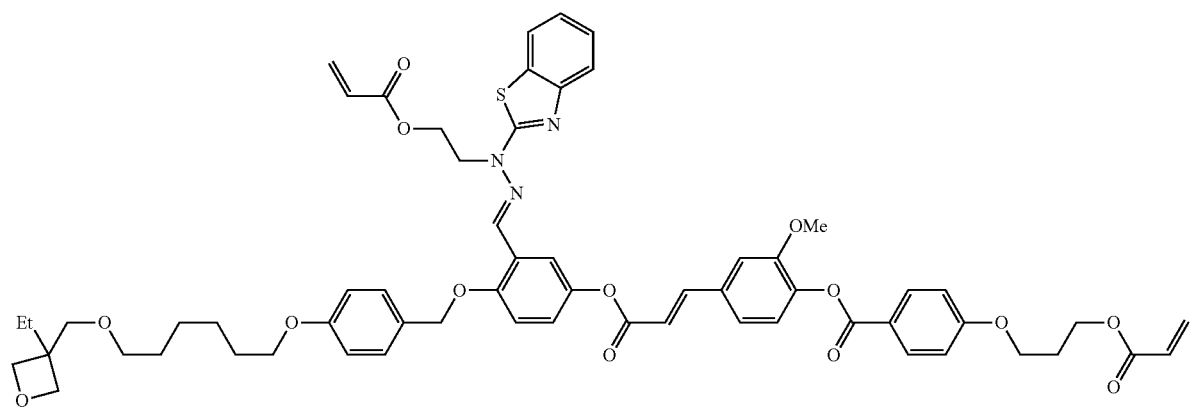
(I-47)
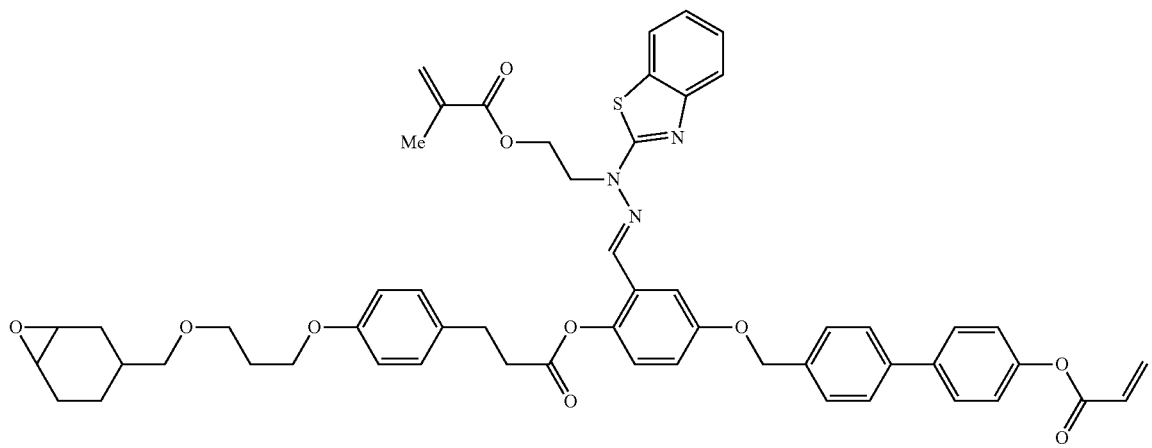
(I-48)
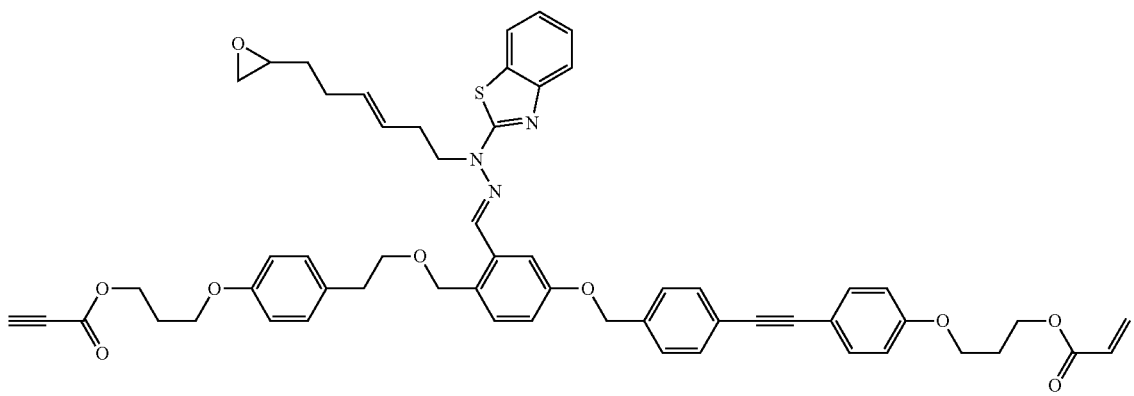

(I-49)
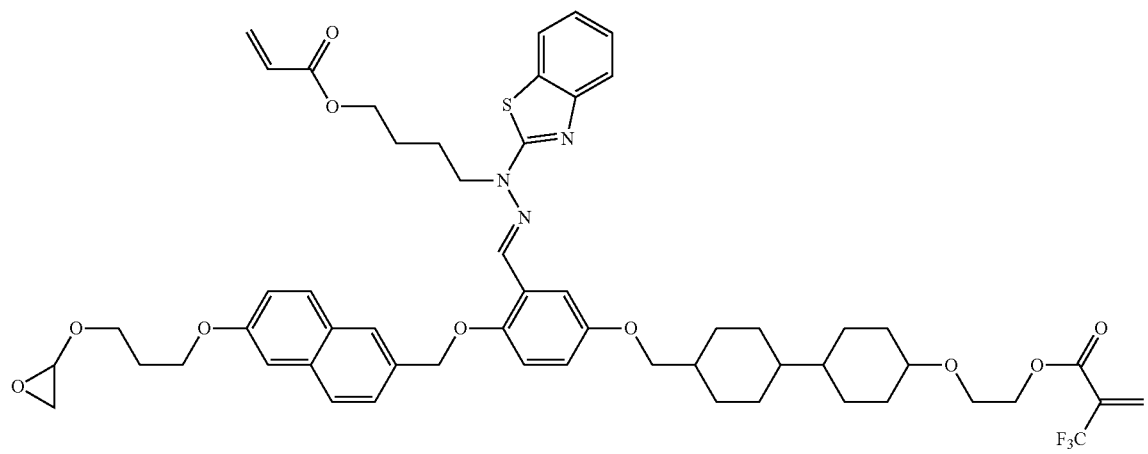
(I-50)
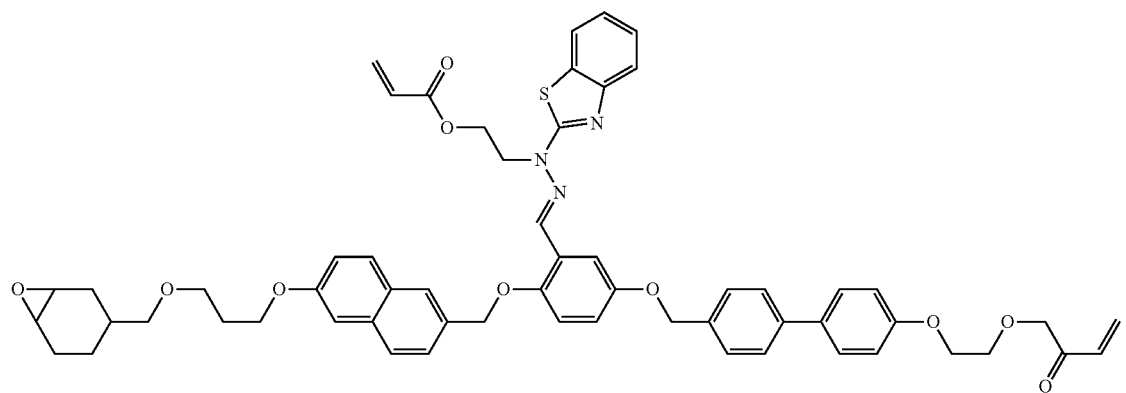
[Chem. 45]
(I-51)
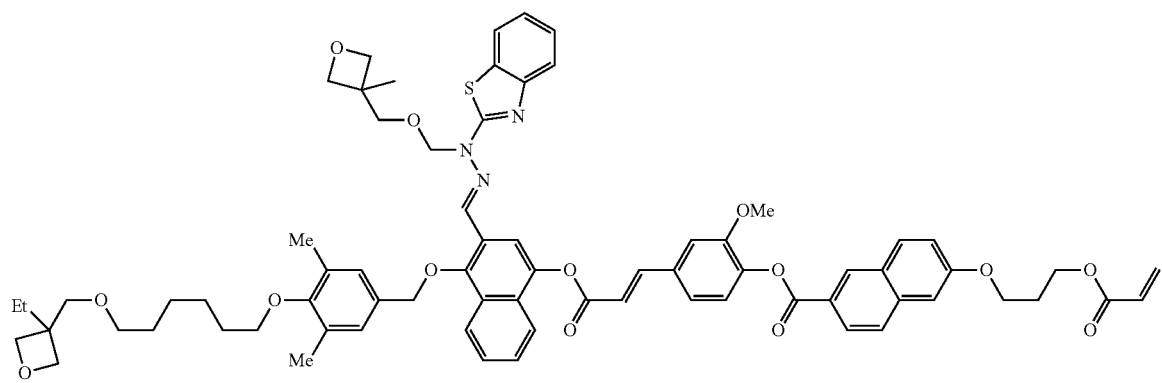
(I-52)
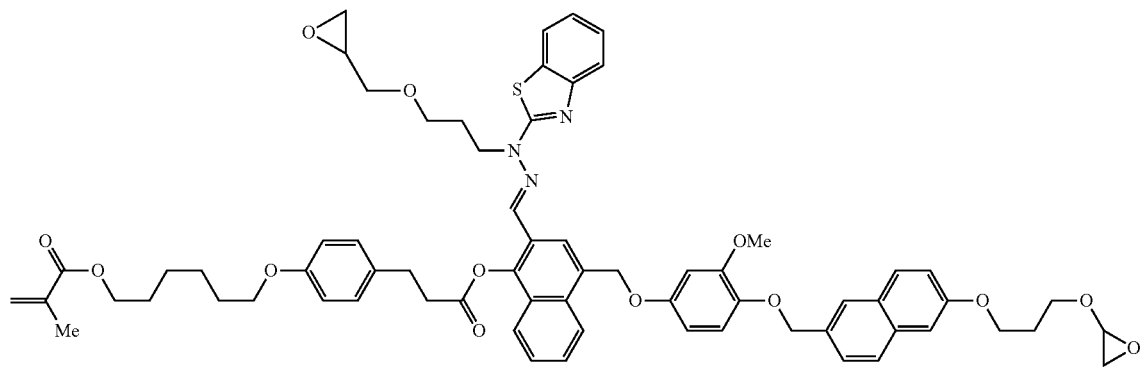

-continued
(I-53)
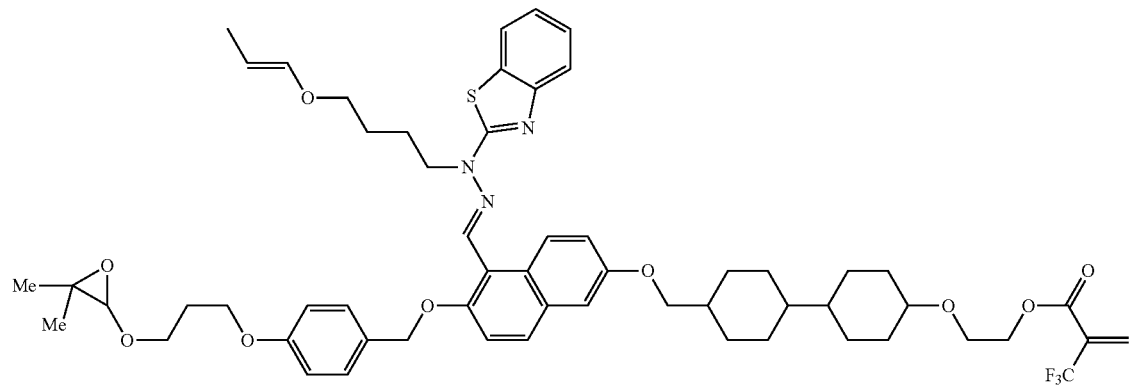
(I-54)
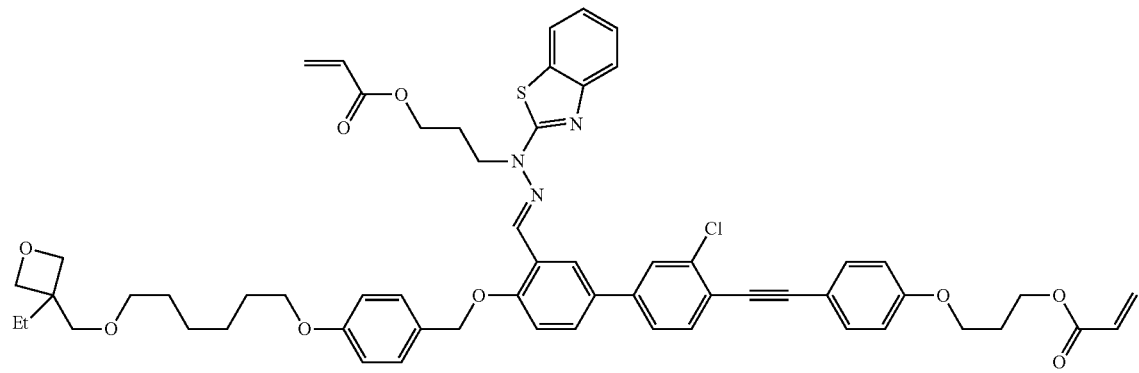
(I-55)
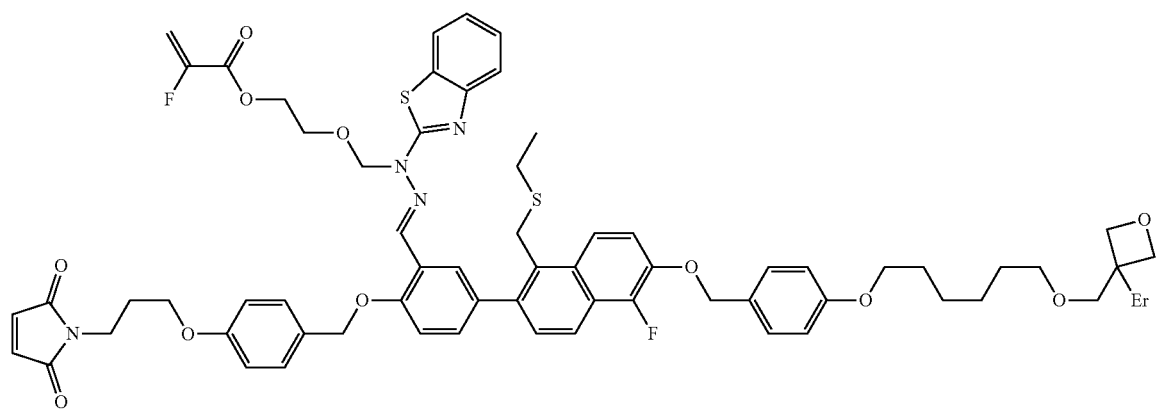

(I-56)
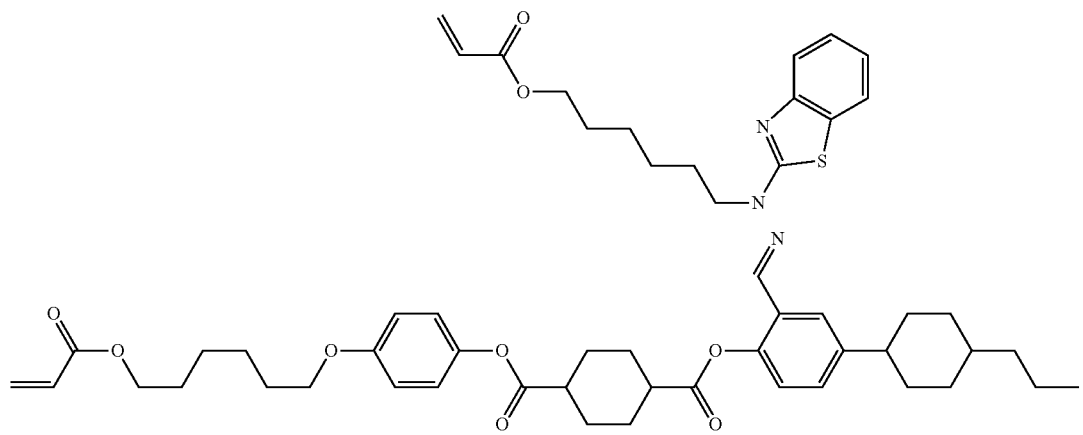
(I-57)
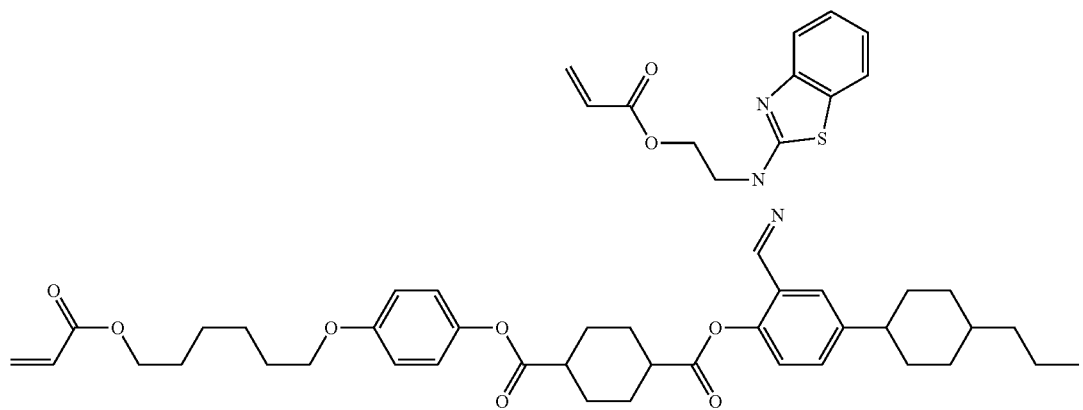
(I-58)
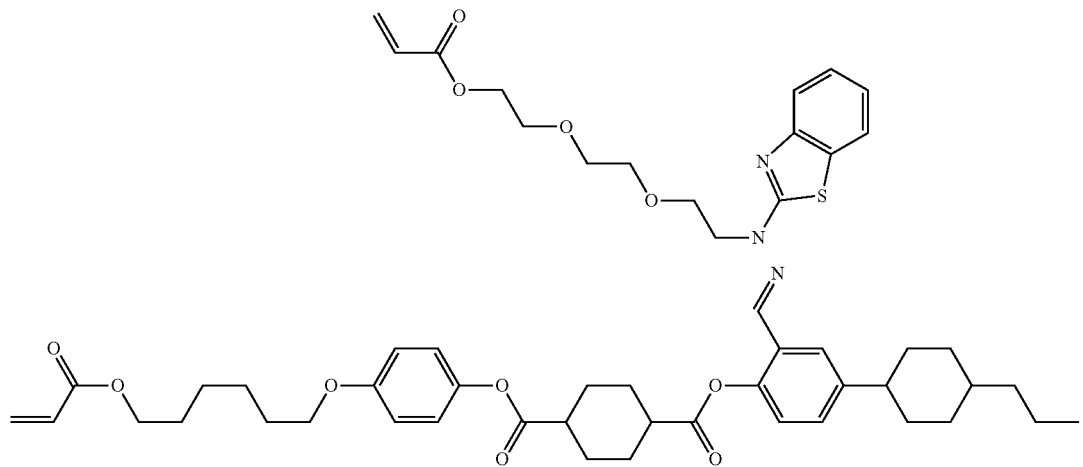

(I-59)
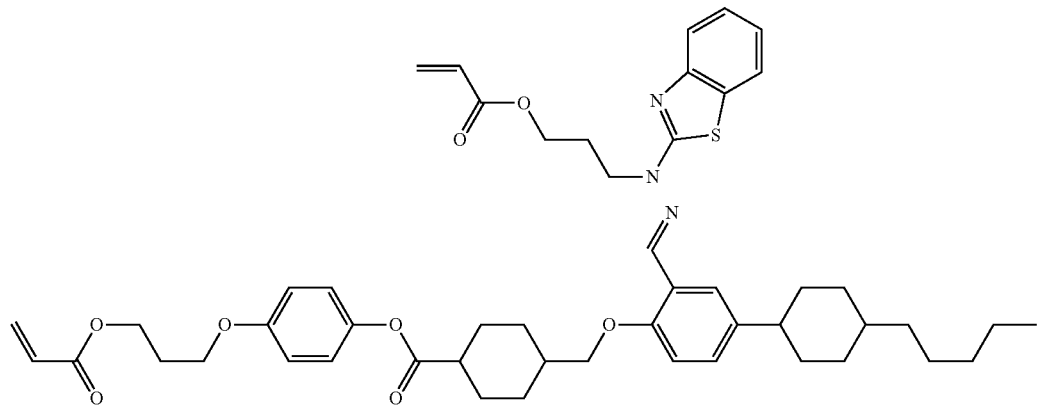
(I-60)
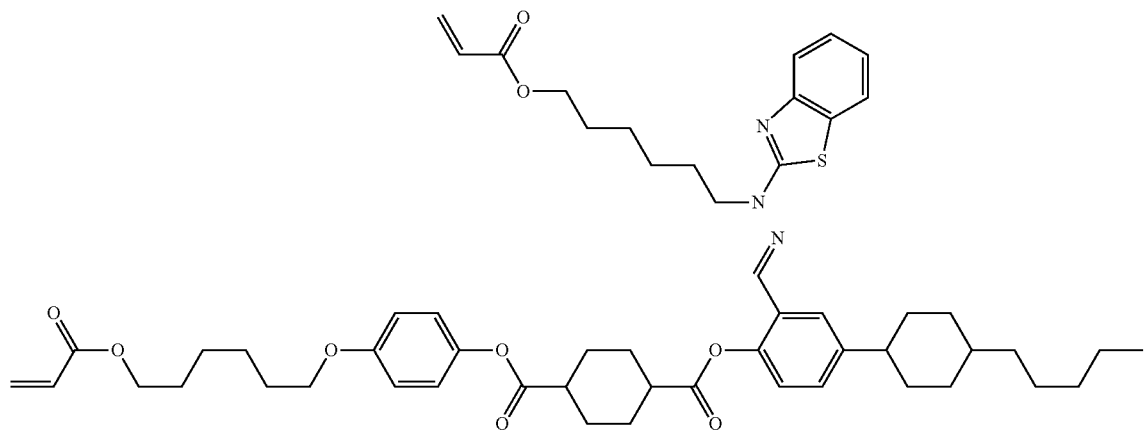
[Chem. 47]
(I-61)
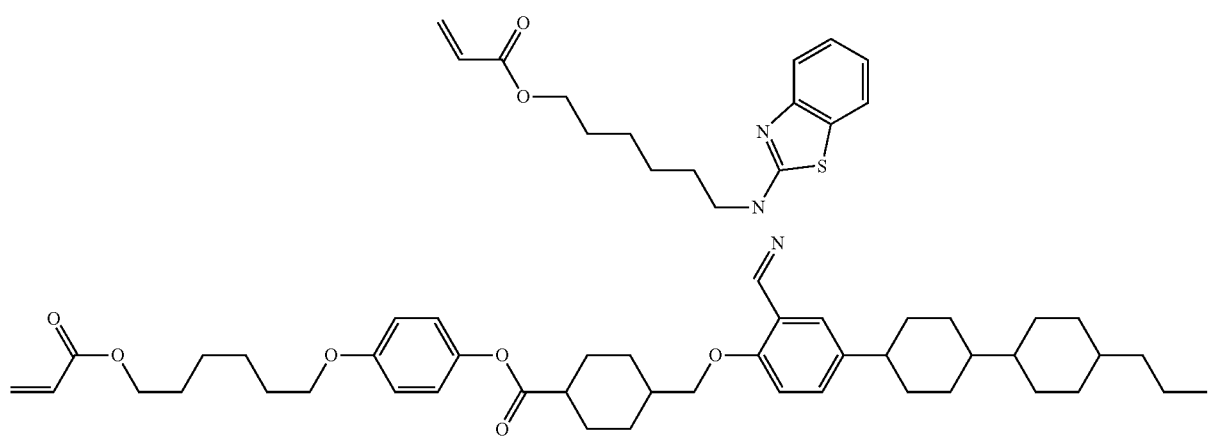

(I-62)
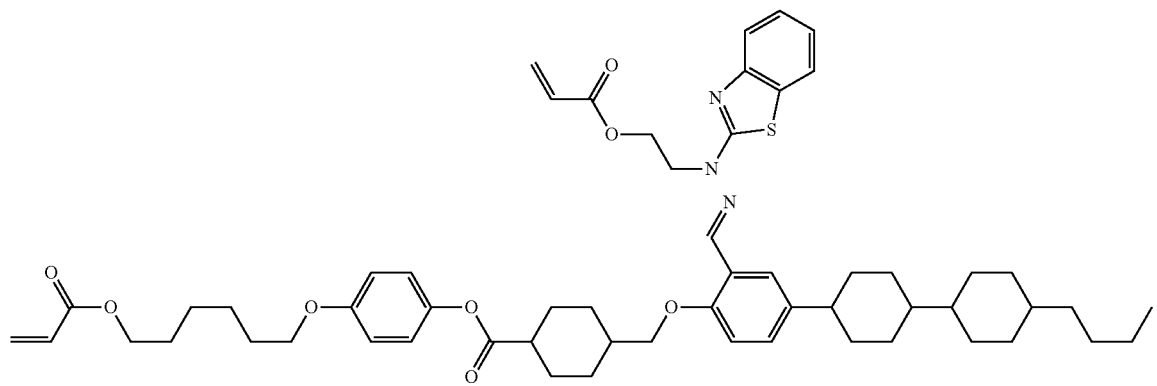
(I-63)
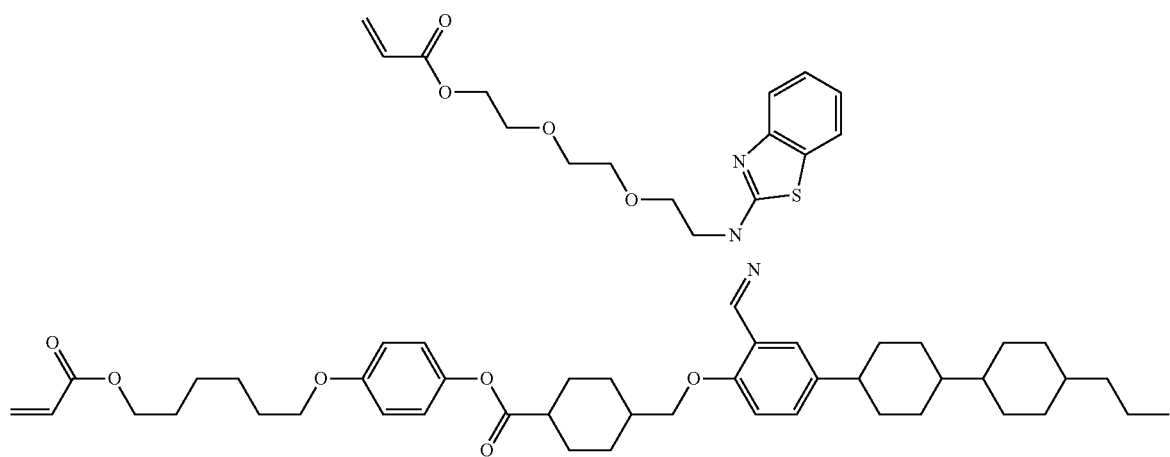
(I-64)
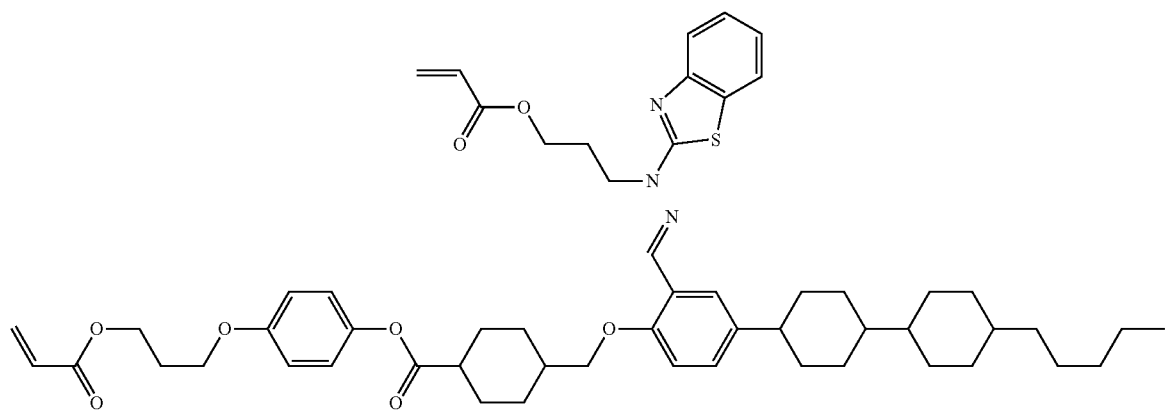

(I-65)
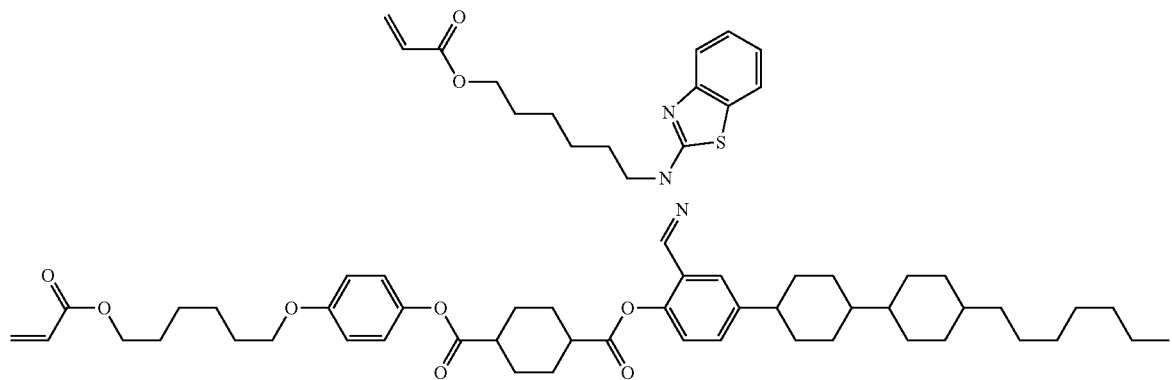
[Chem. 48]
(I-66)
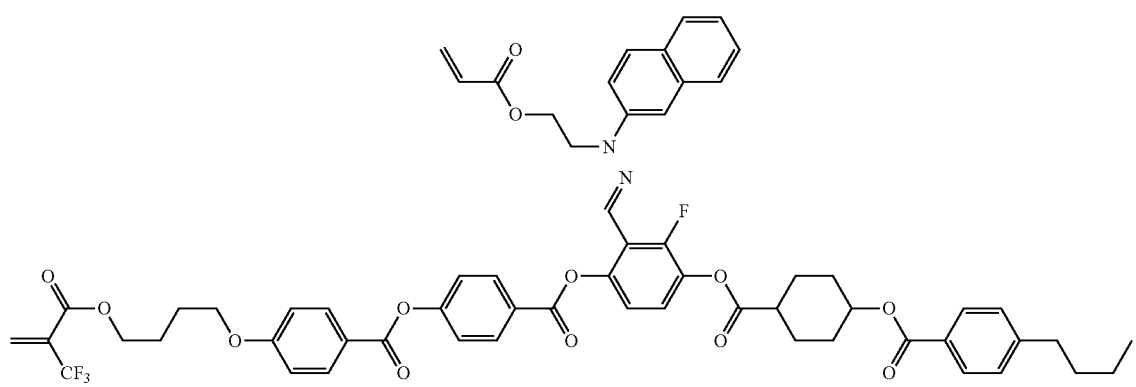
(I-67)
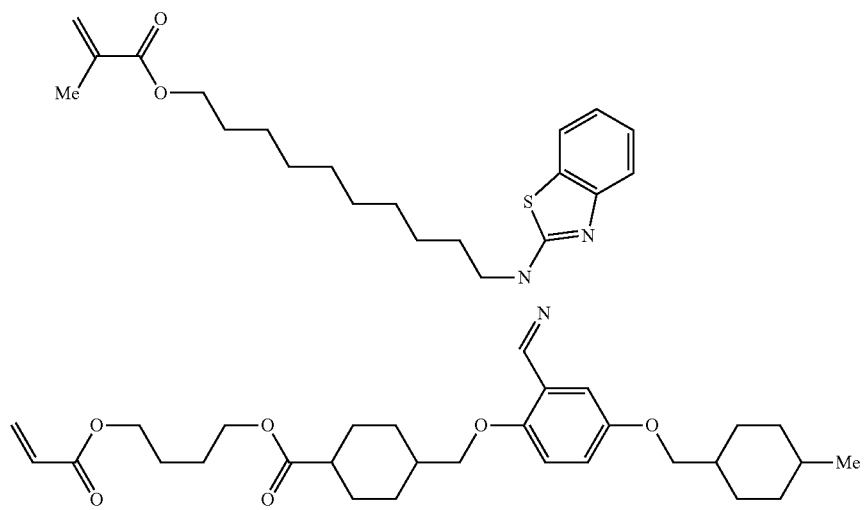

(I-68)
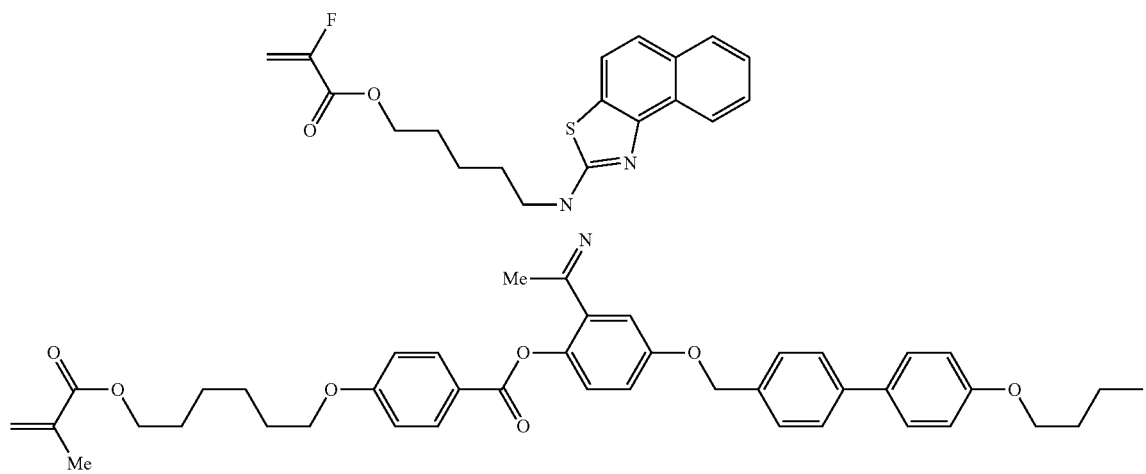
(I-69)
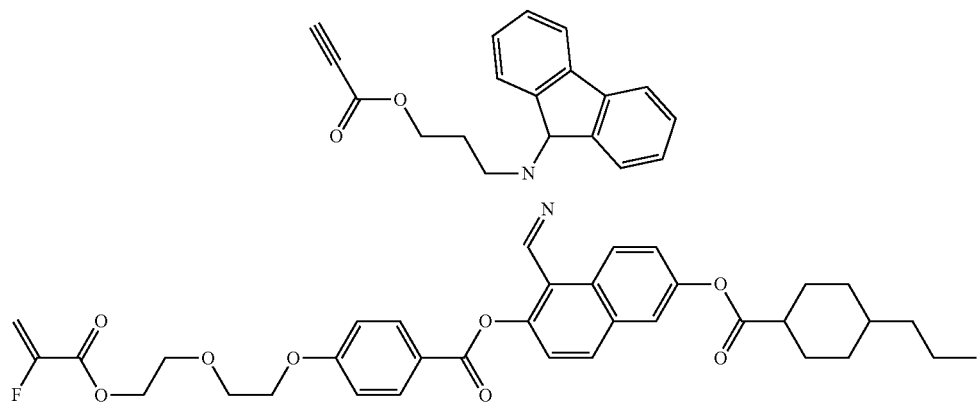
(I-70)
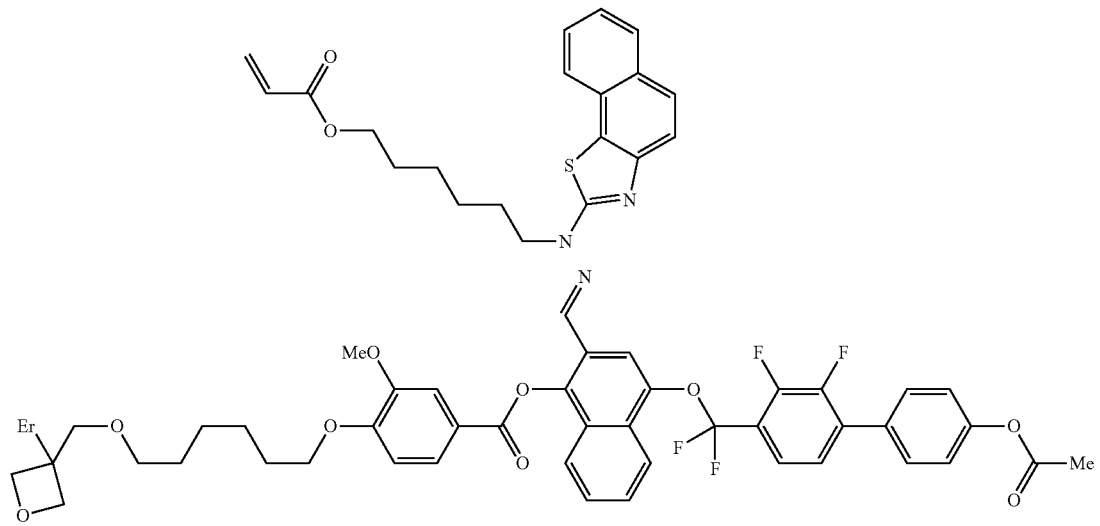

[Chem. 49]
(I-71)
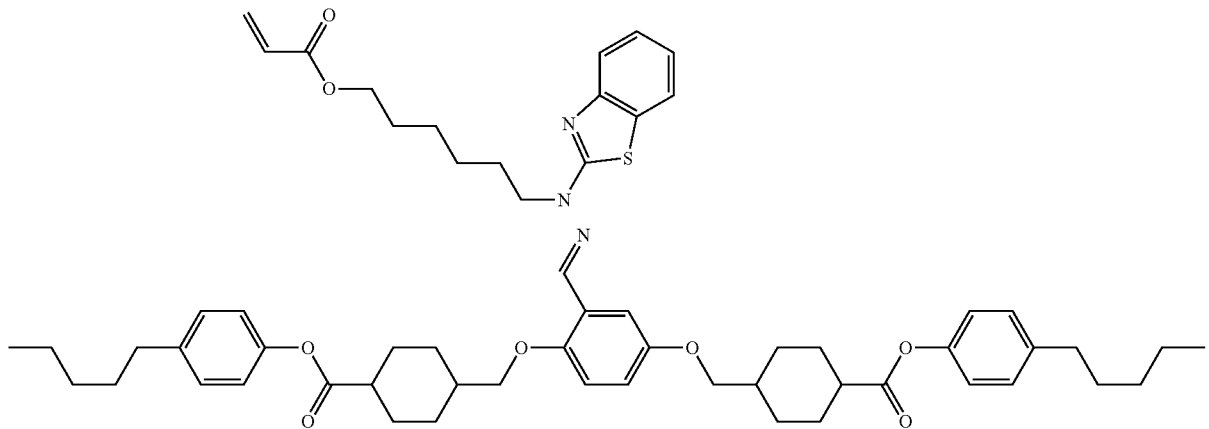
(I-72)
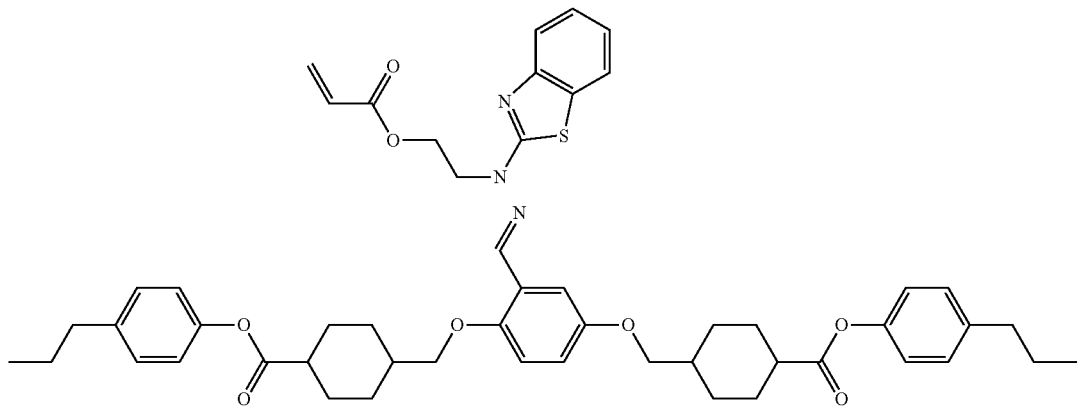
(I-73)
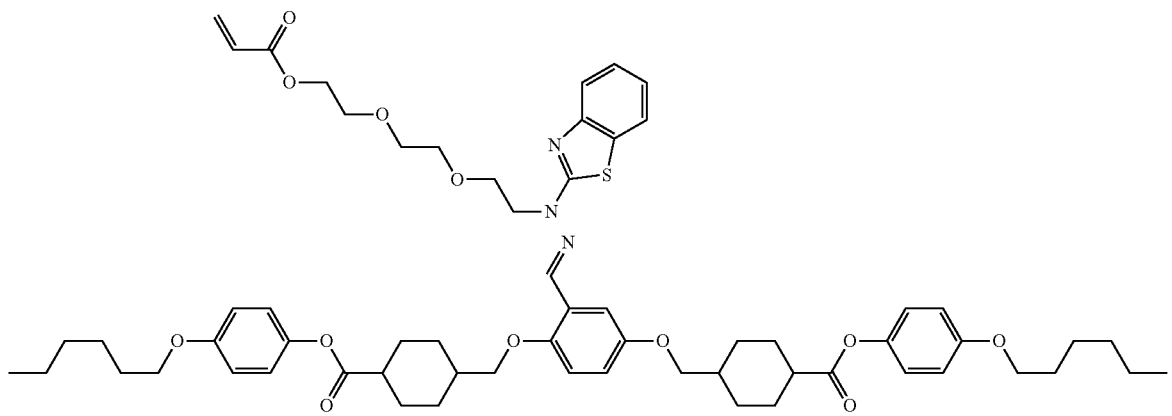

-continued
(I-74)
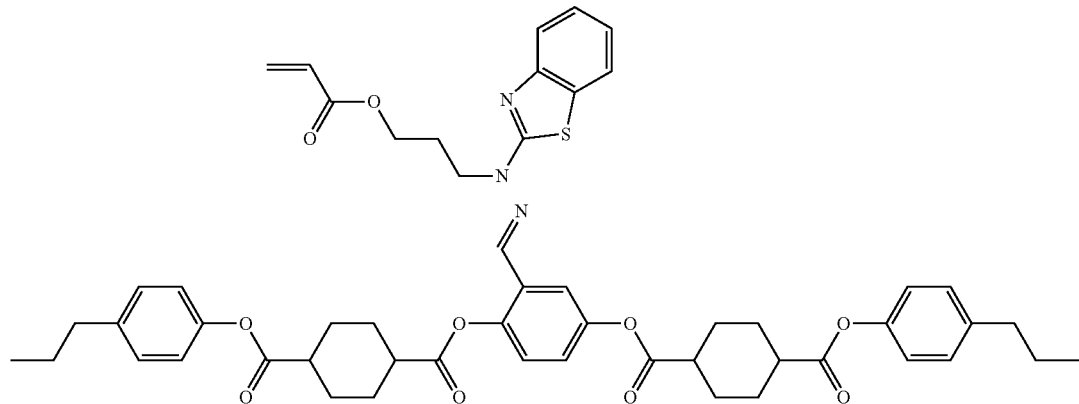
(I-75)
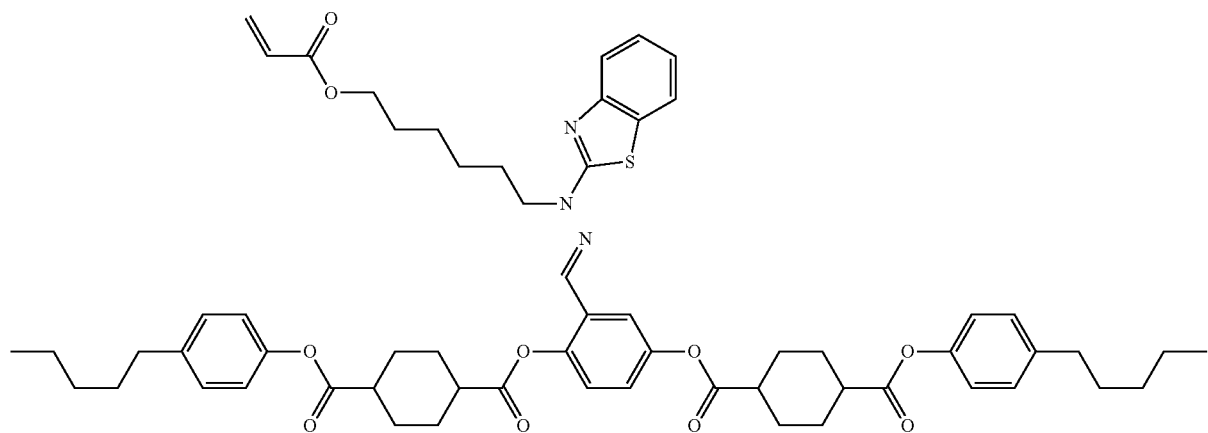
[Chem. 50]
(I-76)
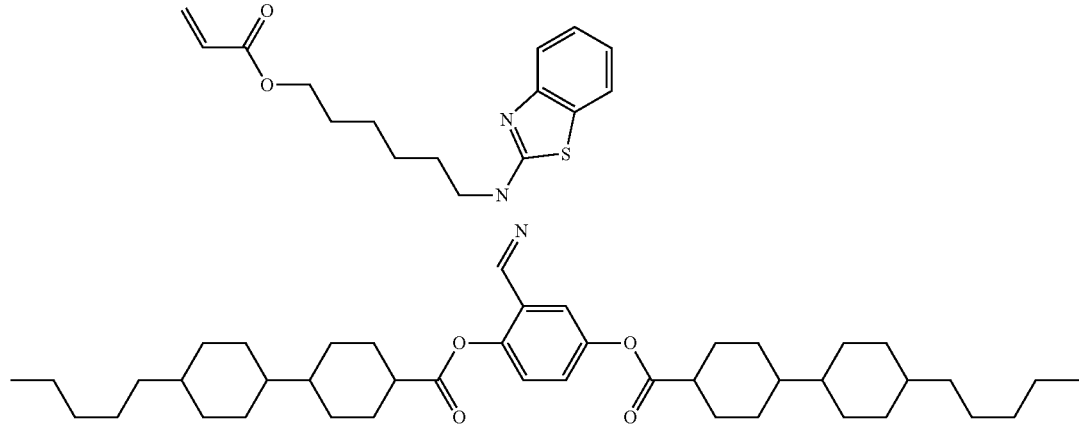

(I-77)
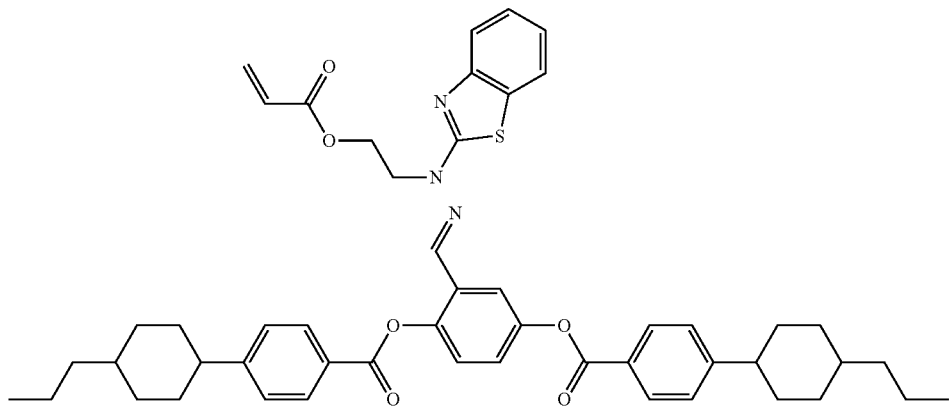
(I-78)
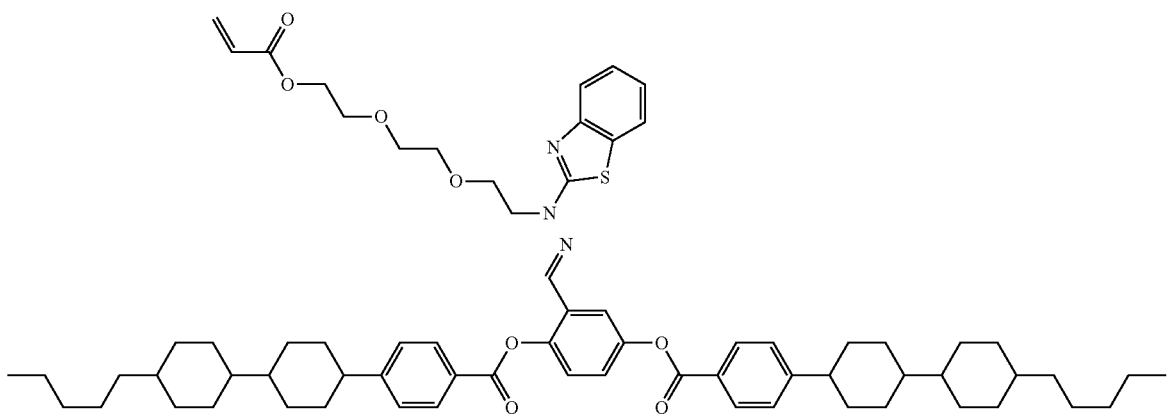
(I-79)
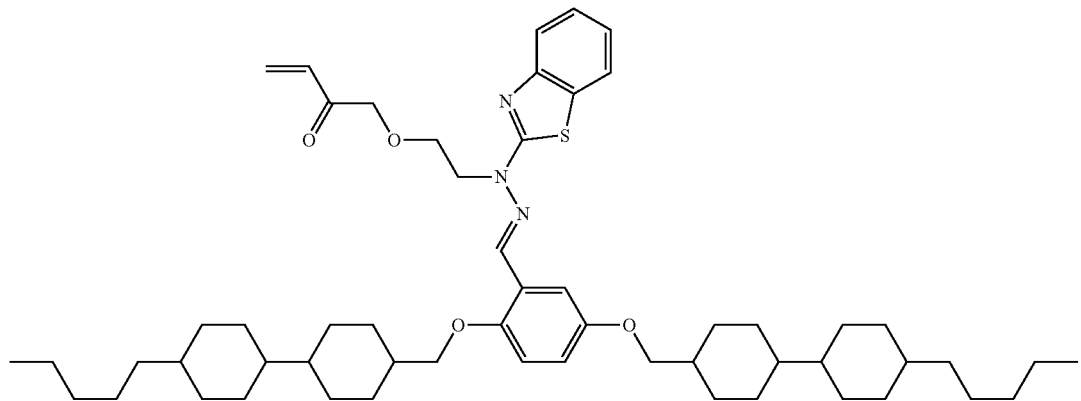

(I-80)
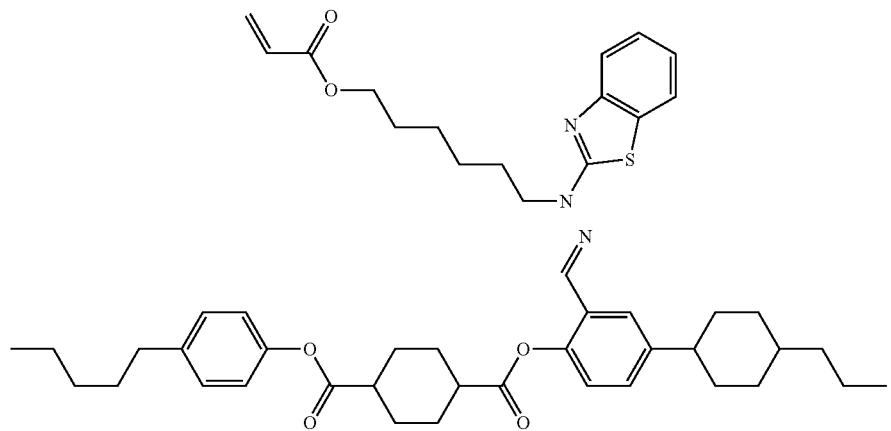
[Chem. 51]
(I-81)
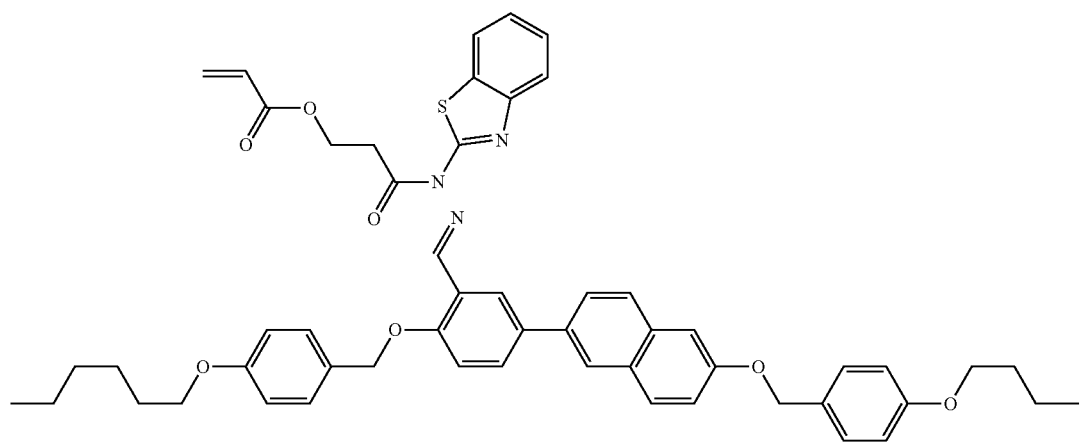
(I-82)
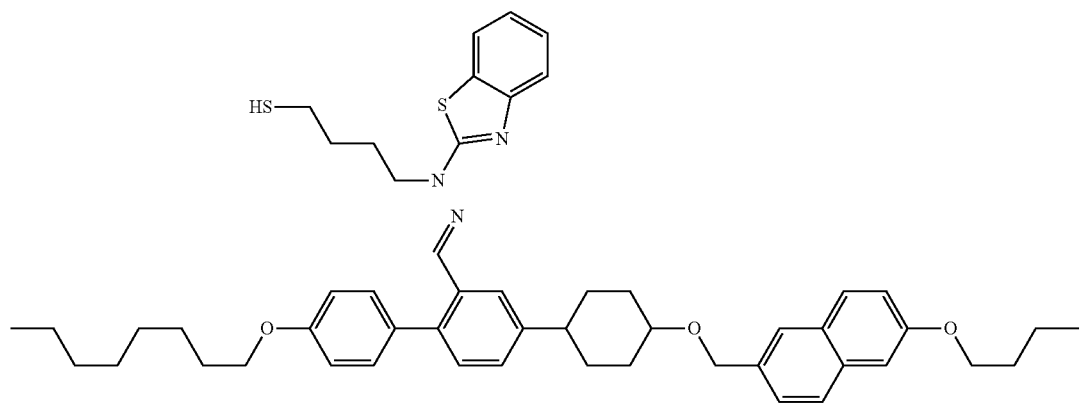

(I-83)
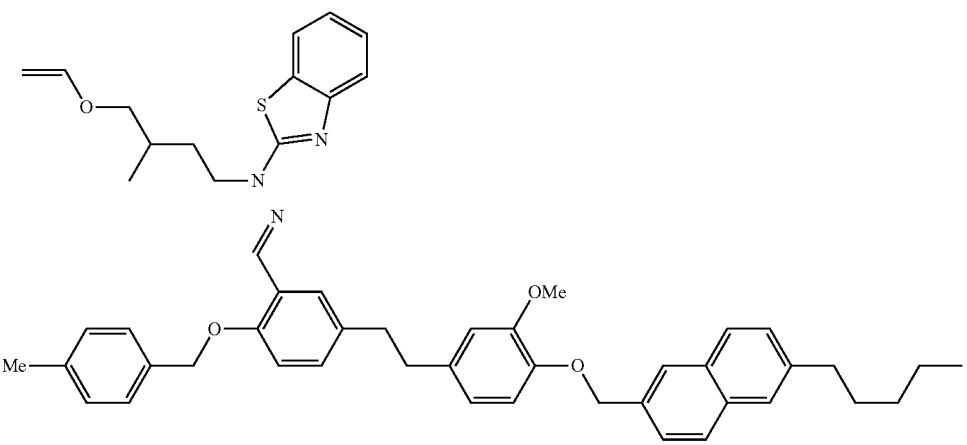
(I-84)
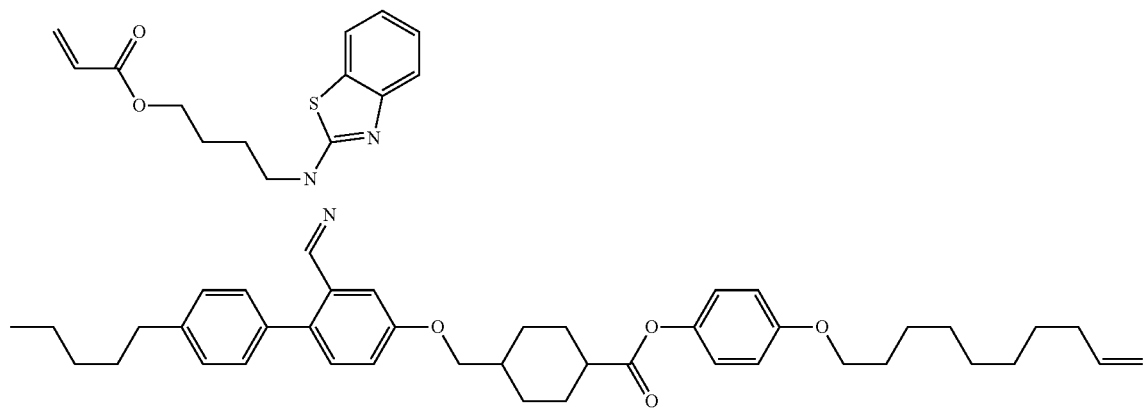
(I-85)
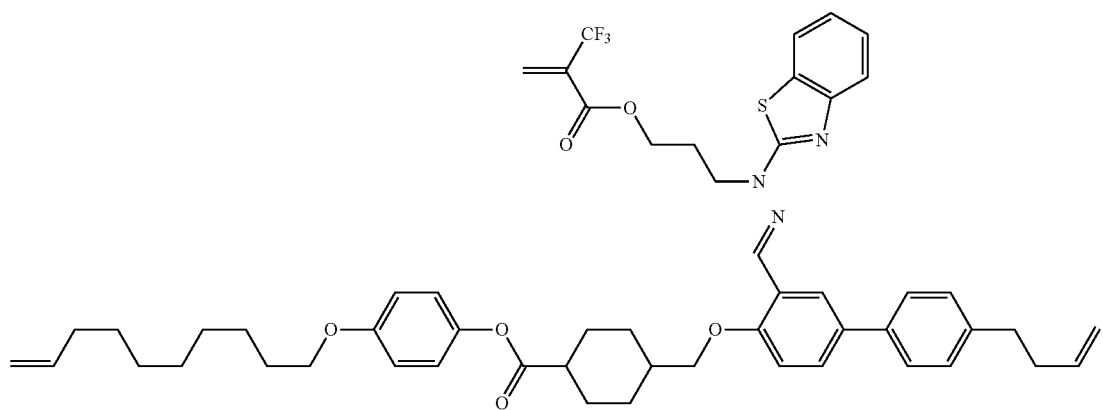

[Chem. 52]
(I-86)
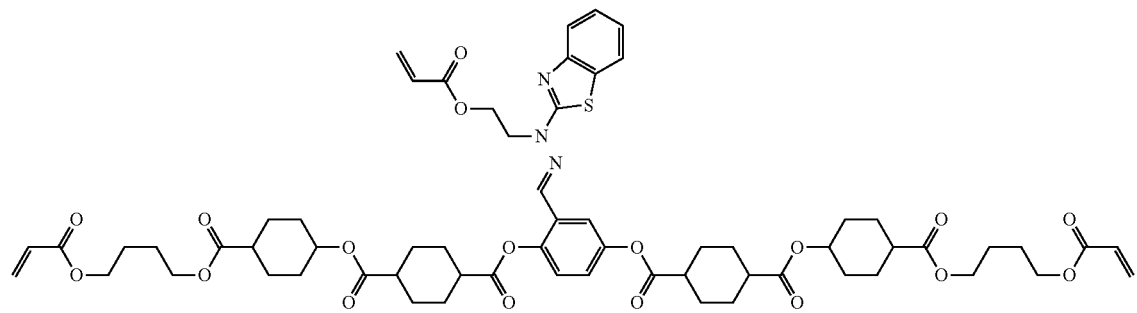
(I-87)
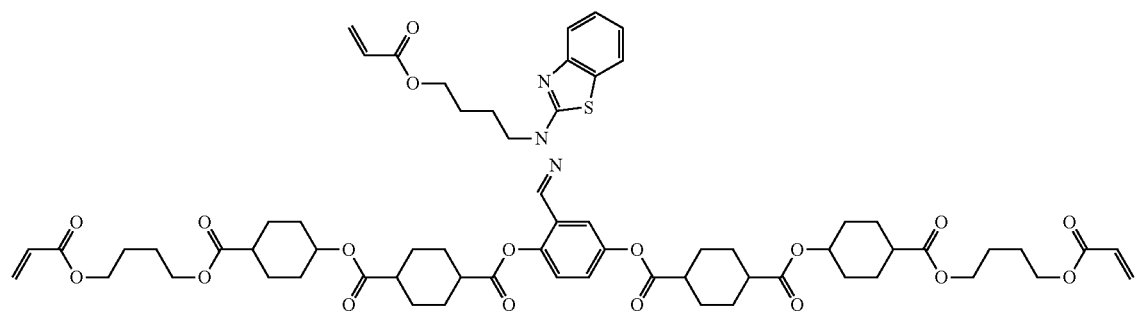
(I-88)
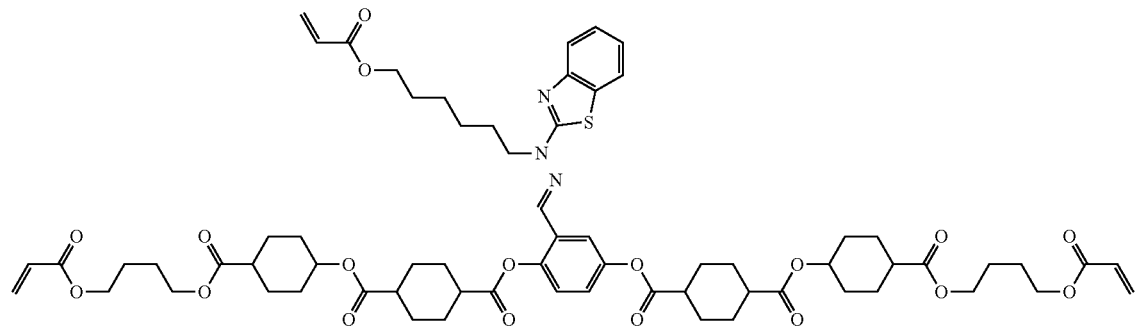
(I-89)
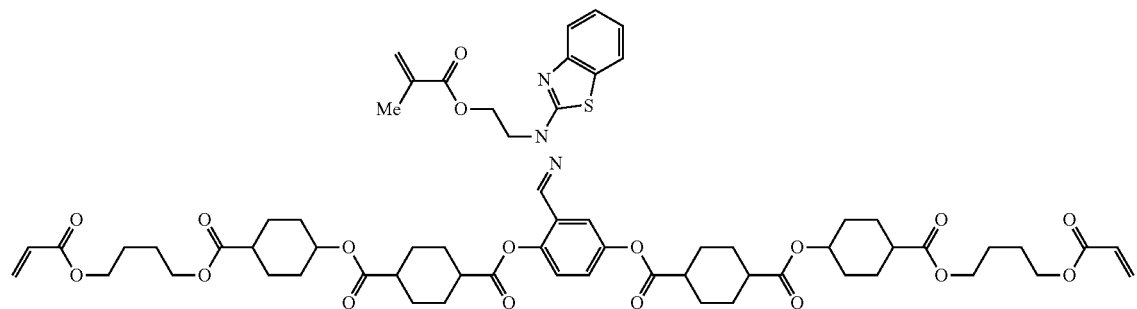

(I-90)
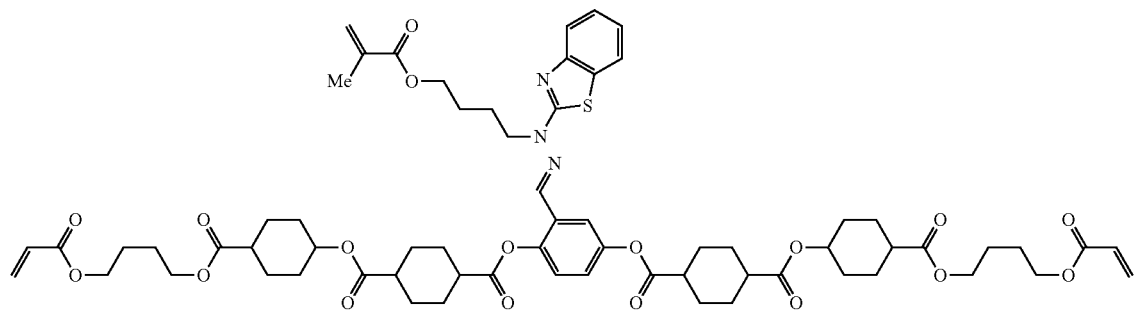
[Chem. 53]
(I-91)
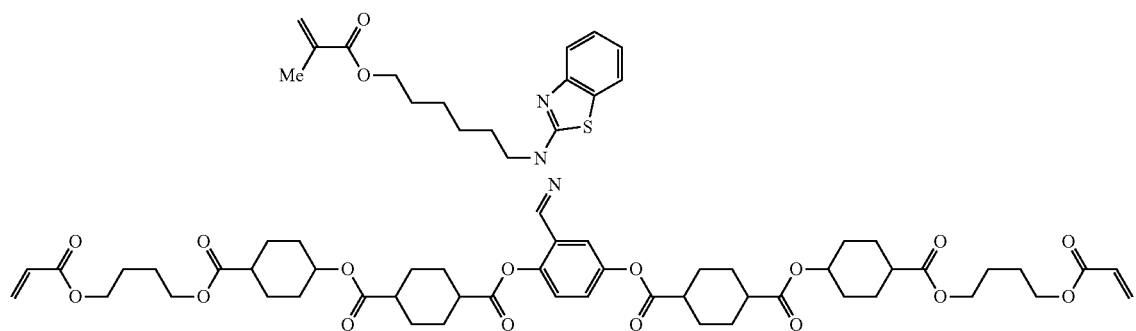
(I-92)
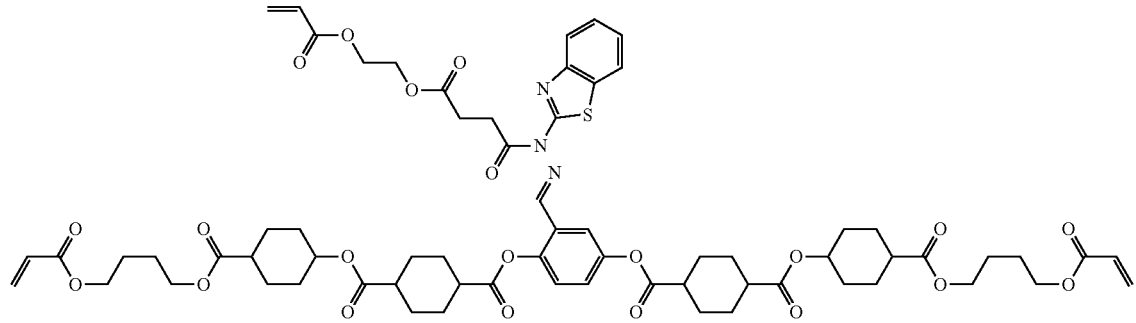
(I-93)
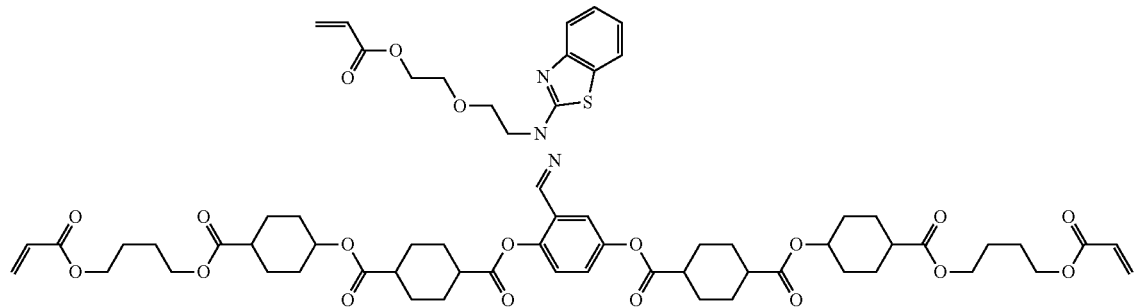

(I-94)
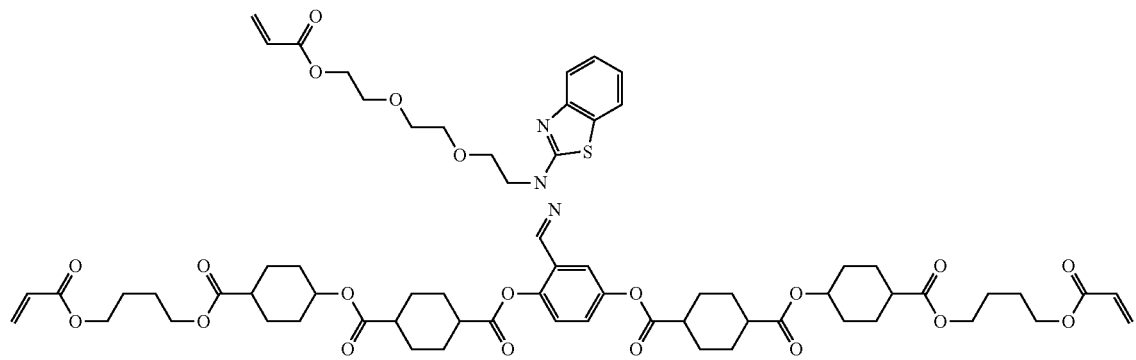
(I-95)
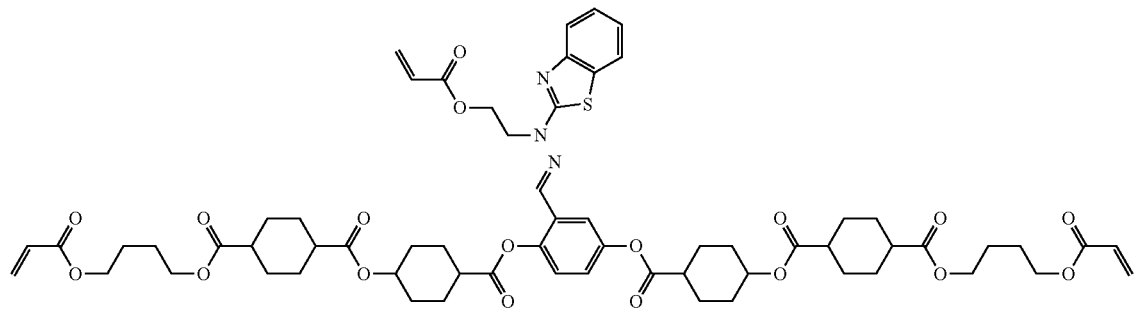
[Chem. 54]
(I-96)
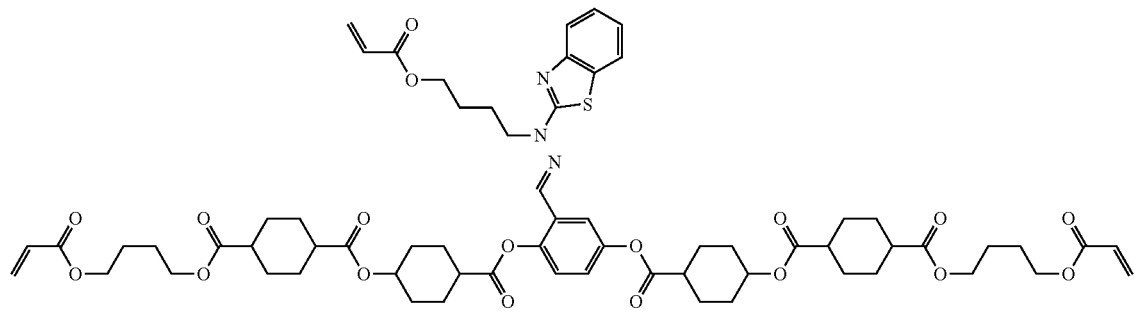
(I-97)
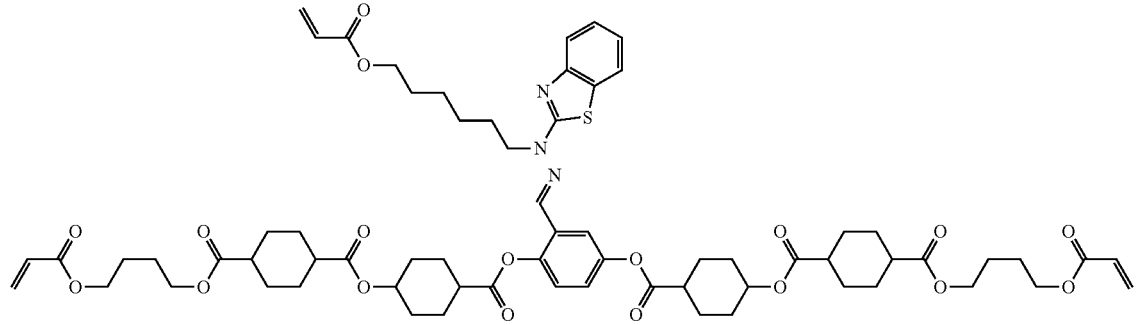

(I-98)
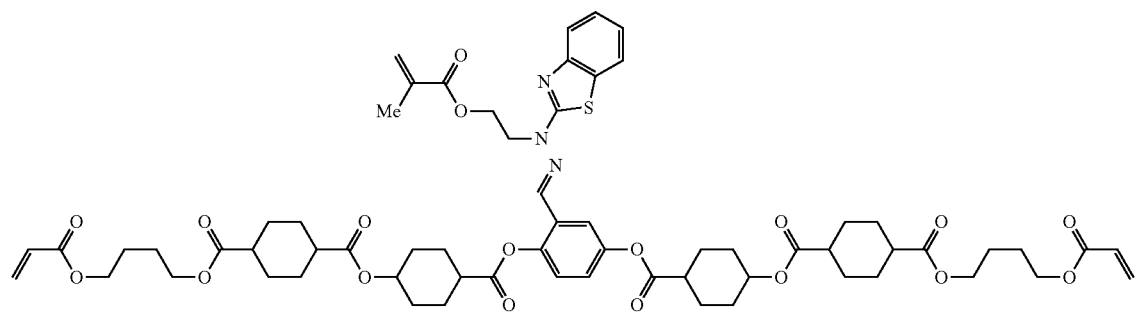
(I-99)
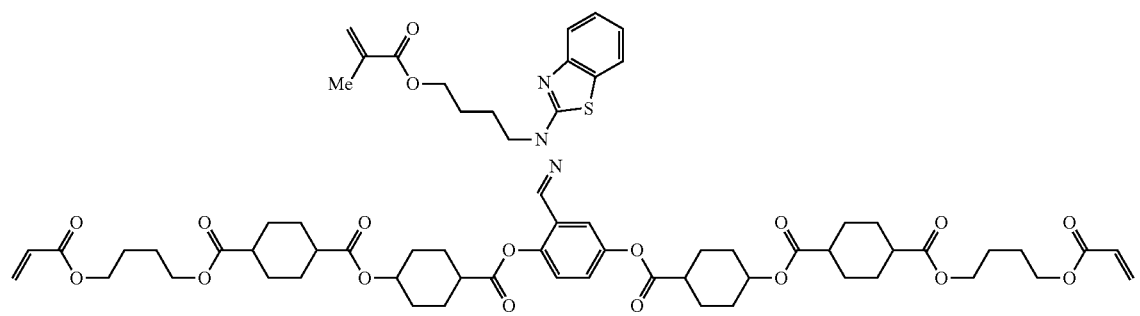
(I-100)
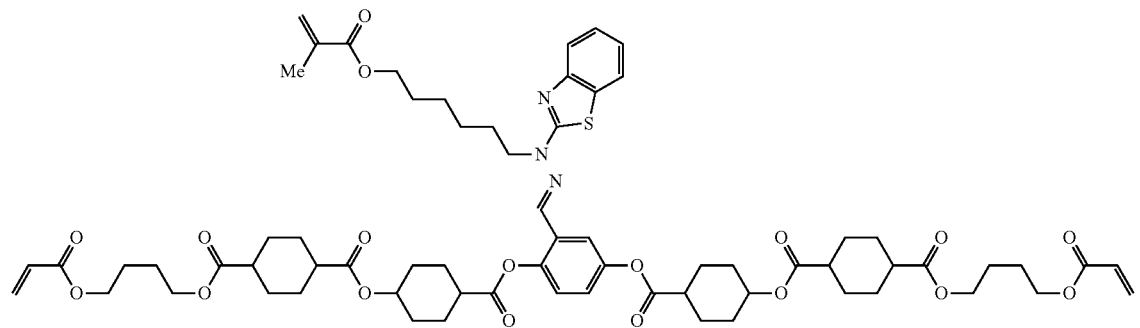
[Chem. 55]
(I-101)
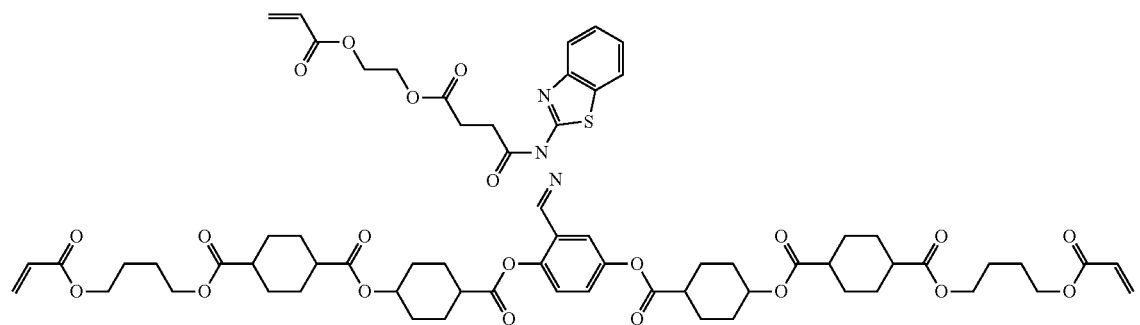

(I-102)
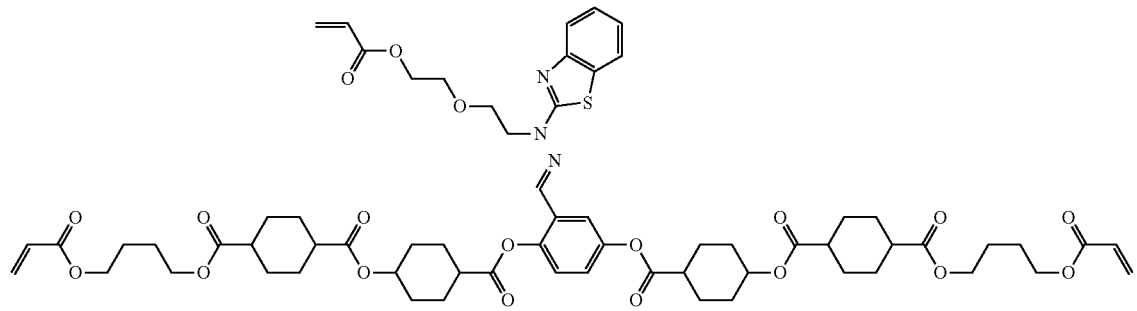
(I-103)
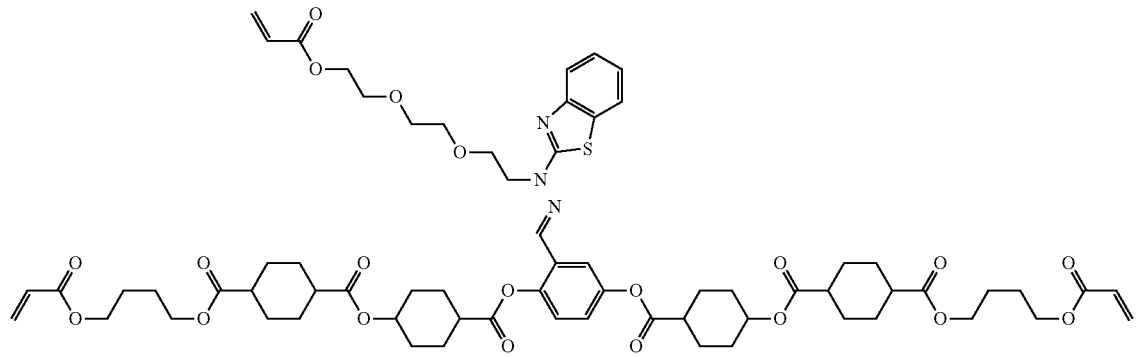
The compounds of the present invention can be produced according to the following production methods.
(Production Method 1) Production of Compounds Represented by the Following Formula (S-12):
[Chem. 56]
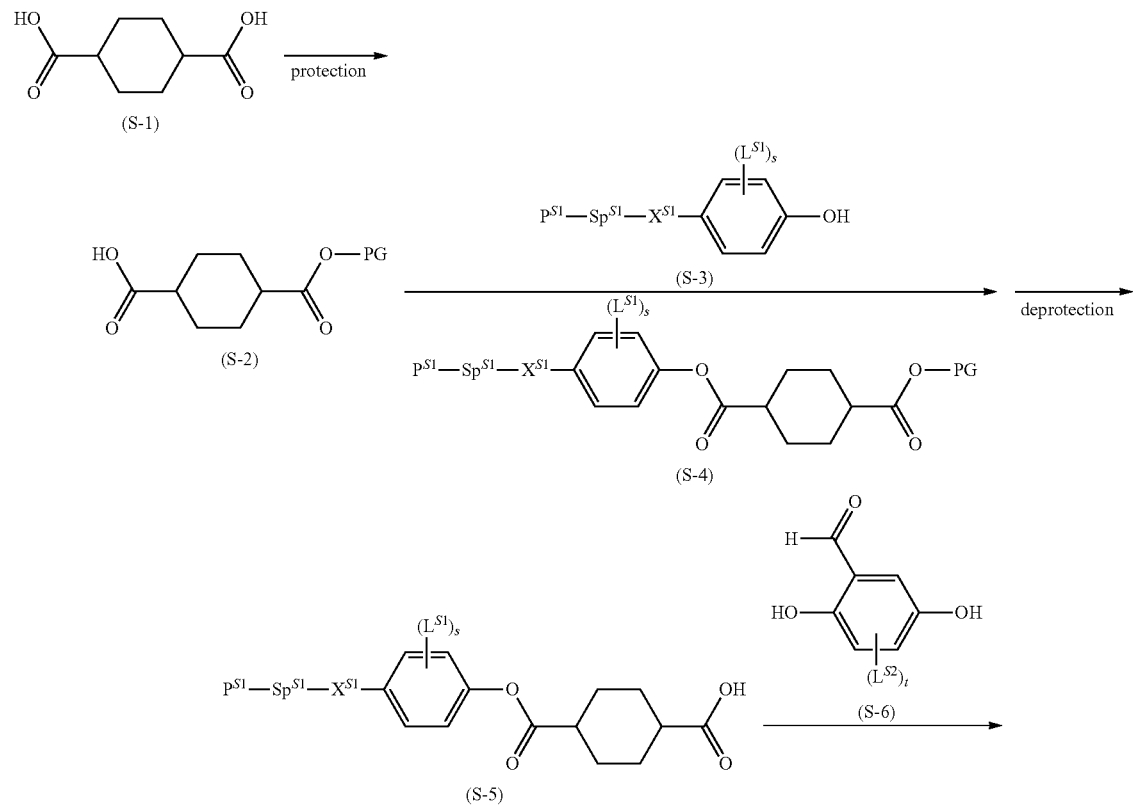

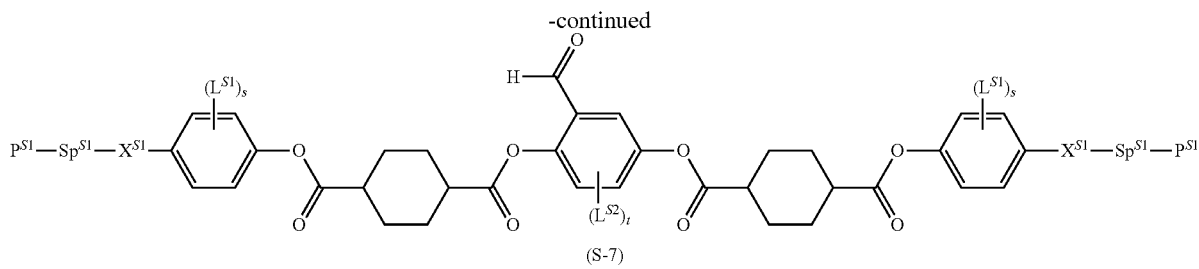

(S-7)

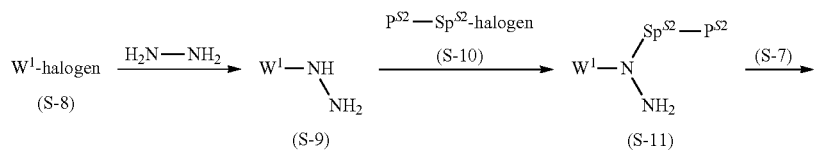

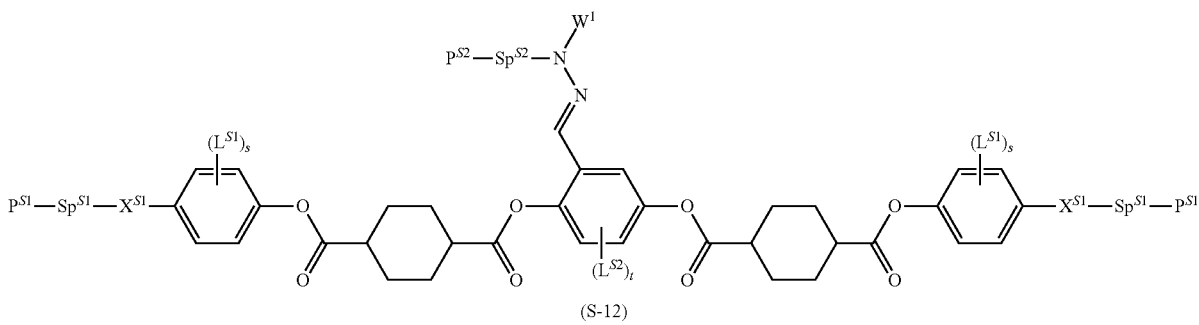

(S-12)

(wherein $P^{S1}$ and $P^{S2}$ each have the same meaning as $P^1$, $P^2$ or $P^3$ in the general formula (I), $Sp^{S1}$ and $Sp^{S2}$ each have the same meaning as $Sp^1$, $Sp^2$ or $Sp^3$ in the general formula (I), $X^{S1}$ has the same meaning as $X^1$ or $X^2$ in the general formula (I), $W^1$ has the same meaning as $W^1$ in the general formula (I), $L^{S1}$ has the same meaning as L in the general formula (I), $L^{S2}$ has the same meaning as $L^M$ in the general formula (I), s each independently represents an integer of 0 to 4, t represents an integer of 0 to 3, PG represents a protective group, "halogen" represents a halogen atom or a halogen equivalent.)

The carboxyl group in the compound represented by the formula (S-1) is protected with a protective group (PG). With no specific limitation, the protective group (PG) may be any one capable of attaining stable protection until the deprotection step, and for example, the protective groups (PG) shown in GREENE's PROTECTIVE GROUPS IN ORGANIC SYNTHESIS ((Fourth Edition), co-edited by PETER G. M. WUTS, and THEODORA W. GREENE, John Wiley & Sons, Inc., Publication) and others are preferred. Specific examples of the protective group include a tetrahydropyranyl group, a tert-butyl group, a methoxymethyl group and an ethoxymethyl group.

The compound represented by the formula (S-2) is reacted the compound represented by the formula (S-3) to give the compound represented by the formula (S-4). Regarding the reaction conditions, for example, a method using a condensing agent or a method including converting the compound represented by the formula (S-2) into an acid chloride, a mixed acid anhydride or a carboxylic acid anhydride thereof, and then reacting it with the compound represented by the general formula (S-3) in the presence of a base may be employed. In the case of using a condensing agent, the condensing agent includes, for example, N,N'-dicyclohexylcarbodiimide, N,N'-diisopropylcarbodiimide, and 1-ethyl-3-(3-dimethylaminopropyl)carbodiimide hydrochloride. The base includes, for example, triethylamine, diisopropylethylamine, etc.

The protective group (PG) of the compound represented by the formula (S-4) is deprotected. Regarding the deprotection reaction conditions, any one capable of giving the compound represented by the formula (S-5) is employable with no specific limitation, but those shown in the above-mentioned literature are preferred.

The compound represented by the formula (S-5) is reacted with the compound represented by the formula (S-6) to give the compound represented by the formula (S-7). Regarding the reaction conditions, for example, those mentioned hereinabove are employable.

The compound represented by the formula (S-8) is reacted with, for example, hydrazine monohydrate to give the compound represented by the formula (S-9).

The compound represented by the formula (S-9) is reacted with the compound represented by the formula (S-10) in the presence of a base to give the compound represented by the formula (S-11). The base includes, for example, potassium carbonate, cesium carbonate, triethylamine, etc.

The compound represented by the formula (S-11) is reacted with the compound represented by the formula (S-7) in the presence of an acid catalyst to give the compound represented by the formula (S-12). The acid includes, for example, p-toluenesulfonic acid, pyridinium p-toluenesulfonate, 10-camphorsulfonic acid, etc.

(Production Method 2) Production of Compounds Represented by the Following Formula (S-24):
[Chem. 57]
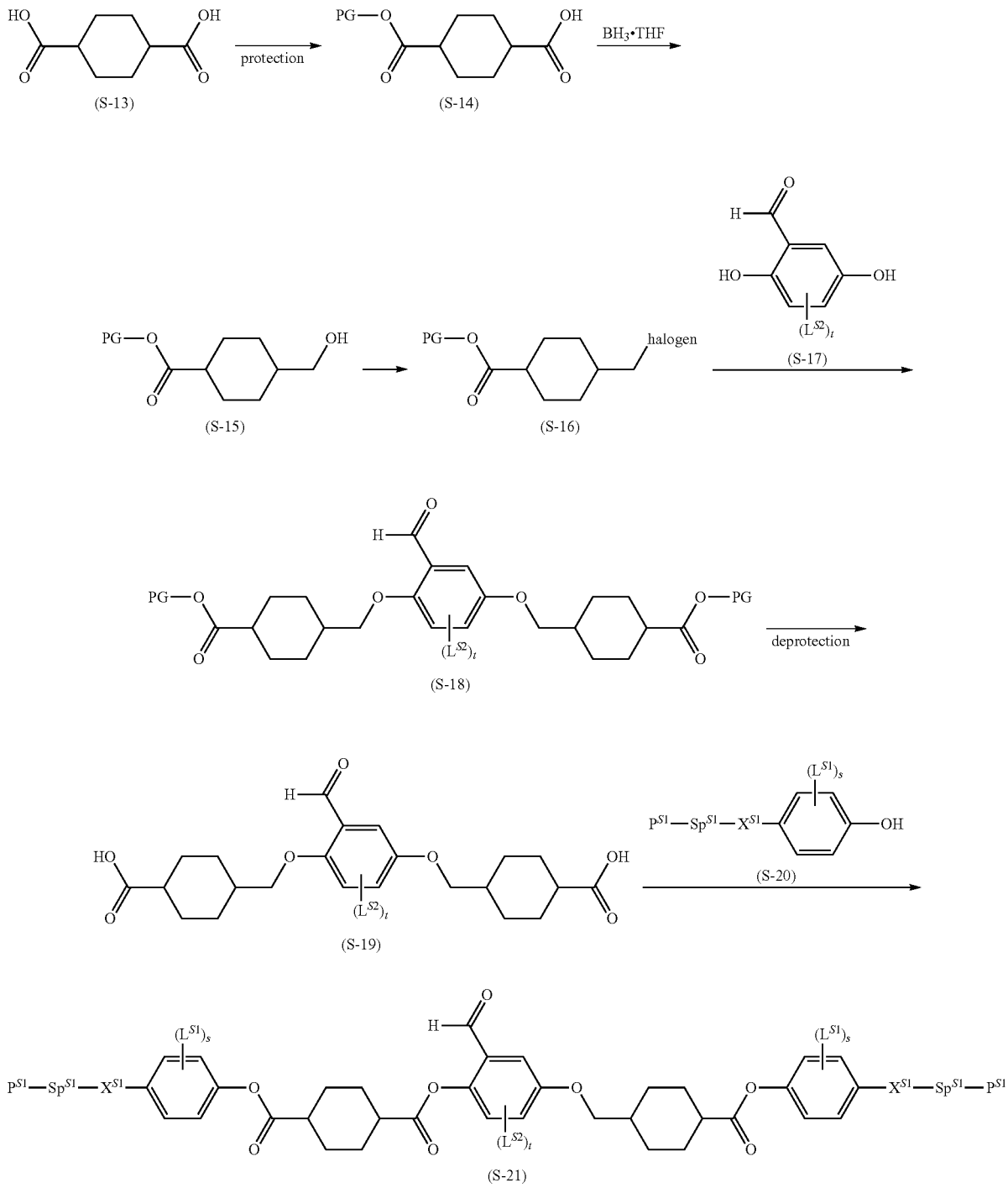
[Chem. 58]
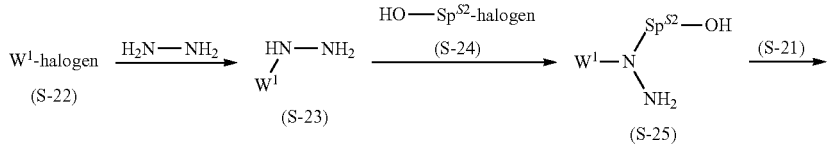

-continued

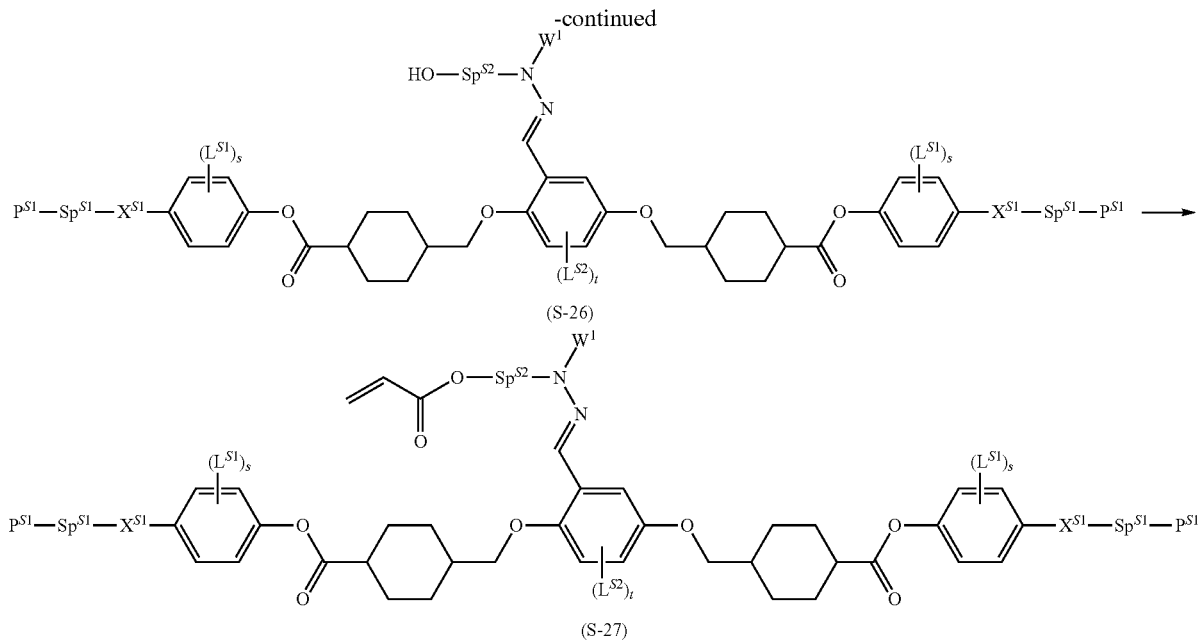

(wherein $P^{S1}$ has the same meaning as $P^1$ or $P^2$ in the general formula (I), $Sp^{S1}$ and $Sp^{S2}$ each have the same meaning as $Sp^1$, $Sp^2$ or $Sp^3$ in the general formula (I), $X^{s1}$ has the same meaning as $X^1$ or $X^2$ in the general formula (I), $W^1$ has the same meaning as $W^1$ in the general formula (I), $L^{S1}$ has the same meaning as L in the general formula (I), $L^{S2}$ has the same meaning as L in the general formula (I), s each independently represents an integer of 0 to 4, t represents an integer of 0 to 3, PG represents a protective group, and "halogen" represents a halogen atom or a halogen equivalent.)

The carboxyl group in the compound represented by the formula (S-13) is protected with a protective group (PG). The protective group (PG) includes, for example, those described in the production method 1.

By reducing the compound represented by the formula (S-14), the compound represented by the formula (S-15) is produced. The reducing agent includes, for example, borane complexes such as a borane-tetrahydrofuran complex, a borane-dimethyl sulfide complex, etc., and diborane, etc.

The compound represented by the formula (S-15) is halogenated to give the compound represented by the formula (S-16). Regarding the halogenation conditions, a method of reacting with iodine in the presence of triphenyl phosphine and imidazole, a method of reacting with carbon tetrabromide or N-bromosuccinimide in the presence of triphenyl phosphine, or a method of reacting with lithium chloride in the presence of a base may be employed. In addition, a method of reacting with methanesulfonyl chloride or p-toluenesulfonyl chloride in the presence of a base to derive into a halogen equivalent is also employable.

The compound represented by the general formula (S-16) is reacted with the compound represented by the formula (S-17) in the presence of a base to give the compound represented by the formula (S-18). The base includes, for example, those mentioned for the production method 1.

The protective group (PG) in the compound represented by the formula (S-18) is deprotected. Regarding the deprotection reaction conditions, any one capable of giving the compound represented by the formula (S-19) is employable with no specific limitation, but those shown in the above-mentioned literature are preferred.

The compound represented by the formula (S-19) is reacted with the compound represented by the formula (S-20) to give the compound represented by the formula (S-21). Regarding the reaction conditions, for example, those mentioned for the production method 1 are employable.

The compound represented by the formula (S-22) is reacted with, for example, a hydrazine monohydrate to give the compound represented by the formula (S-23).

The compound represented by the formula (S-23) is reacted with the compound represented by the formula (S-24) in the presence of a base to give the compound represented by the formula (S-25). The base includes, for example, potassium carbonate, cesium carbonate, triethylamine, etc.

The compound represented by the formula (S-25) is reacted with the compound represented by the formula (S-21) in the presence of an acid catalyst to give the compound represented by the formula (S-26). The acid includes, for example, p-toluenesulfonic acid, pyridinium p-toluenesulfonate, 10-camphorsulfonic acid, etc.

An acrylic group is introduced into the compound represented by the formula (S-26) to give the compound represented by the formula (S-27). Regarding the reaction conditions, for example, a method of using an acrylic acid and a condensing agent, or a method of reacting with an acrylic acid chloride in the presence of a base is employable. The condensing agent includes those mentioned hereinabove. The base includes, for example, triethylamine, triisopropylamine, diisopropylethylamine, etc.

As other reaction conditions than those described in each step of the production method 1 and the production method 2, for example, those described in literature such as Experimental Chemistry Course (edited by the Chemical Society of Japan, published by Maruzen Corporation), Organic Syntheses (John Wiley & Sons, Inc., Publication), Beilstein Handbook of Organic Chemistry (Beilstein-Institut fuer Literatur der Organischen Chemie, Springer-Verlag Berlin and Heidelberg GmbH & Co. K), Fiesers' Reagents for Organic Synthesis (John Wiley & Sons, Inc.), etc., or those provided by online search service such as SciFinder (Chemical Abstracts Service, American Chemical Society) or Reaxys (Elsevier Ltd.), etc. can be employed.

A reaction solvent can be appropriately used in each step. The solvent is not specifically limited so far as target compounds can be given, and includes, for example, isopropyl alcohol, ethylene glycol, diethylene glycol, methanol, ethanol, propanol, chloroform, dichloromethane, 1,2-dichloroethane, acetone, acetonitrile, N,N-dimethylformamide, N,N-dimethylacetamide, dimethyl sulfoxide, diethyl ether, ethylene glycol monoethyl ether, xylene, ethyl acetate, butyl acetate, propyl acetate, methyl acetate, cyclohexanone, 1,4-dioxane, dichloromethane, styrene, tetrahydrofuran, pyridine, 1-methyl-2-pyrrolidinone, toluene, hexane, cyclohexane, heptane, benzene, methyl isobutyl ketone, tert-butylmethyl ether, methyl ethyl ketone, etc. In the case where the reaction is carried out in a two-phase system of an organic solvent and water, a phase transfer catalyst may be added. The phase transfer catalyst includes, for example, benzyltrimethylammonium chloride, polyoxyethylene(20) sorbitanmonolaurate [Tween 20], sorbitan monooleate [Span 80], etc.

In each step, as needed, purification may be carried out. The purification method includes chromatography, recrystallization, distillation, sublimation, reprecipitation, adsorption, liquid separation, etc. In the case where a purifying agent is used, the purifying agent includes silica gel, alumina, active carbon, active clay, Celite, zeolite, mesoporous silica, carbon nanotube, carbon nanohorn, binchotan charcoal, wood charcoal, graphene, ion-exchange resin, acid clay, carbon dioxide, diatomaceous earth, pearlite, cellulose, organic polymer, porous gel, etc.

The compound of the present invention is preferably used in a nematic liquid crystal composition, a smectic liquid crystal composition, a chiral smectic liquid crystal composition and a cholesteric liquid crystal composition. Any other compound than the compound of the present invention may be added to the liquid crystal composition containing the reactive compound of the present invention.

As other polymerizable compounds that may be mixed with the polymerizable compound of the present invention for use herein, specifically, compounds represented by a general formula (X-11):

[Chem. 59]

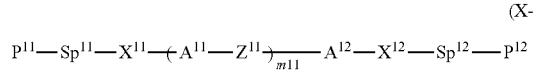
(X-11)

and/or compounds represented by a general formula (X-12):

[Chem. 60]

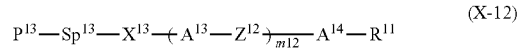
(X-12)

(wherein $P^{11}$, $P^{12}$ and $P^{13}$ each independently represent a polymerizable group, $Sp^1$, $Sp^{12}$ and $Sp^{13}$ each independently represent a single bond or an alkylene group having 1 to 20 carbon atoms in which one —$CH_2$— or two or more (—$CH_2$—)'s not adjacent to each other may be each independently substituted with —O—, —COO—, —OCO— or —OCOO—, $X^{11}$, $X^{12}$ and $X^{13}$ each independently represent —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —CF=CF—, —C≡C— or a single bond, $Z^{11}$ and $Z^{12}$ each independently represent —O—, —S—, —OCH$_2$—, —CH$_2$O—, —COO—, —OCO—, —CO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH$_2$CH$_2$—, —CH$_2$CF$_2$—, —CF$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —CF=CF—, —C≡C— or a single bond, $A^{11}$, $A^{12}$, $A^{13}$ and $A^{14}$ each independently represent a 1,4-phenylene group, a 1,4-cyclohexylene group, a bicyclo[2.2.2]octane-1,4-diyl group, a pyridine-2,5-diyl group, a pyrimidine-2,5-diyl group, a naphthalene-2,6-diyl group, a naphthalene-1,4-diyl group, a tetrahydronaphthalene-2,6-diyl group or a 1,3-dioxane-2,5-diyl group, and $A^{11}$, $A^{12}$, $A^{13}$ and $A^{14}$ may be each independently unsubstituted or substituted with an alkyl group, a halogenoalkyl group, an alkoxy group, a halogenoalkoxy group, a halogen atom, a cyano group or a nitro group, R represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms in which one —CH$_2$— or two or more (—CH$_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, m11 and m12 each represent 0, 1, 2 or 3, and in the case where m11 and/or m12 each are 2 or 3, two or three existing groups with respect to each of $A^{11}$, $A^{13}$, $Z^{11}$ and $Z^{12}$ may be the same or different) are preferred; and those where $P^{11}$, $P^{12}$ and $P^{13}$ each are an acrylic group or a methacrylic group are especially preferred. Specifically, the compounds represented by the general formula (X-11) are preferably those represented by a general formula (X-11a):

[Chem. 61]

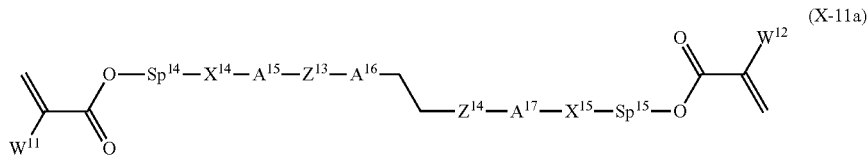

(X-11a)

(wherein $W^{11}$ and $W^{12}$ each independently represent a hydrogen atom or a methyl group, $Sp^{14}$ and $Sp^{15}$ each independently represent an alkylene group having 2 to 18 carbon atoms, $X^{14}$ and $X^{15}$ each independently represent —O—, —COO—, —OCO— or a single bond, $Z^{13}$ and $Z^{14}$ each independently represent —COO— or —OCO—, $A^{15}$, $A^{16}$ and $A^{17}$ each independently represent a 1,4-phenylene group which is unsubstituted or optionally substituted with a fluorine atom, a chlorine atom, a linear or branched alkyl group having 1 to 4 carbon atoms, or a linear or branched alkoxy group having 1 to 4 carbon atoms); and those represented by the following formulae (X-11a-1) to (X-11a-4):

[Chem. 62]

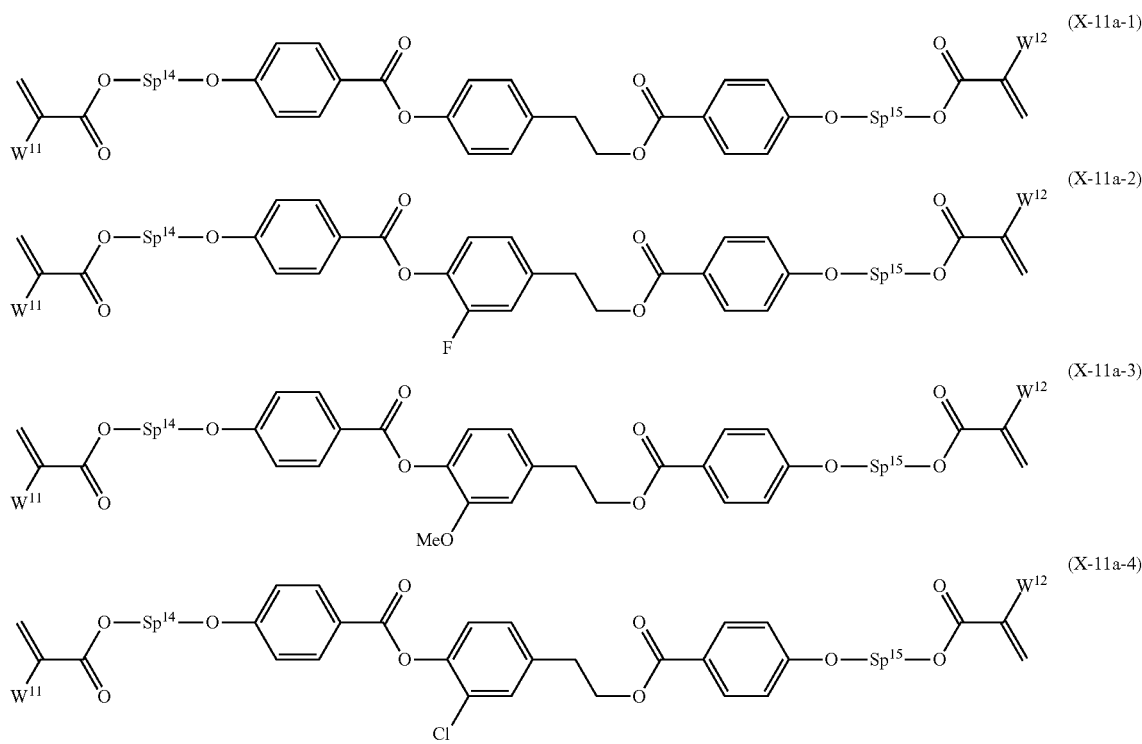

(wherein $W^{11}$, $W^{12}$, $Sp^{14}$ and $Sp^{15}$ each have the same meaning as in the general formula (X-11a) are especially preferred. Compounds of the above formulae (X-11a-1) to (X-11a-4) where $Sp^{14}$ and $Sp^{15}$ each are an alkylene group having 2 to 8 carbon atoms are especially preferred.

In addition, as preferred bifunctional polymerizable compounds, there are mentioned compounds represented by the following general formulae (X-11b-1) to (X-11b-3):

[Chem. 63]

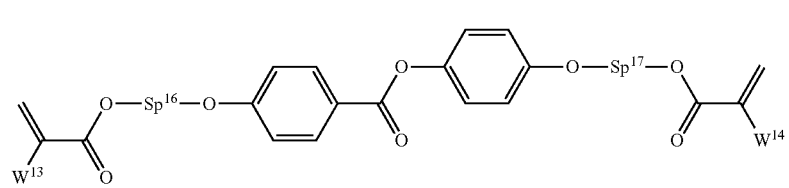

(X-11b-1)

-continued

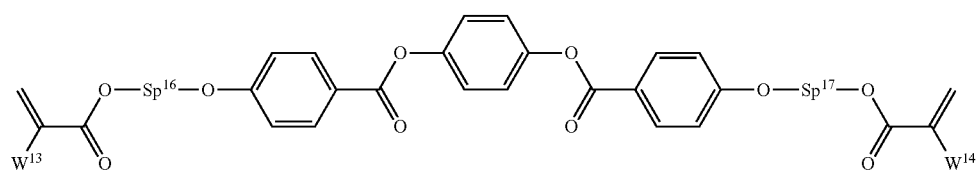
(X-11b-2)

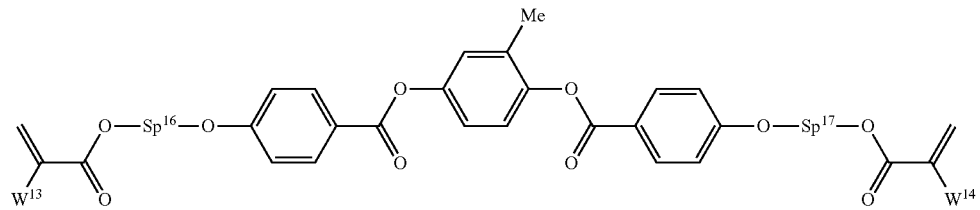
(X-11b-3)

(wherein $W^{13}$ and $W^{14}$ each independently represent a hydrogen atom or a methyl group, $Sp^{16}$ and $Sp^{17}$ each independently represent an alkylene group having 2 to 18 carbon atom). Compounds of the above formulae (X-11b-1) to (X-11b-3) where $Sp^{16}$ and $Sp^{17}$ each are an alkylene group having 2 to 8 carbon atoms are especially preferred.

Specifically, the compounds represented by the general formula (X-12) include compounds represented by the following general formulae (X-12-1) to (X-12-7):

[Chem. 64]

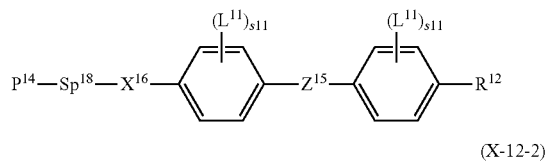
(X-12-1)

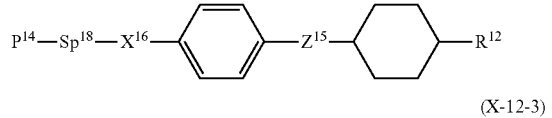
(X-12-2)

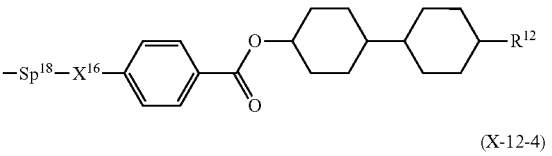
(X-12-3)

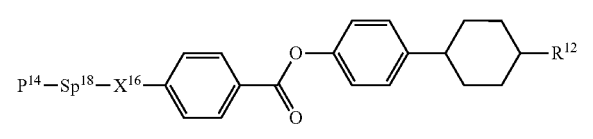
(X-12-4)

(X-12-5)

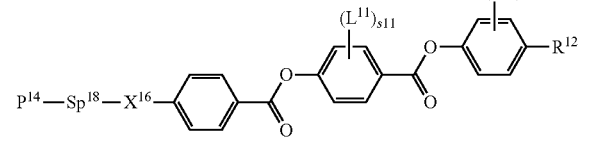

-continued

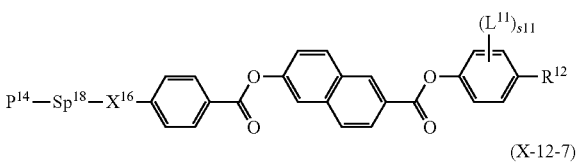
(X-12-6)

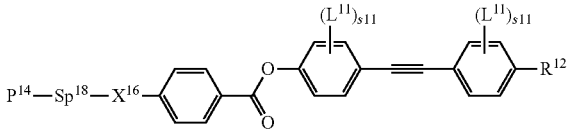
(X-12-7)

(wherein $P^{14}$ represents a polymerizable group, $Sp^{18}$ represents a single bond or an alkylene group having 1 to 20 carbon atoms, in which one —$CH_2$— or two or more (—$CH_2$—)'s not adjacent to each other may be substituted with —O—, —COO—, —OCO— or —O—CO—O—, $X^{16}$ represents a single bond, —O—, —COO—, or —OCO—, $Z^{15}$ represents a single bond, —COO— or —OCO—, $L^{11}$ represents a fluorine atom, a chlorine atom, or a linear or branched alkyl group having 1 to 10 carbon atoms in which one —$CH_2$— or two or more (—$CH_2$—)'s not adjacent to each other may be each independently substituted with —O—, —COO— or —OCO—, s11 represents an integer of 0 to 4, $R^{12}$ represents a hydrogen atom, a fluorine atom, a chlorine atom, a cyano group, a nitro group, or a linear or branched alkyl group having 1 to 20 carbon atoms in which one —$CH_2$— or two or more (—$CH_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—.)

A polymerizable compound not showing liquid crystallinity may be added to the polymerizable liquid crystal composition containing the compound of the present invention within a range not significantly detracting the liquid crystallinity of the composition. Specifically, a compound that can be recognized as a polymer-forming monomer or a polymer-forming oligomer in this technical field can be used with no specific limitation. As specific examples, for example, there are mentioned those described in "Photocurable Technique Data Book, Materials Section (monomer, oligomer, photopolymerization initiator)" (supervised by Kunihiro Ichimura "Kiyoshi Kato, Technonet Co., Ltd.).

The compound of the present invention may be polymerized even though not using a photopolymerization initiator, but depending on the intended purpose, a photopolymerization initiator may be added. In such a case, the concentration of the photopolymerization initiator is preferably 0.1% by mass to 15% by mass relative to the compound of the present invention, more preferably 0.2% by weight to 10% by weight, even more preferably 0.4% by weight to 8% by weight. The photopolymerization initiator includes benzoin ethers, benzophenones, acetophenones, benzyl ketals, acylphosphine oxides, etc. Specific examples of the photopolymerization initiator include 2-methyl-1-(4-methylthiophenyl)-2-morpholinopropan-1-one (IRGACURE 907), [1-[4-(phenylthio)benzoyl]heptylidene]amino-benzoate (IRGACURE OXE 01), etc. A thermal polymerization initiator includes azo compounds, peroxides, etc. Specific examples of the thermal polymerization initiator include 2,2'-azobis(4-methoxy-2,4-dimethylvaleronitrile), 2,2'-azobis(isobutyronitrile), etc. One kind of polymerization initiator may be used, or two or more kinds of polymerization initiators may be used in combination.

A stabilizer may be added to the liquid crystal composition of the present invention for improving the storage stability thereof. Usable stabilizers include, for example, hydroquinones, hydroquinone monoalkyl ethers, tert-butyl catechols, pyrogallols, thiophenols, nitro compounds, β-naphthylamines, β-naphthols, nitroso compounds, etc. In the case where a stabilizer is used, the amount thereof to be added is preferably within a range of 0.005% by mass to 1% by mass relative to the composition, more preferably 0.02% by mass to 0.8% by mass, even more preferably 0.03% by mass to 0.5% by mass. One kind of stabilizer may be used or two or more kinds of stabilizers may be used in combination. As the stabilizer, specifically, compounds represented by formulae (X-13-1) to (X-13-35) are preferred.

[Chem. 65]

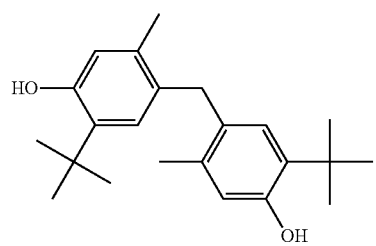

(X-13-1)

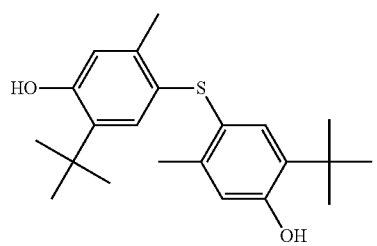

(X-13-2)

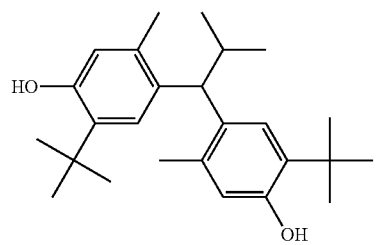

(X-13-3)

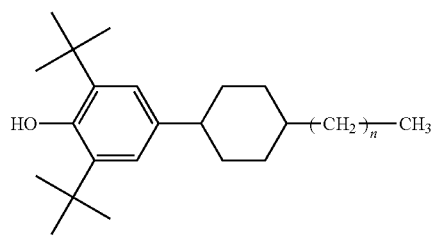

(X-13-4)

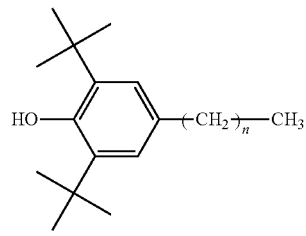

(X-13-5)

[Chem. 66]

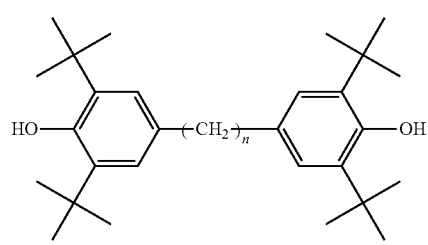

(X-13-6)

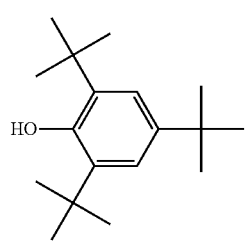

(X-13-7)

(X-13-8)
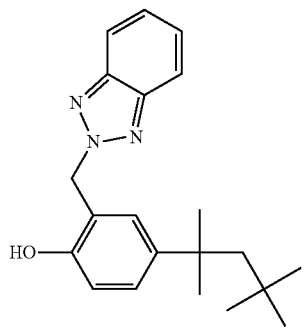
(X-13-9)
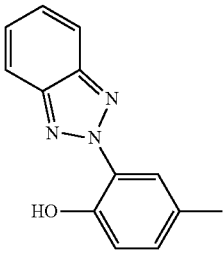
(X-13-10)
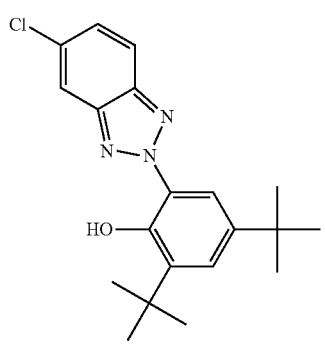
[Chem. 67]
(X-13-11)
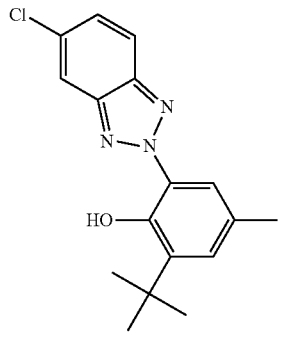
(X-13-12)
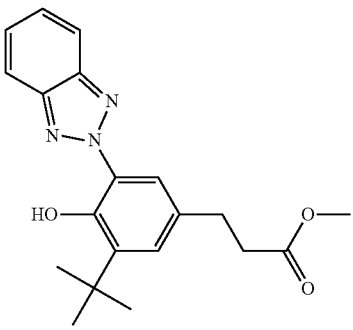
(X-13-13)
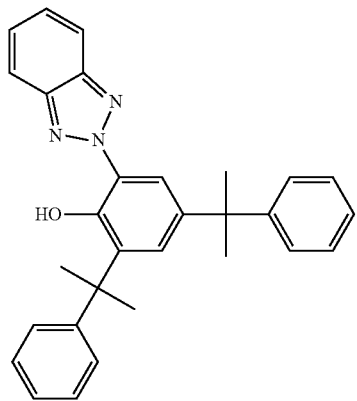
(X-13-14)
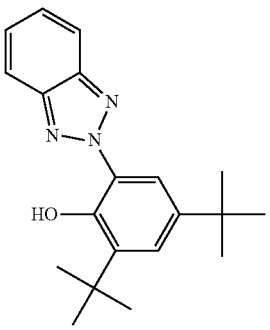

(X-13-15)
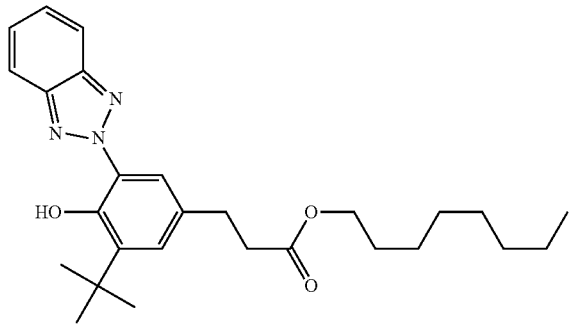
[Chem. 68]
(X-13-16)
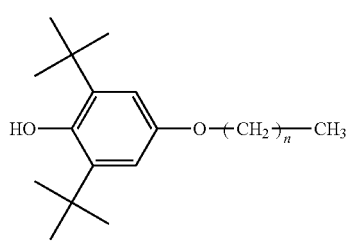
(X-13-17)
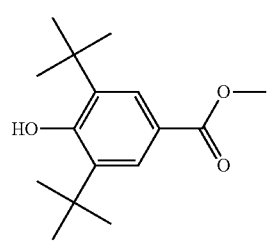
(X-13-18)
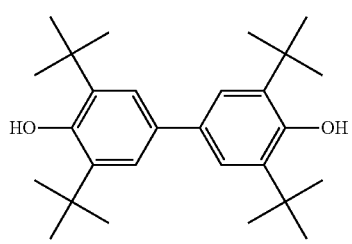
(X-13-19)
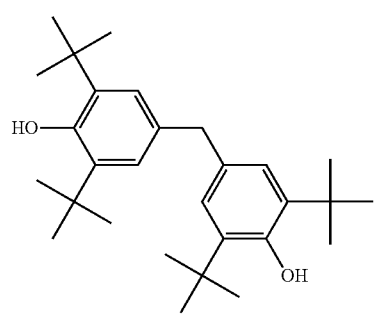
(X-13-20)
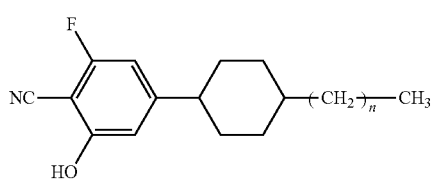
[Chem. 69]
(X-13-21)
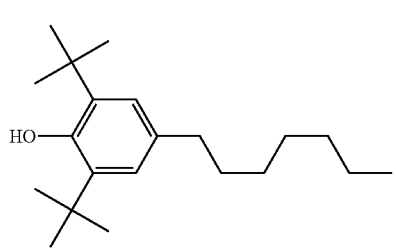
(X-13-22)
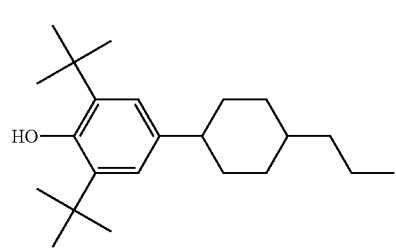
(X-13-23)
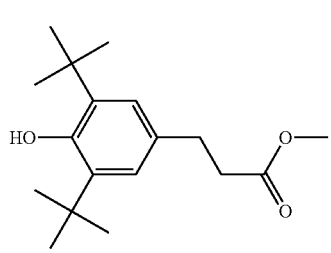
(X-13-24)
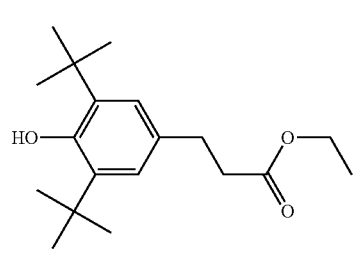

(X-13-25)
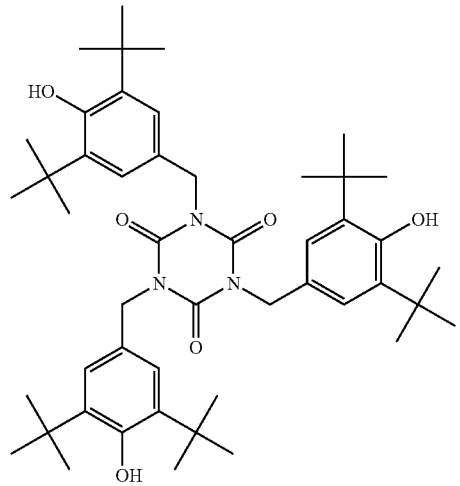
[Chem. 70]
(X-13-26)
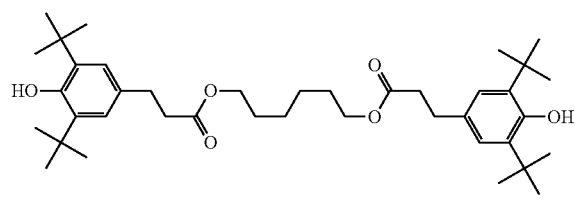
(X-13-27)
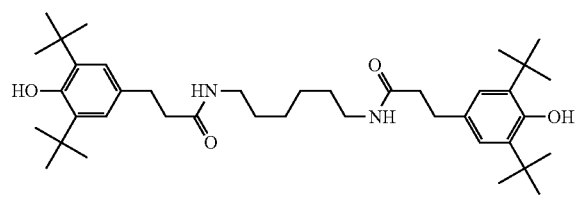
(X-13-28)
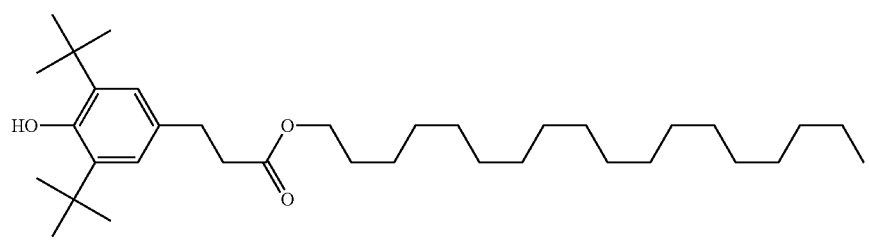
(X-13-29)
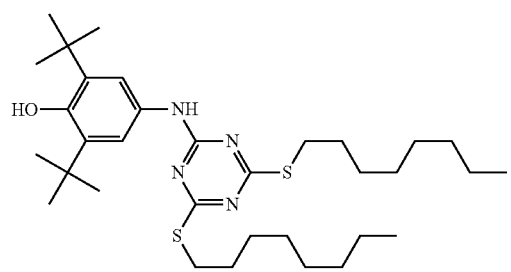
(X-13-30)
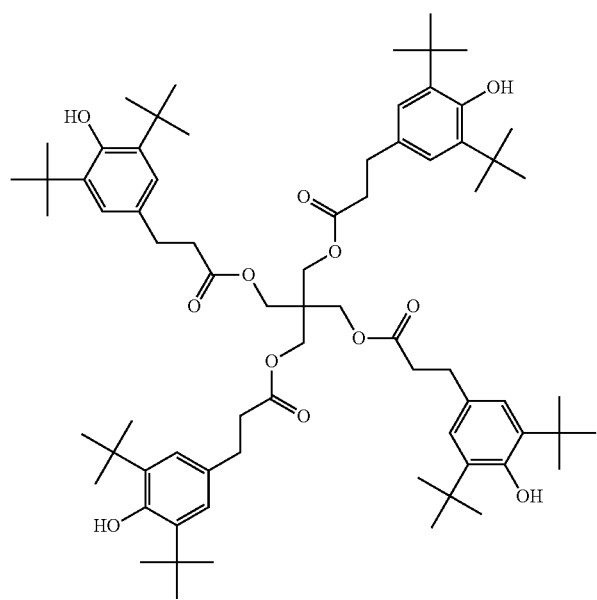

[Chem. 71]

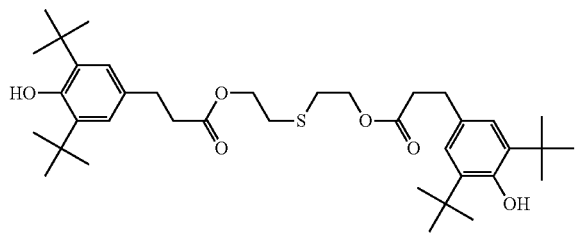
(X-13-31)

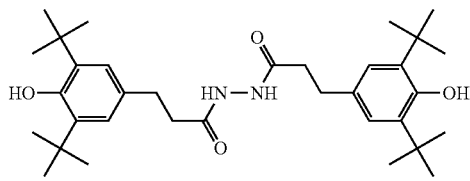
(X-13-32)

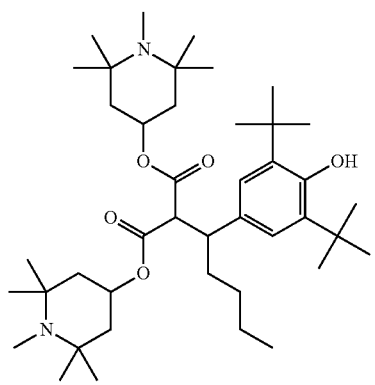
(X-13-33)

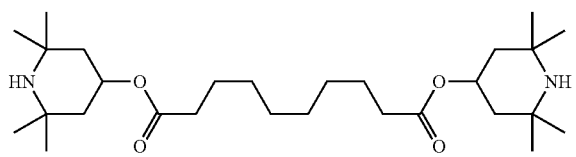
(X-13-34)

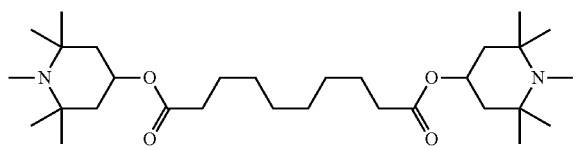
(X-13-35)

(wherein n represents an integer of 0 to 20).

In the case where the polymerizable liquid crystal composition containing the compound of the present invention is used for films, optical elements, functional pigments, medicines, cosmetics, coating agents, synthetic resins and others, a metal, a metal complex, a dye, a pigment, a colorant, a fluorescent material, a phosphorescent material, a surfactant, a leveling agent, a thixotropic agent, a gelling agent, a polysaccharide, a UV absorbent, an IR absorbent, an antioxidant, an ion-exchange resin, a metal oxide such as titanium oxide or the like may be added thereto in accordance with the intended purpose.

Polymers to be obtained through polymerization of the polymerizable liquid crystal composition containing the compound of the present invention can be used in various use applications. For example, polymers obtained through polymerization with no alignment of the polymerizable liquid crystal composition containing the compound of the present invention can be used as light scattering plates, depolarization plates, or moire fringe inhibitor plates. Polymers obtained through polymerization after alignment have optical anisotropy and are useful. Such optically anisotropic bodies can be produced, for example, by applying the polymerizable liquid crystal composition containing the compound of the present invention onto a substrate previously rubbed with cloth or the like, a substrate having an organic thin film formed thereon, or a substrate having, as obliquely deposited thereon, an $SiO_2$ alignment film to thereby make the composition supported by the substrate, or by sandwiching the composition between the substrates, and thereafter polymerizing the polymerizable liquid crystal composition.

As a method of making the polymerizable liquid crystal composition supported by a substrate, there are mentioned methods of spin coating, die coating, extrusion coating, roll coating, wire bar coating, gravure coating, spray coating, dipping, printing, etc. In coating, an organic solvent may be added to the polymerizable liquid crystal composition. The organic solvent usable here include hydrocarbon solvents, halogenohydrocarbon solvents, ether solvents, alcohol solvents, ketone solvents, ester solvents, aprotic solvents, etc. For example, hydrocarbon solvents include toluene and hexane; halogenohydrocarbon solvents include methylene chloride; ether solvents include tetrahydrofuran, acetoxy-2-ethoxyethane and propylene glycol monomethyl ether acetate; alcohol solvents include methanol, ethanol and isopropanol; ketone solvents include acetone, methyl ethyl ketone, cyclohexanone, γ-butyrolactone and N-methylpyrrolidinones; ester solvents include ethyl acetate and cellosolve; and aprotic solvents include dimethylformamide and acetonitrile. These may be used either singly or in combination. In consideration of the vapor pressure thereof and the solubility of the polymerizable liquid crystal composition therein, the solvents may be appropriately selected. As a method of volatilizing the added organic solvent, atmospheric drying, drying under heat, drying under reduced pressure, or drying under heat and reduced pressure may be employed. For further improving the coatability with the polymerizable liquid crystal material, it is also effective to provide an interlayer such as a polyimide thin film or the like on a substrate or to add a leveling agent to the polymerizable liquid crystal material. The method of providing an interlayer such as a polyimide thin film or the like on a substrate is effective for improving the adhesiveness between the polymer obtained through polymerization of the polymerizable liquid crystal material and a substrate.

As the other alignment treatment than the above, there may be mentioned utilization of flow alignment of liquid crystal material, and utilization of electric field or magnetic field. These alignment means may be used singly or may be used in combination. As an alignment treatment method substitutable for rubbing, a photo-alignment method may be employed. Regarding the shape of the substrate, the substrate may have a curved face as a constituent part in addition to a tabular plate. As the material to constitute the substrate, an organic material and an inorganic material may be employed with no limitation. The organic material to constitute the substrate includes, for example, polyethylene terephthalate, polycarbonate, polyimide, polyamide, polymethyl methacrylate, polystyrene, polyvinyl chloride, polytetrafluoroethylene, polychlorotrifluoroethylene, polyarylate, polysulfone, triacetyl cellulose, cellulose, polyether ether ketone, etc. The inorganic material includes, for example, silicon, glass, calcite, etc.

In polymerizing the polymerizable liquid crystal composition containing the compound of the present invention, it is desirable that the polymerization runs on rapidly, and therefore, a method of polymerizing the composition through irradiation with active energy rays such as UV rays, electron beams or the like is preferred. In the case of using UV rays, a polarized light source may be used, or a non-polarized light source may also be used. In the case where the liquid crystal composition is polymerized while kept sandwiched between two substrates, at least the substrate on the irradiation face side must have suitable transparency for the active energy rays. If desired, a method of polymerizing only a specific part of the composition via a mask during photoirradiation, then changing the conditions of electric field, magnetic field, temperature and the like to thereby change the alignment state of the unpolymerized part, and further polymerizing the part through irradiation with active energy rays may be employed. The temperature during irradiation is preferably within a temperature range within which the polymerizable liquid crystal composition of the present invention can maintain the liquid crystal state thereof. In particular, in the case of producing an optically anisotropic body through photopolymerization, the polymerization is carried out at a temperature as near as possible to room temperature, typically at a temperature of 25° C. for the purpose of evading induction of any unintended thermal polymerization. The intensity of the active energy rays is preferably 0.1 mW/cm$^2$ to 2 mW/cm$^2$. When the intensity is less than 0.1 mW/cm$^2$, much time is taken for completing photopolymerization to worsen productivity, and when more than 2 mW/cm$^2$, there is a risk of degradation of the polymerizable liquid crystal compound or the polymerizable liquid crystal composition.

The optically anisotropic body obtained through polymerization may be heat-treated for reducing change in characteristics in the initial stage and for attaining stable characteristics expression. The temperature for the heat treatment is preferably within a range of 50 to 250° C., and the heat-treatment time is preferably within a range of 30 seconds to 12 hours.

The optically anisotropic body thus produced according to the method may be used as a simple body after peeled from a substrate, or may be used without peeled. Alternatively, the resultant optically anisotropic body may be laminated or may be stuck to any other substrate.

EXAMPLES

Hereinunder the present invention is described further with reference to Examples, but the present invention is not limited to these Examples. "%" in the compositions of the following Examples and Comparative Examples means "% by mass". When a substance unstable to oxygen and/or water is handled in each step, preferably, the operation is carried out in an inert gas such as nitrogen gas, argon gas, etc. In addition to the operation specifically described below, as needed, other operations of quenching, liquid separation, extraction, neutralization, washing, separation, purification, drying, concentration and the like that are generally carried out by those skilled in the art may be carried out.

(Example 1) Production of Compound Represented by Formula (I-1)

[Chem. 72]

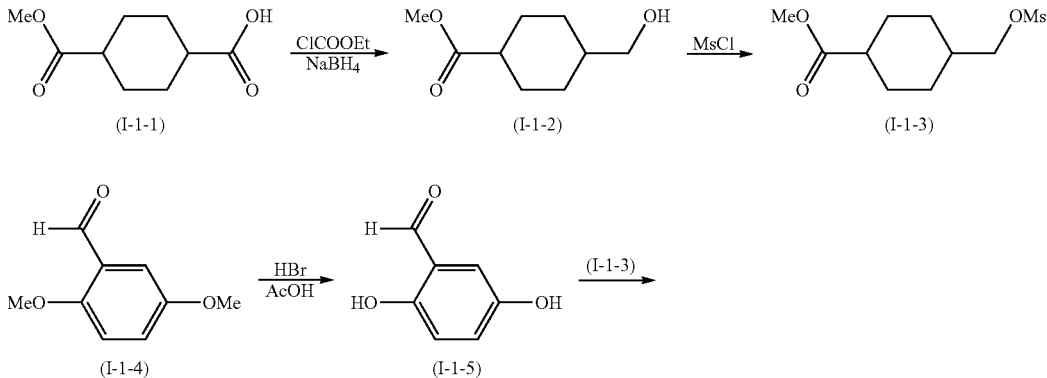

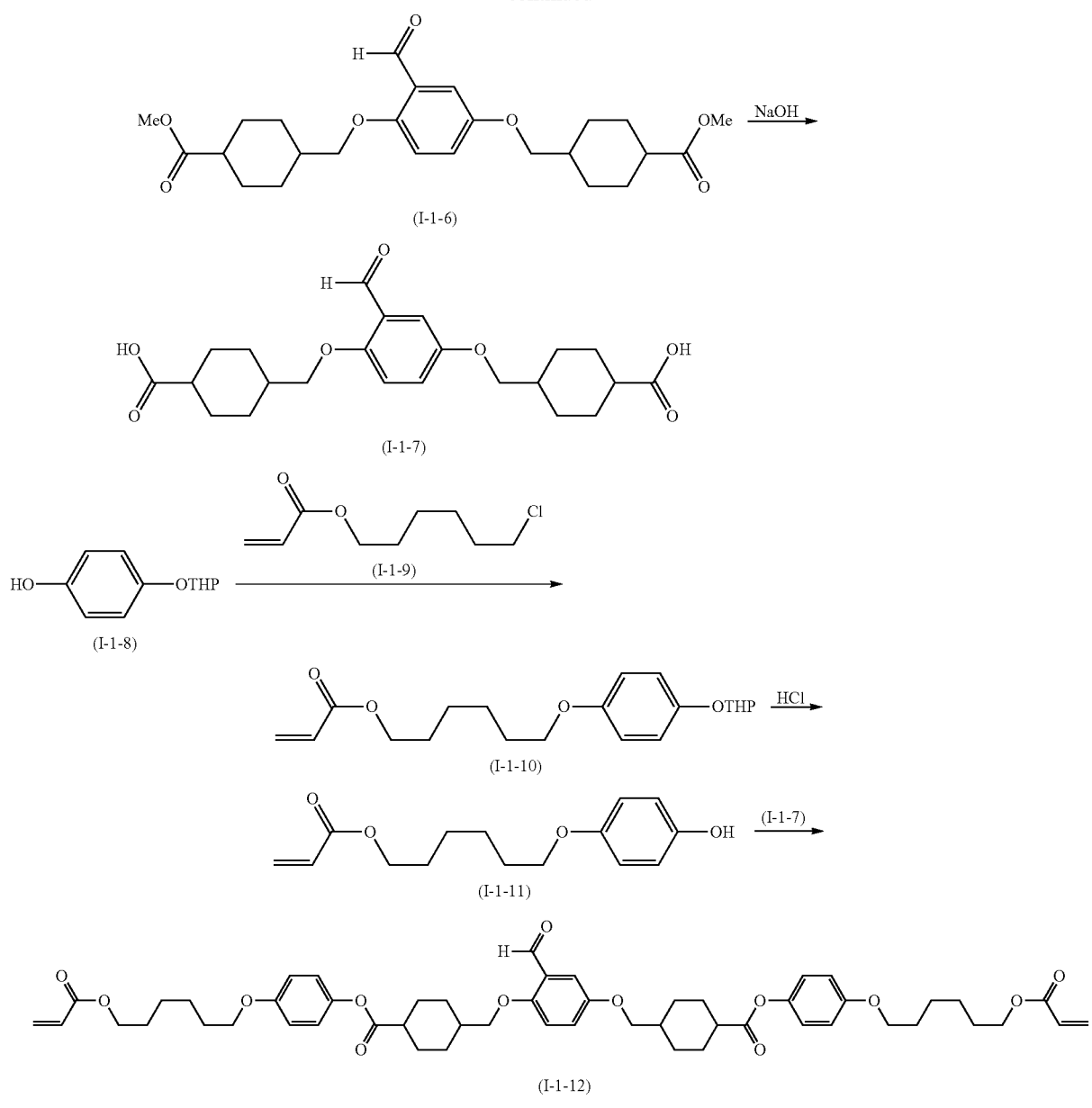
[Chem. 73]
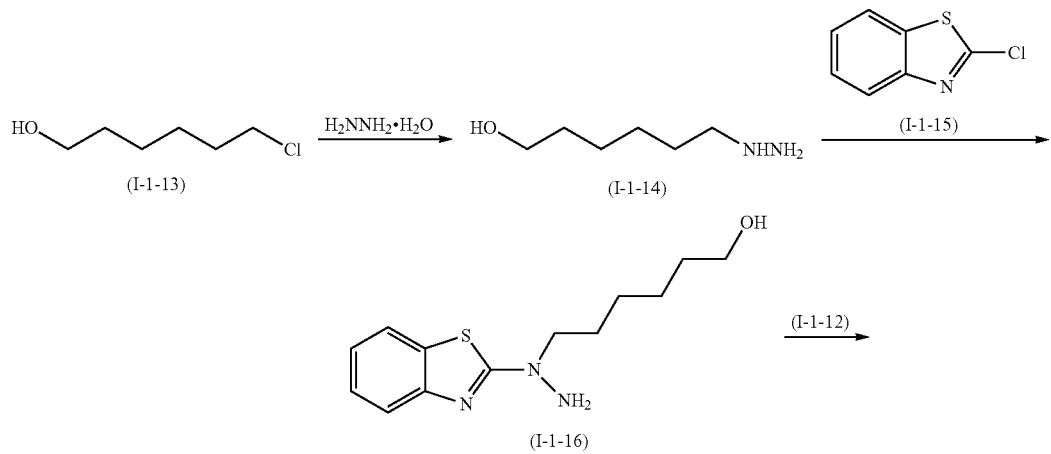

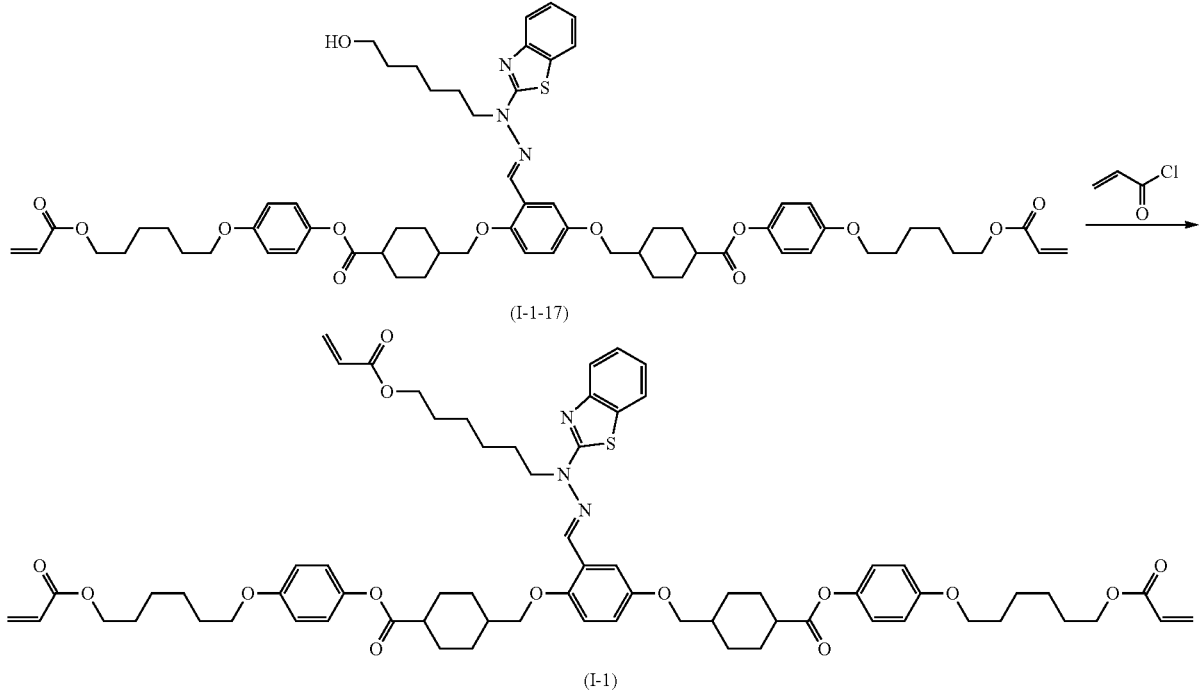

(I-1-17)

(I-1)

In a nitrogen atmosphere, 10.0 g of the compound represented by the formula (I-1-1), 6.0 g of triethylamine and 40 mL of tetrahydrofuran were put into a reactor. With cooling with ice, 6.4 g of ethyl chloroformate was dropwise added thereto and stirred at room temperature for 1 hour. The precipitate was removed through filtration. In a nitrogen atmosphere, 2.2 g of sodium borohydride, and 10 mL of tetrahydrofuran were put into another reactor. With cooling with ice, the previous filtrate was dropwise added thereto. A mixed liquid of 40 mL of methanol and 10 mL of water was dropwise added and stirred at room temperature for 3 hours. After 20 mL of 10% hydrochloric acid was added, this was extracted with ethyl acetate. Purification through column chromatography (silica gel, hexane/ethyl acetate) gave 7.4 g of the compound represented by the formula (I-1-2).

In a nitrogen atmosphere, 7.4 g of the compound represented by the formula (I-12), 4.1 g of pyridine and 35 mL of dichloromethane were put into a reactor. With cooling with ice, 5.4 g of methanesulfonyl chloride was dropwise added thereto, and stirred at room temperature for 3 hours. This was poured into water, and washed sequentially with 5% hydrochloric acid and salt water. Purification through column chromatography (silica gel, hexane/ethyl acetate) and recrystallization (acetone/hexane) gave 7.5 g of the compound represented by the formula (I-1-3).

In a nitrogen atmosphere, 25.0 g of the compound represented by the formula (I-1-4), 100 mL of acetic acid and 100 mL of 48% hydrobromic acid were put into a reactor, and heated under reflux for 12 hours. After cooled, this was poured into 1 L of water. This was extracted with ethyl acetate and washed with salt water. The solvent was distilled away, and the remaining acetic acid was removed through azeotropic removal with toluene. Purification through column chromatography (alumina, ethyl acetate) gave 12.0 g of the compound represented by the formula (I-1-5).

In a nitrogen atmosphere, 2.1 g of the compound represented by the formula (I-1-5), 7.5 g of the compound represented by the formula (I-1-3), 6.2 g of potassium carbonate and 70 mL of N,N-dimethylformamide were put into a reactor and heated with stirring at 90° C. for 3 days. This was poured into water, extracted with toluene and washed with salt water. Purification through column chromatography (silica gel, toluene) and recrystallization (toluene/hexane) gave 4.8 g of the compound represented by the formula (I-1-6).

In a nitrogen atmosphere, 4.8 g of the compound represented by the formula (I-1-6), 20 mL of tetrahydrofuran, 20 mL of methanol and 10 mL of 25% sodium hydroxide were put into a reactor, and heated with stirring at 60° C. for 2 hours. The solvent was distilled away, and the residue was re-dissolved in a mixed solvent of tetrahydrofuran and water. The pH of the solution was made to be 2 by 10% hydrochloric acid added thereto. The solvent was distilled away, water was added and the precipitated solid was filtered out. The resultant solid was washed with water and dried to give 4.0 g of the compound represented by the formula (I-1-7).

15.0 g of the compound represented by the formula (I-1-8), 17.7 g of the compound represented by the formula (I-1-9), 16.0 g of potassium carbonate, and 100 mL of N,N-dimethylformamide were put into a reactor, and heated with stirring at 80° C. for 12 hours. After cooled, this was diluted with dichloromethane, and washed sequentially with water and salt water. Purification through column chromatography (alumina, dichloromethane) gave 24.2 g of the compound represented by the formula (I-1-10).

24.2 g of the compound represented by the formula (I-1-10), 60 mL of tetrahydrofuran, 60 mL of methanol and 1 mL of concentrated hydrochloric acid were put into a reactor, and stirred at room temperature for 8 hours. The solvent was distilled away, then the residue was diluted with ethyl acetate and washed sequentially with water and salt water. Purification through column chromatography (alumina, ethyl acetate) and recrystallization (ethyl acetate/hexane) gave 16.5 g of the compound represented by the formula (I-1-11).

In a nitrogen atmosphere, 3.8 g of the compound represented by the formula (I-1-11), 3.0 g of the compound represented by the formula (I-1-7), 0.9 g of N,N-dimethylaminopyridine and 200 mL of dichloromethane were put into a reactor. With cooling with ice, 2.3 g of diisopropylcarbodiimide was dropwise added thereto and stirred at room temperature for 10 hours. The precipitate was removed through filtration, and the filtrate was sequentially washed with 1% hydrochloric acid, water and salt water. Purification through recrystallization (dichloromethane/methanol) followed by column chromatography (silica gel, dichloromethane) and by recrystallization (dichloromethane/methanol) gave 4.6 g of the compound represented by the formula (I-1-12).

In a nitrogen atmosphere, 100 mL of hydrazinemonohydrate and 100 mL of ethanol were put into a reactor. With heating at 50° C., 10.0 g of the compound represented by the formula (I-1-13) was dropwise added thereto and kept heated with stirring for 3 hours. This was diluted with dichloromethane and washed with salt water. Drying over sodium sulfate followed by removal of solvent through distillation gave 7.7 g of the compound represented by the formula (I-1-14).

In a nitrogen atmosphere, 4.9 g of the compound represented by the formula (I-1-15), 30 mL of 1,2-dimethoxyethane and 3.2 g of triethylamine were put into a reactor. With heating at 60° C., 7.7 g of the compound represented by the formula (I-1-14) was dropwise added thereto, and kept heated with stirring for 2 hours. The reaction liquid was poured into water, and the precipitated solid was filtered out. The solid was washed sequentially with water and hexane, and then dried to give 4.6 g of the compound represented by the formula (I-1-16).

1.5 g of the compound represented by the formula (I-1-16), 5.1 g of the compound represented by the formula (I-1-12), 0.6 g of (±)-10-camphorsulfonic acid, 20 mL of tetrahydrofuran and 20 mL of ethanol were put into a reactor, and heated with stirring at 50° C. for 10 hours. The solvent was distilled away, and the residue was purified through column chromatography (silica gel, dichloromethane) and recrystallization (dichloromethane/methanol) to give 4.6 g of the compound represented by the formula (I-1-17).

In a nitrogen atmosphere, 4.6 g of the compound represented by the formula (I-1-17), 0.6 g of diisopropylethylamine and 50 mL of dichloromethane were put into a reactor. With cooling with ice, 0.4 g of acryloyl chloride was dropwise added thereto and stirred at room temperature for 8 hours. This was washed sequentially with 1% hydrochloric acid and salt water, then recrystallized (methanol), and purified through column chromatography (silica gel, dichloromethane) and recrystallization (dichloromethane/methanol) to give 3.8 g of the compound represented by the formula (I-1).

$^1$H NMR (CDCl$_3$) δ 1.24 (m, 4H), 1.48-1.93 (m, 30H), 2.08 (t, 4H), 2.23 (m, 4H), 2.54 (m, 2H), 3.86 (dd, 4H), 3.94 (t, 4H), 4.17 (t, 4H), 4.53 (t, 2H), 4.65 (t, 2H), 5.82 (dd, 3H), 6.12 (dd, 3H), 6.40 (dd, 3H), 6.88 (m, 6H), 6.97 (dd, 4H), 7.16 (t, 1H), 7.34 (t, 1H), 7.54 (d, 1H), 7.66 (d, 1H), 7.70 (d, 1H), 8.36 (s, 1H) ppm. LCMS: 1212 [M+1]

(Example 2) Production of Compound Represented by Formula (I-2)

[Chem. 74]

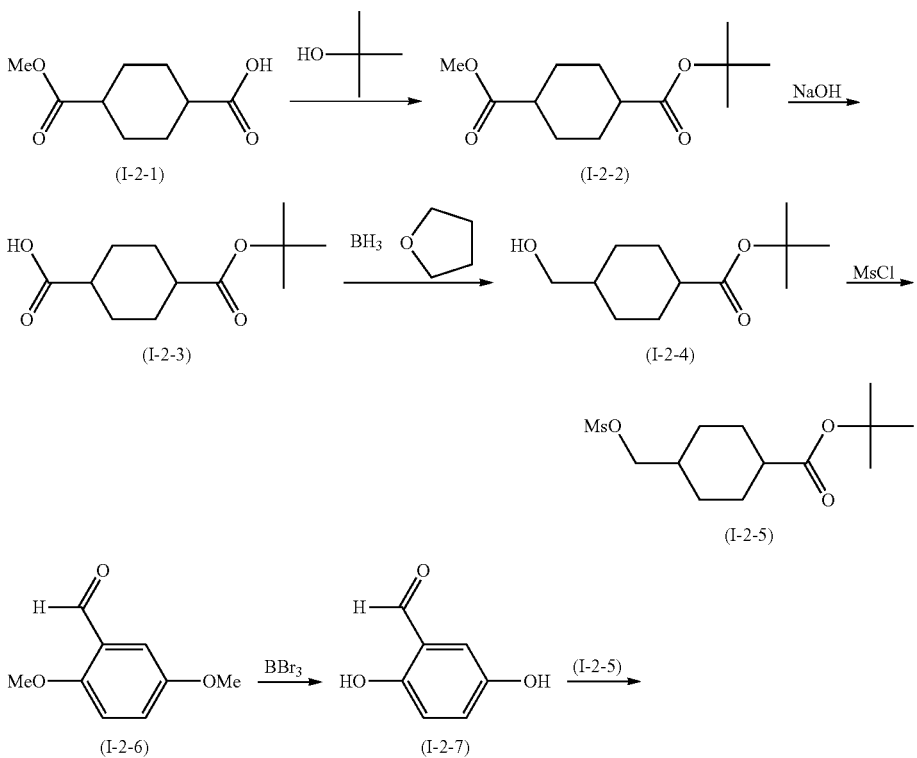

-continued
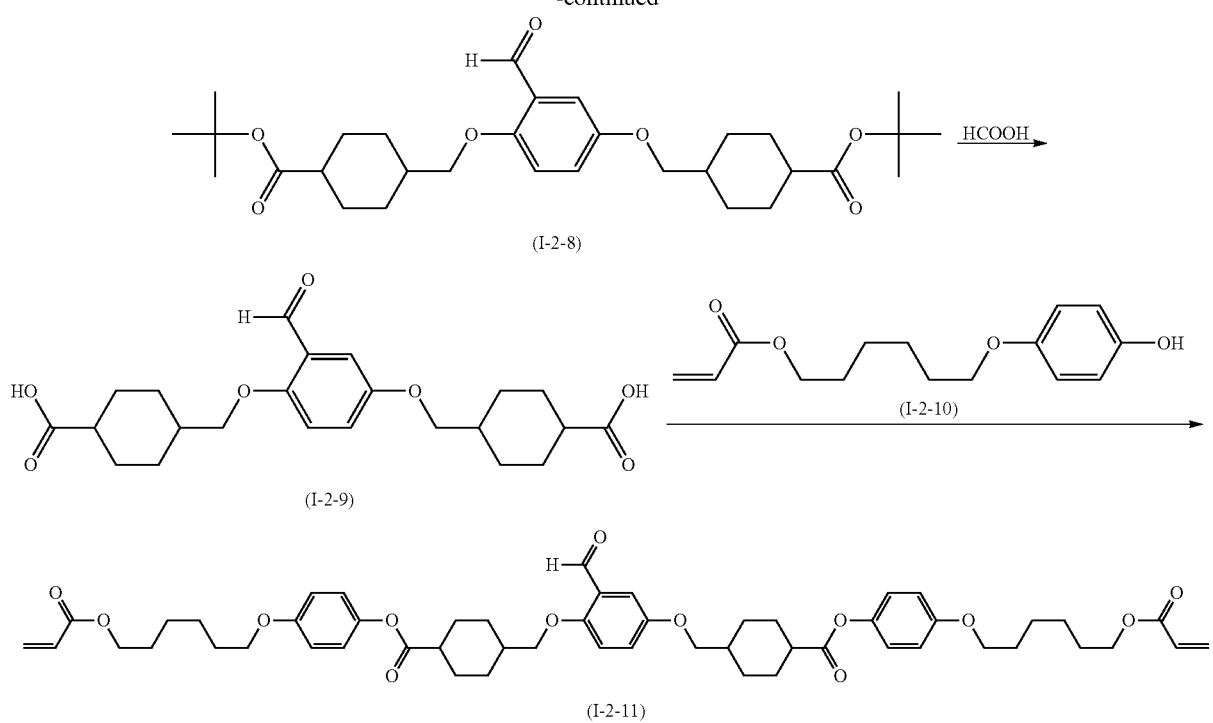
[Chem. 75]
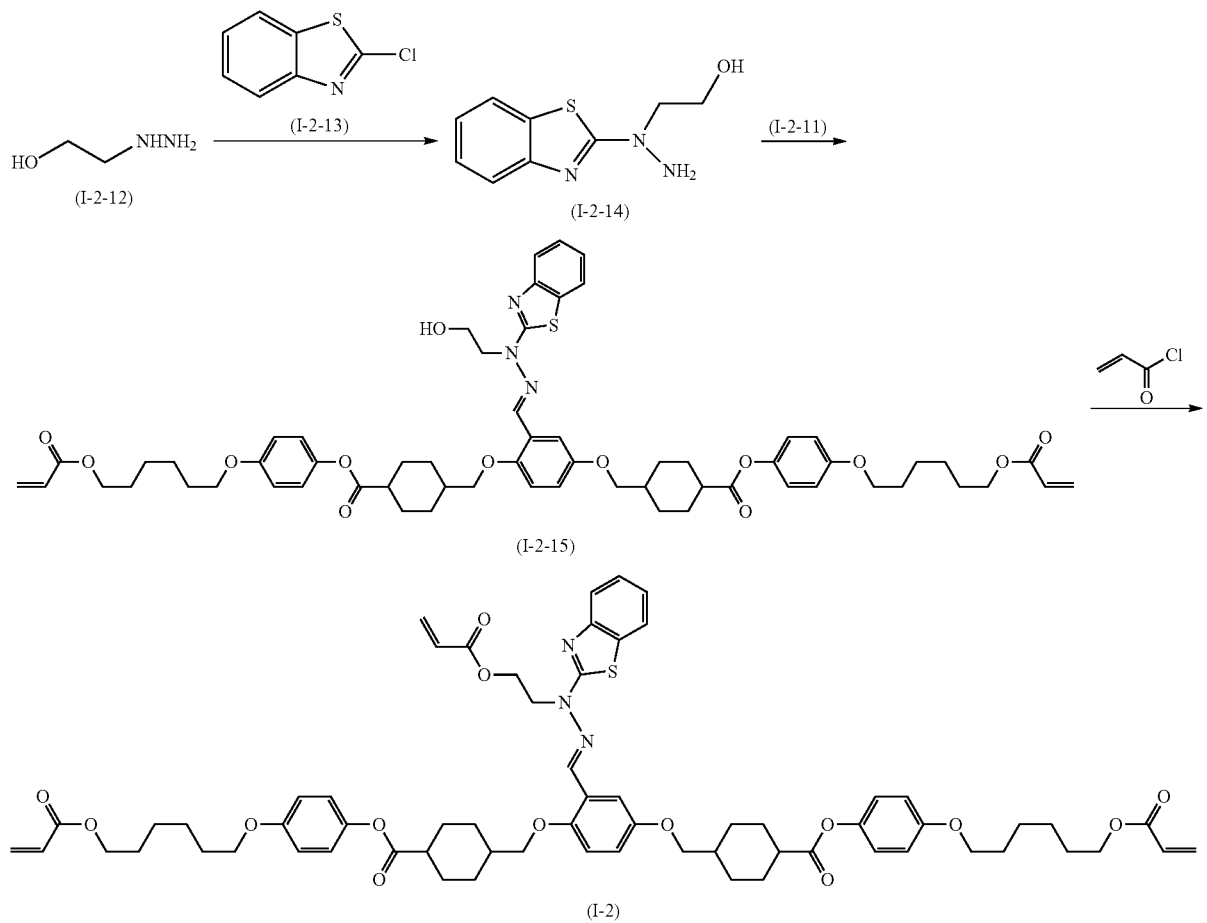

In a nitrogen atmosphere, 20.0 g of the compound represented by the formula (I-2-1), 8.8 g of tert-butyl alcohol, 1.3 g of N,N-dimethylaminopyridine and 100 mL of dichloromethane were put into a reactor. With cooling with ice, 16.3 g of diisopropylcarbodiimide was dropwise added thereto and stirred at room temperature for 8 hours. The precipitate was removed through filtration, and the filtrate was washed sequentially with 5% hydrochloric acid and salt water. Purification through column chromatography (silica gel, dichloromethane) gave 20.8 g of the compound represented by the formula (I-2-2).

20.8 g of the compound represented by the formula (I-2-2), 200 mL of methanol and 30 mL of an aqueous solution of 25% sodium hydroxide were put into a reactor and heated with stirring at 60° C. After this was cooled, chloroform was added thereto. 10% hydrochloric acid was added to make the aqueous layer have a pH of 4 to 5, and treated for liquid separation. The organic layer was washed with salt water, and dried over sodium sulfate. The insolubles were removed by filtration through Celite, then the solvent was distilled away, and the residue was dried to give 17.7 g of the compound represented by the formula (I-2-3).

In a nitrogen atmosphere, 17.7 g of the compound represented by the formula (I-2-3) and 100 mL of tetrahydrofuran were put into a reactor. With cooling with ice, 103 mL of 0.9 mol/L borane-tetrahydrofuran complex was dropwise added thereto and stirred for 1 hour. After 5% hydrochloric acid was dropwise added, this was extracted with ethyl acetate, and washed with salt water. This was dried over sodium sulfate and the solvent was distilled away to give 14.9 g of the compound represented by the formula (I-2-4).

In a nitrogen atmosphere, 14.9 g of the compound represented by the formula (I-2-4), 7.2 g of pyridine and 150 mL of dichloromethane were put into a reactor. With cooling with ice, 8.8 g of methanesulfonyl chloride was dropwise added, and stirred at room temperature for 3 hours. This was poured into water, and washed sequentially with 5% hydrochloric acid and salt water. Purification through column chromatography (silica gel, hexane/ethyl acetate) and recrystallization (acetone/hexane) gave 16.3 g of the compound represented by the formula (I-2-5).

In a nitrogen atmosphere, 25.0 g of the compound represented by the formula (I-2-6), and 200 mL of dichloromethane were put into a reactor. With cooling with ice, 113.1 g of boron tribromide was dropwise added and stirred for 2 hours. This was poured into water with ice, then extracted with ethyl acetate, and washed sequentially with water and salt water. Purification through column chromatography (alumina, ethyl acetate) gave 18.7 g of the compound represented by the formula (I-2-7).

In a nitrogen atmosphere, 2.5 g of the compound represented by the formula (I-2-7), 10.6 g of the compound represented by the formula (I-2-5), 7.5 g of potassium carbonate and 70 mL of N,N-dimethylformamide were put into a reactor, and heated with stirring at 90° C. for 3 days. This was poured into water, extracted with toluene and washed with salt water. Purification through column chromatography (silica gel, toluene) and recrystallization (acetone/methanol) gave 7.7 g of the compound represented by the formula (I-2-8).

7.7 g of the compound represented by the formula (I-2-8), 150 mL of dichloromethane and 100 mL of formic acid were put into a reactor, and heated under reflux for 8 hours. The solvent was distilled away, and the resultant solid was washed with water and dried to give 5.5 g of the compound represented by the formula (I-2-9).

In a nitrogen atmosphere, 5.5 g of the compound represented by the formula (I-2-9), 6.9 g of the compound represented by the formula (I-2-10), 0.8 g of N,N-dimethylaminopyridine and 200 mL of dichloromethane were put into a reactor. With cooling with ice, 4.1 g of diisopropylcarbodiimide was dropwise added and stirred at room temperature for 10 hours. The precipitate was removed through filtration, and then the filtrate was washed sequentially with 1% hydrochloric acid, water and salt water. Purification through recrystallization (dichloromethane/methanol) followed by column chromatography (silica gel, dichloromethane) and further by recrystallization (dichloromethane/methanol) gave 8.4 g of the compound represented by the formula (I-2-11).

In a nitrogen atmosphere, 7.0 g of the compound represented by the formula (I-2-13), 70 mL of 1,2-dimethoxymethane and 5.0 g of triethylamine were put into a reactor. With heating at 60° C., 3.5 g of the compound represented by the formula (I-2-12) was dropwise added and kept heated with stirring for 2 hours. The reaction liquid was poured into water, and the precipitated solid was filtered out. The solid was washed sequentially with water and hexane, and then dried to give 6.0 g of the compound represented by the formula (I-2-14).

1.1 g of the compound represented by the formula (I-2-14), 5.0 g of the compound represented by the formula (I-2-11), 0.6 g of (±)-10-camphorsulfonic acid, 20 mL of tetrahydrofuran and 20 mL of ethanol were put into a reactor, and heated with stirring at 50° C. for 10 hours. The solvent was distilled away, and the residue was purified through column chromatography (silica gel, dichloromethane) followed by recrystallization (dichloromethane/methanol) to give 4.2 g of the compound represented by the formula (I-2-15).

In a nitrogen atmosphere, 4.2 g of the compound represented by the formula (I-2-15), 0.6 g of diisopropylethylamine and 50 mL of dichloromethane were put into a reactor. With cooling with ice, 0.4 g of acryloyl chloride was dropwise added and stirred at room temperature for 8 hours. This was washed sequentially with 1% hydrochloric acid and salt water, and re-precipitated (methanol). Purification through column chromatography (silica gel, dichloromethane) and recrystallization (dichloromethane/methanol) gave 3.5 g of the compound represented by the formula (I-2).

Transition temperature (heating speed 5° C./min) C, 122 N, 142 I 1H NMR (CDCl$_3$) δ 1.24 (m, 4H), 1.48 (m, 8H), 1.60-1.83 (m, 12H), 1.93 (m, 2H), 2.08 (t, 4H), 2.23 (m, 4H), 2.54 (m, 2H), 3.86 (dd, 4H), 3.94 (t, 4H), 4.17 (t, 4H), 4.53 (t, 2H), 4.65 (t, 2H), 5.78 (dd, 1H), 5.82 (dd, 2H), 6.08 (dd, 1H), 6.12 (dd, 2H), 6.39 (dd, 1H), 6.40 (dd, 2H), 6.88 (m, 6H), 6.97 (dd, 4H), 7.16 (t, 1H), 7.34 (t, 1H), 7.54 (d, 1H), 7.66 (d, 1H), 7.70 (d, 1H), 8.36 (s, 1H) ppm.

LCMS: 1156 [M+1]

(Example 3) Production of Compound Represented by Formula (I-3)

[Chem. 76]

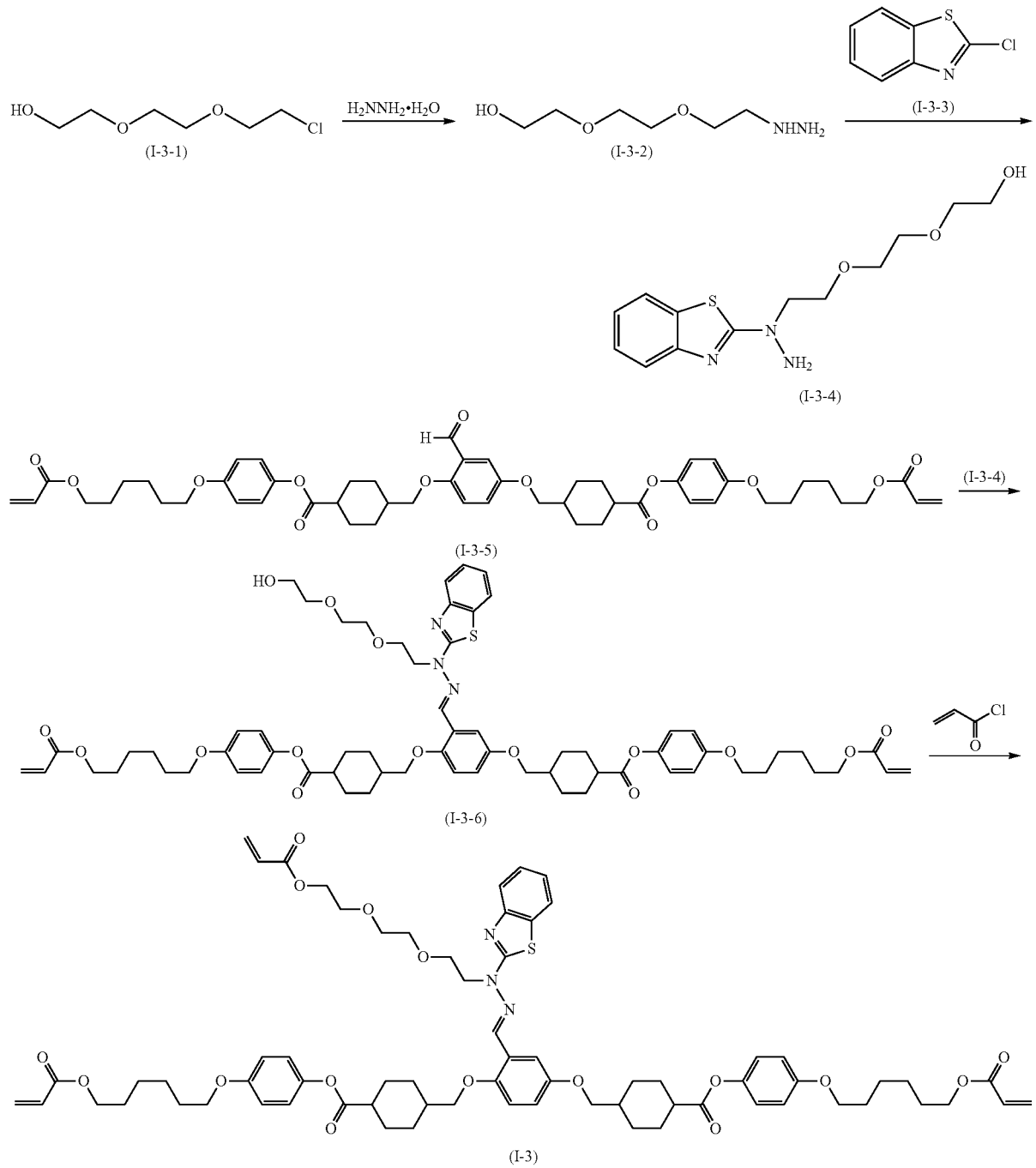

In a nitrogen atmosphere, 100 mL of hydrazine monohydrate, and 100 mL of ethanol were put into a reactor. With heating at 50° C., 10.0 g of the compound represented by the formula (I-3-1) was dropwise added and kept heated with stirring for 3 hours. The solvent was distilled away to give a mixture containing the compound represented by the formula (I-3-2).

In a nitrogen atmosphere, 5.0 g of the compound represented by the formula (I-3-3), 30 mL of 1,2-dimethoxyethane, and 3.6 g of triethylamine were put into a reactor. With heating at 60° C., the mixture containing the compound represented by the formula (I-3-2) was added and kept heated with stirring for 2 hours. The reaction liquid was diluted with dichloromethane, and then washed sequentially with water and salt water. This was dried over sodium sulfate, and the solvent was distilled away to give 7.0 g of the compound represented by the formula (I-3-4).

5.0 g of the compound represented by the formula (I-3-5), 1.6 g of the compound represented by the formula (I-3-4), 0.6 g of (±)-10-camphorsulfonic acid, 20 mL of tetrahydrofuran and 20 mL of ethanol were put into a reactor and heated with stirring at 50° C. for 10 hours. The solvent was distilled away, and the residue was purified through column chromatography (silica gel, dichloromethane) and recrystallization (dichloromethane/methanol) to give 3.9 g of the compound represented by the formula (I-3-6).

In a nitrogen atmosphere, 3.9 g of the compound represented by the formula (I-3-6), 0.6 g of diisopropylethylamine and 80 mL of dichloromethane were put into a reactor. With cooling with ice, 0.4 g of acryloyl chloride was dropwise added and stirred at room temperature for 8 hours. This was washed sequentially with 1% hydrochloric acid and salt water and re-precipitated (methanol). Purification through column chromatography (silica gel, dichloromethane) and recrystallization (dichloromethane/methanol) gave 2.5 g of the compound represented by the formula (I-3).

Transition temperature (heating speed 5° C./min) C, 71 N, 115 I $^1$H NMR (CDCl$_3$) δ 1.19-1.29 (m, 4H), 1.41-1.82 (m, 22H), 1.91 (m, 2H), 2.08 (m, 4H), 2.24 (m, 4H), 2.53 (m, 2H), 3.62 (m, 3H), 3.67 (m, 2H), 3.84-3.90 (m, 5H), 3.94 (t, 4H), 4.15-4.19 (m, 6H), 4.53 (t, 2H), 5.76 (dd, 1H), 5.82 (dd, 2H), 6.08 (dd, 1H), 6.12 (dd, 2H), 6.37 (dd, 1H), 6.40 (dd, 2H), 6.84-6.90 (m, 6H), 6.95-6.98 (m, 4H), 7.14 (t, 1H), 7.32 (t, 1H), 7.53 (d, 1H), 7.65 (d, 1H), 7.69 (d, 1H), 8.34 (s, 1H) ppm.

LCMS: 1244 [M+1]

(Example 4) Production of Compound Represented by Formula (I-4)

[Chem. 77]

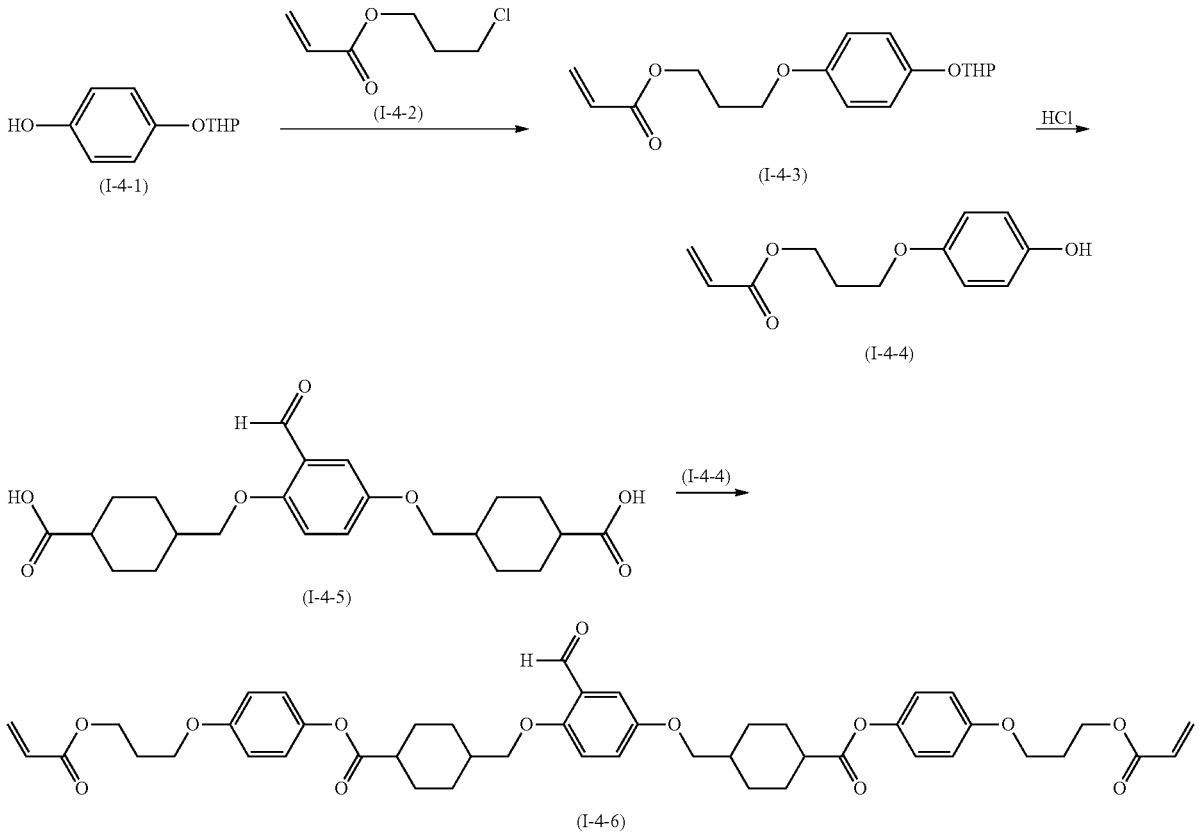

[Chem. 78]

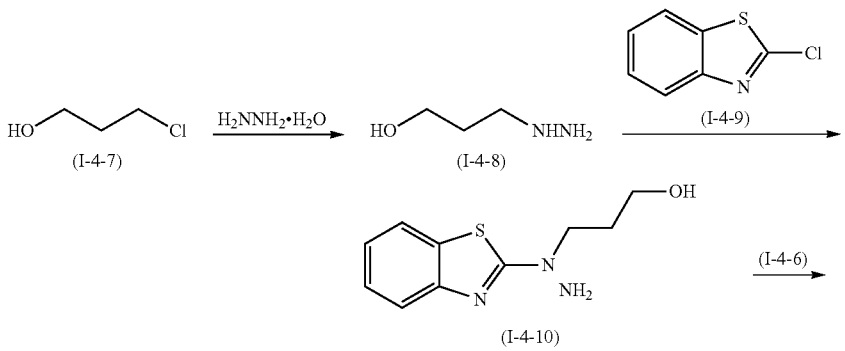

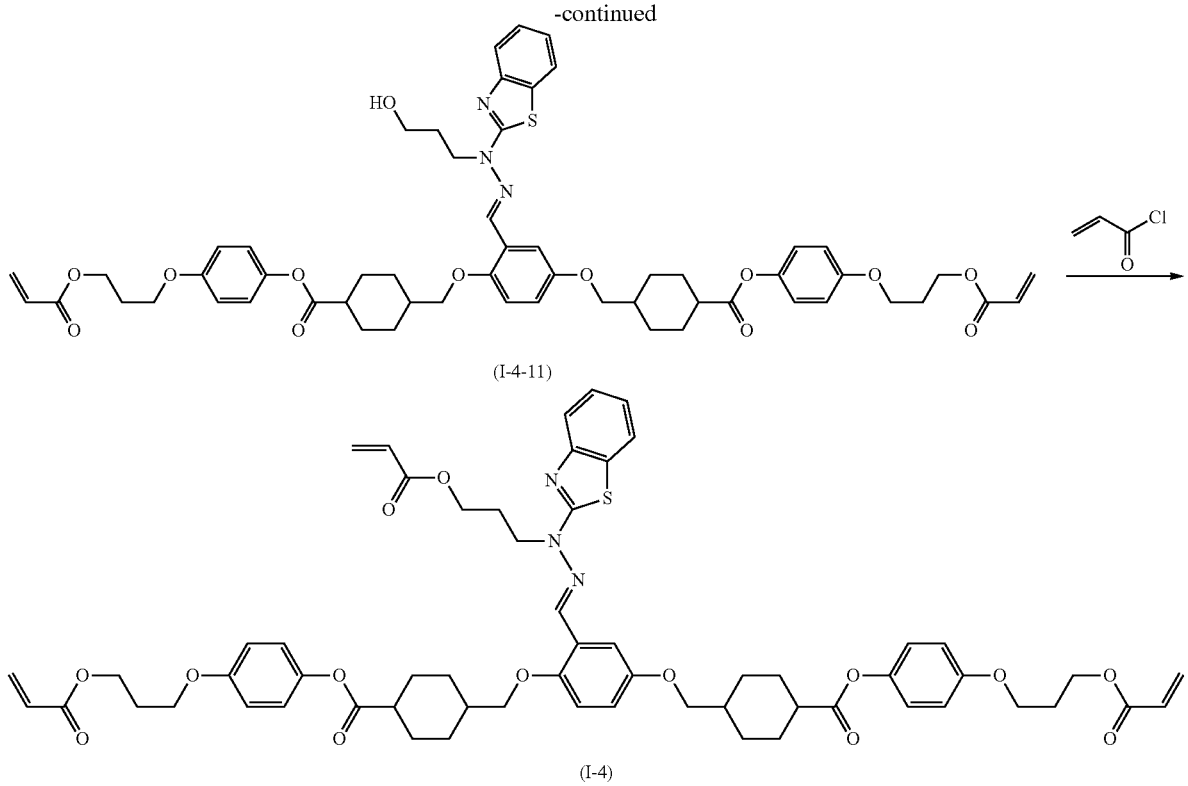

15.0 g of the compound represented by the formula (I-4-1), 13.8 g of the compound represented by the formula (I-4-2), 37.7 g of cesium carbonate and 100 mL of dimethyl sulfoxide were put into a reactor, and heated with stirring at 70° C. for 8 hours. After cooled, this was diluted with dichloromethane, and then washed sequentially with water and salt water. Purification through column chromatography (alumina, dichloromethane) gave 18.9 g of the compound represented by the formula (I-4-3).

18.9 g of the compound represented by the formula (I-4-3), 80 mL of tetrahydrofuran, 80 mL of methanol and 1 mL of concentrated hydrochloric acid were put into a reactor, and stirred at room temperature for 8 hours. The solvent was distilled away, and the residue was diluted with ethyl acetate, and washed sequentially with water and salt water. Purification through column chromatography (alumina, ethyl acetate) gave 11.0 g of the compound represented by the formula (I-4-4).

In a nitrogen atmosphere, 5.0 g of the compound represented by the formula (I-4-5), 5.3 g of the compound represented by the formula (I-4-4), 0.7 g of N,N-dimethylaminopyridine and 200 mL of dichloromethane were put into a reactor. With cooling with ice, 3.8 g of diisopropylcarbodiimide was dropwise added, and stirred at room temperature for 10 hours. The precipitate was removed through filtration, and the filtrate was washed sequentially with 1% hydrochloric acid, water and salt water. After recrystallization (dichloromethane/methanol), purification through column chromatography (silica gel, dichloromethane) and recrystallization (dichloromethane/methanol) gave 6.9 g of the compound represented by the formula (I-4-6).

In a nitrogen atmosphere, 100 mL of hydrazinemonohydrate and 100 mL of ethanol were put into a reactor. With heating at 50° C., 10.0 g of the compound represented by the formula (I-4-7) was dropwise added and kept heated with stirring for 3 hours. This was diluted with dichloromethane and washed with salt water. This was dried over sodium sulfate and the solvent was distilled away to give 8.6 g of the compound represented by the formula (I-4-8).

In a nitrogen atmosphere, 10.8 g of the compound represented by the formula (I-4-9), 100 mL of 1,2-dimethoxyethane and 7.7 g of triethylamine were put into a reactor. With heating at 60° C., 8.6 g of the compound represented by the formula (I-4-8) was dropwise added and kept heated with stirring for 2 hours. Water was poured into the reaction liquid, and the precipitated solid was filtered out. The solid was washed sequentially with water and hexane and then dried to give 8.5 g of the compound represented by the formula (I-4-10).

1.4 g of the compound represented by the formula (I-4-10), 5.0 g of the compound represented by the formula (I-4-6), 0.6 g of (±)-10-camphorsulfonic acid, 20 mL of tetrahydrofuran and 20 mL of ethanol were put into a reactor, and heated with stirring at 50° C. for 8 hours. The solvent was distilled away, and purification through column chromatography (silica gel, dichloromethane) and recrystallization (dichloromethane/methanol) gave 5.0 g of the compound represented by the formula (I-4-11).

In a nitrogen atmosphere, 5.0 g of the compound represented by the formula (I-4-11), 0.8 g of diisopropylethylamine and 80 mL of dichloromethane were put into a reactor. With cooling with ice, 0.5 g of acryloyl chloride was dropwise added and stirred at room temperature for 12 hours. This was washed sequentially with 1% hydrochloric acid and salt water and re-precipitated (methanol). Purification through column chromatography (silica gel, dichloromethane) and recrystallization (dichloromethane/methanol) gave 3.2 g of the compound represented by the formula (I-4).

LCMS: 1086 [M+1]

(Example 5) Production of Compound Represented by Formula (I-5)
[Chem. 79]
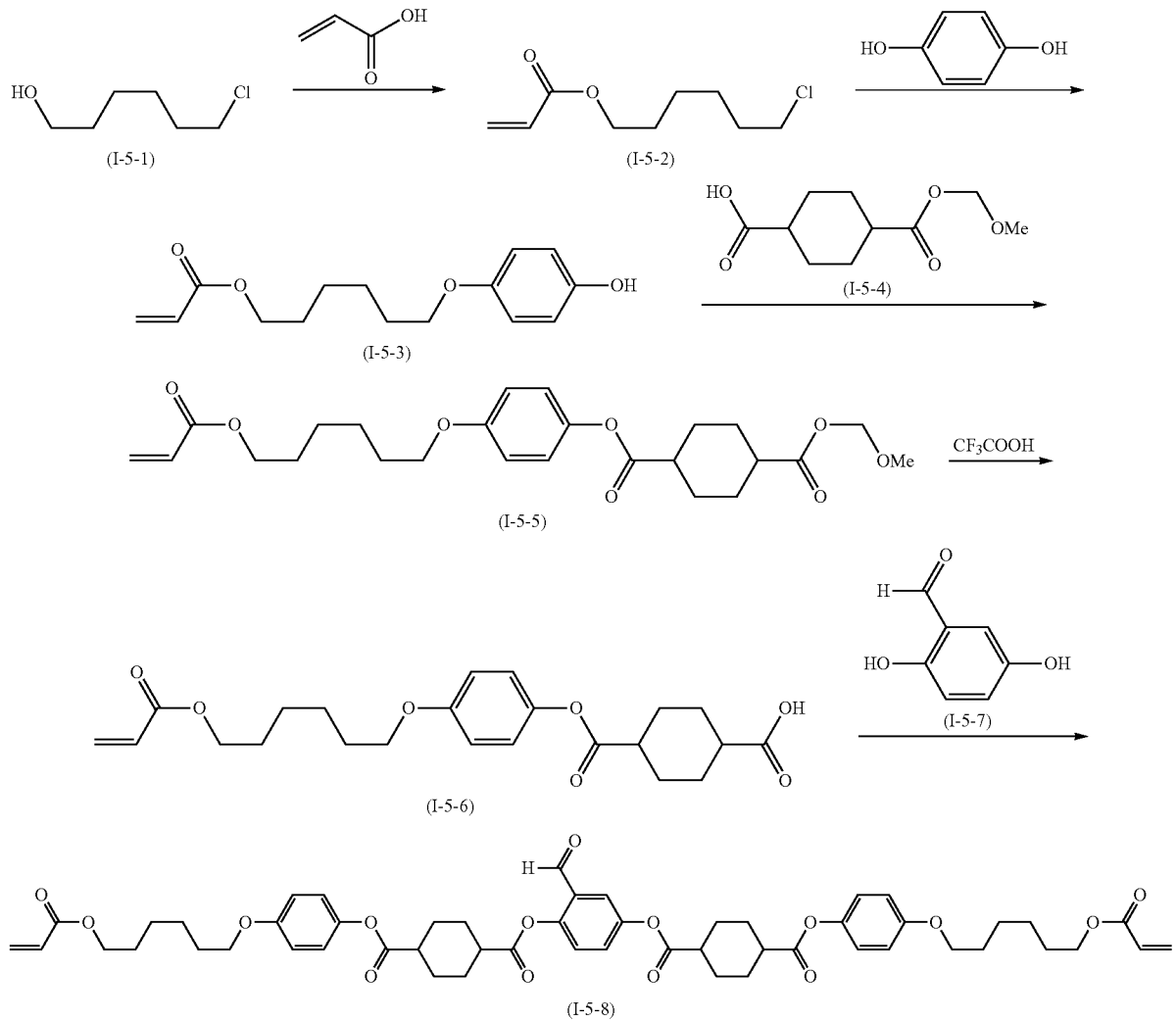
[Chem. 80]
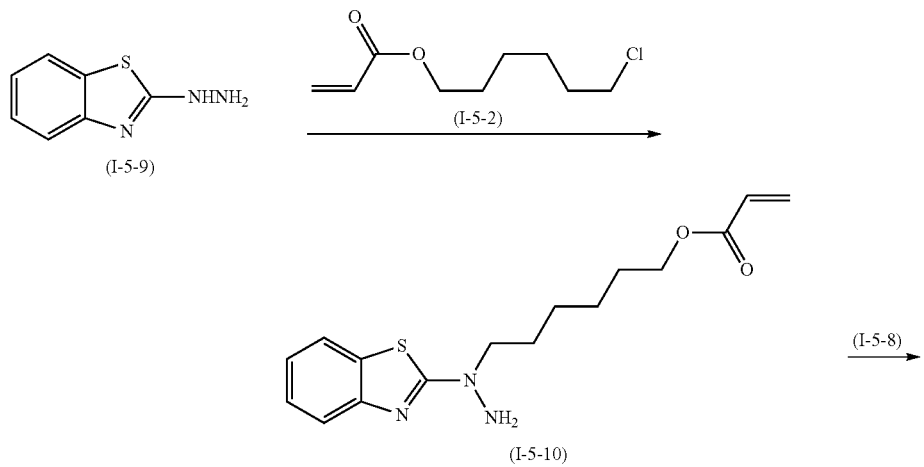

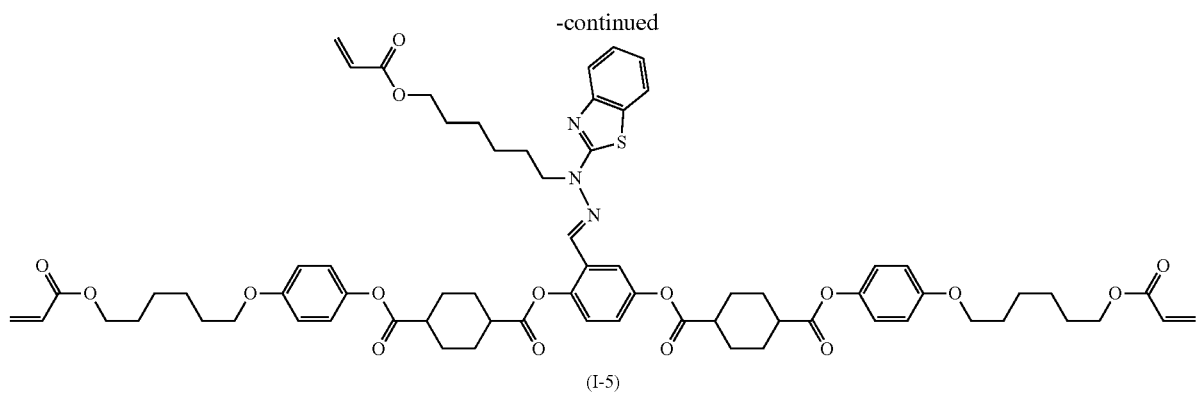

(I-5)

30.0 g of the compound represented by the formula (I-5-1), 19.0 g of acrylic acid 2.1 g of p-toluenesulfonic acid monohydrate, 300 mL of cyclohexane and 150 mL of diisopropyl ether were put into a reactor equipped with a Dean-Stark apparatus. While removing water, this was heated under reflux for 12 hours. After diluted with dichloromethane, this was washed sequentially with an aqueous solution of 5% sodium hydrogencarbonate and salt water. Purification through column chromatography (silica gel, dichloromethane) gave 33.5 g of the compound represented by the formula (I-5-2).

10.0 g of the compound represented by the formula (I-5-2), 28.9 g of hydroquinone, 21.7 g of potassium carbonate, and 150 mL of acetone were put into a reactor, and heated under reflux for 8 hours. After poured into 5% hydrochloric acid, this was extracted with dichloromethane, and washed with salt water. Purification through column chromatography (alumina, dichloromethane) and recrystallization (dichloromethane/hexane) gave 9.7 g of the compound represented by the formula (I-5-3).

In a nitrogen atmosphere, 9.7 g of the compound represented by the formula (I-5-3), 7.9 g of the compound represented by the formula (I-5-4), 0.4 g of N,N-dimethylaminopyridine and 100 mL of dichloromethane were put into a reactor. With cooling with ice, 5.6 g of diisopropylcarbodiimide was dropwise added and stirred at room temperature for 6 hours. The precipitate was removed through filtration, and the filtrate was washed sequentially with 1% hydrochloric acid, water and salt water. Purification through column chromatography (alumina, dichloromethane) and recrystallization (dichloromethane/methanol) gave 11.9 g of the compound represented by the formula (I-5-5).

11.9 g of the compound represented by the formula (I-5-5), and 80 mL of dichloromethane were put into a reactor. 20 mL of trifluoroacetic acid was dropwise added and stirred for 8 hours. The solvent was distilled away, and diisopropyl ether was added, and the precipitated solid was filtrated out. The resultant solid was washed with diisopropyl ether and dried to give 10.7 g of the compound represented by the formula (I-5-6).

In a nitrogen atmosphere, 9.1 g of the compound represented by the formula (I-5-6), 1.5 g of the compound represented by the formula (I-5-7), 0.1 g of N,N-dimethylaminopyridine and 150 mL of dichloromethane were put into a reactor. With cooling with ice, 3.4 g of diisopropylcarbodiimide was dropwise added and stirred at room temperature for 10 hours. The precipitate was removed through filtration, and the filtrate was washed sequentially with 1% hydrochloric acid, water and salt water. After recrystallization (dichloromethane/methanol), purification through column chromatography (silica gel, dichloromethane) and recrystallization (dichloromethane/methanol) gave 7.1 g of the compound represented by the formula (I-5-8).

10.0 g of the compound represented by the formula (I-5-9), 13.8 g of the compound represented by the formula (I-5-2), 12.5 g of potassium carbonate and 100 mL of N,N-dimethylformamide were put into a reactor, and heated with stirring at 70° C. for 8 hours. After diluted with dichloromethane, this was washed sequentially with water and salt water. Purification through column chromatography (alumina, dichloromethane) gave 11.6 g of the compound represented by the formula (I-5-10).

2.0 g of the compound represented by the formula (I-5-10), 5.9 g of the compound represented by the formula (I-5-8), 0.7 g of (±)-10-camphorsulfonic acid, 24 mL of tetrahydrofuran and 24 mL of ethanol were put into a reactor, and heated with stirring at 50° C. for 8 hours. The solvent was distilled away, and purification of the residue through column chromatography (silica gel, dichloromethane) and recrystallization (dichloromethane/methanol) gave 5.4 g of the compound represented by the formula (I-5).

$^{1}$H NMR (CDCl$_3$) δ 1.24 (m, 4H), 1.48-1.93 (m, 28H), 2.08 (t, 4H), 2.23 (m, 4H), 2.54 (m, 4H), 3.94 (t, 4H), 4.17 (t, 4H), 4.53 (t, 2H), 4.65 (t, 2H), 5.82 (dd, 3H), 6.12 (dd, 3H), 6.40 (dd, 3H), 6.88 (m, 6H), 6.97 (dd, 4H), 7.16 (t, 1H), 7.34 (t, 1H), 7.54 (d, 1H), 7.66 (d, 1H), 7.70 (d, 1H), 8.36 (s, 1H) ppm.

LCMS: 1240 [M+1]

(Example 6) Production of Compound Represented by Formula (I-6)
[Chem. 81]
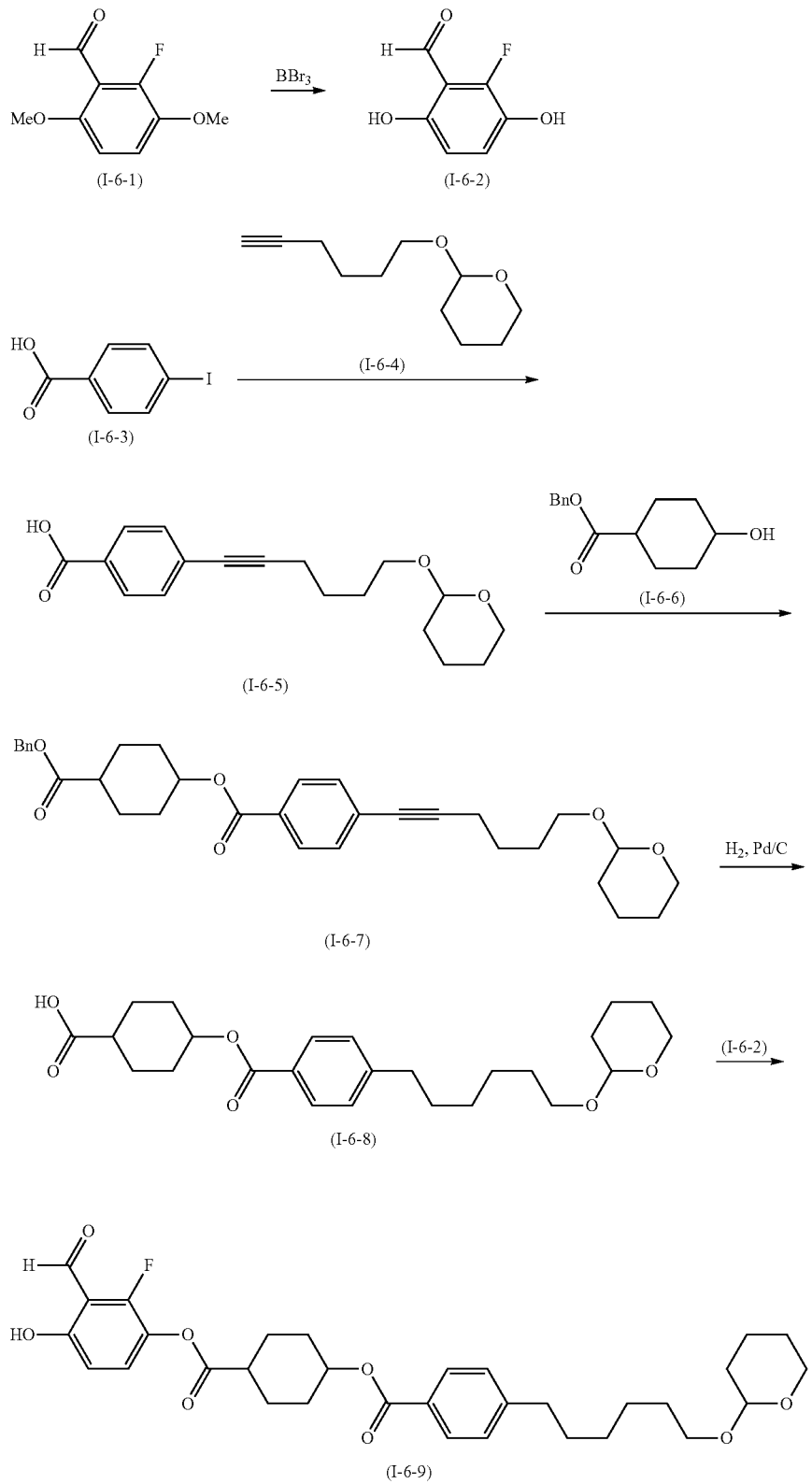

[Chem. 82]
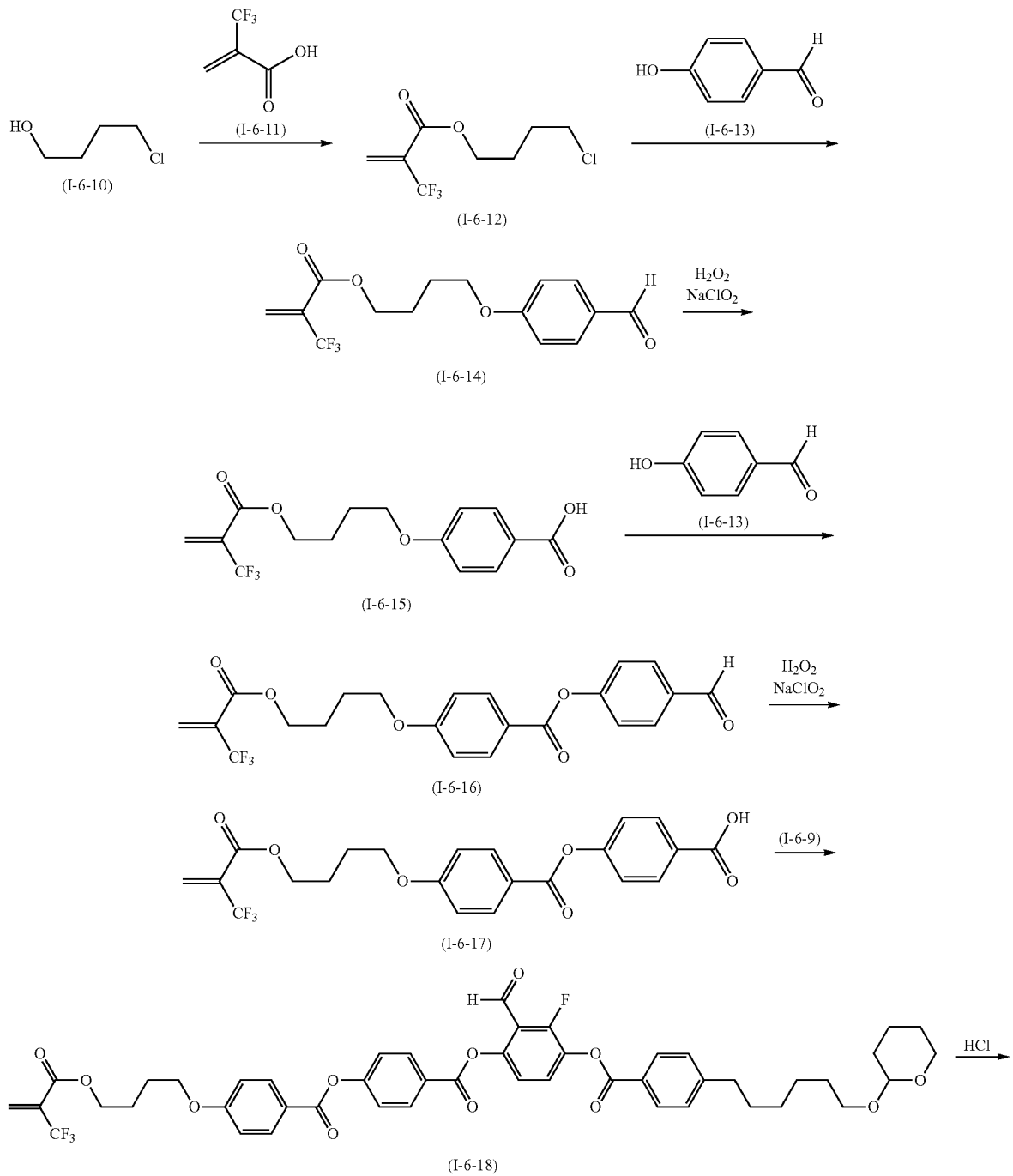
[Chem. 83]
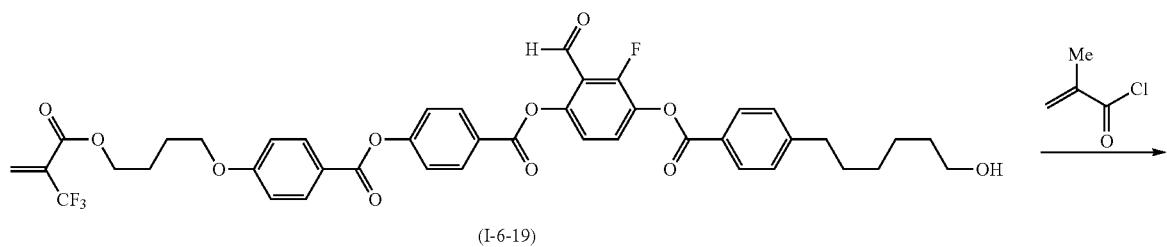

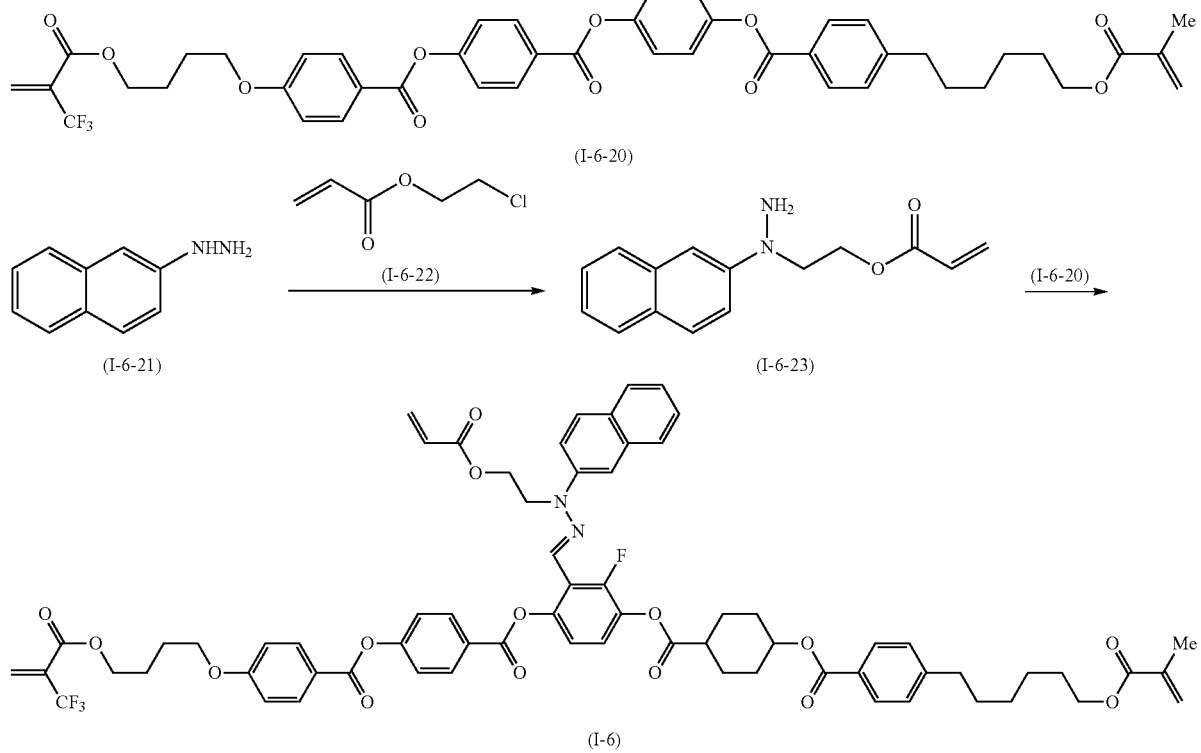

In a nitrogen atmosphere, 5.0 g of the compound represented by the formula (I-6-1), and 50 mL of dichloromethane were put into a reactor. With cooling with ice, 20.4 g of boron tribromide was dropwise added and stirred for 3 hours. After poured into water with ice, this was extracted with ethyl acetate, and washed sequentially with water and salt water. This was dried over sodium sulfate and the solvent was distilled away to give 3.4 g of the compound of the formula (I-6-2).

In a nitrogen atmosphere, 5.0 g of the compound represented by the formula (I-6-3), 4.0 g of the compound represented by the formula (I-6-4), 0.1 g of copper(I) iodide, 30 mL of triethylamine, 90 mL of N,N-dimethylformamide, and 0.2 g of tetrakis(triphenylphosphine)palladium(0) were put into a reactor, and heated with stirring at 90° C. for 5 hours. This was diluted with ethyl acetate and washed sequentially with 5% hydrochloric acid, water and salt water. Purification through column chromatography (silica gel, dichloromethane/ethyl acetate) gave 3.7 g of the compound represented by the formula (I-6-5).

In a nitrogen atmosphere, 3.7 g of the compound represented by the formula (I-6-5), 2.8 g of the compound represented by the formula (I-6-6), 0.1 g of N,N-dimethylaminopyridine and 100 mL of dichloromethane were put into a reactor. With cooling with ice, 1.8 g of diisopropylcarbodiimide was dropwise added and stirred at room temperature for 10 hours. The precipitate was removed through filtration, and the filtrate was washed sequentially with 1% hydrochloric acid, water and salt water. Purification through column chromatography (silica gel, dichloromethane) and recrystallization (dichloromethane/methanol) gave 4.4 g of the compound represented by the formula (I-6-7).

4.4 g of the compound represented by the formula (I-6-7), 30 mL of tetrahydrofuran, 30 mL of ethanol and 0.4 g of 5% palladium carbon were put into an autoclave. Under a hydrogen pressure of 0.5 MPa therein, these were heated with stirring at 50° C. for 6 hours. Palladium was removed through filtration, and the solvent was distilled away to give 5.2 g of the compound represented by the formula (I-6-8).

In a nitrogen atmosphere, 5.2 g of the compound represented by the formula (I-6-8), 1.9 g of the compound represented by the formula (I-6-2), 0.1 g of N,N-dimethylaminopyridine and 60 mL of dichloromethane were put into a reactor. With cooling with ice, 1.8 g of diisopropylcarbodiimide was dropwise added and stirred at room temperature for 10 hours. The precipitate was removed through filtration, and the filtrate was washed sequentially with 1% hydrochloric acid, water and salt water. Purification through column chromatography (silica gel, dichloromethane) and recrystallization (dichloromethane/hexane) gave 2.8 g of the compound represented by the formula (I-6-9).

20.0 g of the compound represented by the formula (I-6-10), 28.4 g of acrylic acid, 1.8 g of p-toluenesulfonic acid monohydrate, 300 mL of cyclohexane and 150 mL of diisopropyl ether were put into a reactor equipped with a Dean-Stark apparatus, and heated under reflux for 12 hours while removing water. This was diluted with dichloromethane, and washed sequentially with an aqueous solution of 5% sodium hydrogencarbonate, and salt water. Purification through column chromatography (silica gel, dichloromethane) gave 34.0 g of the compound of the formula (I-6-12).

11.3 g of the compound represented by the formula (I-6-12), 5.0 g of the compound represented by the formula (I-6-13), 8.5 g of potassium carbonate, and 200 mL of N,N-dimethylformamide were put into a reactor, and heated under reflux for 12 hours. After poured into 5% hydrochloric acid, this was extracted with dichloromethane and washed with salt water. Purification through column chromatography (silica gel, dichloromethane) gave 10.4 g of the compound represented by the formula (I-6-14).

10.4 g of the compound represented by the formula (I-6-14), 5.1 g of sodium dihydrogenphosphate, 100 mL of methanol, 50 mL of water and 5.4 mL of 35% hydrogen peroxide water were put into a reactor. A solution of 4.4 g of sodium chlorite dissolved in 20 mL of water was dropwise added and heated with stirring at 60° C. for 3 hours. Water was added to cool it, and the precipitate was filtered out. The resultant solid was dried to give 8.7 g of the compound represented by the formula (I-6-15).

In a nitrogen atmosphere, 8.7 g of the compound represented by the formula (I-6-15), 3.2 g of the compound represented by the formula (I-6-13), 0.1 g of N,N-dimethylaminopyridine and 60 mL of dichloromethane were put into a reactor. With cooling with ice, 4.0 g of diisopropylcarbodiimide was dropwise added and stirred at room temperature for 6 hours. The precipitate was removed through filtration, and the filtrate was washed sequentially with 1% hydrochloric acid, water and salt water. Purification through column chromatography (silica gel, dichloromethane) and recrystallization (dichloromethane/methanol) gave 9.1 g of the compound represented by the formula (I-6-16).

9.1 g of the compound represented by the formula (I-6-16), 5.1 g of sodium dihydrogenphosphate dihydrate, 100 mL of methanol, 50 mL of water, and 3.5 mL of 35% hydrogen peroxide water were put into a reactor. A solution of 3.4 g of sodium chlorite dissolved in 15 mL of water was dropwise added and heated with stirring at 60° C. for 3 hours. Water was added to cool it, and the precipitate was filtered out. The resultant solid was dried to give 7.6 g of the compound represented by the formula (I-6-17).

In a nitrogen atmosphere, 2.2 g of the compound represented by the formula (I-6-17), 2.8 g of the compound represented by the formula (I-6-9), 0.1 g of N,N-dimethylaminopyridine and 50 mL of dichloromethane were put into a reactor. With cooling with ice, 0.7 g of diisopropylcarbodiimide was dropwise added and stirred at room temperature for 6 hours. The precipitate was removed through filtration, and the filtrate was washed sequentially with 1% hydrochloric acid, water and salt water. Purification through column chromatography (silica gel, dichloromethane) and recrystallization (dichloromethane/methanol) gave 3.4 g of the compound represented by the formula (I-6-18).

3.4 g of the compound represented by the formula (I-6-18), 15 mL of tetrahydrofuran, 15 mL of methanol and 5 mL of concentrated hydrochloric acid were put into a reactor, and heated with stirring at 50° C. for 5 hours. After added with dichloromethane, this was washed sequentially with water and salt water. Purification through column chromatography (silica gel, dichloromethane) and recrystallization (dichloromethane/methanol) gave 2.2 g of the compound represented by the formula (I-6-19).

In a nitrogen atmosphere, 2.2 g of the compound represented by the formula (I-6-19), 0.5 g of diisopropylethylamine, and 40 mL of dichloromethane were put into a reactor. With cooling with ice, 0.3 g of methacryloyl chloride was dropwise added and stirred at room temperature for 6 hours. This was washed sequentially with 1% hydrochloric acid and salt water and re-precipitated (methanol). Purification through column chromatography (silica gel, dichloromethane) and recrystallization (dichloromethane/methanol) gave 1.9 g of the compound represented by the formula (I-6-20).

3.0 g of the compound represented by the formula (I-6-21), 3.3 g of the compound represented by the formula (I-6-22), 3.9 g of potassium carbonate and 30 mL of acetone were put into a reactor and heated under reflux for 5 hours. After cooled and added with dichloromethane, this was washed with salt water. This was dried over sodium sulfate, and the solvent was distilled away to give 2.9 g of the compound represented by the formula (I-6-23).

0.6 g of the compound represented by the formula (I-6-23), 1.9 g of the compound represented by the formula (I-6-20), 0.3 g of (±)-10-camphorsulfonic acid, 20 mL of tetrahydrofuran and 20 mL of ethanol were put into a reactor, and heated with stirring at 50° C. for 8 hours. After solvent removal through distillation, purification through column chromatography (silica gel, dichloromethane) and recrystallization (dichloromethane/methanol) gave 1.9 g of the compound represented by the formula (I-6).

LCMS: 1227 [M+1]

(Example 7) Production of Compound Represented by Formula (I-7)

[Chem. 84]

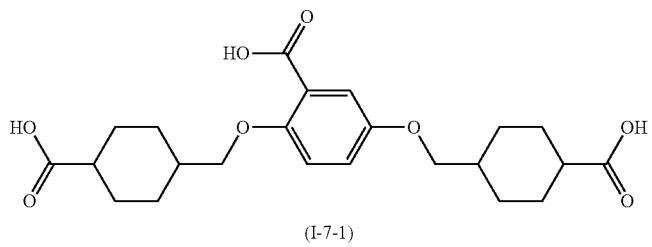

(I-7-1)

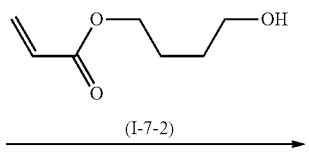

(I-7-2)

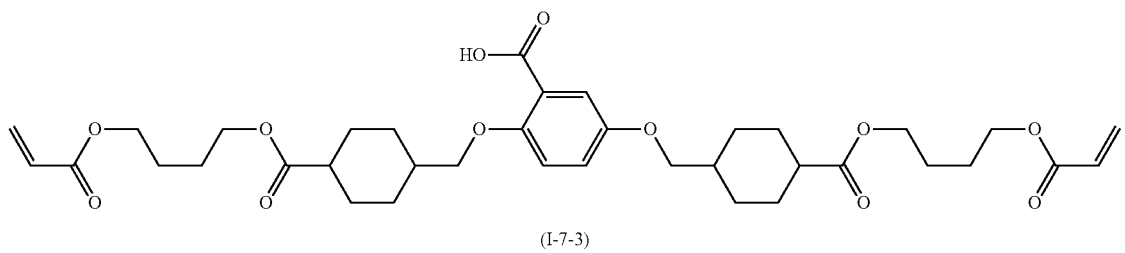

(I-7-3)

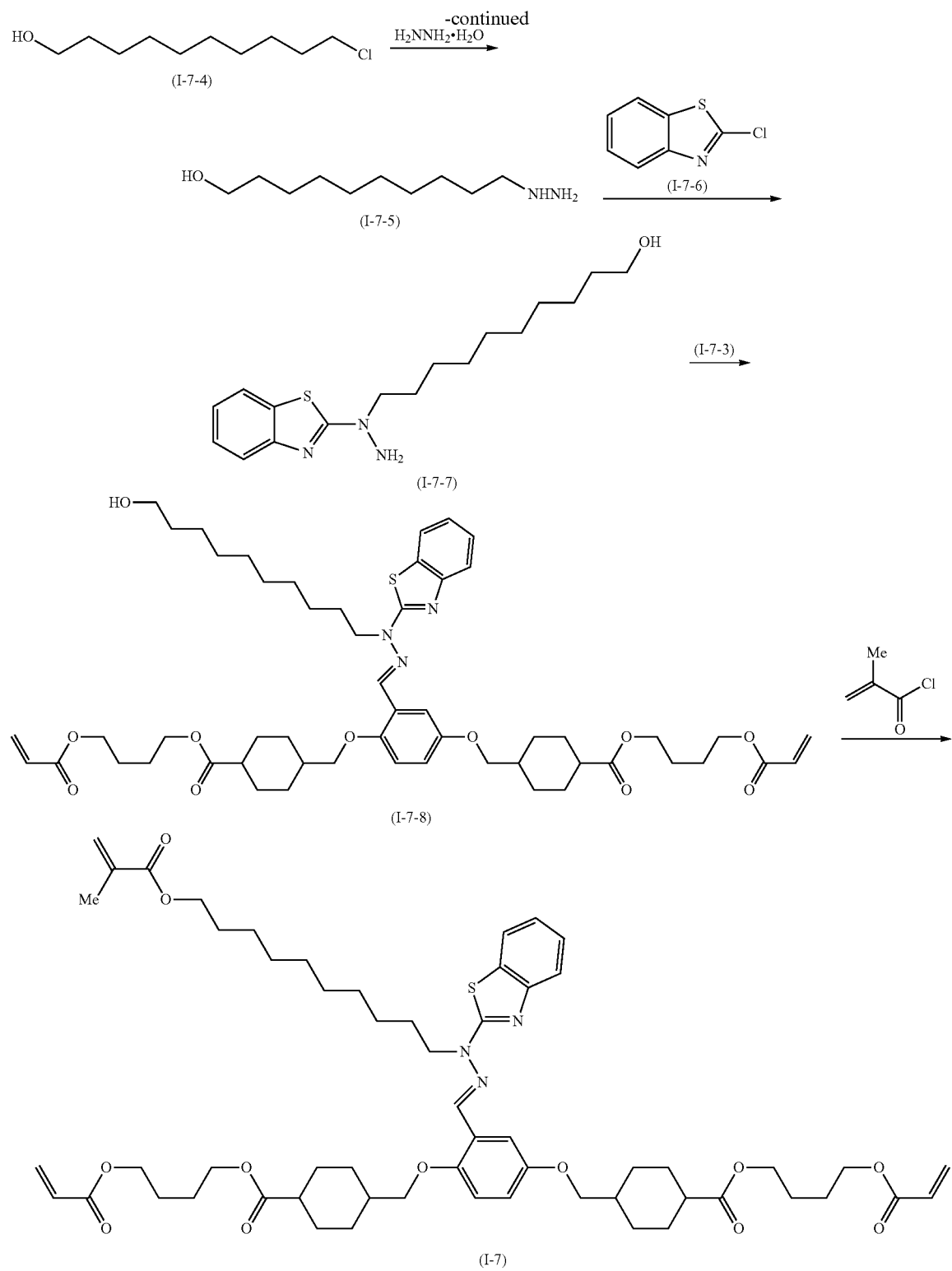

In a nitrogen atmosphere, 5.0 g of the compound represented by the formula (I-7-1), 3.8 g of the compound represented by the formula (I-7-2), 0.1 g of N,N-dimethylaminopyridine and 100 mL of dichloromethane were put into a reactor. With cooling with ice, 3.8 g of diisopropylcarbodiimide was dropwise added and stirred at room temperature for 10 hours. The precipitate was removed through filtration, and the filtrate was washed sequentially with 1% hydrochloric acid, water and salt water. Purification through column chromatography (silica gel, dichloromethane) and recrystallization (dichloromethane/methanol) gave 5.6 g of the compound represented by the formula (I-7-3).

In a nitrogen atmosphere, 150 mL of hydrazinemonohydrate, and 150 mL of ethanol were put into a reactor. With heating at 50° C., 10.0 g of the compound represented by the formula (I-7-4) was dropwise added and kept heated with stirring for 3 hours. This was diluted with dichloromethane and washed with salt water. This was dried over sodium sulfate and the solvent was distilled away to give 7.8 g of the compound represented by the formula (I-7-5).

In a nitrogen atmosphere, 4.7 g of the compound represented by the formula (I-7-6), 30 mL of 1,2-dimethoxyethane and 3.2 g of triethylamine were put into a reactor. With heating at 60° C., 7.8 g of the compound represented by the formula (I-7-5) was dropwise added and kept heated with stirring form 2 hours. The reaction liquid was poured into water, and the precipitated solid was filtered out. The solid was washed sequentially with water and hexane and dried to give 6.2 g of the compound represented by the formula (I-7-7).

5.6 g of the compound represented by the formula (I-7-3), 2.7 g of the compound represented by the formula (I-7-7), 0.6 g of (±)-10-camphorsulfonic acid, 20 mL of tetrahydrofuran, and 20 mL of ethanol were put into a reactor and heated with stirring at 50° C. for 10 hours. The solvent was distilled away, and the residue was purified through column chromatography (silica gel, dichloromethane) and recrystallization (dichloromethane/methanol) to give 5.7 g of the compound represented by the formula (I-7-8).

In a nitrogen atmosphere, 5.7 g of the compound represented by the formula (I-7-8), 0.9 g of diisopropylethylamine and 50 mL of dichloromethane were put into a reactor. With cooling with ice, 0.7 g of methacryloyl chloride was dropwise added, and stirred at room temperature for 8 hours. This was washed sequentially with 1% hydrochloric acid and salt water, and then purified through column chromatography (silica gel, dichloromethane) and recrystallization (dichloromethane/methanol) to give 3.7 g of the compound represented by the formula (I-7).

LCMS: 1042 [M+1]

(Example 8) Production of Compound Represented by Formula (I-8)

[Chem. 85]

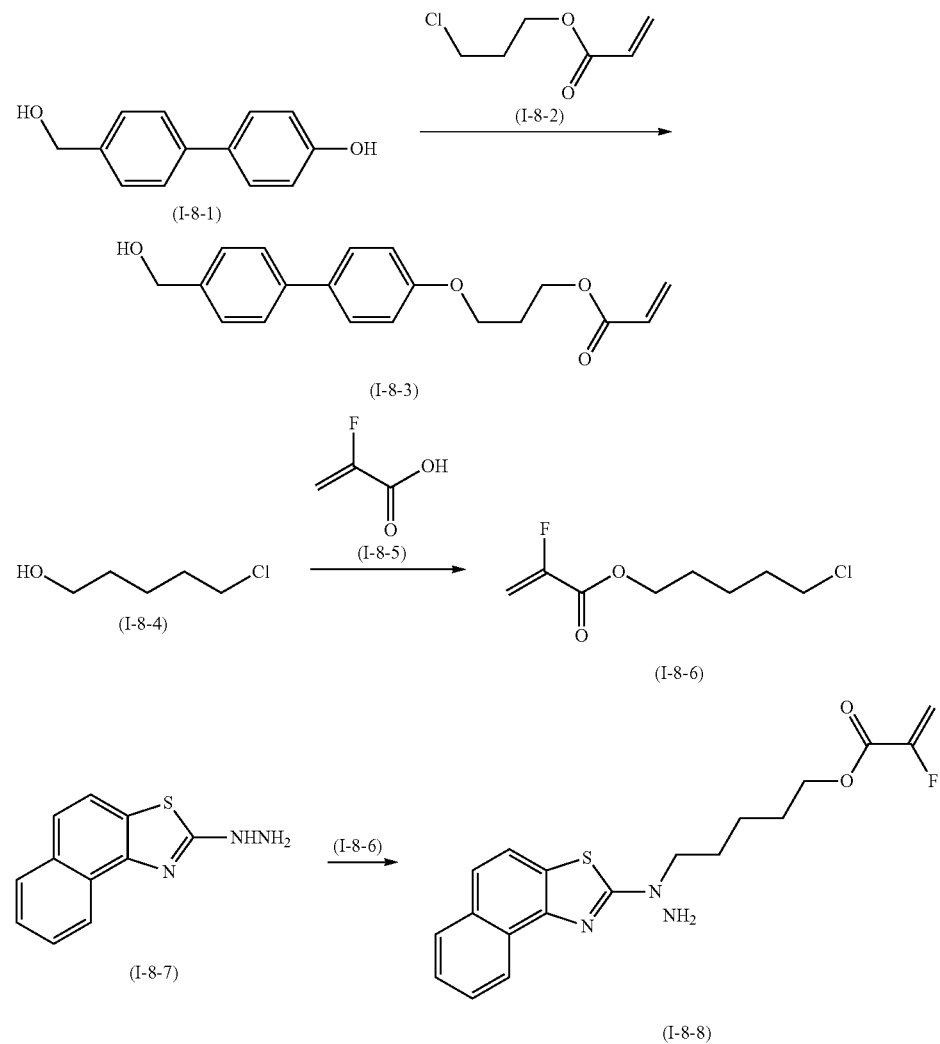

[Chem. 86]

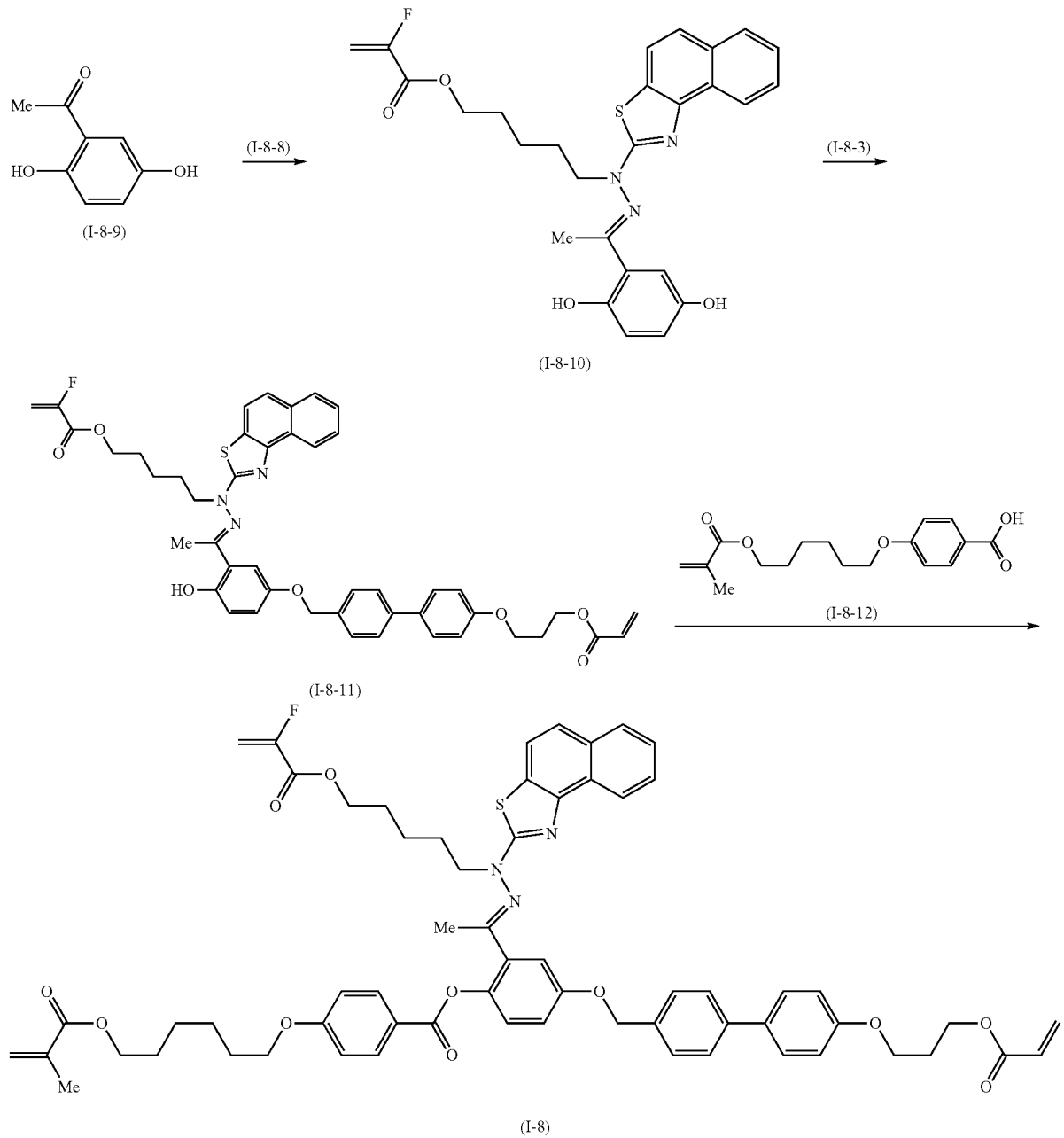

5.0 g of the compound represented by the formula (I-8-1), 4.8 g of the compound represented by the formula (I-8-2), 12.2 g of cesium carbonate and 50 mL of dimethyl sulfoxide were put into a reactor, and heated with attiring at 60° C. for 5 hours. This was poured into 5% hydrochloric acid, then extracted with dichloromethane, and washed sequentially with water and salt water. Purification through column chromatography (silica gel, dichloromethane) gave 4.6 g of the compound represented by the formula (I-8-3).

10.0 g of the compound represented by the formula (I-8-4), 11.0 g of the compound represented by the formula (I-8-5), 0.8 g of p-toluenesulfonic acid monohydrate, 100 mL of cyclohexane and 100 mL of diisopropyl ether were put into a reactor equipped with a Dean-Stark apparatus. While removing water, this was heated under reflux for 12 hours. This was diluted with dichloromethane, and washed sequentially with an aqueous solution of 5% sodium hydrogencarbonate and salt water. Purification through column chromatography (silica gel, dichloromethane) gave 11.1 g of the compound represented by the formula (I-6-8).

5.0 g of the compound represented by the formula (I-8-7), 5.4 g of the compound represented by the formula (I-8-6), 4.8 g of potassium carbonate and 50 mL of acetone were put into a reactor, and heated under reflux for 5 hours. After cooled, dichloromethane was added thereto and washed with salt water. This was dried over sodium sulfate, and the solvent was distilled away to give 5.2 g of the compound represented by the formula (I-8-8).

2.0 g of the compound represented by the formula (I-8-9), 4.9 g of the compound represented by the formula (I-8-8), 20 mL of tetrahydrofuran and 20 mL of ethanol were put into a reactor, and heated with stirring at 50° C. for 8 hours. After added with ethyl acetate, this was washed sequentially with water and salt water. This was dried over sodium sulfate, and the solvent was distilled away to give 5.3 g of the compound represented by the formula (I-8-10).

In a nitrogen atmosphere, 5.3 g of the compound represented by the formula (I-8-10), 3.3 g of the compound represented by the formula (I-8-3), 3.6 g of triphenyl phosphine and 70 mL of tetrahydrofuran were put into a reactor. With cooling with ice, 2.6 g of diisopropyl azodicarboxylate was dropwise added and stirred at room temperature for 5 hours. Added with dichloromethane, this was washed with salt water. Purification through column chromatography (silica gel, dichloromethane) and recrystallization (dichloromethane/hexane) gave 4.2 g of the compound represented by the formula (I-8-11).

In a nitrogen atmosphere, 4.2 g of the compound represented by the formula (I-8-11), 1.6 g of the compound represented by the formula (I-8-12), 0.1 g of N,N-dimethylaminopyridine and 50 mL of dichloromethane were put into a reactor. With cooling with ice, 0.8 g of diisopropylcarbodiimide was dropwise added and stirred at room temperature for 10 hours. The precipitate was removed through filtration, and the filtrate was washed sequentially with 1% hydrochloric acid, water and salt water. Purification through column chromatography (silica gel, dichloromethane) and recrystallization (dichloromethane/methanol) gave 4.0 g of the compound represented by the formula (I-8).

LCMS: 1090 [M+1]

(Example 9) Production of Compound Represented by Formula (I-58)

[Chem. 87]

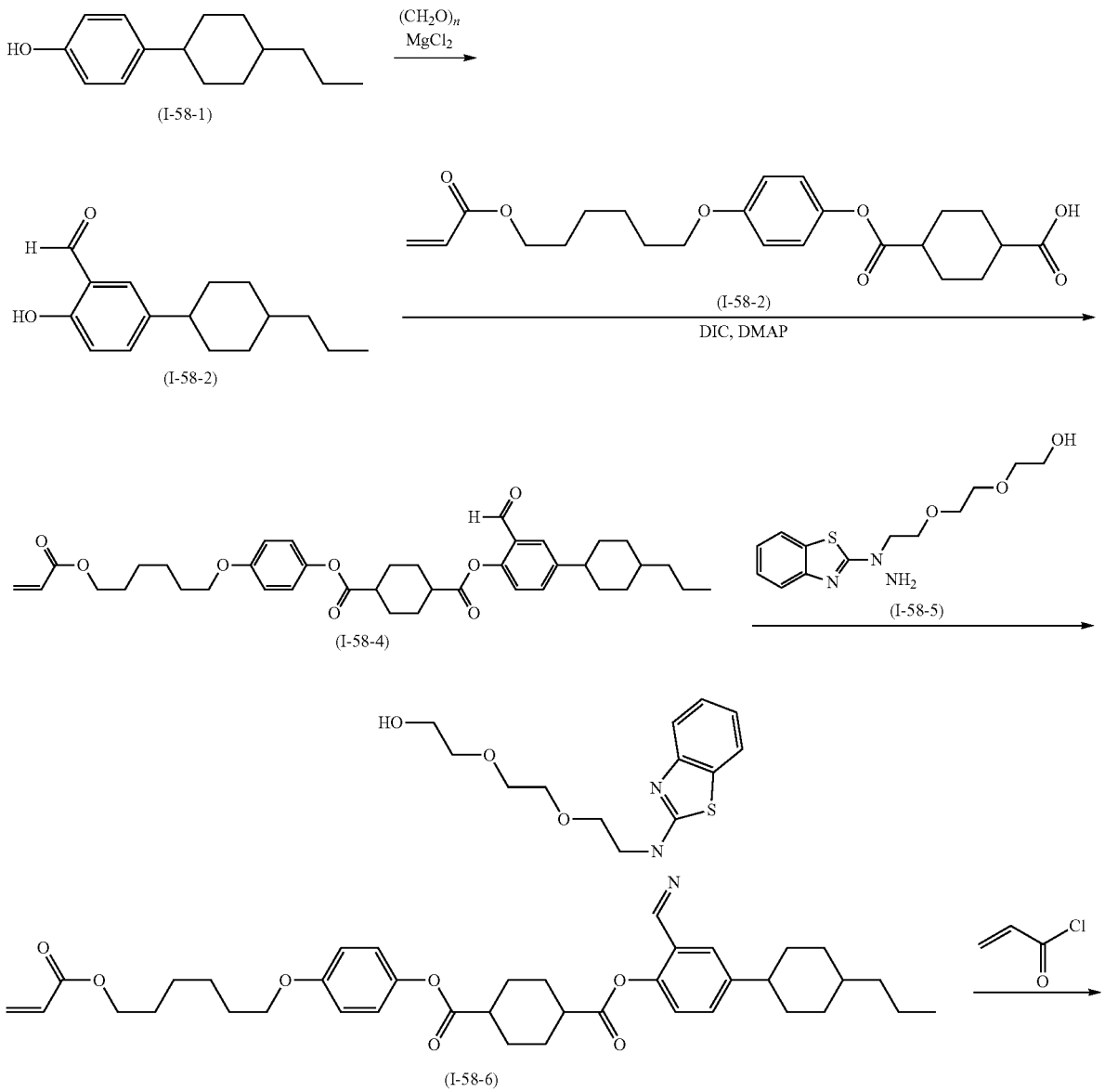

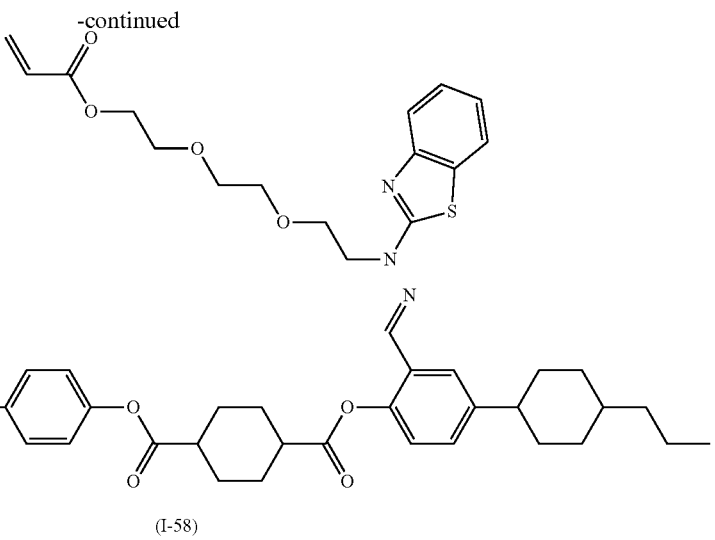

(I-58)

5.0 g of the compound represented by the formula (I-58-1), 3.2 g of magnesium chloride, 2.0 g of paraformaldehyde, 20 mL of triethylamine and 80 mL of acetonitrile were put into a reactor. With stirring at 60° C., paraformaldehyde was appropriately added. This was diluted with ethyl acetate and washed sequentially with 5% hydrochloric acid and salt water. Purification through column chromatography (silica gel, dichloromethane/hexane) gave 5.3 g of the compound represented by the formula (I-58-2).

In a nitrogen atmosphere, 2.0 g of the compound represented by the formula (I-58-2), 3.4 g of the compound represented by the formula (I-58-3), 0.1 g of N,N-dimethylaminopyridine and 30 mL of dichloromethane were put into a reactor. 1.2 g of diisopropylcarbodiimide was dropwise added and stirred at room temperature for 8 hours. The precipitate was removed through filtration, and the filtrate was washed sequentially with 5% hydrochloric acid and salt water. Purification trough column chromatography (silica gel, dichloromethane) and recrystallization (dichloromethane/methanol) gave 4.2 g of the compound represented by the formula (I-58-4).

4.2 g of the compound represented by the formula (I-58-4), 1.9 g of the compound represented by the formula (I-58-5), 0.5 g of (±)-10-camphorsulfonic acid, 20 mL of tetrahydrofuran and 20 mL of ethanol were put into a reactor. This was heated with stirring at 50° C. for 8 hours, the solvent was distilled away, and the residue was washed through dispersion with methanol. Purification through column chromatography (dichloromethane) and recrystallization (dichloromethane/methanol) gave 4.2 g of the compound represented by the formula (I-58-6).

In a nitrogen atmosphere, 4.2 g of the compound represented by the formula (I-58-6), 0.9 g of diisopropylethylamine and 40 mL of dichloromethane were put into a reactor. With cooling with ice, 0.7 g of acryloyl chloride was dropwise added and stirred at room temperature for 8 hours. This was washed sequentially with 1% hydrochloric acid and salt water, the solvent was distilled away, and the residue was washed through diversion (methanol). Purification through column chromatography (silica gel, dichloromethane) and recrystallization (dichloromethane/methanol) gave 3.5 g of the compound represented by the formula (I-58).

LCMS: 980 [M+1]

(Example 10) Production of Compound Represented by Formula (I-69)

[Chem. 88]

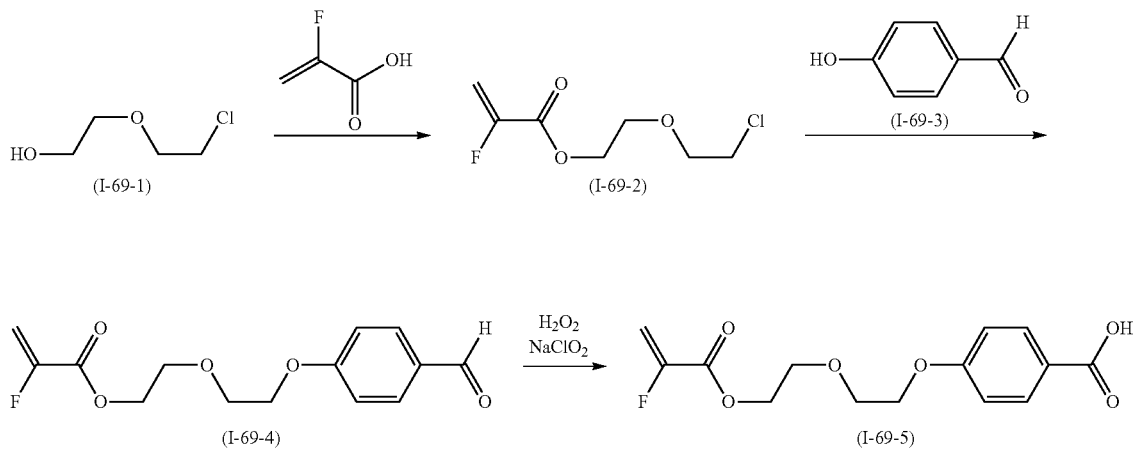

-continued
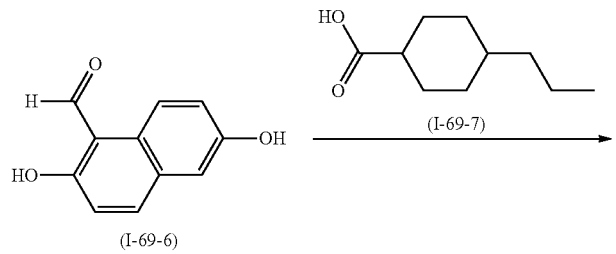
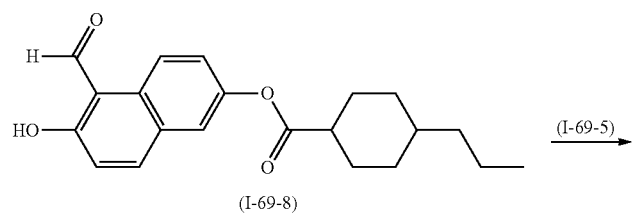
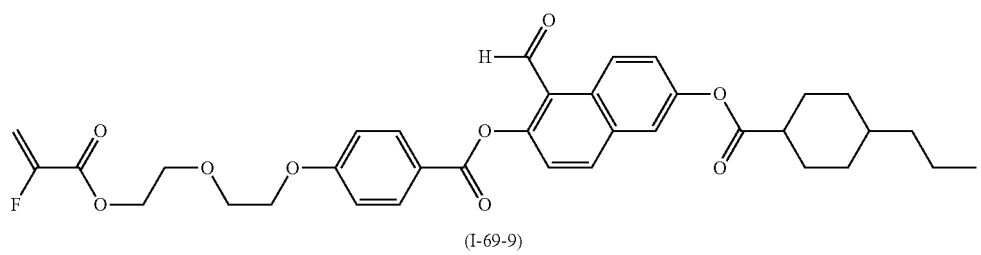
[Chem. 89]
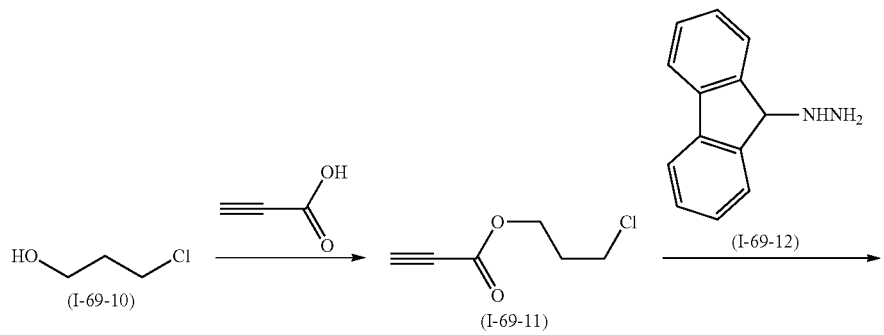
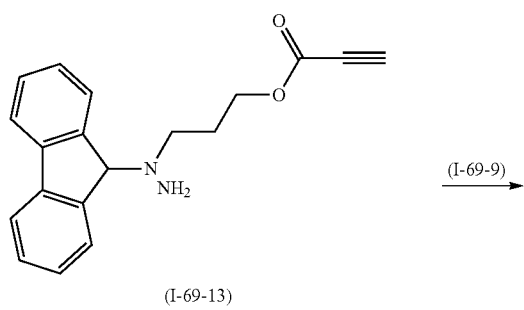

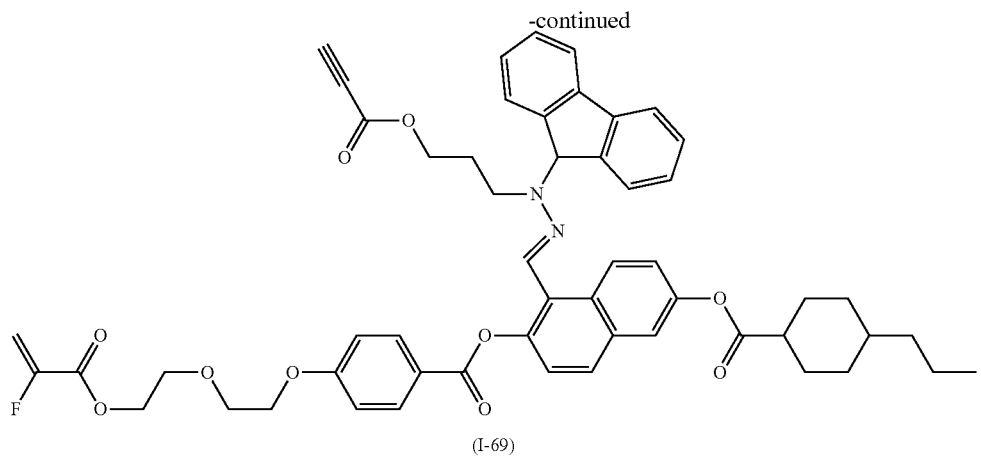

(I-69)

8.0 g of the compound represented by the formula (I-69-1), 8.7 g of 2-fluoroacrylic acid, 0.6 g of p-toluenesulfonic acid monohydrate, 100 mL of cyclohexane and 50 mL of diisopropyl ether were put into a reactor equipped with a Dean-Stark apparatus. While removing water, this was heated under reflux for 12 hours. This was diluted with dichloromethane, and washed sequentially with an aqueous solution of 5% sodium hydrogencarbonate and salt water. Purification through column chromatography (silica gel, dichloromethane) gave 10.1 g of the compound represented by the formula (I-69-2).

10.1 g of the compound represented by the formula (I-69-2), 4.8 g of the compound represented by the formula (I-69-3), 19.2 g of cesium carbonate, and 70 mL of dimethyl sulfoxide were put into a reactor, and heated with stirring at 60° C. for 6 hours. After poured into 5% hydrochloric acid, this was extracted with dichloromethane and washed sequentially with water and salt water. Purification through column chromatography (silica gel, dichloromethane) gave 7.8 g of the compound represented by the formula (I-69-4).

7.8 g of the compound represented by the formula (I-69-4), 5.1 g of sodium dihydrogenphosphate dihydrate, 100 mL of methanol, 50 mL of water and 4.8 mL of 35% hydrogen peroxide water were put into a reactor. A solution of 4.2 g of sodium chloride dissolved in 20 mL of water was dropwise added and heated with stirring at 60° C. for 3 hours. This was cooled with water added thereto, and the precipitate was filtered out. The resultant solid was dried to give 6.6 g of the compound represented by the formula (I-69-5).

In a nitrogen atmosphere, 2.5 g of the compound represented by the formula (I-69-6), 2.3 g of the compound represented by the formula (I-69-7), 0.1 g of N,N-dimethylaminopyridine and 50 mL of dichloromethane were put into a reactor. With cooling with ice, 2.0 g of diisopropylcarbodiimide was dropwise added and stirred at room temperature for 8 hours. The precipitate was removed through filtration, and the filtrate was washed sequentially with 1% hydrochloric acid, water and salt water. Purification through column chromatography (silica gel, dichloromethane) gave 3.2 g of the compound represented by the formula (I-69-8).

In a nitrogen atmosphere, 3.2 g of the compound represented by the formula (I-69-8), 2.8 g of the compound represented by the formula (I-69-5), 0.1 g of N,N-dimethylaminopyridine and 50 mL of dichloromethane were put into a reactor. With cooling with ice, 1.4 g of diisopropylcarbodiimide was dropwise added and stirred at room temperature for 8 hours. The precipitate was removed through filtration, and the filtrate was washed sequentially with 1% hydrochloric acid, water and salt water. Purification through column chromatography (silica gel, dichloromethane) and recrystallization (dichloromethane/methanol) gave 4.0 g of the compound represented by the formula (I-69-9).

5.0 g of the compound represented by the formula (I-69-10), 5.6 g of propiolic acid, 0.5 g of p-toluenesulfonic acid monohydrate, 80 mL of cyclohexane and 50 mL of diisopropyl ether were put into a reactor equipped with a Dean-Stark apparatus. While removing water, this was heated under reflux for 12 hours. After diluted with dichloromethane, this was washed sequentially with an aqueous solution of 5% sodium hydrogencarbonate and salt water. Purification through column chromatography (silica gel, dichloromethane) gave 6.2 g of the compound represented by the formula (I-69-11).

4.5 g of the compound represented by the formula (I-69-11), 5.0 g of the compound represented by the formula (I-69-12), 5.3 g of potassium carbonate and 50 mL of acetone were put into a reactor, and heated under reflux for 5 hours. After cooled, this was added with dichloromethane and washed with salt water. After this was dried over sodium sulfate, the solvent was distilled away to give 3.9 g of the compound represented by the formula (I-69-13).

1.4 g of the compound represented by the formula (I-69-13), 2.8 g of the compound represented by the formula (I-69-9), 0.5 g of (+)-10-camphorsulfonic acid, 20 mL of tetrahydrofuran and 20 mL of ethanol were put into a reactor, and heated with stirring at 50° C. for 10 hours. The solvent was distilled away, and the residue was purified through column chromatography (silica gel, dichloromethane) and recrystallization (dichloromethane/methanol) to give 3.1 g of the compound represented by the formula (I-69).

LCMS: 909 [M+1]

(Example 11) Production of Compound Represented by Formula (I-70)
[Chem. 90]
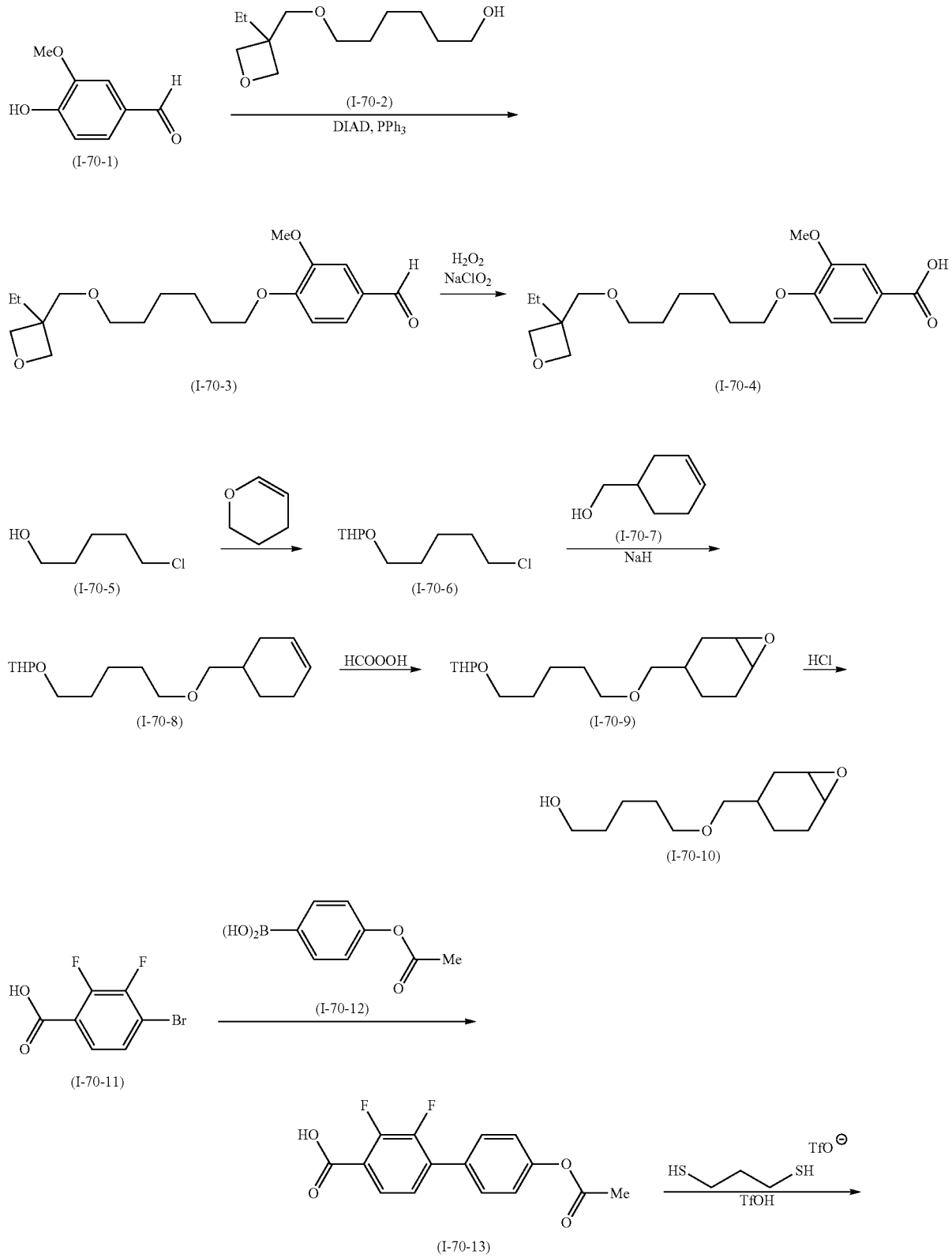

[Chem. 91]
-continued
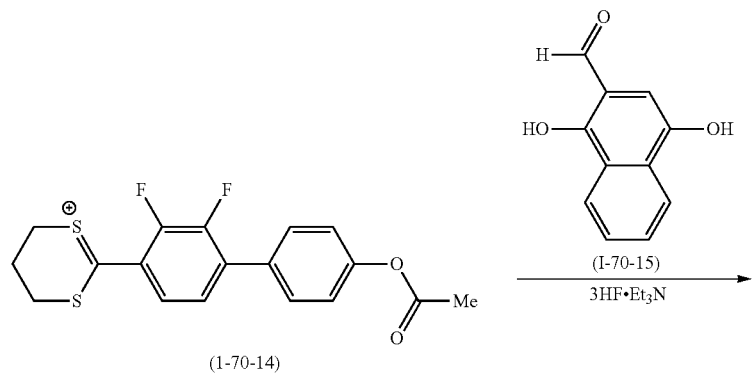
(I-70-14)     (I-70-15)
3HF·Et₃N
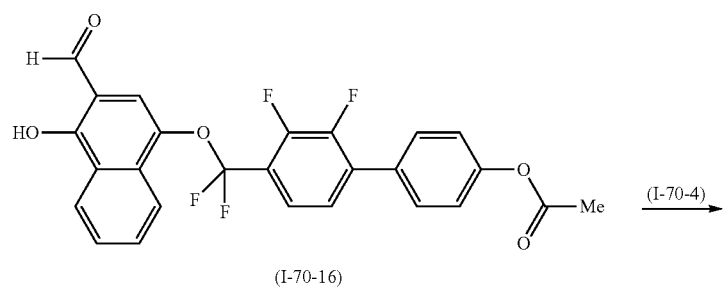
(I-70-16) → (I-70-4)
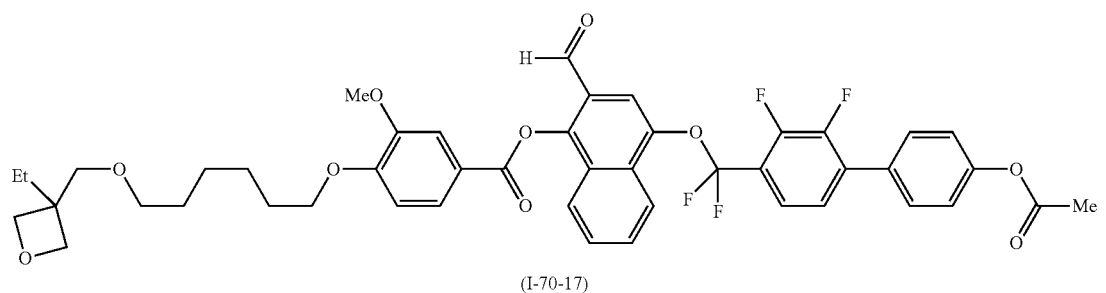
(I-70-17)
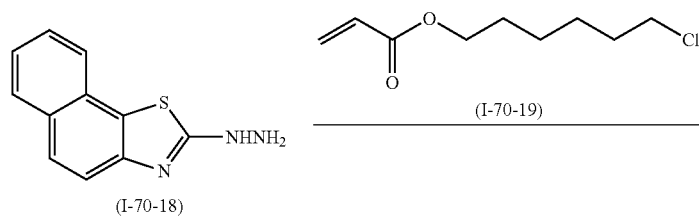
(I-70-18)     (I-70-19) →
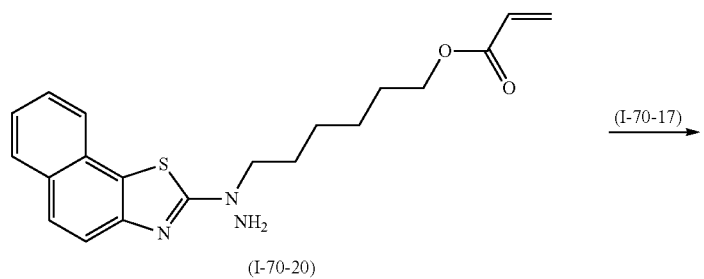
(I-70-20) → (I-70-17)

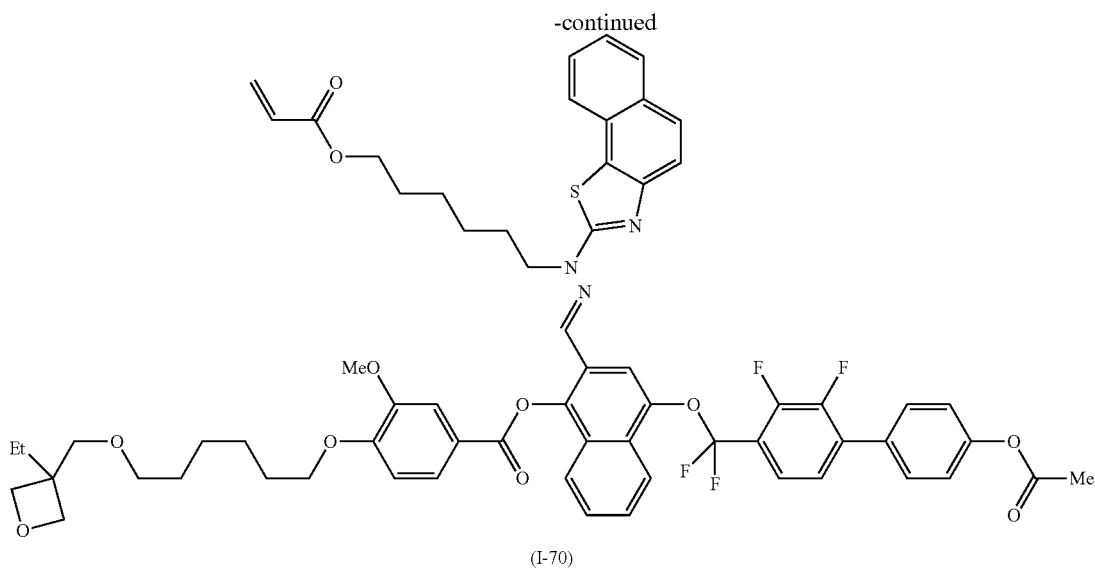

(I-70)

According to the method described in a journal of "Macromolecular Chemistry and Physics", 2009, Vol. 210, No. 7, pp. 531-541, the compound represented by the formula (I-70-2) was produced. In a nitrogen atmosphere, 5.0 g of the compound represented by the formula (I-70-1), 7.1 g of the compound represented by the formula (I-70-2), 11.2 g of triphenyl phosphine, and 30 mL of tetrahydrofuran were put into a reactor. With cooling with ice, 8.0 g of diisopropyl azodicarboxylate was added thereto, and stirred at room temperature for 3 hours. After added with water, this was extracted with dichloromethane and washed with salt water. Purification through column chromatography (silica gel, dichloromethane) gave 8.1 g of the compound represented by the formula (I-70-3).

8.1 g of the compound represented by the formula (I-70-3), 5.5 g of sodium dihydrogenphosphate, 100 mL of methanol, 50 mL of water and 5.0 mL of 35% hydrogen peroxide water were put into a reactor. A solution of 4.7 g of sodium chlorite dissolved in 20 mL of water was dropwise added and heated with stirring at 60° C. for 2 hours. Water was added for cooling, and the precipitate was filtered out. The resultant so lid was dried to give 6.7 g of the compound represented by the formula (I-70-4).

In a nitrogen atmosphere, 7.0 g of the compound represented by the formula (I-70-5), 0.7 g of pyridinium p-toluenesulfonate, and 70 mL of dichloromethane were put into a reactor. With cooling with ice, 5.8 g of 3,4-dihydro-2H-pyran was dropwise added, and stirred at room temperature for 8 hours. This was washed sequentially with an aqueous solution of 5% sodium hydrogencarbonate and salt water, and purified through column chromatography (silica gel, dichloromethane) to give 10.6 g of the compound represented by the formula (I-70-6).

In a nitrogen atmosphere, 6.3 g of the compound represented by the formula (I-70-7), 30 mL of tetrahydrofuran, and 1.9 g of sodium hydride were put into a reactor and stirred. With cooling with ice, a solution of 10.6 g of the compound represented by the formula (I-70-6) dissolved in 20 mL of tetrahydrofuran was dropwise added, and heated with stirring at 50° C. for 8 hours. After poured into water, this was extracted with dichloromethane, and washed with salt water. Purification through column chromatography (silica gel, dichloromethane) gave 8.1 g of the compound represented by the formula (I-70-8).

80 mL of formic acid, 80 mL of dichloromethane, and 10 mL of 35% hydrogen peroxide water were put into a reactor and stirred. With cooling with ice, a solution of 8.1 g of the compound represented by the formula (I-70-8) dissolved in 16 mL of dichloromethane was dropwise added, and heated with stirring at 40° C. for 10 hours. After added with an aqueous solution of sodium sulfite, this was extracted with dichloromethane, and washed sequentially with water and salt water. Purification through column chromatography (silica gel, dichloromethane) gave 7.7 g of the compound represented by the formula (I-70-9).

7.7 g of the compound represented by the formula (I-70-9), 30 mL of methanol, 30 mL of tetrahydrofuran and 5 mL of concentrated hydrochloric acid were put into a reactor, and heated with stirring at 50° C. for 8 hours. After diluted with ethyl acetate, this was washed sequentially with water and salt water. Purification through column chromatography (silica gel, hexane/ethyl acetate) gave 4.4 g of the compound represented by the formula (I-70-10).

In a nitrogen atmosphere, 10.0 g of the compound represented by the formula (I-70-11), 7.6 g of the compound represented by the formula (I-70-12), 8.7 of potassium carbonate, 50 mL of tetrahydrofuran, 25 mL of water and 0.5 g of tetrakis(triphenylphosphine)palladium(0) were put into a reactor, and heated under reflux for 8 hours. After poured into 5% hydrochloric acid, this was extracted with ethyl acetate and washed sequentially with water and salt water. Purification through column chromatography (silica gel, toluene/ethyl acetate) and recrystallization gave 8.6 g of the compound represented by the formula (I-70-13).

In a nitrogen atmosphere, 8.6 g of the compound represented by the formula (I-70-13), 9.6 g of 1,3-propanedithiol, and 50 mL of trifluoroacetic acid were put into a reactor, and heated with stirring at 60° C. for 3 hours. After cooling, tert-butylmethyl ether was added, and the precipitate was filtered out. The resultant solid was washed with tert-butylmethyl ether and dried to give 13.7 g of the compound represented by the formula (I-70-14).

In a nitrogen atmosphere, 13.7 g of the compound represented by the formula (I-70-14), 5.0 g of the compound represented by the formula (I-70-15), and 100 mL of dichloromethane were put into a reactor. At −65° C., 12.9 g of triethylamine tri-hydrofluoride and 12.7 g of bromine were sequentially dropwise added, and stirred for 2 hours. At room temperature, after added with an aqueous solution of sodium hydroxide, this was processed for liquid separation and washed sequentially with water and salt water. Purification through column chromatography (silica gel, dichloromethane/ethyl acetate) and recrystallization (acetone/hexane) gave 7.7 g of the compound represented by the formula (I-70-16).

In a nitrogen atmosphere, 4.0 g of the compound represented by the formula (I-70-16), 3.0 g of the compound represented by the formula (I-70-4), 0.1 g of N,N-dimethylaminopyridine, and 50 mL of dichloromethane were put into a reactor. With cooling with ice, 1.4 g of diisopropylcarbodiimide was dropwise added, and stirred at room temperature for 8 hours. The precipitate was removed through filtration, and the filtrate was washed sequentially with 5% hydrochloric acid, water and salt water. Purification through column chromatography (silica gel, dichloromethane) and recrystallization (dichloromethane/methanol) gave 4.8 g of the compound represented by the formula (I-70-17).

5.0 g of the compound represented by the formula (I-70-18), 5.3 g of the compound represented by the formula (I-70-19), 4.8 g of potassium carbonate, and 50 mL of acetone were put into a reactor, and heated under reflux for 5 hours. After cooled, this was added with dichloromethane, and washed with salt water. This was dried over sodium sulfate, and the solvent was distilled away to give 5.1 g of the compound represented by the formula (I-70-20).

2.1 g of the compound represented by the formula (I-70-20), 4.8 g of the compound represented by the formula (I-70-17), 0.5 g of (±)-10-camphorsulfonic acid, 20 mL of tetrahydrofuran, and 20 mL of ethanol were put into a reactor, and heated with stirring at 50° C. for 10 hours. The solvent was distilled away and the residue was purified through column chromatography (silica gel, dichloromethane) and recrystallization (dichloromethane/methanol) to give 5.5 g of the compound represented by the formula (I-70).

LCMS: 1184 [M+1]

(Example 12) Production of Compound Represented by Formula (I-71)

[Chem. 92]

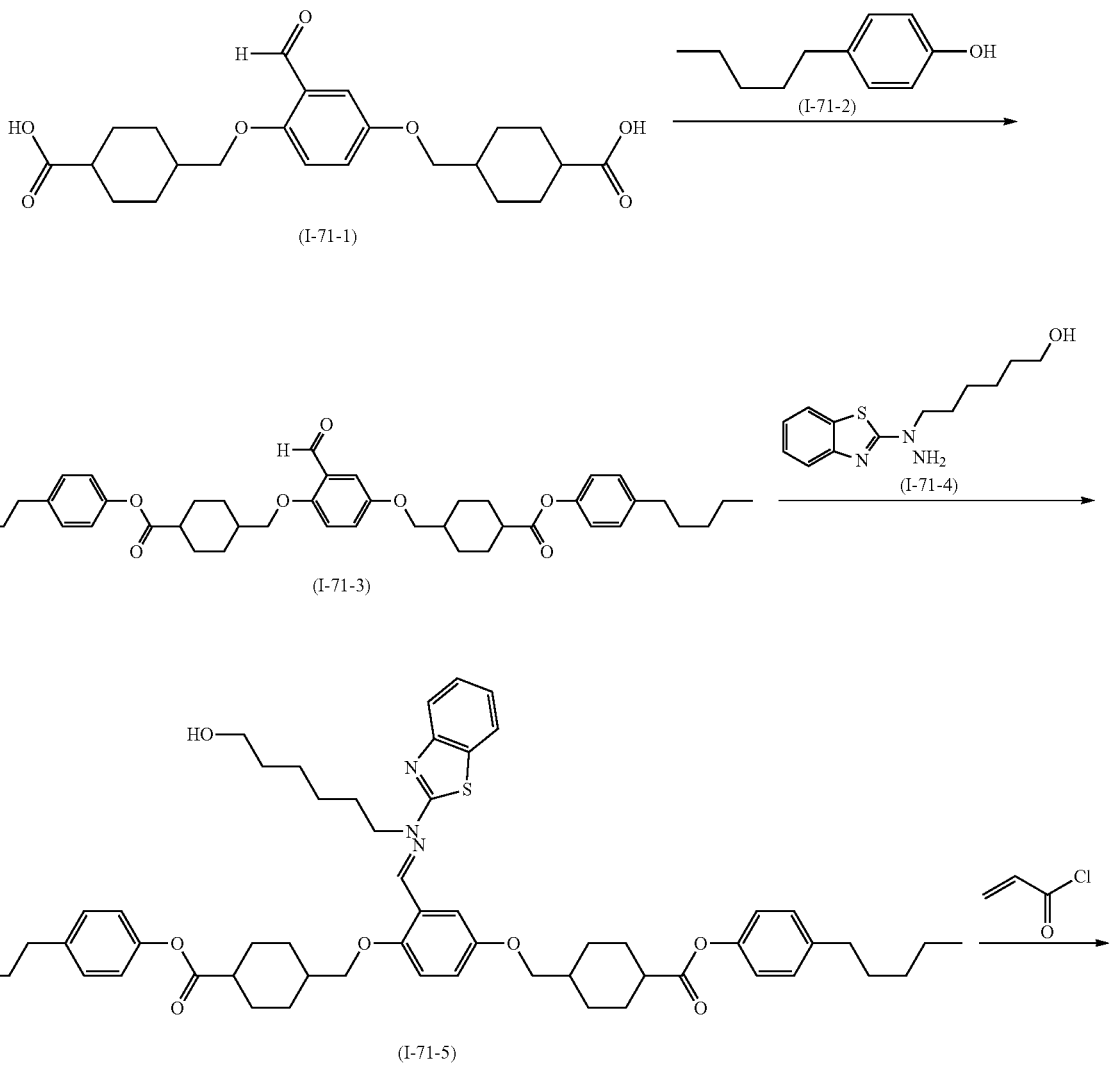

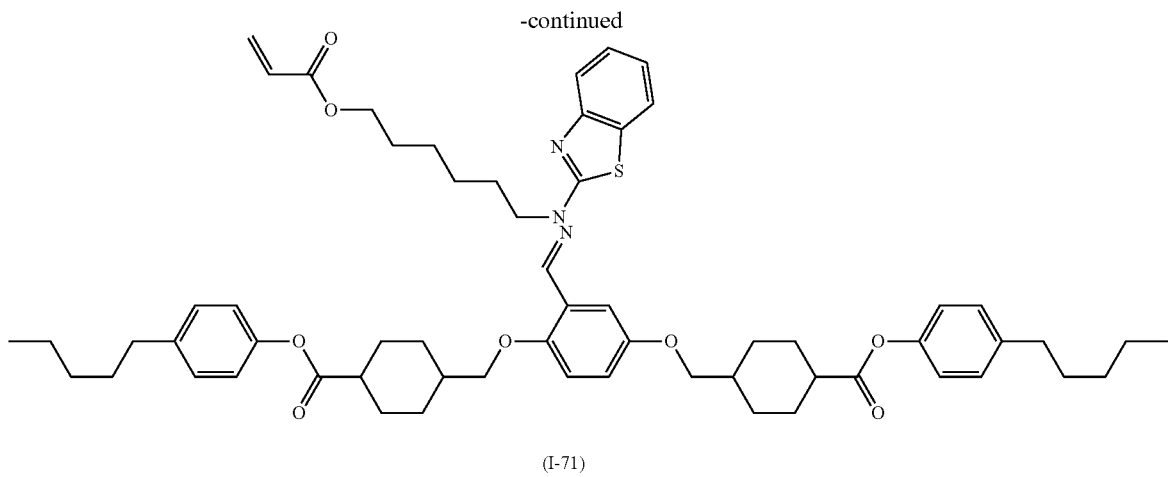

(I-71)

In a nitrogen atmosphere, 3.0 g of the compound represented by the formula (I-71-1), 2.4 g of the compound represented by the formula (I-71-2), 0.4 g of N,N-dimethylaminopyridine, and 150 mL of dichloromethane were put into a reactor. With cooling with ice, 2.2 g of diisopropylcarbodiimide was dropwise added, and stirred at room temperature for 10 hours. The precipitate was removed through filtration, and the filtrate was washed sequentially with 1% hydrochloric acid, water and salt water. After reprecipitation, (methanol), purification through column chromatography (silica gel, dichloromethane) and recrystallization (dichloromethane/methanol) gave 3.6 g of the compound represented by the formula (I-71-3).

3.6 g of the compound represented by the formula (I-71-3), 1.3 g of the compound represented by the formula (I-71-4), 0.5 g of (±)-10-camphorsulfonic acid, 20 mL of tetrahydrofuran, and 20 mL of ethanol were put into a reactor, and heated with stirring at 50° C. for 10 hours. The solvent was distilled away, and the residue was washed through dispersion (methanol). Purification through column chromatography (silica gel, dichloromethane) and recrystallization (dichloromethane/methanol) gave 3.4 g of the compound represented by the formula (I-71-5).

In a nitrogen atmosphere, 3.4 g of the compound represented by the formula (I-71-5), 0.6 g of diisopropylethylamine, and 40 mL of dichloromethane were put into a reactor. With cooling with ice, 0.4 g of acryloyl chloride was dropwise added, and stirred at room temperature for 8 hours. This was washed sequentially with 1% hydrochloric acid and salt water, the solvent was distilled away, and the residue was washed through dispersion (methanol). Purification through column chromatography (silica gel, dichloromethane) and recrystallization (dichloromethane/methanol) gave 2.8 g of the compound represented by the formula (I-71).

LCMS: 1012 [M+1]

(Example 13) Production of Compound Represented by Formula (I-77)

[Chem. 93]

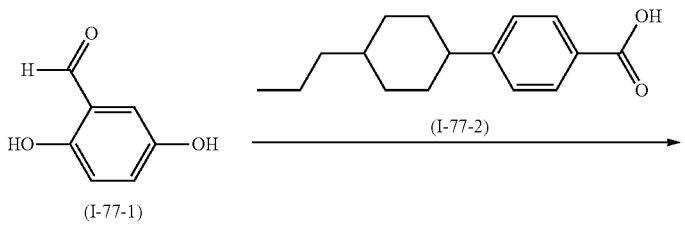

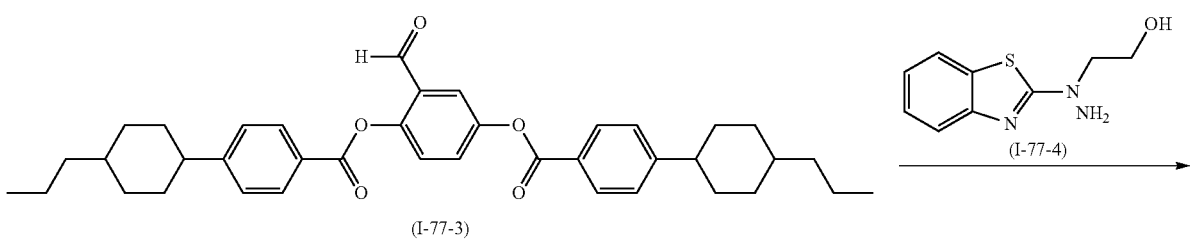

-continued

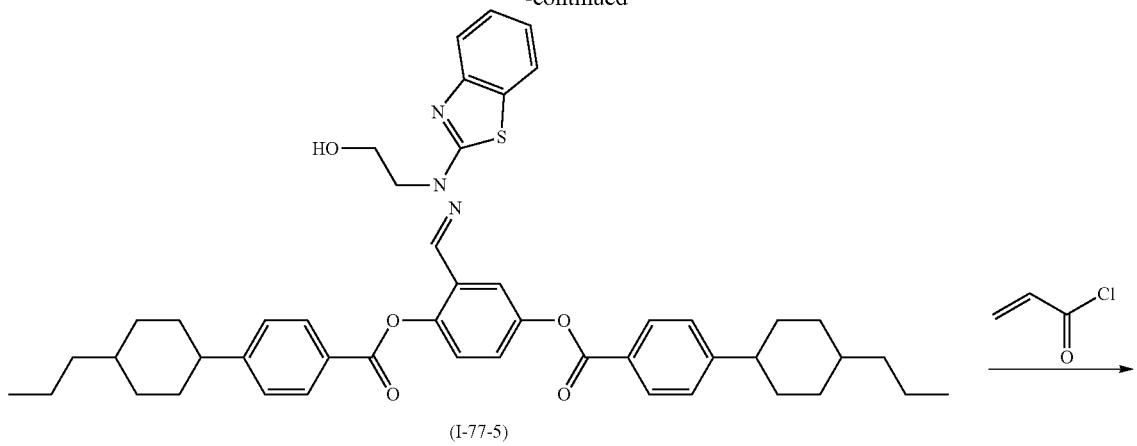

(I-77-5)

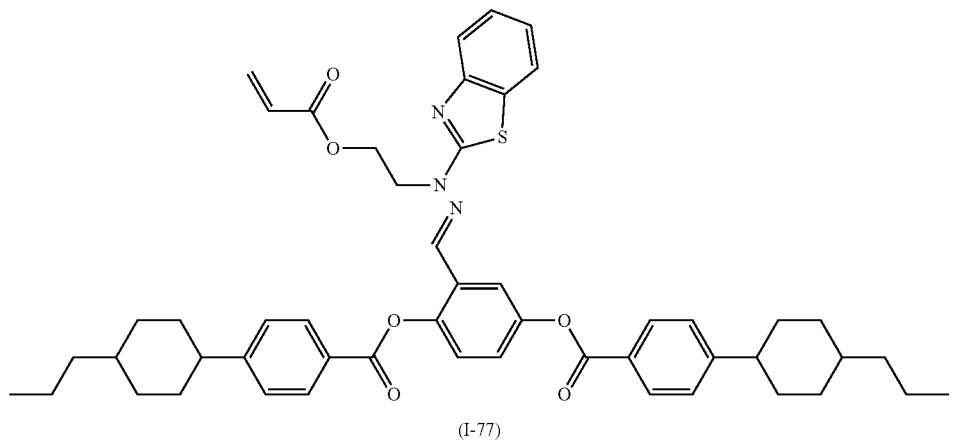

(I-77)

In a nitrogen atmosphere, 1.0 g of the compound represented by the formula (I-77-1), 3.6 g of the compound represented by the formula (I-77-2), 0.4 g of N,N-dimethylaminopyridine, and 20 mL of dichloromethane were put into a reactor. With cooling with ice, 2.2 g of diisopropylcarbodiimide was dropwise added, and stirred at room temperature for 10 hours. The precipitate was removed through filtration, and the filtrate was washed sequentially with 1% hydrochloric acid, water and salt water. After reprecipitation (methanol), purification through column chromatography (silica gel, dichloromethane) and recrystallization (dichloromethane/methanol) gave 3.0 g of the compound represented by the formula (I-77-3).

3.0 g of the compound represented by the formula (I-77-3), 1.1 g of the compound represented by the formula (I-77-4), 0.5 g of (±)-10-camphorsulfonic acid, 20 mL of tetrahydrofuran, and 20 mL of ethanol were put into a reactor, and heated with stirring at 50° C. for 10 hours. The solvent was distilled away, and the residue was washed through dispersion (methanol). Purification through column chromatography (silica gel, dichloromethane) and recrystallization (dichloromethane/methanol) gave 3.2 g of the compound represented by the formula (I-77-5).

In a nitrogen atmosphere, 3.2 g of the compound represented by the formula (I-77-5), 0.6 g of diisopropylethylamine, and 40 mL of dichloromethane were put into a reactor. With cooling with ice, 0.4 g of acryloyl chloride was dropwise added, and stirred at room temperature for 8 hours. This was washed sequentially with 1% hydrochloric acid and salt water, then re-precipitated (methanol), and purified through column chromatography (silica gel, dichloromethane) and recrystallization (dichloromethane/methanol) gave 2.7 g of the compound represented by the formula (I-77).

LCMS: 840 [M+1]

According to the same method as in Example 1 to Example 13 and according to a known method, compounds represented by the formulae (I-9) to (I-57), the formulae (I-59) to (I-68), the formulae (I-72) to (I-76), and the formulae (I-78) to (I-103) were produced.

Examples 14 to 39, Comparative Examples 1 to 6

The compounds represented by the formulae (I-1) to (I-8), the formula (I-58), the formula (I-69), the formula (I-70), the formula (I-71) and the formula (I-77) in Examples 1 to 13, and the compound (R-1) described in PTL 1, the compound (R-2) described in PTL 2, and the compound (R-3) described in PTL 3 were tested as compounds to be evaluated.

[Chem. 94]

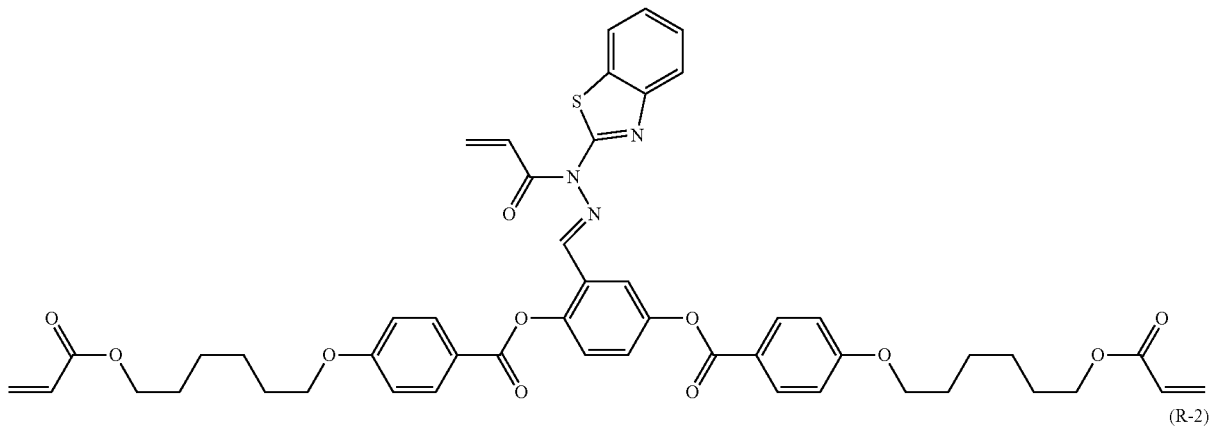
(R-1)

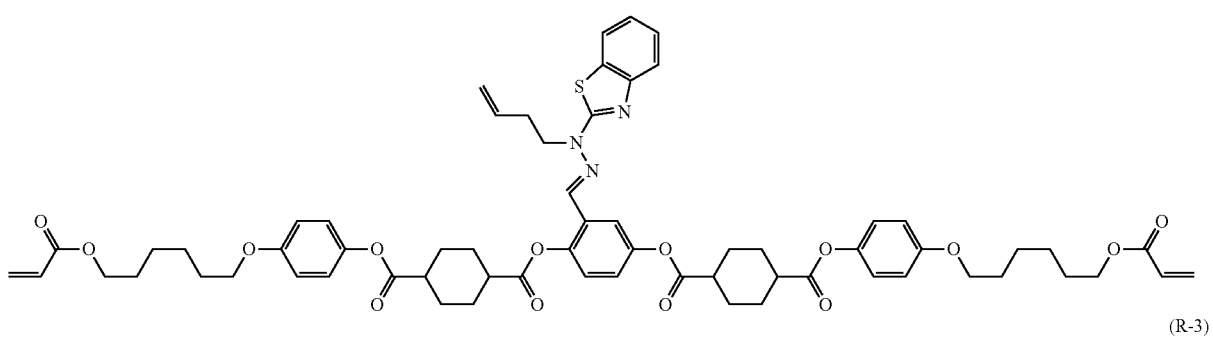
(R-2)

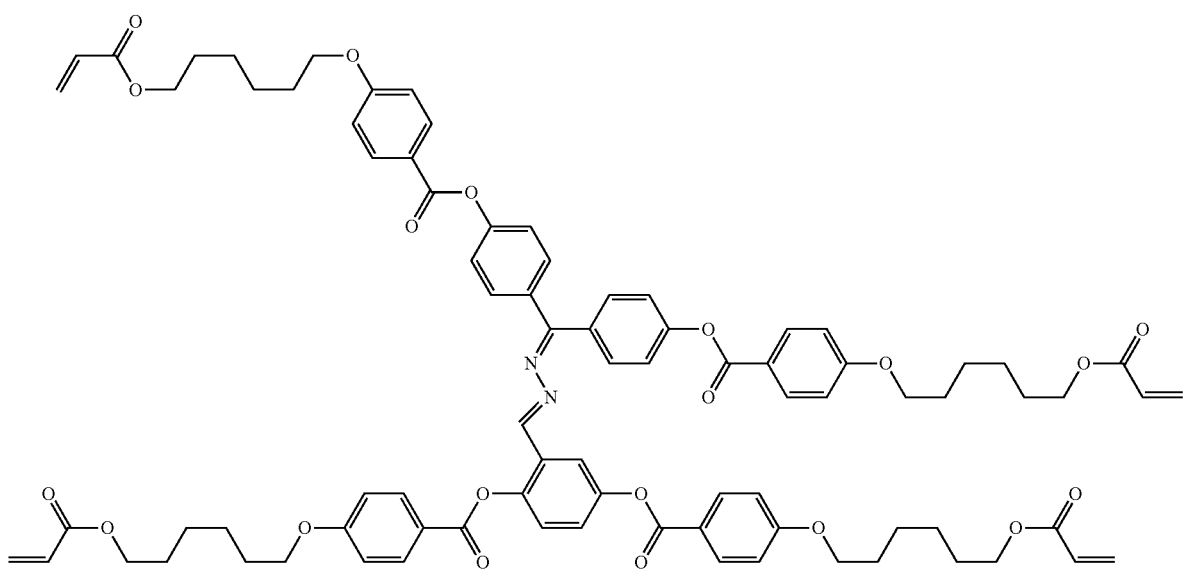
(R-3)

A polyimide solution for alignment film was applied onto a glass substrate having a thickness of 0.7 mm according to a spin coating method, dried at 100° C. for 10 minutes, and then baked at 200° C. for 60 minutes to form a coating film thereon. The resultant coating film was rubbed. For the rubbing, a commercially-available rubbing apparatus was used.

1% of a photopolymerization initiator Irgacure 907 (manufactured by BASF), 0.1% of 4-methoxyphenol and 80% of chloroform were added to the compound to be evaluated to prepare a coating liquid. The coating liquid was applied onto the rubbed glass substrate according to a spin coating method. This was dried at the temperature shown in the Table below for 2 minutes, and, using a high-pressure mercury lamp, irradiated with UV rays at an intensity of 40 mW/cm$^2$ for 25 seconds to produce a film to be evaluated.

The film to be evaluated was heat-treated at 90° C. for 1000 hours. The in-plane phase difference at a wavelength of 450 nm (Re(450)) and the in-plane phase difference at a wavelength of 550 nm (Re(550)) before the heat treatment, and the in-plane phase difference at a wavelength of 450 nm (Re'(450)) and the in-plane phase difference at a wavelength of 550 nm (Re'(550)) after the heat treatment were measured, and the reverse wavelength dispersion change rate (%)={Re'(450)/Re'(550)}/{Re(450)/Re(550)}×100 was calculated. In addition, the phase difference change rate (%)=Re'(550)/Re(550)×100 was calculated. The results are shown in the following Table.

TABLE 1

| Compound to be Evaluated | | Reverse wavelength Dispersion Change Rate | Phase Difference Change Rate |
|---|---|---|---|
| Example 14 | Compound (I-1) of the Invention | 99% | 100% |
| Example 15 | Compound (I-2) of the Invention | 100% | 99% |
| Example 16 | Compound (I-3) of the Invention | 99% | 100% |
| Example 17 | Compound (I-4) of the Invention | 99% | 99% |
| Example 18 | Compound (I-5) of the Invention | 98% | 98% |
| Example 19 | Compound (I-6) of the Invention | 96% | 97% |
| Example 20 | Compound (I-7) of the Invention | 97% | 97% |
| Example 21 | Compound (I-8) of the Invention | 95% | 96% |
| Example 22 | Compound (I-58) of the Invention | 96% | 95% |
| Example 23 | Compound (I-69) of the Invention | 95% | 95% |
| Example 24 | Compound (I-70) of the Invention | 96% | 95% |
| Example 25 | Compound (I-71) of the Invention | 95% | 94% |
| Example 26 | Compound (I-77) of the Invention | 95% | 94% |
| Comparative Example 1 | Comparative Compound (R-1) | 107% | 108% |
| Comparative Example 2 | Comparative Compound (R-2) | 93% | 93% |
| Comparative Example 3 | Comparative Compound (R-3) | 116% | 114% |

As in the Table, the compounds represented by the formulae (I-1) to (I-8), the formula (I-58), the formula (I-69), the formula (I-70), the formula (I-71) and the formula (I-77) of the present invention all have a reverse wavelength dispersion change rate of not more than 100%, and it can be seen that the reverse wavelength dispersion of these compounds after heat treatment was improved. In addition, the phase difference change rate of these compounds is also not more than 100%, and it can be seen that the phase difference of these compounds changed small after heat treatment. On the other hand, the comparative compounds (R-1) and (R-3) had a reverse wavelength dispersion change rate of more than 100%, and it can be seen that the reverse wavelength dispersion of these compounds lowered after heat treatment. In addition, the phase difference change rate of these compounds was larger than 100%, and it can be seen that the phase difference of these compounds changed large after heat treatment.

Further as in the Table, the degree of the reverse wavelength dispersion change (Ireverse wavelength dispersion change rate (%)−100%1) and the degree of phase difference change (Iphase difference change rate (%)−100%1) before and after heat treatment of the compounds represented by the formulae (I-1) to (I-8), the formula (I-58), the formula (I-69), the formula (I-70), the formula (I-71) and the formula (I-77) of the present invention were smaller than those of the comparative compounds (R-1) to (R-3), and it can be seen that the compounds of the present invention are unlikely to cause change in the reverse wavelength dispersion and the phase difference due to heating and are stable with time.

The film to be evaluated was tested as a sun test of 120 J, using a xenon lamp exposure test machine (SUNTEST XLS by Atlas) at 60 mW/cm$^2$ at 28° C. The test film after the sun test was sectioned into 10 cuts in length×10 cuts in width, totaling 100 cuts, and the number of the peeled cuts was counted. The ratio of the number of the peeled cuts (%) is shown in the following Table.

TABLE 2

| | Compound to be Evaluated | Peeled Cuts |
|---|---|---|
| Example 27 | Compound (I-1) of the Invention | 0% |
| Example 28 | Compound (I-2) of the Invention | 0% |
| Example 29 | Compound (I-3) of the Invention | 0% |
| Example 30 | Compound (I-4) of the Invention | 0% |
| Example 31 | Compound (I-5) of the Invention | 2% |
| Example 32 | Compound (I-6) of the Invention | 5% |
| Example 33 | Compound (I-7) of the Invention | 4% |
| Example 34 | Compound (I-8) of the Invention | 7% |
| Example 35 | Compound (I-58) of the Invention | 8% |
| Example 36 | Compound (I-69) of the Invention | 8% |
| Example 37 | Compound (I-70) of the Invention | 7% |
| Example 38 | Compound (I-71) of the Invention | 9% |
| Example 39 | Compound (I-77) of the Invention | 9% |
| Comparative Example 4 | Comparative Compound (R-1) | 15% |
| Comparative Example 5 | Comparative Compound (R-2) | 9% |
| Comparative Example 6 | Comparative Compound (R-3) | 11% |

From the Table, it can be seen that, regarding the degree of peeling, the compounds represented by the formulae (I-1) to (I-8), the formula (I-58), the formula (I-69), the formula (I-70), the formula (I-71) and the formula (I-77) of the present invention were comparable to or were more hardly peeled than the comparative compounds (R-1) to (R-3). Accordingly, the compounds of the present invention are useful as a constituent member of a polymerizable composition. In addition, the optically anisotropic body using the polymerizable liquid crystal composition that contains the compound of the present invention is useful for an optical film, etc.

The invention claimed is:

1. A compound represented by the following general formula (I):

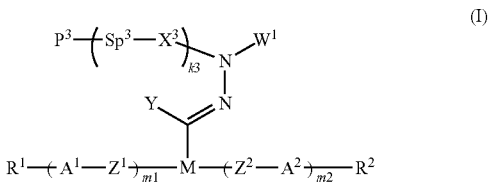

(wherein P$^3$ represents a group selected from the formulae (P-1) to (P-3), the formula (P-6), the formula (P-10), the formula (P-12), and the formula (P-17) shown below:

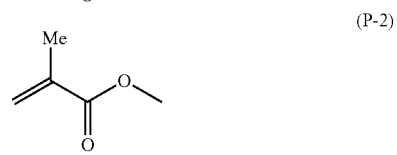

-continued

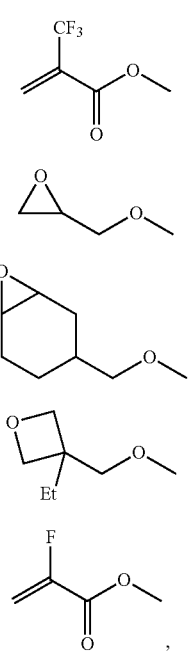

(P-3)

(P-6)

(P-10)

(P-12)

(P-17)

Sp³ represents a linear alkylene group having 1 to 20 carbon atoms in which one —CH₂— or two or more (—CH₂—)'s not adjacent to each other may be each independently substituted with —O—, —COO—, —OCO— or —OCO—O—, and plural Sp³'s, if any, may be the same or different;

X³ represents —O—, —S—, —OCH₂—, —CH₂O—, —COO—, —OCO—, —CO—S—, —S—CO—, —O—CO—O—, —COO—CH₂CH₂—, —OCO—CH₂CH₂—, —CH₂CH₂—COO—, —CH₂CH₂—OCO— or a single bond;

k3 represents an integer of 1 to 10;

A¹ and A² each independently represent a 1,4-phenylene group, a 1,4-cyclohexylene group or a naphthalene-2,6-diyl group, and these groups may be unsubstituted or substituted with one or more substituents L's;

L represents a fluorine atom, a chlorine atom, or a linear or branched alkyl group having 1 to 12 carbon atoms in which one —CH₂— or two or more (—CH₂—)'s not adjacent to each other may be each independently substituted with —O—, —OCO— or —OCO—, and arbitrary hydrogen atoms in the alkyl group may be substituted with a fluorine atom;

Z¹ and Z² each independently represent —OCH₂—, —CH₂O—, —CH₂CH₂—, —COO—, —OCO—, —CF₂O—, —OCF₂—, —COO—CH₂CH₂—, —OCO—CH₂CH₂—, —CH₂CH₂—COO—, —CH₂CH₂—OCO—, or a single bond, plural Z¹'s, if any, may be the same or different, and plural Z²'s, if any, may be the same or different;

m1 and m2 each independently represent an integer of 0 to 6, provided that m1+m2 represents an integer of 0 to 6;

M represents a group selected from the following formulae (M-1) to (M-6):

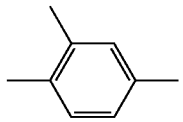

(M-1)

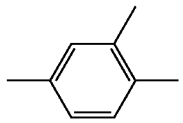

(M-2)

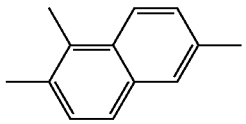

(M-3)

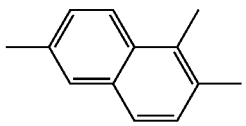

(M-4)

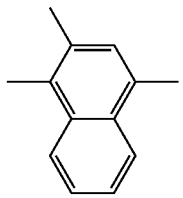

(M-5)

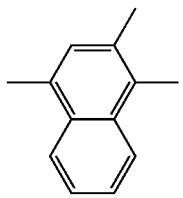

(M-6)

(wherein the two bonds in the horizontal direction each mean a bond to $R^1$-$(A^1$-$Z^1)_{m1}$— or —$(Z^2$-$A^2)_{m2}$-$R^2$, the upper bond means a bond to the remaining group, these groups may be unsubstituted or substituted with one or more substituents $L^M$'s ($L^M$ represents a fluorine atom, a chlorine atom, a nitro group, a cyano group, a dimethylamino group, or a linear or branched alkyl group having 1 to 12 carbon atoms in which one —CH₂— or two or more (—CH₂—)'s not adjacent to each other may be each independently substituted with —O—, —COO— or —OCO—, and arbitrary hydrogen atoms in the alkyl group may be substituted with a fluorine atom, or $L^M$ represents a group represented by $P^{LM}(Sp^{LM}$-$X^{LM})_{kLM}$— in which $P^{LM}$ represents a polymerizable group, the polymerizable group has the same meaning as $P^3$, $Sp^{LM}$ represents a spacer group or a single bond, plural $Sp^{LM}$'s, if any, may be the same or different, the spacer group has the same meaning as $Sp^3$, $X^{LM}$ has the same meaning as $X^3$, plural $X^{LM}$'s, if any, may be the same or different, provided that $P^{LM}$—$(Sp^{LM}$—$X^{LM})_{kLM}$— does not contain an —O—O— bond, kLM represents an integer of 0 to 10, plural $L^M$'s, if any, in the compound may be the same or different), and arbitrary (—CH═)'s may be each independently substituted with —N═);

Y represents a hydrogen atom, a fluorine atom, a chlorine atom, a nitro group, a cyano group or a linear or branched alkyl group having 1 to 20 carbon atoms in which one —CH₂— or two or more (—CH₂—)'s not adjacent to each other may be each independently substituted with —O—, —S—, —CO—, —COO—, —OCO—, —CO—S—, —S—CO—, —O—CO—O—, —CO—NH—, or —NH—CO—, and arbitrary hydrogen atoms in the alkyl group may be substituted with a fluorine atom;

W¹ represents a group selected from the following formulae (W-7-7-1) to (W-14-7-1):

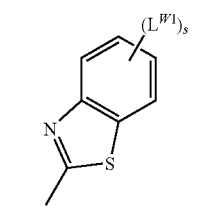
(W-7-7-1)

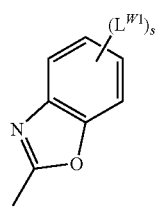
(W-7-6-1)

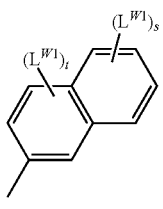
(W-9-1-1)

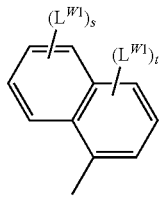
(W-9-1-2)

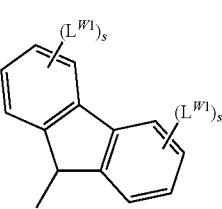
(W-12-1-1)

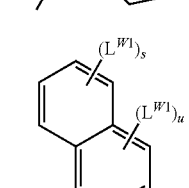
(W-13-7-1)

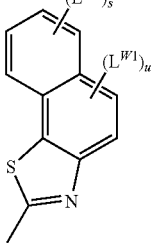

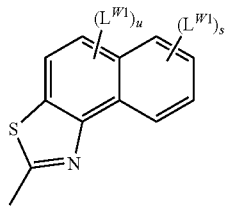
(W-14-7-1)

(wherein $L^{W1}$ represents a fluorine atom, a chlorine atom, a nitro group, a cyano group, or a linear or branched alkyl group having 1 to 20 carbon atoms in which one —CH₂— or two or more (—CH₂—)'s not adjacent to each other may be each independently substituted with —O—, —S—, —CO—, —COO— or —OCO—, arbitrary hydrogen atoms in the alkyl group may be substituted with a fluorine atom, plural $L^{W1}$'s, if any, in the compound may be the same or different, s represents an integer of 0 to 4, t represents an integer of 0 to 3, and u represents an integer of 0 to 2), provided that the group W¹ does not contain an —O—O— bond;

R¹ represents a hydrogen atom, a fluorine atom, a chlorine atom, a cyano group, or a linear or branched alkyl group having 1 to 12 carbon atoms in which one —CH₂— or two or more (—CH₂—)'s not adjacent to each other may be each independently substituted with —O—, —COO—, —OCO—, or —O—CO—O—, and arbitrary hydrogen atoms in the alkyl group may be substituted with a fluorine atom, or R¹ represents a group represented by $P^1$—$(Sp^1-X^1)_{k1}$— (where P¹ represents a polymerizable group, the polymerizable group has the same meaning as P³, Sp¹ represents a spacer group, plural Sp¹'s, if any, may be the same or different, the spacer group has the same meaning as Sp³, X¹ has the same meaning as X³, plural X¹'s, if any, may be the same or different, provided that $P^1$—$(Sp^1-X^1)_{k1}$— does not contain an —O—O— bond, and k1 represents an integer of 0 to 10); and R² represents a hydrogen atom, a fluorine atom, a chlorine atom, a cyano group, or a linear or branched alkyl group having 1 to 12 carbon atoms in which one —CH₂— or two or more (—CH₂—)'s not adjacent to each other may be each independently substituted with —O—, —COO—, —OCO—, or —O—CO—O—, and arbitrary hydrogen atoms in the alkyl group may be substituted with a fluorine atom, or R² represents a group represented by $P^2$-$(Sp^2-X^2)_{k2}$—(where P² represents a polymerizable group, the polymerizable group has the same meaning as P³, Sp² represents a spacer group, plural Sp²'s, if any, may be the same or different, the space group has the same meaning as Sp³, X² has the same meaning as X³, plural X²'s, if any, may be the same or different, provided that $P^2$-$(Sp^2-X^2)_{k2}$— does not contain an —O—O— bond, and k2 represents an integer of 0 to 10), provided that when R¹ represents a group represented by $P^1$—$(Sp^1-X^1)_{k1}$— and R² represents a group represented by $P^2$—$(Sp^2-X^2)_{k2}$—, at least one of Z¹ and Z² directly bonding to M represents —OCH₂—, —CH₂O—, —CH₂CH₂—, —CF₂O—, —OCF₂—, —COO—CH₂CH₂—, —OCO—CH₂CH₂—, —CH₂CH₂—COO— or —CH₂CH₂—OCO—).

2. The compound according to claim 1, wherein P¹ and P², if present, and P³ in the general formula (I), each independently represent the group selected from the formulae (P-1) to (P3).

3. The compound according to claim 1, wherein $Sp^1$ and $Sp^2$, if present, and $Sp^3$ in the general formula (I), each independently represent a linear alkylene group having 1 to 12 carbon atoms in which one —$CH_2$— or two or more (—$CH_2$—)'s not adjacent to each other may be each independently substituted with —O—.

4. The compound according to claim 1, wherein in the general formula (I), $R^1$ represents a group represented by $P^1$—$(Sp^1\text{-}X^1)_{k1}$— and $R^2$ represents any other group than a group represented by $P^2$—$(Sp^2\text{-}X^2)_{k2}$—, or $R^1$ represents any other group than a group represented by $P^1$—$(Sp^1\text{-}X^1)_{k1}$— and $R^2$ represents a group represented by $P^2$—$(Sp^2\text{-}X^2)_{k2}$—.

5. The compound according to claim 1, wherein in the general formula (I), at least one of $R^1$ and $R^2$ represents a linear or branched alkyl group having 1 to 12 carbon atoms in which one —$CH_2$— or two or more (—$CH_2$—)'s not adjacent to each other may be each independently substituted with —O—, —COO—, —OCO— or —O—CO—O—.

6. A composition comprising the compound of claim 1.

7. A liquid crystal composition comprising the compound of claim 1.

8. A polymer obtained through polymerization of the composition of claim 6.

9. An optically anisotropic body using the polymer of claim 8.

10. A cured product of the compound of claim 1, the cure product having a utility selected from the group consisting of resins, resin additives, oils, filters, adhesives, pressure-sensitive adhesives, oils and fats, inks, medicines, cosmetics, detergents, building materials, wrapping materials, liquid crystal materials, organic EL materials, organic semiconductor materials, electronic materials, di splay elements, electronic devices, communication devices, automotive parts, aircraft parts, machine parts, agricultural chemicals and foods.

* * * * *